US012187797B2

United States Patent
Panicker et al.

(10) Patent No.: US 12,187,797 B2
(45) Date of Patent: Jan. 7, 2025

(54) SIRP α, SIRP β 1, AND SIRP γ ANTIBODIES AND USES THEREOF

(71) Applicant: Electra Therapeutics, Inc., South San Francisco, CA (US)

(72) Inventors: Sandip Panicker, South San Francisco, CA (US); Adam David Rosenthal, South San Francisco, CA (US); Eileen Lingshu Rose, South San Francisco, CA (US)

(73) Assignee: Electra Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 18/590,865

(22) Filed: Feb. 28, 2024

(65) Prior Publication Data

US 2024/0239888 A1 Jul. 18, 2024

Related U.S. Application Data

(63) Continuation of application No. 17/923,778, filed as application No. PCT/US2021/031605 on May 10, 2021.

(60) Provisional application No. 63/022,309, filed on May 8, 2020.

(51) Int. Cl.
| | |
|---|---|
| *A61K 39/395* | (2006.01) |
| *A61P 37/06* | (2006.01) |
| *C07K 16/28* | (2006.01) |
| *C12N 15/63* | (2006.01) |

(52) U.S. Cl.
CPC .......... *C07K 16/2803* (2013.01); *A61P 37/06* (2018.01); *C12N 15/63* (2013.01); *C07K 2317/24* (2013.01); *C07K 2317/52* (2013.01); *C07K 2317/565* (2013.01); *C07K 2317/73* (2013.01); *C07K 2317/732* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 2023/0174648 A1 | 6/2023 | Panicker et al. |
| 2023/0303685 A1 | 9/2023 | Panicker et al. |

FOREIGN PATENT DOCUMENTS

| | | |
|---|---|---|
| WO | WO-2018118887 A1 | 6/2018 |
| WO | WO-2018149938 A1 | 8/2018 |
| WO | WO-2018190719 A2 | 10/2018 |
| WO | WO-2019073080 A1 | 4/2019 |
| WO | WO-2020263793 A1 | 12/2020 |
| WO | WO-2021226576 A1 | 11/2021 |
| WO | WO-2021226591 A1 | 11/2021 |
| WO | WO-2023086906 A2 | 5/2023 |

OTHER PUBLICATIONS

Almagro & Fransson, Frontiers in Bioscience 2008; 13:1619-33 (Year: 2008).*
Rudikoff et al. (Proc Natl Acad Sci USA 1982 vol. 79 p. 1979). (Year: 1979).*
MacCallum et al. J. Mol. Biol. (1996) 262, 732-745 (Year: 1996).*
Pascalis et al. (The Journal of Immunology (2002) 169, 3076-3084) (Year: 2002).*
Casset et al. (BBRC 2003, 307:198-205) (Year: 2003).*
Vajdos et al. (J. Mol. Biol. (2002) 320, 415-428) (Year: 2002).*
Chen et al. (J. Mol. Bio. (1999) 293, 865-881) (Year: 1999).*
Wu et al. (J. Mol. Biol. (1999) 294, 151-162) (Year: 1999).*
Lamminmaki et al. (JBC 2001, 276:36687-36694) (Year: 2001).*
Padlan et al. (PNAS 1989, 86:5938-5942) (Year: 1989).*
Absolute Antibody, (Jan. 1, 2023) "Anti-SIRP g [OX-119]," [online]. Retrieved from: https://absoluteantibody.com/product/a nti-sirp-g-ox-119/ [retrieved on Oct. 19, 2023], 2 pages.
Brooke et al., "Human lymphocytes interact directly with CD47 through a novel member of the signal regulatory protein (SIRP) family," The Journal of Immunology (2004); 173(4): 2562-2570.
ClinicalTrials.gov, ID NCT05416307. Evaluation of the Safety and Efficacy of ELA026 in Participants with Secondary Hemophagocytic Lymphohistiocytosis [online], Version 1, dated Jun. 8, 2022 [retrieved on Nov. 29, 2023]. Retrieved from the Internet: https://clinicaltrials.gov/study/NCT05416307?term=Electratherapeutics&intr=ELA026&rank=2&tab=history&a=1, 10 printed pages.
ClinicalTrials.gov, ID NCT05416307. Evaluation of the Safety and Efficacy of ELA026 in Participants with Secondary Hemophagocytic Lymphohistiocytosis [online], Version 7, dated Oct. 18, 2023 [retrieved on Nov. 29, 2023]. Retrieved from the Internet: https://clinicaltrials.gov/study/NCT05416307?term=Electratherapeutics&intr=ELA026&rank=2&tab=history&a=7, 11 printed pages.
ClinicalTrials.gov, ID NCT05556863. Evaluation of the Safety, Tolerability, Pharmacokinetics and Pharmacodynamics of ELA026 in Single and Multiple Doses in Healthy [online], Version 1, dated Sep. 23, 2022 [retrieved on Nov. 29, 2023]. Retrieved from the Internet: https://clinicaltrials.gov/study/NCT05556863?term=NCT05556863&rank=1&tab=history&a=1, 10 printed pages.
ClinicalTrials.gov, ID NCT05556863. Evaluation of the Safety, Tolerability, Pharmacokinetics and Pharmacodynamics of ELA026 in Single and Multiple Doses in Healthy [online], Version 2, dated Oct. 18, 2023 [retrieved on Nov. 29, 2023]. Retrieved from the Internet: https://clinicaltrials.gov/study/NCT05556863?term=NCT05556863&rank=1&tab=history&a=2, 10 printed pages.

(Continued)

*Primary Examiner* — Meera Natarajan
(74) *Attorney, Agent, or Firm* — Cooley LLP

(57) ABSTRACT

Provided herein are antibodies that bind signal regulatory protein gamma (SIRPγ), as well as SIRPα and/or SIRPβ1, and methods of using such antibodies (referred to as SIRP antibodies). In some embodiments, the SIRP antibodies are human monoclonal antibodies that bind human SIRPγ as well as SIRPα and/or SIRPβ1. In some embodiments, the SIRP antibodies provided herein are useful for treating a disease or condition associated with overactivation and/or hyperproliferation of lymphocytes, myeloid cells, or a combination thereof, or a disease or condition associated with SIRPα, SIRPβ1 and/or SIRPγ activity.

29 Claims, 39 Drawing Sheets
Specification includes a Sequence Listing.

(56) References Cited

OTHER PUBLICATIONS

Database GenBank Accession No. EHH65481.1 (Mar. 2015) "Signal-regulatory protein gamma [Macaca fascicularis]" National Library of Medicine, National Center for Biotechnology Information (NCBI) [online]. Retrieved from: https://www.ncbi.nlm.nih.gov/protein/EHH65481.1/; retrieved on Nov. 22, 2023, 5 printed pages.
Database UniProtKB ID Q9P1W8 (Jan. 23, 2007), "SIRPG_Human", including Isoform 1, Isoform 2, Isoform 3, and Isoform 4. UniProt consortium [online]. Retrieved from: https://www.uniprot.org/uniprotkb/Q9P1W8/entry#sequences; retrieved on Nov. 22, 2023, 11 printed pages.
Hatherley et al., (Apr. 2014) "Polymorphisms in the human inhibitory signal-regulatory protein α do not affect binding to its ligand CD47," J Biol Chem, 289(14):10024-10028.
Henter, J-I. et al. "HLH-2004: Diagnostic and therapeutic guidelines for hemophagocytic lymphohistiocytosis" Pediatr Blood Cancer, vol. 48, p. 124-131 (2007).
Locatelli et al., (May 2020) "Emapalumab in Children with Primary Hemophagocytic Lymphohistiocytosis," The New England Journal of Medicine, 382(19):1811-1822.
PCT/US2021/031541 International Search Repot and Written Opinion mailed Oct. 5, 2021, 20 pages.
PCT/US2021/031605 International Search Report and Written Opinion mailed Sep. 30, 2021, 19 pages.
PCT/US2022/079668 International Search Report and Written Opinion dated May 16, 2023, 18 pages.
Piccio et al., "Adhesion of human T cells to antigen-presenting cells through SIRPβ2-CD47 interaction costimulates T-cell proliferation," Blood (2005); 105(6):2421-2427.
Ring et al., "Anti-SIRP[alpha] antibody immunotherapy enhances neutrophil and macrophage antitumor activity," PNAS USA (Nov. 2017); 114(49):E10578-E10585, 8 pages.
Tabata et al. (Jan. 2012) "Possible prediction of underlying lymphoma by high sIL-2R/ferritin ratio in hemophagocytic syndrome." Annals of Hematology, 91(1):63-71. doi:10.1007/s00277-011-1239-7.
Zoref-Lorenz, et al., (Feb. 2022) "An improved index for diagnosis and mortality prediction in malignancy-associated hemophagocytic lymphohistiocytosis," Blood, 139(7):1098-1110.
Zou, et al. (Sep. 2023) "Serum sCD25/ferritin ratio combined with MCP-1 is a valid predictor for identifying LAHS with HLH as the first manifestation," J Cancer Res Clin Oncol, 149(11):8521-8533.
Co-pending U.S. Appl. No. 18/660,086, inventor Sandip Panicker; et al., filed May 9, 2024.

* cited by examiner

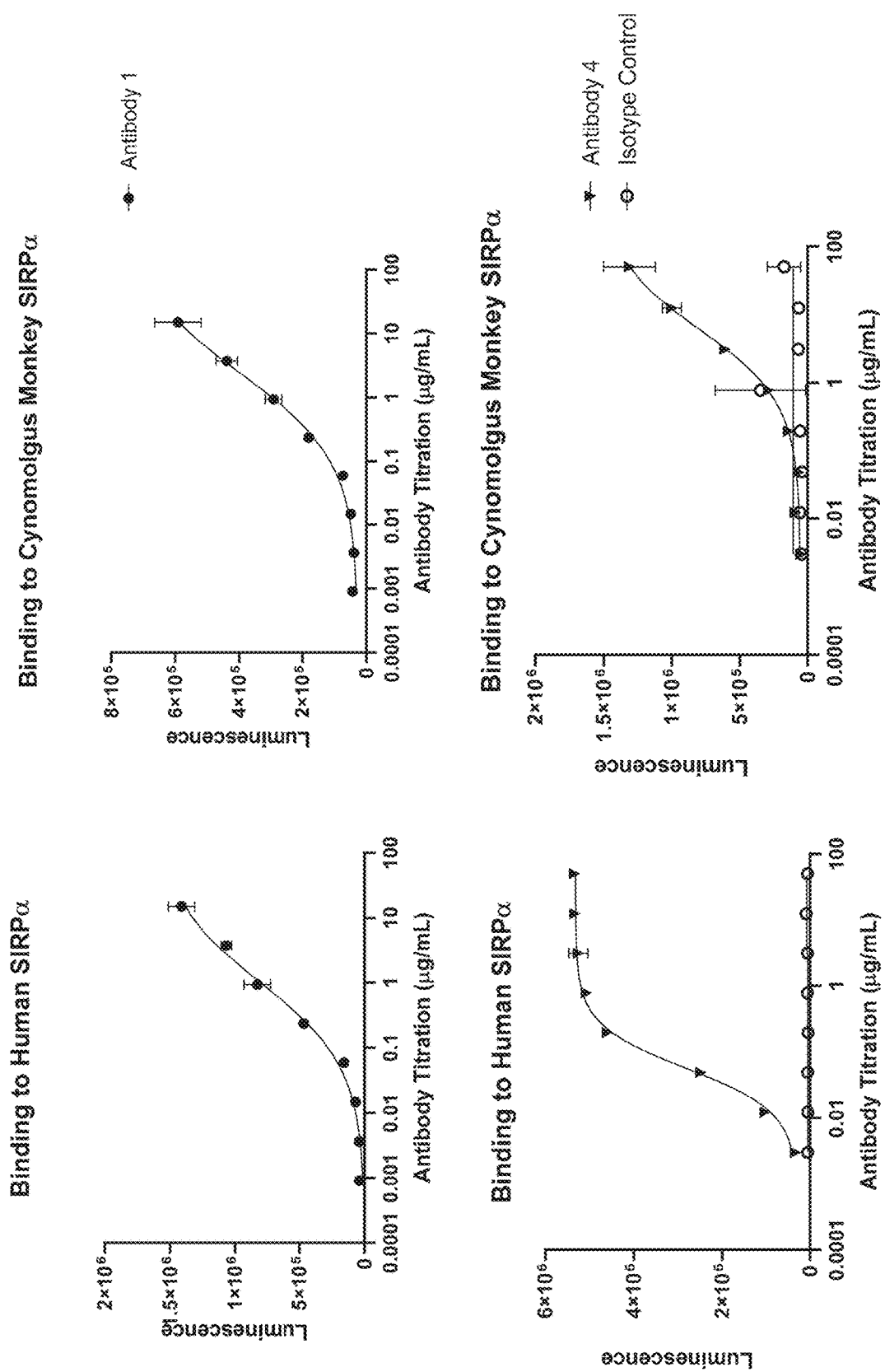

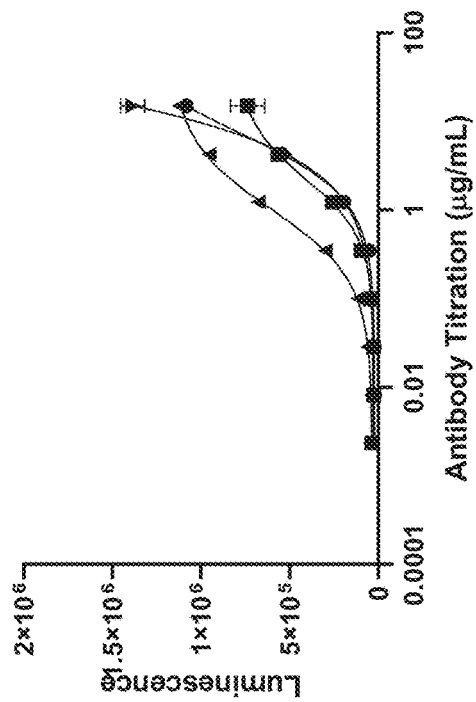
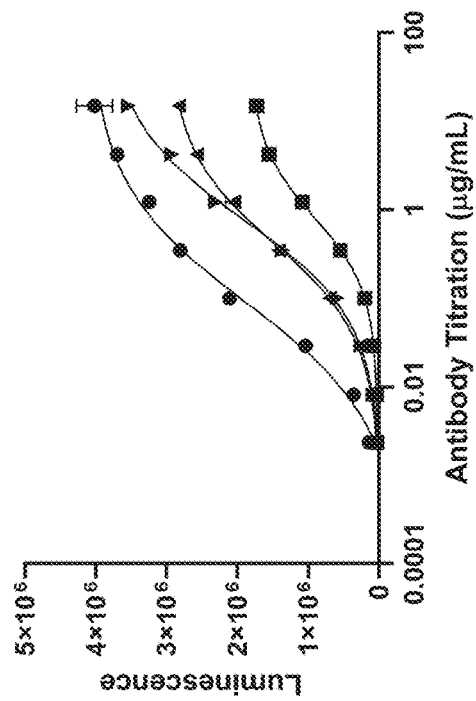
FIG. 2B

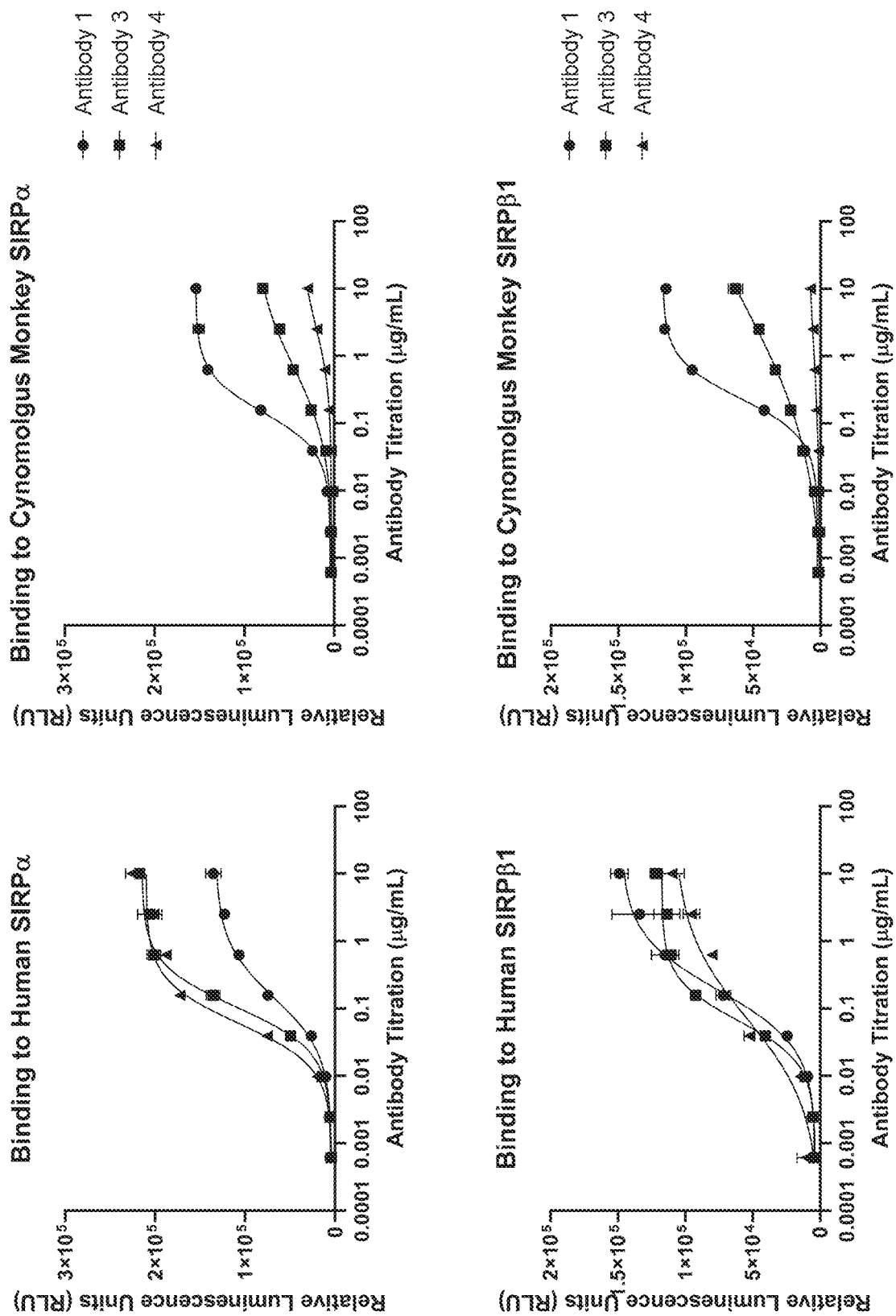

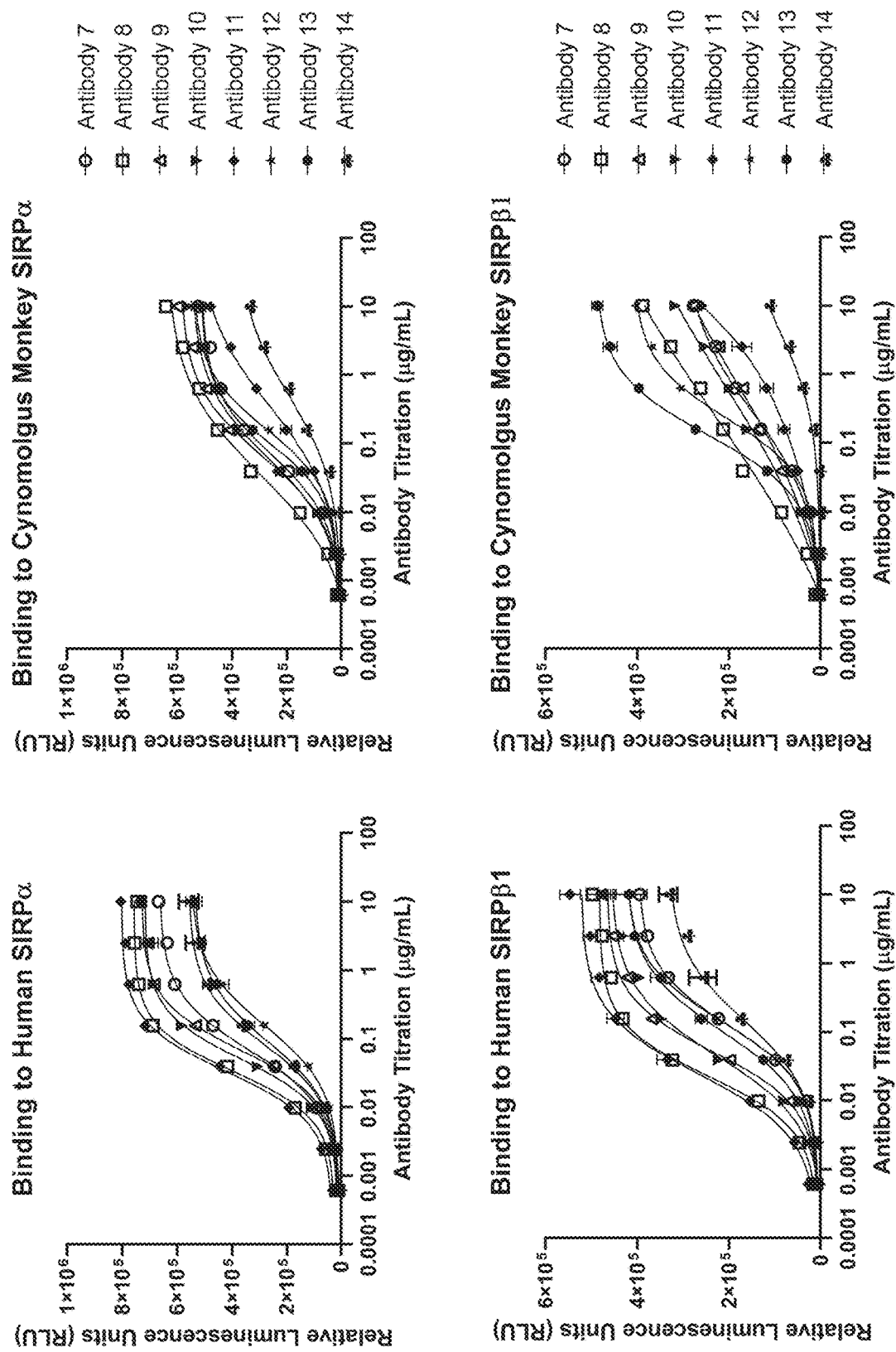

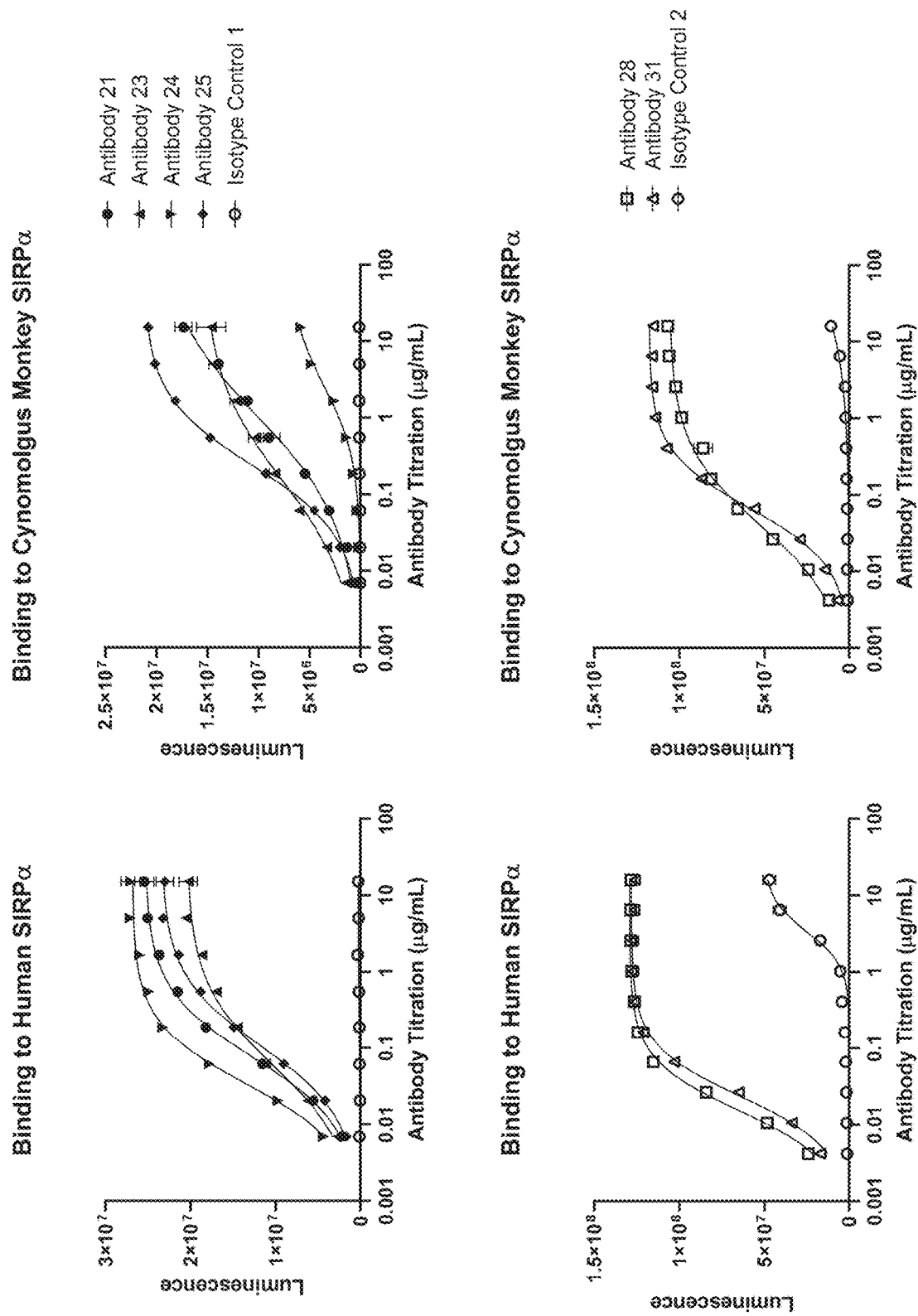

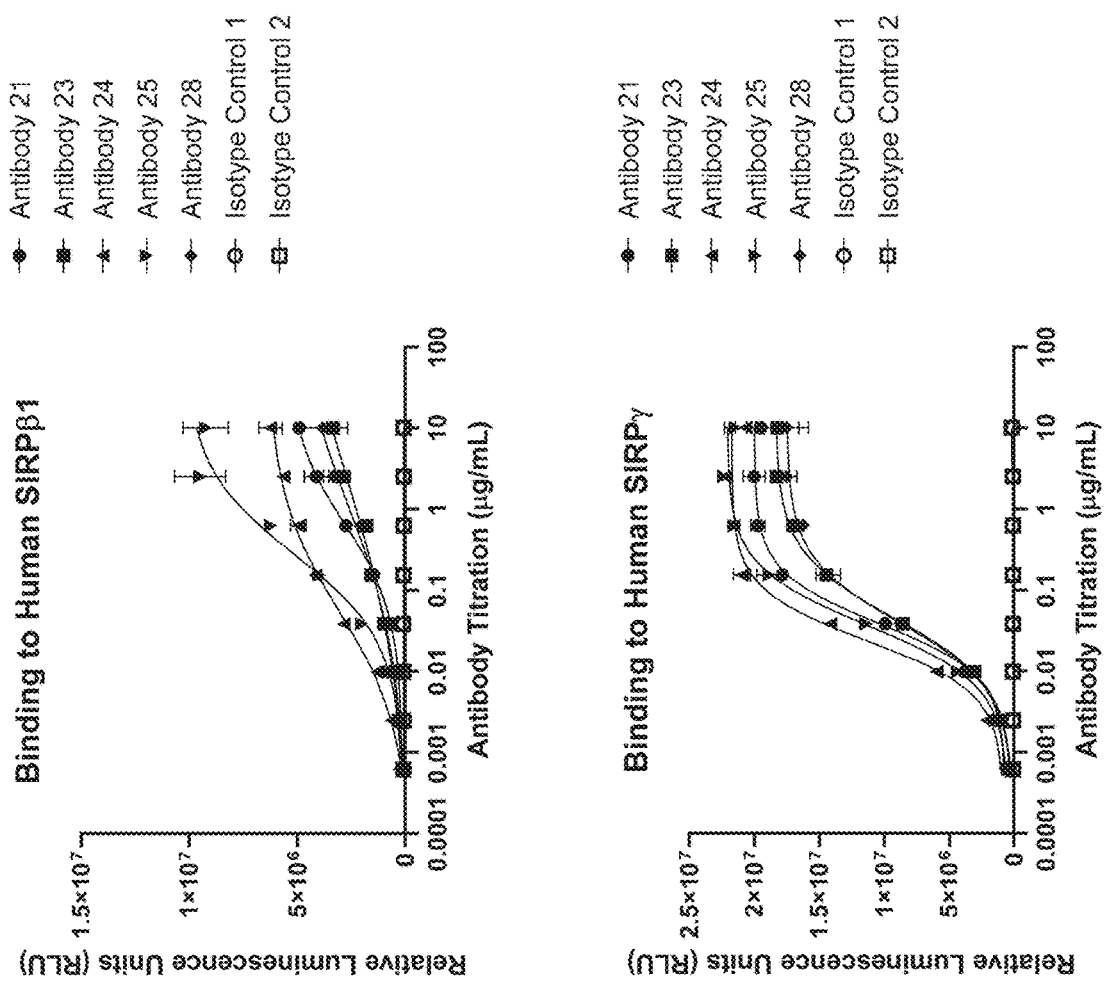

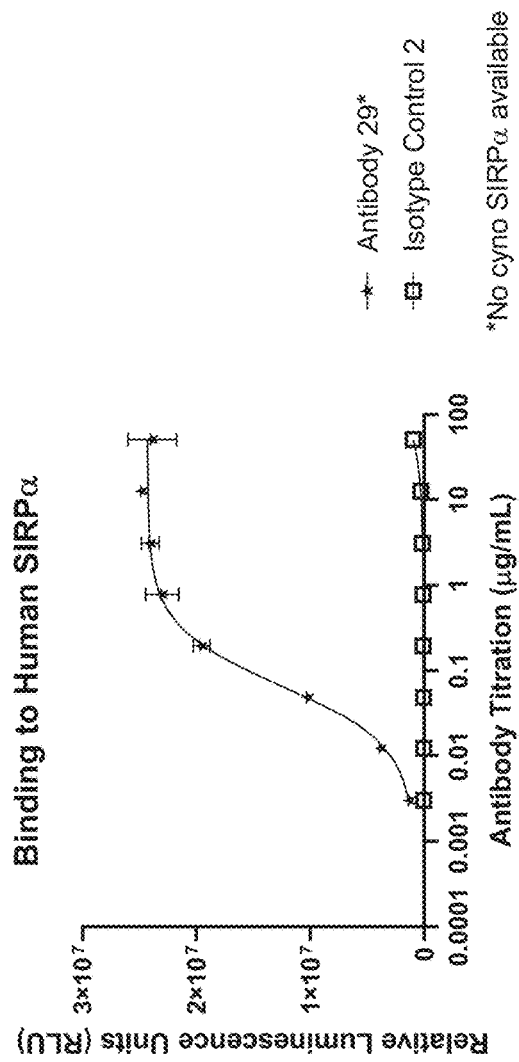
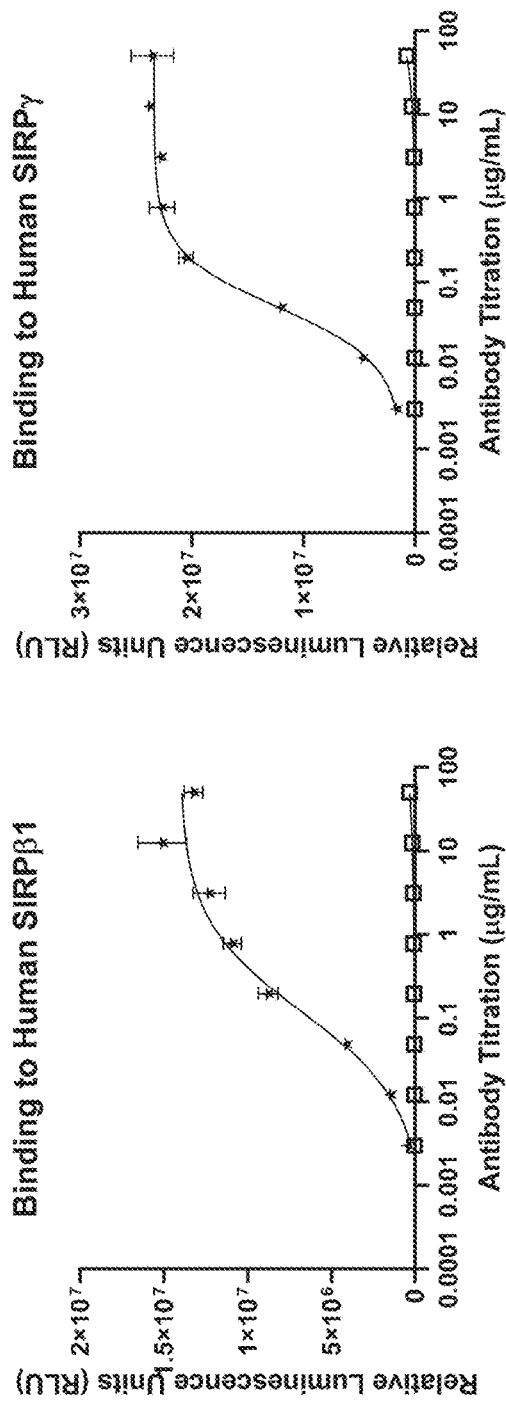
FIG. 3C

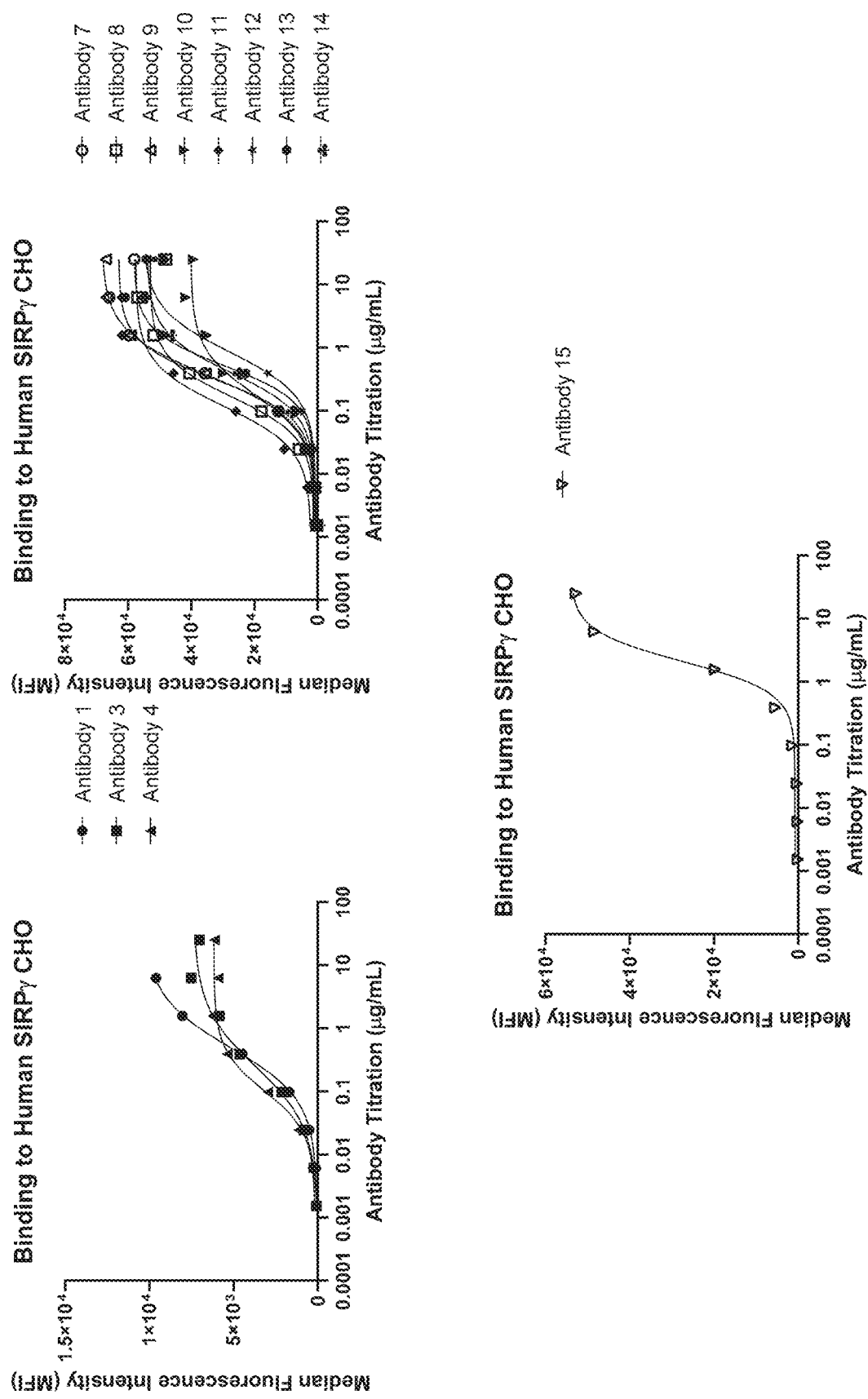

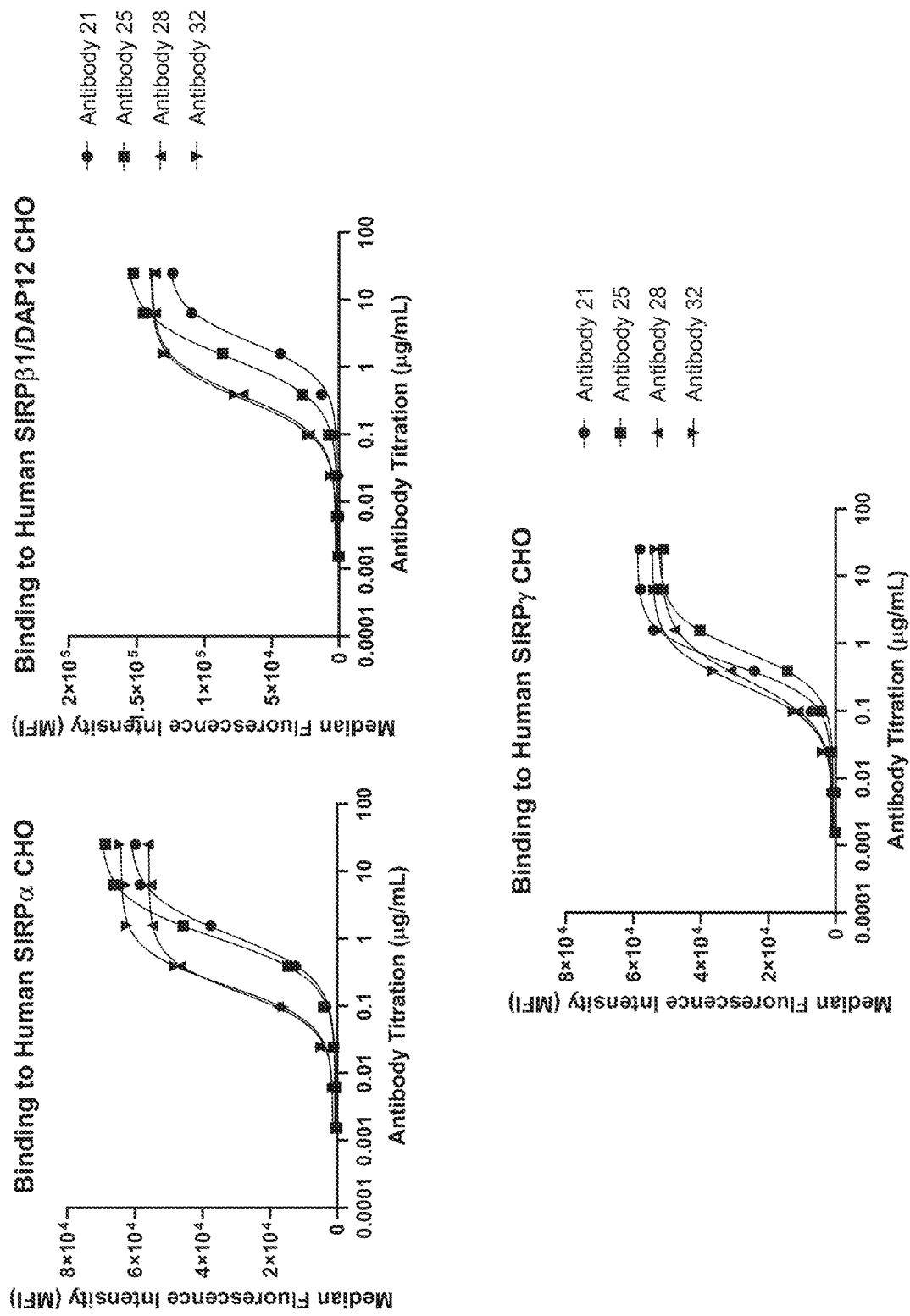

FIG. 6C
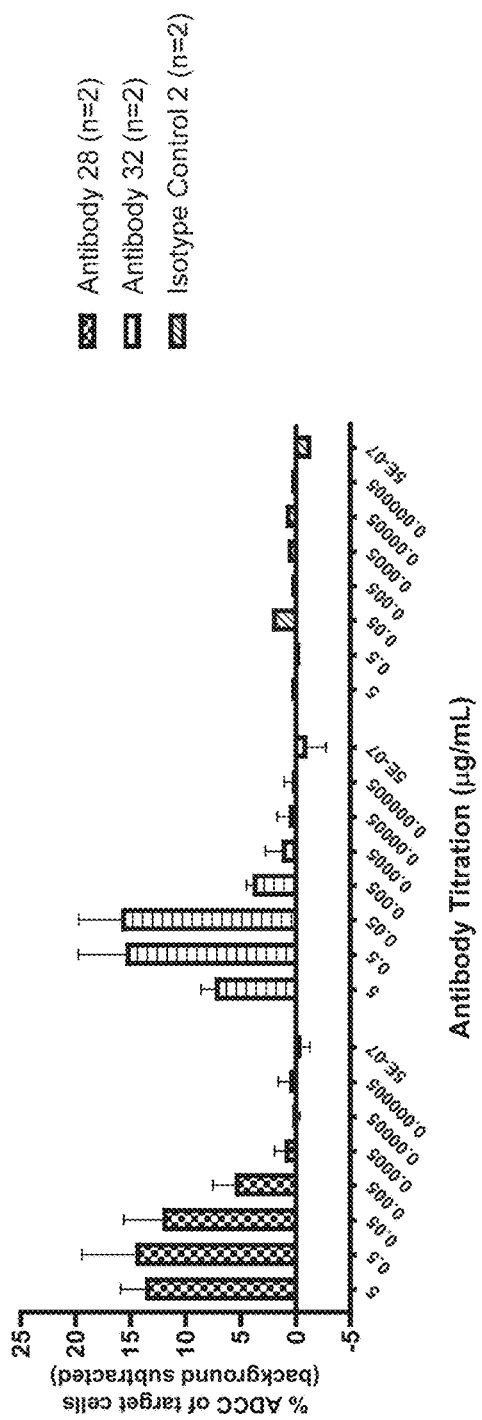
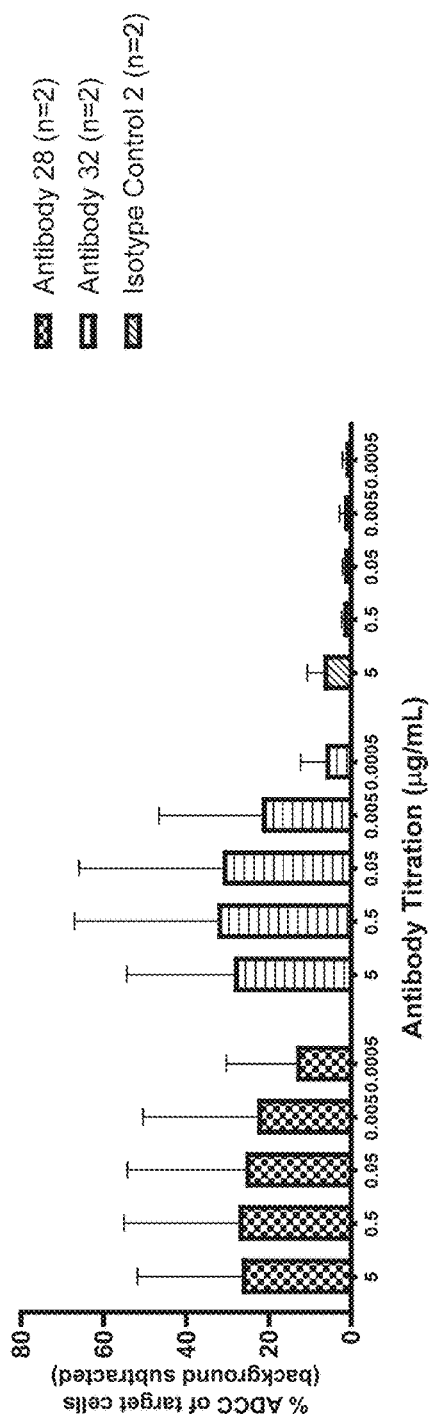

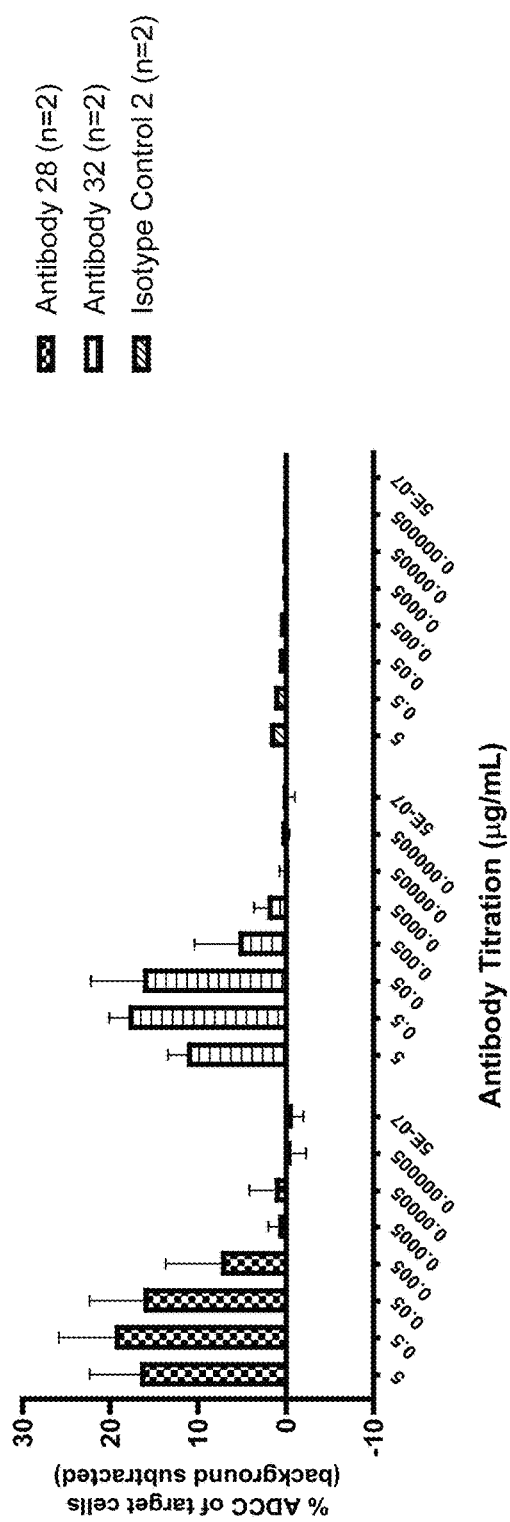
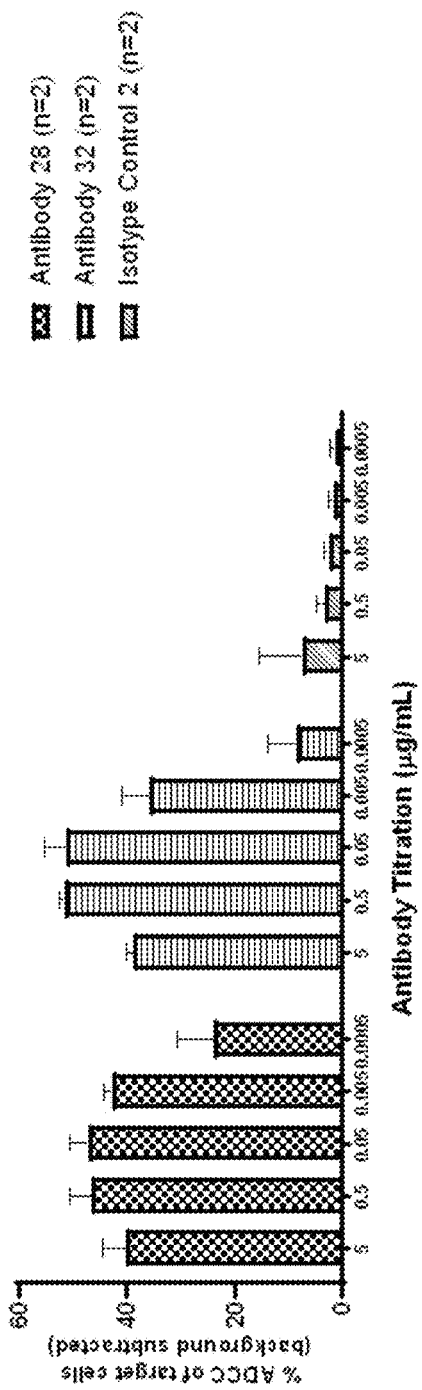
FIG. 6D

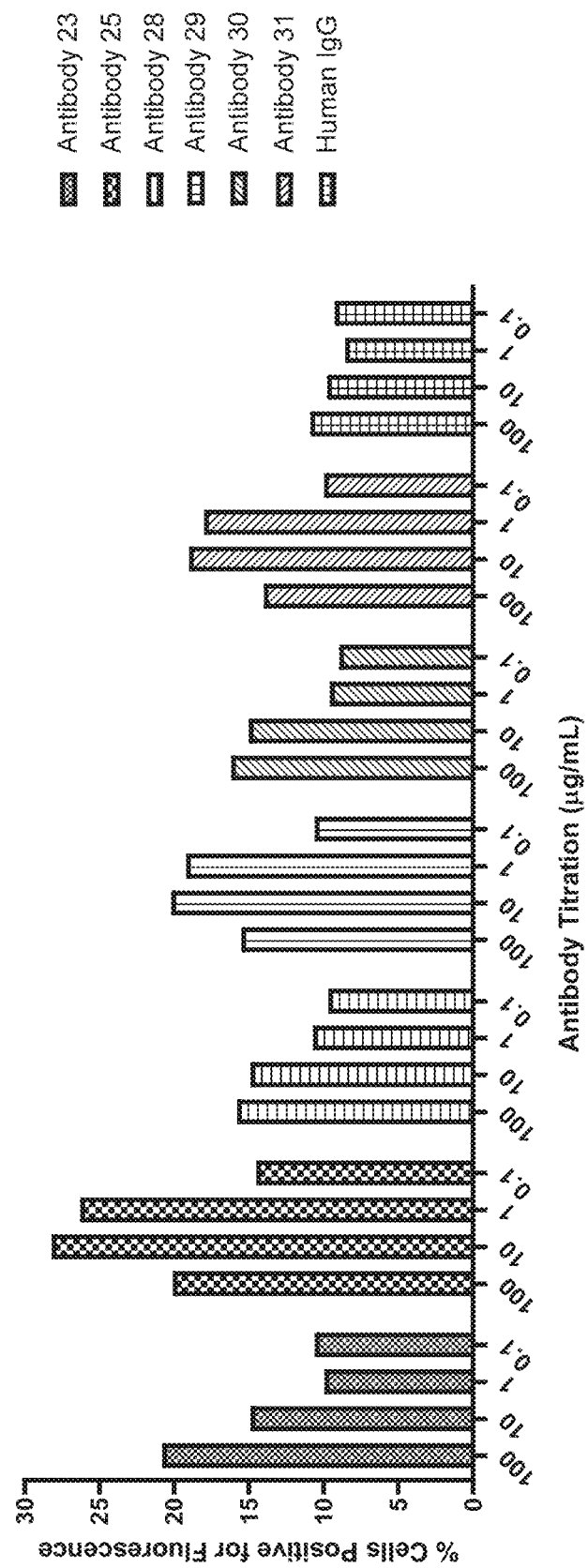

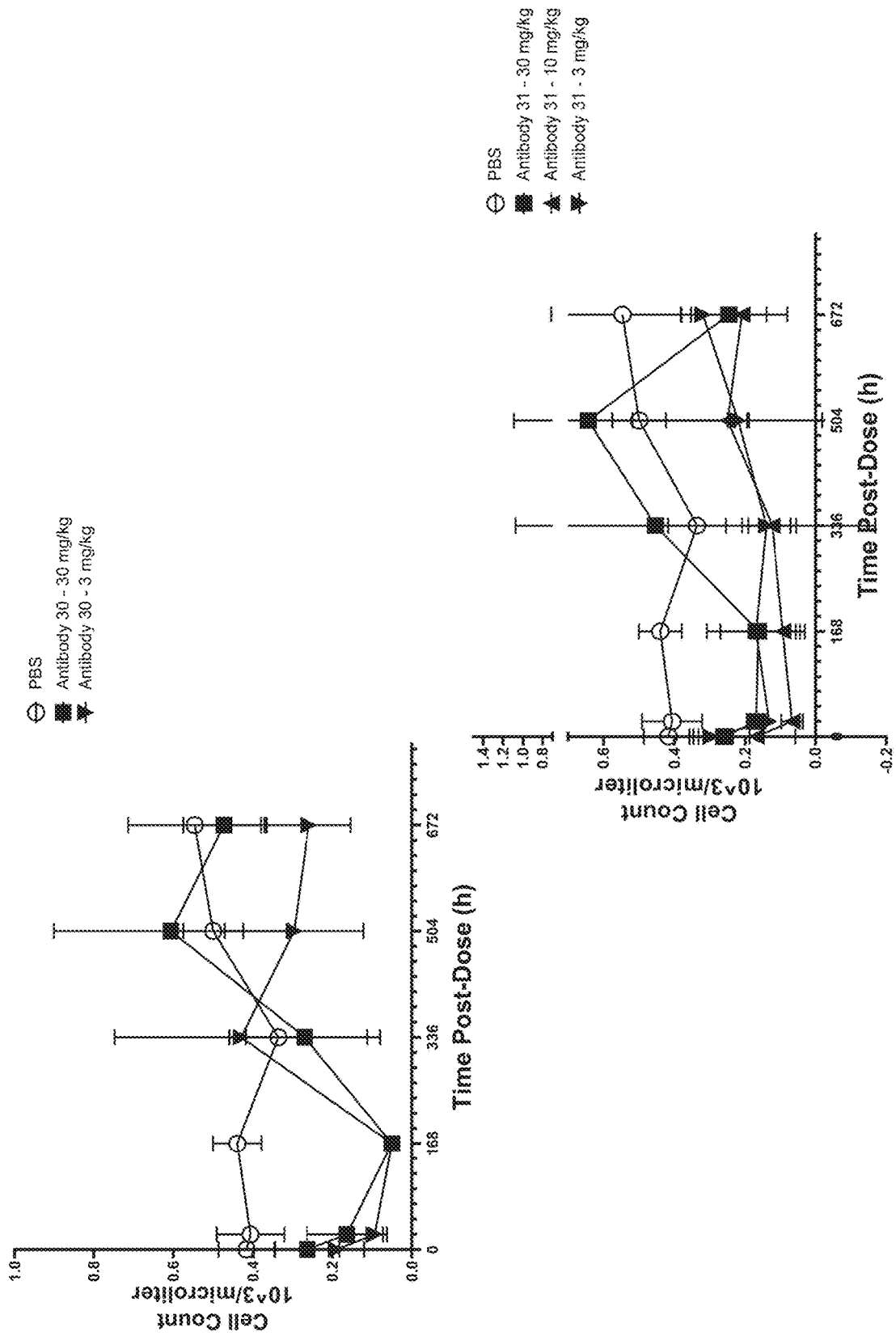

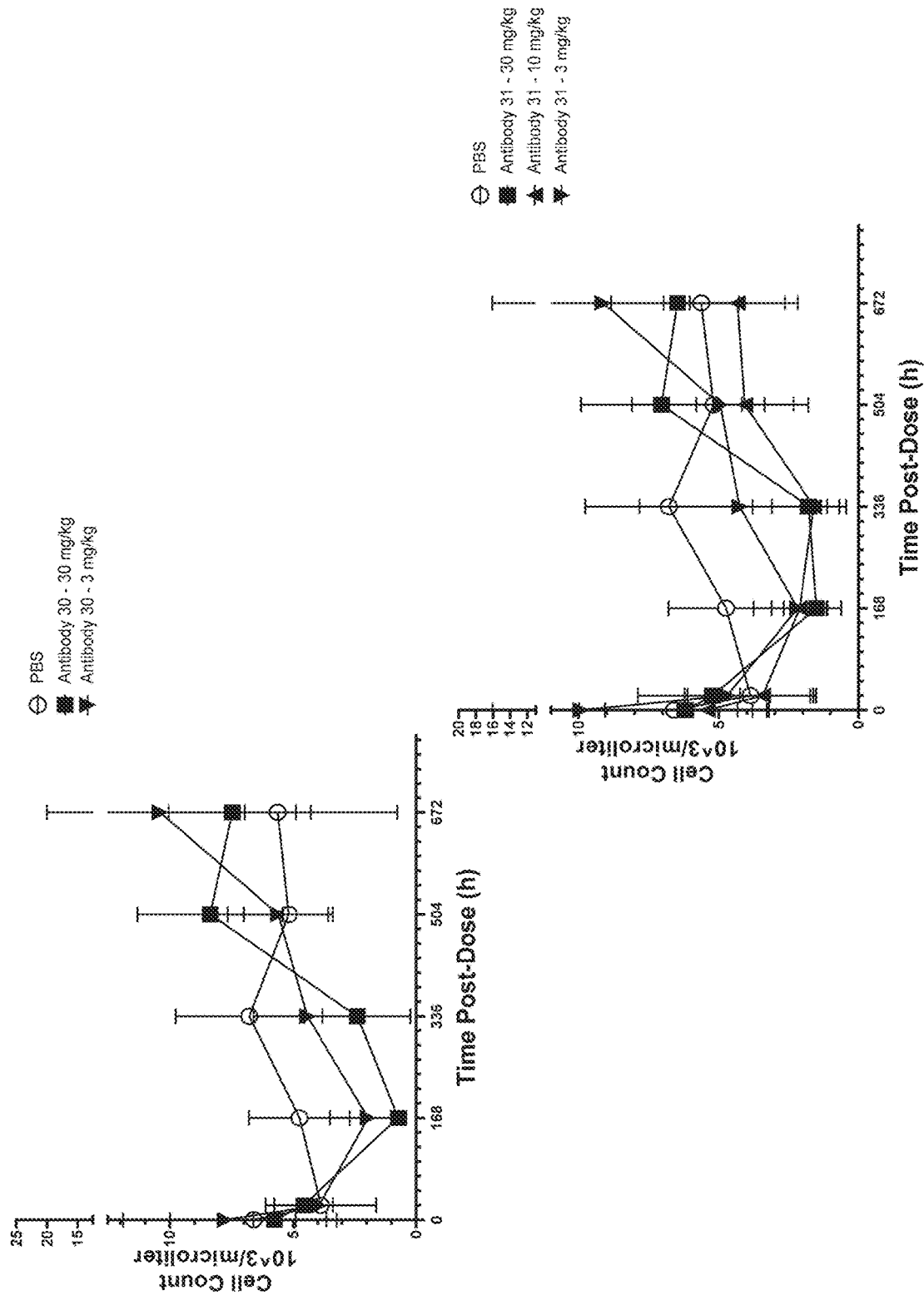

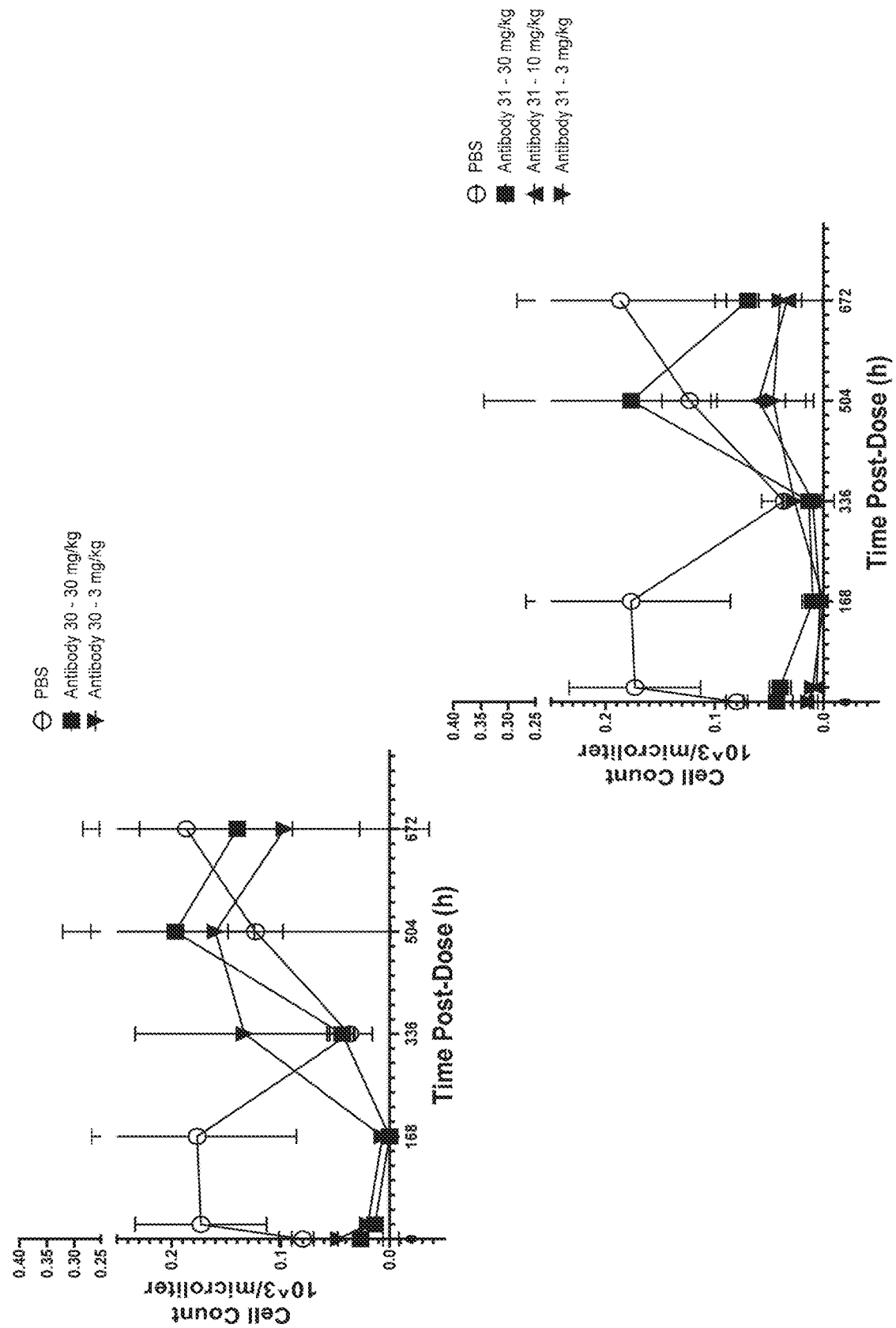

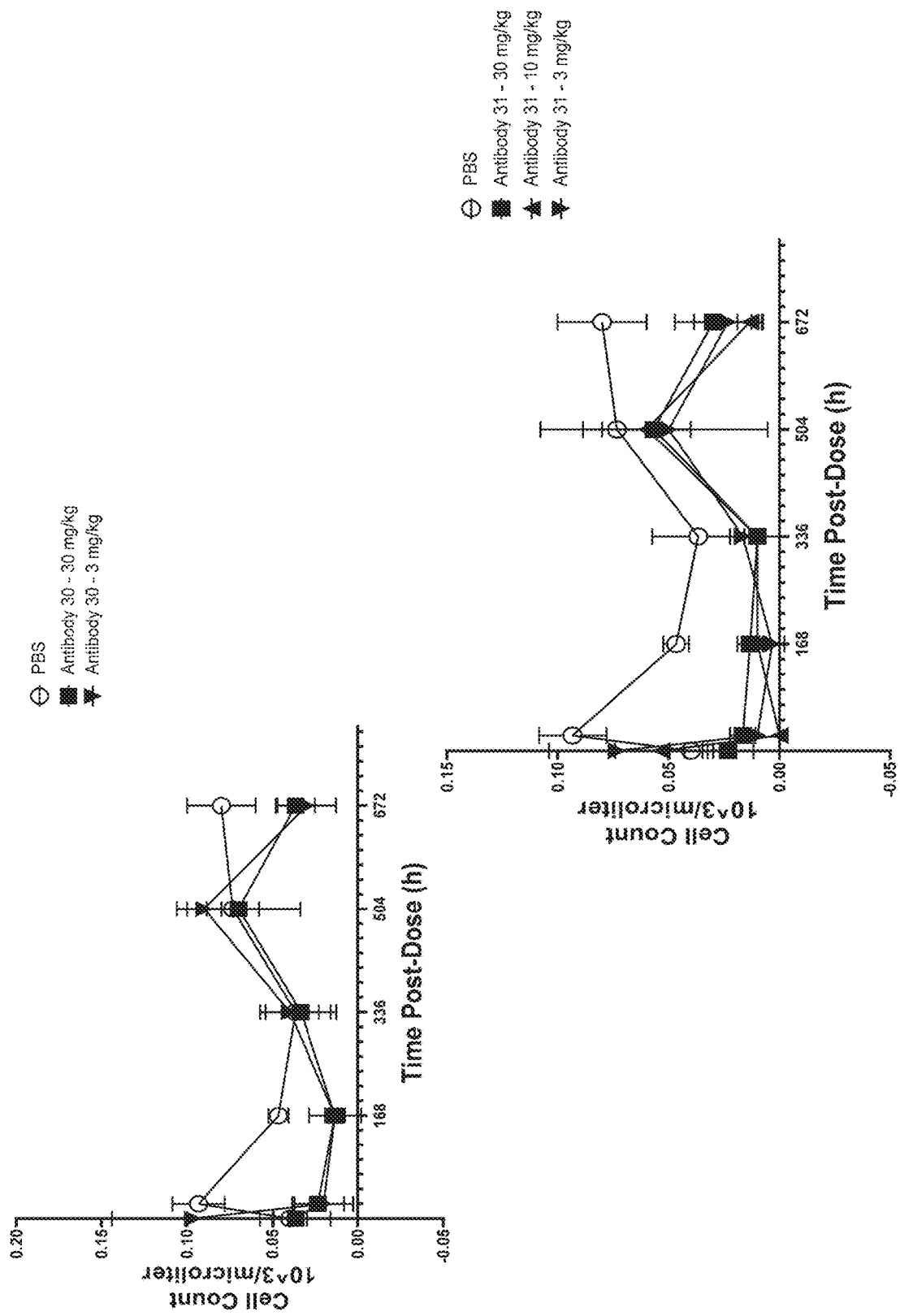

```
                              SEQUENCE LISTING

Sequence total quantity: 175
SEQ ID NO: 1            moltype = AA  length = 504
FEATURE                 Location/Qualifiers
source                  1..504
                        mol_type = protein
                        organism = Homo sapiens
SEQUENCE: 1
MEPAGPAPGR LGPLLCLLLA ASCAWSGVAG EEELQVIQPD KSVLVAAGET ATLRCTATSL   60
IPVGPIQWFR GAGPGRELIY NQKEGHFPRV TTVSDLTKRN NMDFSIRIGN ITPADAGTYY  120
CVKFRKGSPD DVEFKSGAGT ELSVRAKPSA PVVSGPAARA TPQHTVSFTC ESHGFSPRDI  180
TLKWFKNGNE LSDFQTNVDP VGESVSYSIH STAKVVLTRE DVHSQVICEV AHVTLQGDPL  240
RGTANLSETI RVPPTLEVTQ QPVRAENQVN VTCQVRKFYP QRLQLTWLEN GNVSRTETAS  300
TVTENKDGTY NWMSWLLVNV SAHRDDVKLT CQVEHDGQPA VSKSHDLKVS AHPKEQGSNT  360
AAENTGSNER NIYIVVGVVC TLLVALLMAA LYLVRIRQKK AQGSTSSTRL HEPEKNAREI  420
TQDTNDITYA DLNLPKGKKP APQAAEPNNH TEYASIQTSP QPASEDTLTY ADLDMVHLNR  480
TPKQPAPKPE PSFSEYASVQ VPRK                                        504

SEQ ID NO: 2            moltype = AA  length = 507
FEATURE                 Location/Qualifiers
source                  1..507
                        mol_type = protein
                        organism = Homo sapiens
SEQUENCE: 2
MEPAGPAPGR LGPLLCLLLA ASCAWSGVAG EEELQVIQPD KSVSVAAGES AILHCTVTSL   60
IPVGPIQWFR GAGPARELIY NQKEGHFPRV TTVSESTKRE NMDFSISISN ITPADAGTYY  120
CVKFRKGSPD TEFKSGAGTE LSVRAKPSAP VVSGPAARAT PQHTVSFTCE SHGFSPRDIT  180
LKWFKNGNEL SDFQTNVDPV GESVSYSIHS TAKVVLTRED VHSQVICEVA HVTLQGDPLR  240
GTANLSETIR VPPTLEVTQQ PVRAENQVNV TCQVRKFYPQ RLQLTWLENG NVSRTETAST  300
VTENKDGTYN WMSWLLVNVS AHRDDVKLTC QVEHDGQPAV SKSHDLKVSA HPKEQGSNTA  360
AENTGSNERN IYIVVGVVCT LLVALLMAAL YLVRIRQKKA QGSTSSTRLH EPEKNAREIT  420
QVQSLDTNDI TYADLNLPKG KKPAPQAAEP NNHTEYASIQ TSPQPASEDT LTYADLDMVH  480
LNRTPKQPAP KPEPSFSEYA SVQVPRK                                     507

SEQ ID NO: 3            moltype = AA  length = 330
FEATURE                 Location/Qualifiers
REGION                  1..330
                        note = Fc domain
source                  1..330
                        mol_type = protein
                        organism = synthetic construct
SEQUENCE: 3
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 4            moltype = AA  length = 330
FEATURE                 Location/Qualifiers
REGION                  1..330
                        note = Fc domain
source                  1..330
                        mol_type = protein
                        organism = synthetic construct
SEQUENCE: 4
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 5            moltype = AA  length = 11
FEATURE                 Location/Qualifiers
REGION                  1..11
                        note = CDR-L1
```

```
source                      1..11
                            mol_type = protein
                            organism = synthetic construct
SEQUENCE: 5
QSLLHGNGFN Y                                                                    11

SEQ ID NO: 6                moltype = AA   length = 508
FEATURE                     Location/Qualifiers
source                      1..508
                            mol_type = protein
                            organism = Homo sapiens
SEQUENCE: 6
MEPAGPAPGR LGPLLCLLLA ASCAWSGVAG EEELQVIQPD KSVLVAAGET ATLRCTATSL        60
IPVGPIQWFR GAGPGRELIY NQKEGHFPRV TTVSDLTKRN NMDFSIRIGN ITPADAGTYY       120
CVKFRKGSPD DVEFKSGAGT ELSVRAKPSA PVVSGPAARA TPQHTVSFTC ESHGFSPRDI       180
TLKWFKNGNE LSDFQTNVDP VGESVSYSIH STAKVVLTRE DVHSQVICEV AHVTLQGDPL       240
RGTANLSETI RVPPTLEVTQ QPVRAENQVN VTCQVRKFYP QRLQLTWLEN GNVSRTETAS       300
TVTENKDGTY NWMSWLLVNV SAHRDDVKLT CQVEHDGQPA VSKSHDLKVS AHPKEQGSNT       360
AAENTGSNER NIYIVVGVVC TLLVALLMAA LYLVRIRQKK AQGSTSSTRL HEPEKNAREI       420
TQVQSLDTND ITYADLNLPK GKKPAPQAAE PNNHTEYASI QTSPQPASED TLTYADLDMV       480
HLNRTPKQPA PKPEPSFSEY ASVQVPRK                                          508

SEQ ID NO: 7                moltype = AA   length = 6
FEATURE                     Location/Qualifiers
REGION                      1..6
                            note = CDR-L1
source                      1..6
                            mol_type = protein
                            organism = synthetic construct
SEQUENCE: 7
QGISGY                                                                    6

SEQ ID NO: 8                moltype = AA   length = 6
FEATURE                     Location/Qualifiers
REGION                      1..6
                            note = CDR-L1
source                      1..6
                            mol_type = protein
                            organism = synthetic construct
SEQUENCE: 8
QDFSNY                                                                    6

SEQ ID NO: 9                moltype = AA   length = 398
FEATURE                     Location/Qualifiers
source                      1..398
                            mol_type = protein
                            organism = Homo sapiens
SEQUENCE: 9
MPVPASWPHL PSPFLLMTLL LGRLTGVAGE DELQVIQPEK SVSVAAGESA TLRCAMTSLI        60
PVGPIMWFRG AGAGRELIYN QKEGHFPRVT TVSELTKRNN LDFSISISNI TPADAGTYYC       120
VKFRKGSPDD VEFKSGAGTE LSVRAKPSAP VVSGPAVRAT PEHTVSFTCE SHGFSPRDIT       180
LKWFKNGNEL SDFQTNVDPA GDSVSYSIHS TARVVLTRGD VHSQVICEIA HITLQGDPLR       240
GTANLSEAIR VPPTLEVTQQ PMRAENQANV TCQVSNFYPR GLQLTWLENG NVSRTETAST       300
LIENKDGTYN WMSWLLVNTC AHRDDVVLTC QVEHDGQQAV SKSYALEISA HQKEHGSDIT       360
HEAALAPTAP LLVALLLGPK LLLVVGVSAI YICWKQKA                               398

SEQ ID NO: 10               moltype = AA   length = 387
FEATURE                     Location/Qualifiers
source                      1..387
                            mol_type = protein
                            organism = Homo sapiens
SEQUENCE: 10
MPVPASWPHP PGPFLLLTLL LGLTEVAGEE ELQMIQPEKL LLVTVGKTAT LHCTVTSLLP        60
VGPVLWFRGV GPGRELIYNQ KEGHFPRVTT VSDLTKRNNM DFSIRISSIT PADVGTYYCV       120
KFRKGSPENV EFKSGPGTEM ALGAKPSAPV VLGPAARTTP EHTVSFTCES HGFSPRDITL       180
KWFKNGNELS DFQTNVDPTG QSVAYSIRST ARVVLDPWDV RSQVICEVAH VTLQGDPLRG       240
TANLSEAIRV PPTLEVTQQP MRVGNQVNVT CQVRKFYPQS LQLTWSENGN VCQRETASTL       300
TENKDGTYNW TSWFLVNISD QRDDVVLTCQ VKHDGQLAVS KRLALEVTVH QKDQSSDATP       360
GPASSLTALL LIAVLLGPIY VPWKQKT                                           387

SEQ ID NO: 11               moltype = AA   length = 6
FEATURE                     Location/Qualifiers
REGION                      1..6
                            note = CDR-L1
source                      1..6
                            mol_type = protein
                            organism = synthetic construct
SEQUENCE: 11
NIGSKS                                                                    6
```

```
SEQ ID NO: 12             moltype = AA   length = 6
FEATURE                   Location/Qualifiers
REGION                    1..6
                          note = CDR-L1
source                    1..6
                          mol_type = protein
                          organism = synthetic construct
SEQUENCE: 12
KLGDKY                                                                    6

SEQ ID NO: 13             moltype = AA   length = 6
FEATURE                   Location/Qualifiers
REGION                    1..6
                          note = CDR-L1
source                    1..6
                          mol_type = protein
                          organism = synthetic construct
SEQUENCE: 13
KLGDRY                                                                    6

SEQ ID NO: 14             moltype = AA   length = 6
FEATURE                   Location/Qualifiers
REGION                    1..6
                          note = CDR-L1
source                    1..6
                          mol_type = protein
                          organism = synthetic construct
SEQUENCE: 14
QDISSW                                                                    6

SEQ ID NO: 15             moltype = AA   length = 6
FEATURE                   Location/Qualifiers
REGION                    1..6
                          note = CDR-L1
source                    1..6
                          mol_type = protein
                          organism = synthetic construct
SEQUENCE: 15
QSVSSN                                                                    6

SEQ ID NO: 16             moltype = AA   length = 6
FEATURE                   Location/Qualifiers
REGION                    1..6
                          note = CDR-L1
source                    1..6
                          mol_type = protein
                          organism = synthetic construct
SEQUENCE: 16
QSVSRN                                                                    6

SEQ ID NO: 17             moltype = AA   length = 12
FEATURE                   Location/Qualifiers
REGION                    1..12
                          note = CDR-L1
source                    1..12
                          mol_type = protein
                          organism = synthetic construct
SEQUENCE: 17
QTVLNSSNNK NY                                                            12

SEQ ID NO: 18             moltype = AA   length = 6
FEATURE                   Location/Qualifiers
REGION                    1..6
                          note = CDR-L1
source                    1..6
                          mol_type = protein
                          organism = synthetic construct
SEQUENCE: 18
QDINRY                                                                    6

SEQ ID NO: 19             moltype = AA   length = 330
FEATURE                   Location/Qualifiers
REGION                    1..330
                          note = IgG1 Fc domain
source                    1..330
                          mol_type = protein
                          organism = synthetic construct
```

```
SEQUENCE: 19
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKAEP KSCDKTHTCP PCPAPELLAG   120
PDVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPEEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 20           moltype = AA  length = 330
FEATURE                 Location/Qualifiers
REGION                  1..330
                        note = IgG1 Fc domain
VARIANT                 98
                        note = Xaa is Val or Ala
source                  1..330
                        mol_type = protein
                        organism = synthetic construct
SEQUENCE: 20
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKXEP KSCDKTHTCP PCPAPELLAG   120
PDVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPEEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 21           moltype = AA  length = 330
FEATURE                 Location/Qualifiers
REGION                  1..330
                        note = IgG1 Fc domain
VARIANT                 98
                        note = Xaa is Val or Ala
VARIANT                 119
                        note = Xaa is Gly or Ala
VARIANT                 122
                        note = Xaa is Ser or Asp
VARIANT                 215
                        note = Xaa is Ile or Glu
source                  1..330
                        mol_type = protein
                        organism = synthetic construct
SEQUENCE: 21
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKXEP KSCDKTHTCP PCPAPELLXG   120
PXVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPXEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 22           moltype = AA  length = 330
FEATURE                 Location/Qualifiers
REGION                  1..330
                        note = IgG1 Fc domain
VARIANT                 98
                        note = Xaa is Val or Ala
source                  1..330
                        mol_type = protein
                        organism = synthetic construct
SEQUENCE: 22
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKXEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV LHEALHSHYT QKSLSLSPGK                                   330

SEQ ID NO: 23           moltype =    length =
SEQUENCE: 23
000

SEQ ID NO: 24           moltype =    length =
SEQUENCE: 24
000

SEQ ID NO: 25           moltype = AA  length = 330
FEATURE                 Location/Qualifiers
REGION                  1..330
                        note = IgG1 Fc domain
VARIANT                 98
                        note = Xaa is Val or Ala
```

```
VARIANT                 311
                        note = Xaa is Met or Leu
VARIANT                 317
                        note = Xaa is Asn or Ser
source                  1..330
                        mol_type = protein
                        organism = synthetic construct
SEQUENCE: 25
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKXEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV XHEALHXHYT QKSLSLSPGK                                  330

SEQ ID NO: 26           moltype = AA  length = 330
FEATURE                 Location/Qualifiers
REGION                  1..330
                        note = IgG1 Fc domain
VARIANT                 97
                        note = Xaa is Lys or Arg
VARIANT                 239
                        note = Xaa is Asp or Glu
VARIANT                 241
                        note = Xaa is Leu or Met
source                  1..330
                        mol_type = protein
                        organism = synthetic construct
SEQUENCE: 26
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKXVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRXE  240
XTKNQVSLTC LVKGFYPSDI AVEWESNGQP ENNYKTTPPV LDSDGSFFLY SKLTVDKSRW  300
QQGNVFSCSM MHEALHNHYT QKSLSLSPGK                                  330

SEQ ID NO: 27           moltype =  length =
SEQUENCE: 27
000

SEQ ID NO: 28           moltype =  length =
SEQUENCE: 28
000

SEQ ID NO: 29           moltype =  length =
SEQUENCE: 29
000

SEQ ID NO: 30           moltype =  length =
SEQUENCE: 30
000

SEQ ID NO: 31           moltype =  length =
SEQUENCE: 31
000

SEQ ID NO: 32           moltype =  length =
SEQUENCE: 32
000

SEQ ID NO: 33           moltype =  length =
SEQUENCE: 33
000

SEQ ID NO: 34           moltype = AA  length = 327
FEATURE                 Location/Qualifiers
REGION                  1..327
                        note = IgG4 Fc domain
source                  1..327
                        mol_type = protein
                        organism = synthetic construct
SEQUENCE: 34
ASTKGPSVFP LAPCSRSTSE STAALGCLVK DYFPEPVTVS WNSGALTSGV HTFPAVLQSS   60
GLYSLSSVVT VPSSSLGTKT YTCNVDHKPS NTKVDKRVES KYGPPCPSCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
NQVSLTCLVK GFYPSDIAVE WESNGQPENN YKTTPPVLDS DGSFFLYSRL TVDKSRWQEG  300
NVFSCSVMHE ALHNHYTQKS LSLSLGK                                     327
```

```
SEQ ID NO: 35               moltype = AA   length = 327
FEATURE                     Location/Qualifiers
REGION                      1..327
                            note = IgG4 Fc domain
source                      1..327
                            mol_type = protein
                            organism = synthetic construct
SEQUENCE: 35
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 36               moltype = AA   length = 9
FEATURE                     Location/Qualifiers
REGION                      1..9
                            note = CDR-L3
source                      1..9
                            mol_type = protein
                            organism = synthetic construct
SEQUENCE: 36
MQGLQTPRT                                                             9

SEQ ID NO: 37               moltype = AA   length = 327
FEATURE                     Location/Qualifiers
REGION                      1..327
                            note = IgG4 Fc domain
VARIANT                     108
                            note = Xaa is Ser or Pro
VARIANT                     115
                            note = Xaa is Leu or Glu
source                      1..327
                            mol_type = protein
                            organism = synthetic construct
SEQUENCE: 37
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPXCP APEFXGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 38               moltype = AA   length = 9
FEATURE                     Location/Qualifiers
REGION                      1..9
                            note = CDR-L3
source                      1..9
                            mol_type = protein
                            organism = synthetic construct
SEQUENCE: 38
QQFTSDLIT                                                             9

SEQ ID NO: 39               moltype = AA   length = 9
FEATURE                     Location/Qualifiers
REGION                      1..9
                            note = CDR-L3
source                      1..9
                            mol_type = protein
                            organism = synthetic construct
SEQUENCE: 39
QQYDNLPYT                                                             9

SEQ ID NO: 40               moltype = AA   length = 503
FEATURE                     Location/Qualifiers
source                      1..503
                            mol_type = protein
                            organism = Homo sapiens
SEQUENCE: 40
MEPAGPAPGR LGPLLCLLLA ASCAWSGVAG EEELQVIQPD KSVLVAAGET ATLRCTATSL    60
IPVGPIQWFR GAGPGRELIY NQKEGHFPRV TTVSDLTKRN NMDFSIRIGN ITPADAGTYY   120
CVKFRKGSPD VEFKSGAGTE LSVRAKPSAP VVSGPAARAT PQHTVSFTCE SHGFSPRDIT   180
LKWFKNGNEL SDFQTNVDPV GESVSYSIHS TAKVVLTRED VHSQVICEVA HVTLQGDPLR   240
GTANLSETIR VPPTLEVTQQ PVRAENQVNV TCQVRKFYPQ RLQLTWLENG NVSRTETAST   300
VTENKDGTYN WMSWLLVNVS AHRDDVKLTC QVEHDGQPAV SKSHDLKVSA HPKEQGSNTA   360
AENTGSNERN IYIVVGVVCT LLVALLMAAL YLVRIRQKKA QGSTSSTRLH EPEKNAREIT   420
QDTNDITYAD LNLPKGKKPA PQAAEPNNHT EYASIQTSPQ PASEDTLTYA DLDMVHLNRT   480
PKQPAPKPEP SFSEYASVQV PRK                                          503
```

```
SEQ ID NO: 41          moltype = AA   length = 330
FEATURE                Location/Qualifiers
REGION                 1..330
                       note = IgG1 Fc domain
source                 1..330
                       mol_type = protein
                       organism = synthetic construct
SEQUENCE: 41
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLAG   120
PDVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPEEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 42          moltype = AA   length = 11
FEATURE                Location/Qualifiers
REGION                 1..11
                       note = CDR-L3
source                 1..11
                       mol_type = protein
                       organism = synthetic construct
SEQUENCE: 42
QVWDSSSDHY V                                                        11

SEQ ID NO: 43          moltype = AA   length = 9
FEATURE                Location/Qualifiers
REGION                 1..9
                       note = CDR-L3
source                 1..9
                       mol_type = protein
                       organism = synthetic construct
SEQUENCE: 43
QTWDSSTVV                                                            9

SEQ ID NO: 44          moltype = AA   length = 9
FEATURE                Location/Qualifiers
REGION                 1..9
                       note = CDR-L3
source                 1..9
                       mol_type = protein
                       organism = synthetic construct
SEQUENCE: 44
QAWDSSTAV                                                            9

SEQ ID NO: 45          moltype = AA   length = 9
FEATURE                Location/Qualifiers
REGION                 1..9
                       note = CDR-L3
source                 1..9
                       mol_type = protein
                       organism = synthetic construct
SEQUENCE: 45
QACDSSTAV                                                            9

SEQ ID NO: 46          moltype = AA   length = 9
FEATURE                Location/Qualifiers
REGION                 1..9
                       note = CDR-L3
source                 1..9
                       mol_type = protein
                       organism = synthetic construct
SEQUENCE: 46
QEANSFPYT                                                            9

SEQ ID NO: 47          moltype = AA   length = 9
FEATURE                Location/Qualifiers
REGION                 1..9
                       note = CDR-L3
source                 1..9
                       mol_type = protein
                       organism = synthetic construct
SEQUENCE: 47
QQYNNWPYT                                                            9
```

```
SEQ ID NO: 48              moltype = AA   length = 10
FEATURE                    Location/Qualifiers
REGION                     1..10
                           note = CDR-L3
source                     1..10
                           mol_type = protein
                           organism = synthetic construct
SEQUENCE: 48
QQYYNTPPWT                                                                    10

SEQ ID NO: 49              moltype = AA   length = 9
FEATURE                    Location/Qualifiers
REGION                     1..9
                           note = CDR-L3
source                     1..9
                           mol_type = protein
                           organism = synthetic construct
SEQUENCE: 49
LQYDEFPFT                                                                      9

SEQ ID NO: 50              moltype = AA   length = 330
FEATURE                    Location/Qualifiers
REGION                     1..330
                           note = IgG1 Fc domain
source                     1..330
                           mol_type = protein
                           organism = synthetic construct
SEQUENCE: 50
ASTKGPSVFP LAPSSKSTSG GTAALGCLVK DYFPEPVTVS WNSGALTSGV HTFPAVLQSS               60
GLYSLSSVVT VPSSSLGTQT YICNVNHKPS NTKVDKKVEP KSCDKTHTCP PCPAPELLGG              120
PDVFLFPPKP KDTLMISRTP EVTCVVVDVS HEDPEVKFNW YVDGVEVHNA KTKPREEQYN              180
STYRVVSVLT VLHQDWLNGK EYKCKVSNKA LPAPEEKTIS KAKGQPREPQ VYTLPPSRDE              240
LTKNQVSLTC LVKGFYPSDI AVEWESNGQP ENNYKTTPPV LDSDGSFFLY SKLTVDKSRW              300
QQGNVFSCSV MHEALHNHYT QKSLSLSPGK                                              330

SEQ ID NO: 51              moltype = AA   length = 330
FEATURE                    Location/Qualifiers
REGION                     1..330
                           note = IgG1 Fc domain
source                     1..330
                           mol_type = protein
                           organism = synthetic construct
SEQUENCE: 51
ASTKGPSVFP LAPSSKSTSG GTAALGCLVK DYFPEPVTVS WNSGALTSGV HTFPAVLQSS               60
GLYSLSSVVT VPSSSLGTQT YICNVNHKPS NTKVDKKVEP KSCDKTHTCP PCPAPELLGG              120
PSVFLFPPKP KDTLMISRTP EVTCVVVDVS HEDPEVKFNW YVDGVEVHNA KTKPREEQYN              180
STYRVVSVLT VLHQDWLNGK EYKCKVSNKA LPAPEEKTIS KAKGQPREPQ VYTLPPSRDE              240
LTKNQVSLTC LVKGFYPSDI AVEWESNGQP ENNYKTTPPV LDSDGSFFLY SKLTVDKSRW              300
QQGNVFSCSV MHEALHNHYT QKSLSLSPGK                                              330

SEQ ID NO: 52              moltype = AA   length = 330
FEATURE                    Location/Qualifiers
REGION                     1..330
                           note = IgG1 Fc domain
source                     1..330
                           mol_type = protein
                           organism = synthetic construct
SEQUENCE: 52
ASTKGPSVFP LAPSSKSTSG GTAALGCLVK DYFPEPVTVS WNSGALTSGV HTFPAVLQSS               60
GLYSLSSVVT VPSSSLGTQT YICNVNHKPS NTKVDKKVEP KSCDKTHTCP PCPAPELLGG              120
PDVFLFPPKP KDTLMISRTP EVTCVVVDVS HEDPEVKFNW YVDGVEVHNA KTKPREEQYN              180
STYRVVSVLT VLHQDWLNGK EYKCKVSNKA LPAPIEKTIS KAKGQPREPQ VYTLPPSRDE              240
LTKNQVSLTC LVKGFYPSDI AVEWESNGQP ENNYKTTPPV LDSDGSFFLY SKLTVDKSRW              300
QQGNVFSCSV MHEALHNHYT QKSLSLSPGK                                              330

SEQ ID NO: 53              moltype = AA   length = 330
FEATURE                    Location/Qualifiers
REGION                     1..330
                           note = IgG1 Fc domain
source                     1..330
                           mol_type = protein
                           organism = synthetic construct
SEQUENCE: 53
ASTKGPSVFP LAPSSKSTSG GTAALGCLVK DYFPEPVTVS WNSGALTSGV HTFPAVLQSS               60
GLYSLSSVVT VPSSSLGTQT YICNVNHKPS NTKVDKKAEP KSCDKTHTCP PCPAPELLGG              120
PSVFLFPPKP KDTLMISRTP EVTCVVVDVS HEDPEVKFNW YVDGVEVHNA KTKPREEQYN              180
STYRVVSVLT VLHQDWLNGK EYKCKVSNKA LPAPIEKTIS KAKGQPREPQ VYTLPPSRDE              240
LTKNQVSLTC LVKGFYPSDI AVEWESNGQP ENNYKTTPPV LDSDGSFFLY SKLTVDKSRW              300
QQGNVFSCSV MHEALHNHYT QKSLSLSPGK                                              330
```

```
SEQ ID NO: 54            moltype = AA   length = 9
FEATURE                  Location/Qualifiers
REGION                   1..9
                         note = CDR-H1
source                   1..9
                         mol_type = protein
                         organism = synthetic construct
SEQUENCE: 54
GGSISSSNW                                                                 9

SEQ ID NO: 55            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 55
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                  330

SEQ ID NO: 56            moltype = AA   length = 9
FEATURE                  Location/Qualifiers
REGION                   1..9
                         note = CDR-H1
source                   1..9
                         mol_type = protein
                         organism = synthetic construct
SEQUENCE: 56
DYSISSGYY                                                                 9

SEQ ID NO: 57            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 57
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPGK                                  330

SEQ ID NO: 58            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 58
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV LHEALHNHYT QKSLSLSPGK                                  330

SEQ ID NO: 59            moltype = AA   length = 8
FEATURE                  Location/Qualifiers
REGION                   1..8
                         note = CDR-H1
source                   1..8
                         mol_type = protein
                         organism = synthetic construct
SEQUENCE: 59
GFTFSKFG                                                                  8
```

```
SEQ ID NO: 60            moltype = AA   length = 8
FEATURE                  Location/Qualifiers
REGION                   1..8
                         note = CDR-H1
source                   1..8
                         mol_type = protein
                         organism = synthetic construct
SEQUENCE: 60
GGSFSGYY                                                                  8

SEQ ID NO: 61            moltype = AA   length = 8
FEATURE                  Location/Qualifiers
REGION                   1..8
                         note = CDR-H1
source                   1..8
                         mol_type = protein
                         organism = synthetic construct
SEQUENCE: 61
GGSFSTYY                                                                  8

SEQ ID NO: 62            moltype = AA   length = 8
FEATURE                  Location/Qualifiers
REGION                   1..8
                         note = CDR-H1
source                   1..8
                         mol_type = protein
                         organism = synthetic construct
SEQUENCE: 62
GFTFSSYA                                                                  8

SEQ ID NO: 63            moltype = AA   length = 8
FEATURE                  Location/Qualifiers
REGION                   1..8
                         note = CDR-H1
source                   1..8
                         mol_type = protein
                         organism = synthetic construct
SEQUENCE: 63
GFTFSSYW                                                                  8

SEQ ID NO: 64            moltype = AA   length = 8
FEATURE                  Location/Qualifiers
REGION                   1..8
                         note = CDR-H1
source                   1..8
                         mol_type = protein
                         organism = synthetic construct
SEQUENCE: 64
GFIFSNYG                                                                  8

SEQ ID NO: 65            moltype = AA   length = 8
FEATURE                  Location/Qualifiers
REGION                   1..8
                         note = CDR-H1
source                   1..8
                         mol_type = protein
                         organism = synthetic construct
SEQUENCE: 65
GYTFRNFG                                                                  8

SEQ ID NO: 66            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 66
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHSHYT QKSLSLSPGK                                   330
```

```
SEQ ID NO: 67            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 67
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 68            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 68
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 69            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 69
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
LTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 70            moltype = AA   length = 7
FEATURE                  Location/Qualifiers
REGION                   1..7
                         note = CDR-H2
source                   1..7
                         mol_type = protein
                         organism = synthetic construct
SEQUENCE: 70
IYHSGST                                                              7

SEQ ID NO: 71            moltype = AA   length = 330
FEATURE                  Location/Qualifiers
REGION                   1..330
                         note = IgG1 Fc domain
source                   1..330
                         mol_type = protein
                         organism = synthetic construct
SEQUENCE: 71
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSRDE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPGK                                   330

SEQ ID NO: 72            moltype = AA   length = 7
FEATURE                  Location/Qualifiers
REGION                   1..7
                         note = CDR-H2
source                   1..7
                         mol_type = protein
                         organism = synthetic construct
```

```
SEQUENCE: 72
IYHSGNT                                                                  7

SEQ ID NO: 73           moltype = AA  length = 330
FEATURE                 Location/Qualifiers
REGION                  1..330
                        note = IgG1 Fc domain
source                  1..330
                        mol_type = protein
                        organism = synthetic construct
SEQUENCE: 73
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSRDE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 74           moltype = AA  length = 330
FEATURE                 Location/Qualifiers
REGION                  1..330
                        note = IgG1 Fc domain
source                  1..330
                        mol_type = protein
                        organism = synthetic construct
SEQUENCE: 74
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKAEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPEEKTIS KAKGQPREPQ VYTLPPSRDE  240
LTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 75           moltype = AA  length = 8
FEATURE                 Location/Qualifiers
REGION                  1..8
                        note = CDR-H2
source                  1..8
                        mol_type = protein
                        organism = synthetic construct
SEQUENCE: 75
ISYDGNNK                                                                 8

SEQ ID NO: 76           moltype = AA  length = 7
FEATURE                 Location/Qualifiers
REGION                  1..7
                        note = CDR-H2
source                  1..7
                        mol_type = protein
                        organism = synthetic construct
SEQUENCE: 76
INHSGST                                                                  7

SEQ ID NO: 77           moltype = AA  length = 8
FEATURE                 Location/Qualifiers
REGION                  1..8
                        note = CDR-H2
source                  1..8
                        mol_type = protein
                        organism = synthetic construct
SEQUENCE: 77
ISGSGGDT                                                                 8

SEQ ID NO: 78           moltype = AA  length = 8
FEATURE                 Location/Qualifiers
REGION                  1..8
                        note = CDR-H2
source                  1..8
                        mol_type = protein
                        organism = synthetic construct
SEQUENCE: 78
IHNDGSRT                                                                 8

SEQ ID NO: 79           moltype = AA  length = 8
FEATURE                 Location/Qualifiers
REGION                  1..8
                        note = CDR-H2
```

```
source                    1..8
                          mol_type = protein
                          organism = synthetic construct
SEQUENCE: 79
ISGSGSST                                                                    8

SEQ ID NO: 80             moltype = AA   length = 8
FEATURE                   Location/Qualifiers
REGION                    1..8
                          note = CDR-H2
source                    1..8
                          mol_type = protein
                          organism = synthetic construct
SEQUENCE: 80
ISYDGRNE                                                                    8

SEQ ID NO: 81             moltype = AA   length = 8
FEATURE                   Location/Qualifiers
REGION                    1..8
                          note = CDR-H2
source                    1..8
                          mol_type = protein
                          organism = synthetic construct
SEQUENCE: 81
IDTNTGEP                                                                    8

SEQ ID NO: 82             moltype = AA   length = 327
FEATURE                   Location/Qualifiers
REGION                    1..327
                          note = IgG4 Fc Domain
source                    1..327
                          mol_type = protein
                          organism = synthetic construct
SEQUENCE: 82
ASTKGPSVFP LAPCSRSTSE STAALGCLVK DYFPEPVTVS WNSGALTSGV HTFPAVLQSS            60
GLYSLSSVVT VPSSSLGTKT YTCNVDHKPS NTKVDKRVES KYGPPCPSCP APEFEGGPSV          120
FLFPPKPKDT LMISRTPEVT CVVVDVSQED PEVQFNWYVD GVEVHNAKTK PREEQFNSTY          180
RVVSVLTVLH QDWLNGKEYK CKVSNKGLPS SIEKTISKAK GQPREPQVYT LPPSQEEMTK          240
NQVSLTCLVK GFYPSDIAVE WESNGQPENN YKTTPPVLDS DGSFFLYSRL TVDKSRWQEG          300
NVFSCSVMHE ALHNHYTQKS LSLSLGK                                              327

SEQ ID NO: 83             moltype = AA   length = 327
FEATURE                   Location/Qualifiers
REGION                    1..327
                          note = IgG4 Fc Domain
source                    1..327
                          mol_type = protein
                          organism = synthetic construct
SEQUENCE: 83
ASTKGPSVFP LAPCSRSTSE STAALGCLVK DYFPEPVTVS WNSGALTSGV HTFPAVLQSS            60
GLYSLSSVVT VPSSSLGTKT YTCNVDHKPS NTKVDKRVES KYGPPCPPCP APEFLGGPSV          120
FLFPPKPKDT LMISRTPEVT CVVVDVSQED PEVQFNWYVD GVEVHNAKTK PREEQFNSTY          180
RVVSVLTVLH QDWLNGKEYK CKVSNKGLPS SIEKTISKAK GQPREPQVYT LPPSQEEMTK          240
NQVSLTCLVK GFYPSDIAVE WESNGQPENN YKTTPPVLDS DGSFFLYSRL TVDKSRWQEG          300
NVFSCSVMHE ALHNHYTQKS LSLSLGK                                              327

SEQ ID NO: 84             moltype = AA   length = 327
FEATURE                   Location/Qualifiers
REGION                    1..327
                          note = IgG4 Fc Domain
source                    1..327
                          mol_type = protein
                          organism = synthetic construct
SEQUENCE: 84
ASTKGPSVFP LAPCSRSTSE STAALGCLVK DYFPEPVTVS WNSGALTSGV HTFPAVLQSS            60
GLYSLSSVVT VPSSSLGTKT YTCNVDHKPS NTKVDKRVES KYGPPCPSCP APEALGGPSV          120
FLFPPKPKDT LMISRTPEVT CVVVDVSQED PEVQFNWYVD GVEVHNAKTK PREEQFNSTY          180
RVVSVLTVLH QDWLNGKEYK CKVSNKGLPS SIEKTISKAK GQPREPQVYT LPPSQEEMTK          240
NQVSLTCLVK GFYPSDIAVE WESNGQPENN YKTTPPVLDS DGSFFLYSRL TVDKSRWQEG          300
NVFSCSVMHE ALHNHYTQKS LSLSLGK                                              327

SEQ ID NO: 85             moltype = AA   length = 327
FEATURE                   Location/Qualifiers
REGION                    1..327
                          note = IgG4 Fc Domain
source                    1..327
                          mol_type = protein
                          organism = synthetic construct
```

```
SEQUENCE: 85
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEAAGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 86           moltype = AA  length = 11
FEATURE                 Location/Qualifiers
REGION                  1..11
                        note = CDR-H3
source                  1..11
                        mol_type = protein
                        organism = synthetic construct
SEQUENCE: 86
ARRGIWFGVG P                                                        11

SEQ ID NO: 87           moltype = AA  length = 327
FEATURE                 Location/Qualifiers
REGION                  1..327
                        note = IgG4 Fc Domain
source                  1..327
                        mol_type = protein
                        organism = synthetic construct
SEQUENCE: 87
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFAGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 88           moltype = AA  length = 16
FEATURE                 Location/Qualifiers
REGION                  1..16
                        note = CDR-H3
source                  1..16
                        mol_type = protein
                        organism = synthetic construct
SEQUENCE: 88
AREGIEGYYF YYGMDV                                                   16

SEQ ID NO: 89           moltype = AA  length = 14
FEATURE                 Location/Qualifiers
REGION                  1..14
                        note = CDR-H3
source                  1..14
                        mol_type = protein
                        organism = synthetic construct
SEQUENCE: 89
ARDKCSTTTC SFDY                                                     14

SEQ ID NO: 90           moltype =     length =
SEQUENCE: 90
000

SEQ ID NO: 91           moltype =     length =
SEQUENCE: 91
000

SEQ ID NO: 92           moltype = AA  length = 9
FEATURE                 Location/Qualifiers
REGION                  1..9
                        note = CDR-H3
source                  1..9
                        mol_type = protein
                        organism = synthetic construct
SEQUENCE: 92
WAAAGAFYI                                                            9

SEQ ID NO: 93           moltype = AA  length = 16
FEATURE                 Location/Qualifiers
REGION                  1..16
                        note = CDR-H3
source                  1..16
                        mol_type = protein
                        organism = synthetic construct
```

```
SEQUENCE: 93
SRVDSGSYPY YDGLDV                                                              16

SEQ ID NO: 94           moltype = AA  length = 18
FEATURE                 Location/Qualifiers
REGION                  1..18
                        note = CDR-H3
source                  1..18
                        mol_type = protein
                        organism = synthetic construct
SEQUENCE: 94
ASSHYGSGSF PDSYGMDV                                                            18

SEQ ID NO: 95           moltype = AA  length = 13
FEATURE                 Location/Qualifiers
REGION                  1..13
                        note = CDR-H3
source                  1..13
                        mol_type = protein
                        organism = synthetic construct
SEQUENCE: 95
AKDGGSYYPP FDY                                                                 13

SEQ ID NO: 96           moltype = AA  length = 17
FEATURE                 Location/Qualifiers
REGION                  1..17
                        note = CDR-H3
source                  1..17
                        mol_type = protein
                        organism = synthetic construct
SEQUENCE: 96
TRDPPPYDIL TGYPFDY                                                             17

SEQ ID NO: 97           moltype = AA  length = 14
FEATURE                 Location/Qualifiers
REGION                  1..14
                        note = CDR-H3
source                  1..14
                        mol_type = protein
                        organism = synthetic construct
SEQUENCE: 97
AAYSGSYYYY GMDV                                                                14

SEQ ID NO: 98           moltype = AA  length = 11
FEATURE                 Location/Qualifiers
REGION                  1..11
                        note = CDR-H3
source                  1..11
                        mol_type = protein
                        organism = synthetic construct
SEQUENCE: 98
AKGSGSYYFD Y                                                                   11

SEQ ID NO: 99           moltype = AA  length = 12
FEATURE                 Location/Qualifiers
REGION                  1..12
                        note = CDR-H3
source                  1..12
                        mol_type = protein
                        organism = synthetic construct
SEQUENCE: 99
ARSRGNYFAM EY                                                                  12

SEQ ID NO: 100          moltype =     length =
SEQUENCE: 100
000

SEQ ID NO: 101          moltype =     length =
SEQUENCE: 101
000

SEQ ID NO: 102          moltype =     length =
SEQUENCE: 102
000

SEQ ID NO: 103          moltype =     length =
SEQUENCE: 103
000
```

```
SEQ ID NO: 104          moltype = AA  length = 118
FEATURE                 Location/Qualifiers
REGION                  1..118
                        note = VH sequence
source                  1..118
                        mol_type = protein
                        organism = synthetic construct
SEQUENCE: 104
QVQLQESGPG LVKPSGTLSL TCAVSGGSIS SSNWWSWVRQ PPGKGLEWIG EIYHSGSTNY    60
NPSLKSRVTI SVDKSKNQFS LKLSSVTAAD TAVYYCARRG IWFGVGPWGQ GTLVTVSS    118

SEQ ID NO: 105          moltype =     length =
SEQUENCE: 105
000

SEQ ID NO: 106          moltype = AA  length = 123
FEATURE                 Location/Qualifiers
REGION                  1..123
                        note = VH sequence
source                  1..123
                        mol_type = protein
                        organism = synthetic construct
SEQUENCE: 106
QVQLQESGPG LVKPSGTLSL TCAVSGGSIS SSNWWSWVRQ PPGKGLEWIG EIYHSGNTNY    60
NPSLKSRVTI SVDKSKNQFS LKLSSVTAAD TAVYYCAREG IEGYYFYYGM DVWGQGTTVT   120
VSS                                                                123

SEQ ID NO: 107          moltype = AA  length = 121
FEATURE                 Location/Qualifiers
REGION                  1..121
                        note = VH sequence
source                  1..121
                        mol_type = protein
                        organism = synthetic construct
SEQUENCE: 107
QVQLQESGPG LLKPSETLSL TCAVSDYSIS SGYYWGWIRQ PPGKGLEWIG SIYHSGNTYY    60
NPSLKSRVTI LVDTSKNQFS LKLSSVTAAD TAVYYCARDK CSTTTCSFDY WGQGTLVTVS   120
S                                                                  121

SEQ ID NO: 108          moltype =     length =
SEQUENCE: 108
000

SEQ ID NO: 109          moltype =     length =
SEQUENCE: 109
000

SEQ ID NO: 110          moltype = AA  length = 116
FEATURE                 Location/Qualifiers
REGION                  1..116
                        note = VH sequence
source                  1..116
                        mol_type = protein
                        organism = synthetic construct
SEQUENCE: 110
QVQLVESGGG VVQPGRSLRL SCAASGFTFS KFGMHWVRQA PGKGLEWVAV ISYDGNNKYY    60
TDSVKGRFTI SRDNSRNTLY LQMDSVKPED TAVYYSWAAA GAFYIWGQGT MVTVSS      116

SEQ ID NO: 111          moltype = AA  length = 122
FEATURE                 Location/Qualifiers
REGION                  1..122
                        note = VH sequence
source                  1..122
                        mol_type = protein
                        organism = synthetic construct
SEQUENCE: 111
QVQLQQWGAG LLKPSETLSL TCAVYGGSFS GYYWSWIRQP PGKGLEWIGE INHSGSTNFN    60
PSLKSRVTIS VDTSKNQFSL KLRSVTAADT AVYYCSRVDS GSYPYYDGLD VWGQGTTVTV   120
SS                                                                 122

SEQ ID NO: 112          moltype = AA  length = 124
FEATURE                 Location/Qualifiers
REGION                  1..124
                        note = VH sequence
source                  1..124
                        mol_type = protein
                        organism = synthetic construct
```

```
SEQUENCE: 112
QVQLQQWGAG LLKPSETLSL TCAVYGGSFS TYYWNWIRQP PGKGLEWIGE INHSGSTNYN    60
PSLKSRVIIS VDTSKNQFSL KLSSVTAADT AVYYCASSHY GSGSFPDSYG MDVWGQGTTV   120
TVSA                                                                124

SEQ ID NO: 113          moltype = AA  length = 120
FEATURE                 Location/Qualifiers
REGION                  1..120
                        note = VH sequence
source                  1..120
                        mol_type = protein
                        organism = synthetic construct
SEQUENCE: 113
EVQLLESGGG LVQPGGSLRL SCAASGFTFS SYAMSWVRQA PGKGLEWVSA ISGSGGDTYY    60
ADSVKGRFTI SRDNSKSTLY LQMNSLRAED TAVYYCAKDG GSYYPPFDYW GQGTLVTVSS   120

SEQ ID NO: 114          moltype = AA  length = 124
FEATURE                 Location/Qualifiers
REGION                  1..124
                        note = VH sequence
source                  1..124
                        mol_type = protein
                        organism = synthetic construct
SEQUENCE: 114
EVQLVESGGG LVQPGGSLRL SCAASGFTFS SYWMHWVRQA PGKGLVWVSR IHNDGSRTSY    60
ADSVKGRFTI SRDNAKNTLY LQMSSLRAED TAVYYCTRDP PPYDILTGYP FDWGQGTLV   120
TVSS                                                                124

SEQ ID NO: 115          moltype = AA  length = 121
FEATURE                 Location/Qualifiers
REGION                  1..121
                        note = VH sequence
source                  1..121
                        mol_type = protein
                        organism = synthetic construct
SEQUENCE: 115
EVQVLESGGG LVQPGGSLRL SCAASGFTFS SYAMSWVRQA PGKGLEWVSA ISGSGSSTHY    60
ADSVKGRFTI SRDNSKNTLY LQMNSLRAED TAVYYCAAYS GSYYYYGMDV WGQGTTVTVS   120
S                                                                   121

SEQ ID NO: 116          moltype = AA  length = 121
FEATURE                 Location/Qualifiers
REGION                  1..121
                        note = VH sequence
source                  1..121
                        mol_type = protein
                        organism = synthetic construct
SEQUENCE: 116
EVQMLESGGG LVQPGGSLRL SCAASGFTFS SYAMSWVRQA PGKGLEWVSA ISGSGSSTHY    60
ADSVKGRFTI SRDNSKNTLY LQMNSLRAED TAVYYCAAYS GSYYYYGMDV WGQGTTVTVS   120
S                                                                   121

SEQ ID NO: 117          moltype = AA  length = 118
FEATURE                 Location/Qualifiers
REGION                  1..118
                        note = VH sequence
source                  1..118
                        mol_type = protein
                        organism = synthetic construct
SEQUENCE: 117
QVQLVESGGG VVQPGRSLRL SCVASGFIFS NYGMHWVRQA PGKGLEWVAV ISYDGRNEDH    60
VDSVKGRFTI SRDNSKNTLY LQMNSLRAED TAVYYCAKGS GSYYFDYWGQ GTLVTVSS    118

SEQ ID NO: 118          moltype = AA  length = 119
FEATURE                 Location/Qualifiers
REGION                  1..119
                        note = VH sequence
source                  1..119
                        mol_type = protein
                        organism = synthetic construct
SEQUENCE: 118
QIQLVQSGPE LKKPGETVKI SCKGSGYTFR NFGMNWVKQA PGMGLKWMVW IDTNTGEPTY    60
AEEFKGRFAF SLETSASTAY LQINNLKNED TATYFCARSR GNYFAMEYWG QGTSVTVSS   119

SEQ ID NO: 119          moltype =    length =
SEQUENCE: 119
000
```

```
SEQ ID NO: 120         moltype =     length =
SEQUENCE: 120
000

SEQ ID NO: 121         moltype =     length =
SEQUENCE: 121
000

SEQ ID NO: 122         moltype =     length =
SEQUENCE: 122
000

SEQ ID NO: 123         moltype = AA   length = 112
FEATURE                Location/Qualifiers
REGION                 1..112
                       note = VL sequence
source                 1..112
                       mol_type = protein
                       organism = synthetic construct
SEQUENCE: 123
DIVMTQSPLS LPVTPGEPAS ISCRSSQSLL HGNGFNYLDW YLQKPGQSPQ LLIYLGSNRA   60
SGVPDRFTGS GSGTDFTLKI SRVEAEDVGV YYCMQGLQTP RTFGQGTKVE IK           112

SEQ ID NO: 124         moltype =     length =
SEQUENCE: 124
000

SEQ ID NO: 125         moltype = AA   length = 107
FEATURE                Location/Qualifiers
REGION                 1..107
                       note = VL sequence
source                 1..107
                       mol_type = protein
                       organism = synthetic construct
SEQUENCE: 125
DIQLTQSPSF LSASVGDRVT ITCRASQGIS GYLDWYQQKP GKAPKLLIYA ASTLQRGVPS   60
RFSGSGSGTD FNLTISSLQP EDFATYYCQQ FTSDLITFGQ GTRLEIK                 107

SEQ ID NO: 126         moltype = AA   length = 107
FEATURE                Location/Qualifiers
REGION                 1..107
                       note = VL sequence
source                 1..107
                       mol_type = protein
                       organism = synthetic construct
SEQUENCE: 126
DIQMTQSPSS LSASVGDRVT ITCQASQDFS NYLNWYQQKP GKAPKLLIYA ASNLETGVPS   60
RFSGSGSGTD FTFTISSLQP EDIAVYYCQQ YDNLPYTFGQ GTKLEIK                 107

SEQ ID NO: 127         moltype =     length =
SEQUENCE: 127
000

SEQ ID NO: 128         moltype =     length =
SEQUENCE: 128
000

SEQ ID NO: 129         moltype = AA   length = 108
FEATURE                Location/Qualifiers
REGION                 1..108
                       note = VL sequence
source                 1..108
                       mol_type = protein
                       organism = synthetic construct
SEQUENCE: 129
SYVLTQPPSV SVAPGQTARI TCGGYNIGSK SVHWYQQKAG QAPVLVVYDD SGRPSGIPER   60
LSGSKSGNTA TLTISRVEAG DEADYYCQVW DSSSDHYVFG TGTKVTVL                108

SEQ ID NO: 130         moltype = AA   length = 106
FEATURE                Location/Qualifiers
REGION                 1..106
                       note = VL sequence
source                 1..106
                       mol_type = protein
                       organism = synthetic construct
SEQUENCE: 130
SSELTQPPSV SVSPGQTASI TCSGDKLGDK YVYWYQQKPG QSPVLVIYHD DRRPAGIPER   60
FAGSASGNTA TLTISGTQAM DEADYYCQTW DSSTVVFGGG TKLTVL                  106
```

```
SEQ ID NO: 131          moltype = AA   length = 106
FEATURE                 Location/Qualifiers
REGION                  1..106
                        note = VL sequence
source                  1..106
                        mol_type = protein
                        organism = synthetic construct
SEQUENCE: 131
SYELTQSPSV SVSPGQTASI TCSGDKLGDR YAWWYQQKPG QSPVLVIYQD DKRPSGIPER    60
FSGSNSGNTA TLTISGTQAM DEADYYCQAW DSSTAVFGGG TKLTVL                   106

SEQ ID NO: 132          moltype = AA   length = 106
FEATURE                 Location/Qualifiers
REGION                  1..106
                        note = VL sequence
source                  1..106
                        mol_type = protein
                        organism = synthetic construct
SEQUENCE: 132
SYELTQPPSV SVSPGQTASI TCSGDKLGDR YACWYQQKPG QSPVLVIYQD TKRPSGIPER    60
FSGSNSGNTA TLTISGTQAM DEADYYCQAC DSSTAVFGGG TKLTVL                   106

SEQ ID NO: 133          moltype = AA   length = 107
FEATURE                 Location/Qualifiers
REGION                  1..107
                        note = VL sequence
source                  1..107
                        mol_type = protein
                        organism = synthetic construct
SEQUENCE: 133
DIQMTQSPSS VSASVGDRVT ITCRASQDIS SWLAWFQQKP GKAPKLLIYG ASSLQSGVPS    60
RFSGSGSGTD FTLTISSLQP EDFATYYCQE ANSFPYTFGQ GTKLEIK                  107

SEQ ID NO: 134          moltype = AA   length = 107
FEATURE                 Location/Qualifiers
REGION                  1..107
                        note = VL sequence
source                  1..107
                        mol_type = protein
                        organism = synthetic construct
SEQUENCE: 134
EIVMTQSPAT LSVSPGERAT LSCRASQSVS SNLAWYQQKS GQAPRLLIYG ASTRATGIPA    60
RFSGSGSGTE FTLTISSLQS EDFAGYYCQQ YNNWPYTFGQ GTKLEIK                  107

SEQ ID NO: 135          moltype = AA   length = 107
FEATURE                 Location/Qualifiers
REGION                  1..107
                        note = VL sequence
source                  1..107
                        mol_type = protein
                        organism = synthetic construct
SEQUENCE: 135
EIVMTQSPAT LSVSPGERAT LSCRASQSVS RNLAWYQQKS GQAPRLLIYG ASTRATGIPA    60
RFSGSGSGTE FTLTISSLQS EDFAGYYCQQ YNNWPYTFGQ GTKLEIK                  107

SEQ ID NO: 136          moltype = AA   length = 114
FEATURE                 Location/Qualifiers
REGION                  1..114
                        note = VL sequence
source                  1..114
                        mol_type = protein
                        organism = synthetic construct
SEQUENCE: 136
DIVLTQSPDS LAVSLGERAT INCKSSQTVL NSSNNKNYLA WYQQKPGQPP KLLIYWASIR    60
ESGVPDRFSG SGSGTDFTLT ISSLQAEDVA VYYCQQYYNT PPWTFGQGTK VEIK          114

SEQ ID NO: 137          moltype = AA   length = 107
FEATURE                 Location/Qualifiers
REGION                  1..107
                        note = VL sequence
source                  1..107
                        mol_type = protein
                        organism = synthetic construct
SEQUENCE: 137
DIKMTQSPSS MYASLGERVT VTCKASQDIN RYLSWFQQKP GKSPKTLIYR ANRLVDGVPS    60
RFSGSGSGQD YSLTISSLEY EDMGFYYCLQ YDEFPFTFGS GTKLEIK                  107
```

SEQ ID NO: 138          moltype =     length =
SEQUENCE: 138
000

SEQ ID NO: 139          moltype =     length =
SEQUENCE: 139
000

SEQ ID NO: 140          moltype =     length =
SEQUENCE: 140
000

SEQ ID NO: 141          moltype =     length =
SEQUENCE: 141
000

SEQ ID NO: 142          moltype = DNA   length = 354
FEATURE                 Location/Qualifiers
misc_feature            1..354
                        note = VH sequence
source                  1..354
                        mol_type = other DNA
                        organism = synthetic construct
SEQUENCE: 142
caggtgcagc tgcaggagtc gggcccagga ctggtgaagc cttcggggac cctgtccctc    60
acctgcgctg tctctggtgg ctccatcagc agtagtaact ggtggagttg ggtccgccag   120
cccccaggga aggggctgga atggattggg gaaatctatc atagtgggag caccaactac   180
aacccgtccc tcaagagtcg agtcaccata tcagtagaca gtccaagaa ccagttctcc    240
ctgaagctga gttctgtgac cgccgcggac acggccgtgt attactgtgc gagaagggg    300
atatggttcg ggtcggtcc ctggggccag ggaaccctgg tcaccgtctc ctca          354

SEQ ID NO: 143          moltype =     length =
SEQUENCE: 143
000

SEQ ID NO: 144          moltype = DNA   length = 369
FEATURE                 Location/Qualifiers
misc_feature            1..369
                        note = VH sequence
source                  1..369
                        mol_type = other DNA
                        organism = synthetic construct
SEQUENCE: 144
caggtgcagc tgcaggagtc gggcccagga ctggtgaagc cttcggggac cctgtctctc    60
acctgcgctg tctctggtgg ctccatcagc agtagtaact ggtggagttg ggtccgccag   120
cccccaggga aggggctgga gtggattggg gaaatctatc atagtgggaa caccaactac   180
aacccgtccc tcaagagtcg agtcaccata tcagtagaca gtccaagaa ccagttctcc    240
ctgaagctga gctctgtgac cgccgcggac acggccgtgt attactgtgc gagagagggt   300
atagaggggt actacttcta ctacggtatg gacgtctggg gccaagggac cacggtcacc   360
gtctcctca                                                           369

SEQ ID NO: 145          moltype = DNA   length = 363
FEATURE                 Location/Qualifiers
misc_feature            1..363
                        note = VH sequence
source                  1..363
                        mol_type = other DNA
                        organism = synthetic construct
SEQUENCE: 145
caggtgcagc tgcaggagtc gggcccagga ctgctgaagc cttcggagac cctgtccctc    60
acctgcgctg tctctgatta ctccatcagc agtggttact actggggctg gatccggcag   120
cccccgggga aggggctgga gtggattggg agtatctatc atagtgggaa tacctattat   180
aacccgtccc tcaagagtcg agtcaccata ttagtagaca cgtccaagaa ccagttctcc   240
ctgaagctga gctctgtgac cgccgcagac acggccgtgt attactgtgc gagagataaa   300
tgtagtacta caacctgctc ctttgactac tggggccagg gaaccctggt caccgtctcc   360
tca                                                                 363

SEQ ID NO: 146          moltype =     length =
SEQUENCE: 146
000

SEQ ID NO: 147          moltype =     length =
SEQUENCE: 147
000

SEQ ID NO: 148          moltype = DNA   length = 348
FEATURE                 Location/Qualifiers
misc_feature            1..348
                        note = VH sequence

| | | |
|---|---|---|
| source | 1..348<br>mol_type = other DNA<br>organism = synthetic construct | |

SEQUENCE: 148

```
caggtgcagc tggtggagtc tggggggaggc gtggtccagc ctgggaggtc cctgagactc   60
tcctgtgcag cctctggatt caccttcagt aaatttggca tgcactgggt ccgccaggct  120
ccaggcaagg ggctggagtg gtggcagtt atatcatatg atggaaataa taaatactat  180
acagactccg tgaagggccg attcaccatc tccagagaca attccaggaa cacgctgtat  240
ctgcaaatgg acagcgtgaa acctgaggac acggctgtgt actattcctg ggcagcagct  300
ggtgcttttt atatctgggg ccaagggaca atggtcaccg tctcttca              348
```

| | | |
|---|---|---|
| SEQ ID NO: 149<br>FEATURE<br>misc_feature | moltype = DNA   length = 366<br>Location/Qualifiers<br>1..366<br>note = VH sequence | |
| source | 1..366<br>mol_type = other DNA<br>organism = synthetic construct | |

SEQUENCE: 149

```
caggtgcagc tacagcagtg gggcgcagga ctgttgaagc cttcggagac cctgtccctc   60
acctgcgctg tctatggtgg gtccttcagt ggttactact ggagctggat cgccagccc   120
ccagggaagg ggctggagtg gattgggaa atcaatcata gtgaagcac caacttcaac   180
ccgtccctca agagtcgagt caccatatca gtagacacgt ccaagaacca gttctccctg   240
aagctgagct ctgtgaccgc cgcggacacg gctgtgtatt actgtgcgag agtcgatagt   300
gggagctatc cctactacga cggttttgac gtctggggcc aagggaccac ggtcaccgtc   360
tcctca                                                            366
```

| | | |
|---|---|---|
| SEQ ID NO: 150<br>FEATURE<br>misc_feature | moltype = DNA   length = 372<br>Location/Qualifiers<br>1..372<br>note = VH sequence | |
| source | 1..372<br>mol_type = other DNA<br>organism = synthetic construct | |

SEQUENCE: 150

```
caggtgcagc tacagcagtg gggcgcagga ctgttgaagc cttcggagac cctgtccctc   60
acctgcgctg tctatggtgg gtccttcagt acttactact ggaactggat ccgccagccc  120
ccagggaagg ggctggagtg gattgggaa atcaatcata gtgaagcac caactacaac   180
ccgtccctca agagtcgagt catcatatca gtagacacgt ccaagaacca gttctccctg   240
aagctgagct ctgtgaccgc cgcggacacg gctgtgtatt actgtgcgag cagtcattat   300
ggttcgggga gttttcccga ctcctacggt atggacgtct ggggccaagg gaccacggtc   360
accgtctccg ca                                                    372
```

| | | |
|---|---|---|
| SEQ ID NO: 151<br>FEATURE<br>misc_feature | moltype = DNA   length = 360<br>Location/Qualifiers<br>1..360<br>note = VH sequence | |
| source | 1..360<br>mol_type = other DNA<br>organism = synthetic construct | |

SEQUENCE: 151

```
gaggtgcagc tgttggagtc tgggggaggc ttggtacagc ctgggggtc cctgagactc    60
tcctgtgcag cctctggatt cacgtttagc agctatgcca tgagctgggt ccgccaggct  120
ccagggaagg ggctggagtg ggtctcagct attagtggta gtggtggtga cacttactac  180
gcagactccg tgaagggccg gttcaccatc tccagagaca attccaagag cacgctgtat  240
ctgcaaatga acagcctgag agccgaggac acggccgtat attactgtgc gaagacggt  300
gggagctact acccccccctt tgactactgg ggccaggaa ccctggtcac cgtctcctca   360
```

| | | |
|---|---|---|
| SEQ ID NO: 152<br>FEATURE<br>misc_feature | moltype = DNA   length = 372<br>Location/Qualifiers<br>1..372<br>note = VH sequence | |
| source | 1..372<br>mol_type = other DNA<br>organism = synthetic construct | |

SEQUENCE: 152

```
gaggtgcagc tggtggagtc cggggaggc ttagttcagc ctgggggtc cctgagactc     60
tcttgtgcag cctctggatt caccttcagt agctactgga tgcactgggt ccgccaagct  120
ccagggaagg ggctggtgtg ggtctcacgt attcataatg atggagtag aacaagttac  180
gcggactccg tgaagggccg attcactatc tccagagaca cgccaagaa cacgctgtat  240
ctgcaaatga gcagtctgcg agccgaggac acggctgtgt attactgtac aagagatccc   300
cctccttacg atattttgac tggttacccc tttgactact ggggccaggg aaccctggtc   360
accgtctcct ca                                                    372
```

| | | |
|---|---|---|
| SEQ ID NO: 153<br>FEATURE<br>misc_feature | moltype = DNA   length = 363<br>Location/Qualifiers<br>1..363<br>note = VH sequence | |

```
source              1..363
                    mol_type = other DNA
                    organism = synthetic construct
SEQUENCE: 153
gaggtgcagg tgttggagtc tgggggaggc ttggtacagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtagtag cacacactac   180
gcagactccg tgaagggccg gttcaccatc tccagagaca attccaagaa cacgctgtat   240
ctgcaaatga acagcctgag agccgaggac acggccgtat attactgtgc ggcgtatagt   300
gggagctact actactatgg aatggacgtc tggggacaag gaccacggt caccgtctcc    360
tca                                                                 363

SEQ ID NO: 154          moltype = DNA   length = 363
FEATURE                 Location/Qualifiers
misc_feature            1..363
                        note = VH sequence
source                  1..363
                        mol_type = other DNA
                        organism = synthetic construct
SEQUENCE: 154
gaggtgcaga tgttggagtc tgggggaggc ttggttcagc ctggggggtc cctgagactc    60
tcctgtgcag cctctggatt cacctttagc agctatgcca tgagctgggt ccgccaggct   120
ccagggaagg ggctggagtg ggtctcagct attagtggta gtggtagtag cacacactac   180
gcagactccg tgaagggccg gttcaccatc tccagagaca attccaagaa cacgctgtat   240
ctgcaaatga acagcctgag agccgaggac acggccgttt attactgtgc ggcgtatagt   300
gggagctact actactatgg aatggacgtc tggggacagg gaccacggt caccgtctcc    360
tca                                                                 363

SEQ ID NO: 155          moltype = DNA   length = 354
FEATURE                 Location/Qualifiers
misc_feature            1..354
                        note = VH sequence
source                  1..354
                        mol_type = other DNA
                        organism = synthetic construct
SEQUENCE: 155
caggtgcagc tggtggagtc tgggggaggc gtggtccagc ctgggaggtc cctgagactc    60
tcctgtgtag cctctggatt catcttcagt aactatggca tgcactgggt ccgccaggct   120
ccaggcaagg ggctggagtg ggtggcagtt atatcatatg atggaagaaa tgaagaccat   180
gtagactccg tgaagggccg attcaccatc tccagagaca attccaagaa cacgctgtat   240
ctgcaaatga acagcctgag agctgaggac acggctgtat attactgtgc gaaagggtcg   300
gggagctact actttgacta ctggggccag ggaaccctgg tcaccgtctc ctca         354

SEQ ID NO: 156          moltype = DNA   length = 357
FEATURE                 Location/Qualifiers
misc_feature            1..357
                        note = VH sequence
source                  1..357
                        mol_type = other DNA
                        organism = synthetic construct
SEQUENCE: 156
cagatccagt tggtgcagtc tggacctgag ctgaagaagc ctggagagac agtcaagatc    60
tcctgcaagg gttctgggta taccttcaga aactttggaa tgaattgggt gaagcaggct   120
ccaggaatgg gtttaaagtg gatggtgtgg atagacacca cactggaga gccaacatat   180
gctgaagagt tcaagggacg gttttgcttc tctttggaaa cctctgccag cactgcctat   240
ttgcagatca caacctcaaa aaatgaggac acggctacat atttctgtgc aagatcgaga   300
ggtaactact ttgctatgga gtattgggg caaggaacct cagtcaccgt ctcctca       357

SEQ ID NO: 157          moltype =    length =
SEQUENCE: 157
000

SEQ ID NO: 158          moltype =    length =
SEQUENCE: 158
000

SEQ ID NO: 159          moltype =    length =
SEQUENCE: 159
000

SEQ ID NO: 160          moltype =    length =
SEQUENCE: 160
000

SEQ ID NO: 161          moltype = DNA   length = 336
FEATURE                 Location/Qualifiers
misc_feature            1..336
                        note = VL sequence
```

```
source                  1..336
                        mol_type = other DNA
                        organism = synthetic construct
SEQUENCE: 161
gatattgtga tgactcagtc tccactctcc ctgcccgtca cccctggaga gccggcctcc    60
atctcctgca ggtctagtca gagcctccta catggtaatg gattcaacta tttggattgg   120
tacctgcaga agccagggca gtctccacag ctcctgatct atttgggttc taatcgggcc   180
tccggggtcc ctgacaggtt cactggcagt ggatcaggca cagattttac actgaaaatc   240
agcagagtgg aggctgagga tgttggggtt tattactgca tgcaaggtct acaaactcct   300
cggacgttcg gccaagggac caaggtggaa atcaaa                             336

SEQ ID NO: 162          moltype =    length =
SEQUENCE: 162
000

SEQ ID NO: 163          moltype = DNA   length = 321
FEATURE                 Location/Qualifiers
misc_feature            1..321
                        note = VL sequence
source                  1..321
                        mol_type = other DNA
                        organism = synthetic construct
SEQUENCE: 163
gacatccagt tgacccagtc tccatccttc ctgtctgcat ctgtaggaga cagagtcacc    60
atcacttgcc gggccagtca gggcattagc ggttatttag actggtatca gcaaaaacca   120
gggaaagccc ctaagctcct gatctatgct gcatccactt tacaaagagg ggtcccatca   180
aggttcagcg gcagtggatc tgggacagat ttcaatctca caatcagcag cctgcagcct   240
gaagattttg caacttatta ctgtcaacag tttactagtg acctcatcac cttcggccaa   300
gggacacgac tggagattaa a                                             321

SEQ ID NO: 164          moltype = DNA   length = 321
FEATURE                 Location/Qualifiers
misc_feature            1..321
                        note = VL sequence
source                  1..321
                        mol_type = other DNA
                        organism = synthetic construct
SEQUENCE: 164
gacatccaga tgacccagtc tccatcctcc ctgtctgcat ctgtaggaga cagagtcacc    60
atcacttgcc aggcgagtca ggactttagc aactatttaa attggtatca gcagaaacca   120
gggaaagccc ctaagctcct gatctacgct gcatccaatt tggaaacagg ggtcccatcg   180
aggttcagtg gaagtggatc tgggacagat tttactttca ccatcagcag cctgcagcct   240
gaagatattg cagtatatta ctgtcaacag tatgataatc tcccgtacac ttttggccag   300
gggaccaagc tggagatcaa a                                             321

SEQ ID NO: 165          moltype =    length =
SEQUENCE: 165
000

SEQ ID NO: 166          moltype =    length =
SEQUENCE: 166
000

SEQ ID NO: 167          moltype = DNA   length = 324
FEATURE                 Location/Qualifiers
misc_feature            1..324
                        note = VL sequence
source                  1..324
                        mol_type = other DNA
                        organism = synthetic construct
SEQUENCE: 167
tcctatgtgc tgactcagcc accctcggtg tcagtggccc caggacagac ggccaggatt    60
acctgtgggg gatacaacat tggaagtaaa agtgtgcact ggtaccagca gaaggcaggc   120
caggcccctg tgctggtcgt ctatgatgat agcggccggc cctcagggat ccctgagcga   180
ttgtctggct ccaagtctgg gaacacggcc accctgacca tcagcagggt cgaagccggg   240
gatgaggccg actattactg tcaggtgtgg gatagtagta gtgatcatta tgtcttcgga   300
actgggacca aggtcaccgt ccta                                          324

SEQ ID NO: 168          moltype = DNA   length = 318
FEATURE                 Location/Qualifiers
misc_feature            1..318
                        note = VL sequence
source                  1..318
                        mol_type = other DNA
                        organism = synthetic construct
SEQUENCE: 168
tcctctgaat tgactcagcc accctcagtg tccgtgtccc caggacagac agccagcatc    60
acctgctctg gagataaatt gggggataaa tatgtttact ggtatcaaca gaagccaggc   120
cagtcccctg tgttggtcat ctatcatgat gatcggcggc cgctgggat  ccctgagcga   180
```

```
ttcgctggct ccgcttctgg gaacacagcc actctgacca tcagcgggac ccaggctatg    240
gatgaggctg actattactg tcagacgtgg gacagcagca ctgtggtttt cggcggaggg    300
accaagctga ccgtccta                                                  318
```

SEQ ID NO: 169           moltype = DNA   length = 318
FEATURE                  Location/Qualifiers
misc_feature             1..318
                         note = VL sequence
source                   1..318
                         mol_type = other DNA
                         organism = synthetic construct
SEQUENCE: 169
```
tcctatgaat tgactcagtc accctcagtg tccgtgtccc caggacagac agccagcatc    60
acctgctctg gagataaatt gggggataga tatgcttggt ggtatcagca gaagccaggc    120
cagtcccctg tgctggtcat ctatcaagat gacaagcggc cctcaggat  ccctgagcga    180
ttctctggct ccaactctgg gaacacagcc actctgacca tcagcgggac ccaggctatg    240
gatgaggctg actattactg tcaggcgtgg gacagcagca ctgcggtatt cggcggaggg    300
accaagctga ccgtccta                                                  318
```

SEQ ID NO: 170           moltype = DNA   length = 318
FEATURE                  Location/Qualifiers
misc_feature             1..318
                         note = VL sequence
source                   1..318
                         mol_type = other DNA
                         organism = synthetic construct
SEQUENCE: 170
```
tcctatgagc tgactcagcc accctcagtg tccgtgtccc caggacagac agccagcatc    60
acctgctctg gagataaatt gggggataga tatgcttgct ggtatcagca gaagccaggc    120
cagtcccctg tactggtcat ctatcaagat accaagcggc cctcaggat  ccctgagcga    180
ttctctggct ccaactctgg gaacacagcc actctgacca tcagcgggac ccaggctatg    240
gatgaggctg actattactg tcaggcgtgc gacagcagca ctgcggtgtt cggcggaggg    300
accaagctga ccgtccta                                                  318
```

SEQ ID NO: 171           moltype = DNA   length = 321
FEATURE                  Location/Qualifiers
misc_feature             1..321
                         note = VL sequence
source                   1..321
                         mol_type = other DNA
                         organism = synthetic construct
SEQUENCE: 171
```
gacatccaga tgacccagtc tccgtcttcc gtgtctgcat ctgtaggaga cagagtcacc    60
atcacttgtc gggcgagtca ggatattagc agctggttag cctggtttca gcagaaacca    120
gggaaagccc ctaagctcct gatctatggt gcatccagtt tgcaaagtgg ggtcccatca    180
aggttcagcg gcagtggatc tgggacagat ttcactctca ccatcagcag cctgcagcct    240
gaagattttg caacttacta ttgtcaagag gctaacagtt cccgtatac  ttttggccag    300
gggaccaagc tggagatcaa a                                              321
```

SEQ ID NO: 172           moltype = DNA   length = 321
FEATURE                  Location/Qualifiers
misc_feature             1..321
                         note = VL sequence
source                   1..321
                         mol_type = other DNA
                         organism = synthetic construct
SEQUENCE: 172
```
gaaatagtga tgacgcagtc tccagccacc ctgtctgtgt ctccagggga aagagccacc    60
ctctcctgca gggccagtca gagtgttagc agcaacttag caacctggtacca gcagaaatct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg caggttatta ctgccagcag tataataact ggccgtacac ttttggccag    300
gggaccaagc tggagatcaa a                                              321
```

SEQ ID NO: 173           moltype = DNA   length = 321
FEATURE                  Location/Qualifiers
misc_feature             1..321
                         note = VL sequence
source                   1..321
                         mol_type = other DNA
                         organism = synthetic construct
SEQUENCE: 173
```
gaaatagtga tgacgcagtc tccagccacc ctgtctgtgt ctccagggga aagagccacc    60
ctctcctgca gggccagtca gagtgttagt aggaatttag cctggtacca gcagaaatct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg caggttatta ctgccagcag tataataact ggccgtacac ttttggccag    300
gggaccaagc tggagatcaa a                                              321
```

```
SEQ ID NO: 174         moltype = DNA  length = 342
FEATURE                Location/Qualifiers
misc_feature           1..342
                       note = VL sequence
source                 1..342
                       mol_type = other DNA
                       organism = synthetic construct
SEQUENCE: 174
gacatcgtgc tgacccagtc tccagactcc ctggctgtgt ctctgggcga gagggccacc    60
atcaactgca agtccagcca gactgtttta aacagctcca acaataagaa ctacctagct   120
tggtaccagc agaaaccagg acagcctcct aagctgctca tttactgggc atctatccgg   180
gaatccgggg tccctgaccg attcagtggc agcgggtctg ggacagattt cactctcacc   240
atcagcagcc tgcaggctga agatgtggca gtttattact gtcagcaata ttataatact   300
cctccgtgga cgttcggcca agggaccaag gtggaaatca aa                      342

SEQ ID NO: 175         moltype = DNA  length = 321
FEATURE                Location/Qualifiers
misc_feature           1..321
                       note = VL sequence
source                 1..321
                       mol_type = other DNA
                       organism = synthetic construct
SEQUENCE: 175
gacatcaaga tgacccagtc tccatcttcc atgtatgcat ctctaggaga gagagtcact    60
gtcacttgca aggcgagtca ggacattaat cgctatttaa gctggttcca gcagaaacca   120
gggaaatctc ctaagaccct gatctatcgt gcaaacagat tggtagatgg ggtcccatca   180
aggttcagtg gcagtggatc tgggcaagat tattctctca ccatcagcag cctggagtat   240
gaagatatgg gatttttatta ttgtctacag tatgatgagt ttccattcac gttcggctcg   300
gggacaaagt tggaaataaa a                                              321
```

SIRP α, SIRP β 1, AND SIRP γ ANTIBODIES AND USES THEREOF

CROSS REFERENCE TO RELATED APPLICATIONS

This application is a continuation of U.S. patent application Ser. No. 17/923,778, filed on Nov. 7, 2022, which is a U.S. National Stage Application under 35 U.S.C. § 371 of International Application No. PCT/US2021/031605, filed on May 10, 2021, which claims priority to U.S. Provisional Patent Application No. 63/022,309, filed on May 8, 2020, the contents of each of which are incorporated by reference herein in their entirety.

INCORPORATION OF SEQUENCE LISTING

The Sequence Listing XML associated with this application is provided in XML file format and is hereby incorporated by reference into the specification. The name of the XML file containing the Sequence Listing XML is ELTH_001_02 US_SeqList_ST26.xml. The XML file is 203,436 bytes, and created on Feb. 28, 2024, and is being submitted electronically via USPTO Patent Center.

BACKGROUND

Signal regulatory proteins (SIRPs) are a family of cell-surface immune receptors with Ig-like extracellular domains. The SIRP family contains three inhibitory, activating, and non-signaling members, which have closely related extracellular regions, but differ in their cytoplasmic domains. SIRP family members play a role in immune regulation. Signal regulatory protein alpha (also known as SIRPα, SIRP alpha, CD172a, BIT, MFR, MYD-1, P84, PTPNS1. SHPS1) is a transmembrane glycoprotein and one member of the signal regulatory SIRP family of cell-surface receptors. SIRPα delivers an inhibitory signal via immunoreceptor tyrosine-based inhibition motifs (ITIMs) located in the cytoplasmic domain of the protein that downregulates myeloid cell phagocytic and pro-inflammatory activity. SIRPα on phagocytes interacts with CD47, also known as integrin-associated protein (IAP), a ubiquitously expressed cell surface protein that serves, among other things, as a marker of "self" on viable cells. Thus, CD47/SIRPα signaling acts as a "do not eat me" immune check point to negatively control innate immune cell phagocytosis. SIRPβ1 (also known as SIRPβ, SIRPβ1, and CD172b) delivers an activating signal through association with the DNA polymerase III subunit tau (DNAX) activation protein of 12 kDa (DAP12, also known as transmembrane immune signaling adaptor TYROBP, or TYROBP), a transmembrane adaptor protein with an immunoreceptor tyrosine-based activation motif (ITAM). SIRPα and SIRPβ1 are expressed on myeloid cells of the immune system, as well as other cell types. SIRPγ (also called CD172-antigen-like family member B, CD172g, and SIRP-beta-2) is expressed by lymphocytes such as T cells, and also binds to CD47. There is a need for agents that bind to SIRPα, SIRPβ1, as well as SIRPγ expressing cells for the treatment of a variety of diseases and conditions.

SUMMARY

The disclosure provides Fc-containing antibodies that are specific for one or more of SIRPα and SIRPβ1, and is also specific for SIRPγ, wherein binding of the antibody to one or more of SIRPα, SIRPβ1, and SIRPγ on a cell induces depletion of the cell.

The disclosure provides antibodies that are specific for one or more of SIRPα and SIRPβ1, and antibodies specific for SIRPγ, wherein the antibody comprises a heavy chain variable region and a light chain variable region, and wherein the heavy chain variable region comprises: (i) a complementarity determining region 1 (CDR-H1) sequence selected from the group consisting of SEQ ID NOS: 54, 56, and 59-65; (ii) a CDR-H2 sequence selected from the group consisting of SEQ ID NOS: 70, 72, and 75-81; and (iii) a CDR-H3 sequence selected from the group consisting of SEQ ID NOS: 86, 88-89, and 92-99; and/or wherein the light chain variable region comprises: (i) a light chain CDR 1 (CDR-L1) sequence selected from the group consisting of SEQ ID NOS: 5, 7-8, and 11-18; (ii) a CDR-L2 sequence selected from the group consisting of SEQ ID NOS: 23-24, and 27-33; and (iii) a CDR-H3 sequence selected from the group consisting of SEQ ID NOS: 36, 38-39, and 42-49.

In some embodiments of the antibodies of disclosure, the antibody comprises the heavy and light variable chain CDR sequence combination selected from the group consisting of: (a) SEQ ID NO: 5, SEQ ID NO: 23, SEQ ID NO: 36, SEQ ID NO: 54, SEQ ID NO: 70, and SEQ ID NO: 86; (b) SEQ ID NO: 7, SEQ ID NO: 24, SEQ ID NO: 38, SEQ ID NO: 54, SEQ ID NO: 72, and SEQ ID NO: 88; (c) SEQ ID NO: 8, SEQ ID NO: 24, SEQ ID NO: 39, SEQ ID NO: 56, SEQ ID NO: 72, and SEQ ID NO: 89; (d) SEQ ID NO: 11, SEQ ID NO: 27, SEQ ID NO: 42, SEQ ID NO: 59, SEQ ID NO: 75, and SEQ ID NO: 92; (e) SEQ ID NO: 12, SEQ ID NO: 28, SEQ ID NO: 43. SEQ ID NO: 60. SEQ ID NO: 76, and SEQ ID NO: 93: (f) SEQ ID NO: 13. SEQ ID NO: 29. SEQ ID NO: 44. SEQ ID NO: 61. SEQ ID NO: 76, and SEQ ID NO: 94: (g) SEQ ID NO: 13. SEQ ID NO: 30. SEQ ID NO: 45. SEQ ID NO: 62. SEQ ID NO: 77, and SEQ ID NO: 95: (h) SEQ ID NO: 14. SEQ ID NO: 31. SEQ ID NO: 46. SEQ ID NO: 63. SEQ ID NO: 78, and SEQ ID NO: 96: (i) SEQ ID NO: 15. SEQ ID NO: 31. SEQ ID NO: 47. SEQ ID NO: 62. SEQ ID NO: 79, and SEQ ID NO: 97: (j) SEQ ID NO: 16. SEQ ID NO: 31. SEQ ID NO: 47. SEQ ID NO: 62. SEQ ID NO: 79, and SEQ ID NO: 97: (k) SEQ ID NO: 17. SEQ ID NO: 32. SEQ ID NO: 48. SEQ ID NO: 64. SEQ ID NO: 80, and SEQ ID NO: 98; and (1) SEQ ID NO: 18. SEQ ID NO: 33. SEQ ID NO: 49. SEQ ID NO: 65. SEQ ID NO: 81, and SEQ ID NO: 99. In some embodiments, the heavy chain variable region comprises a sequence selected from the group consisting of SEQ ID NOS: 104, 106-107, and 110-118. In some embodiments, the light chain variable region comprises a sequence selected from the group consisting of SEQ ID NOS: 123, 125-126, and 129-137.

In some embodiments of the antibodies of the disclosure, the heavy chain variable region sequence and the light chain variable region sequence are selected from the group consisting of: (a) SEQ ID NO: 104 and SEQ ID NO: 123; (b) SEQ ID NO: 106 and SEQ ID NO: 125; (c) SEQ ID NO: 107 and SEQ ID NO: 126; (d) SEQ ID NO: 110 and SEQ ID NO: 129; (e) SEQ ID NO: 111 and SEQ ID NO: 130; (f) SEQ ID NO: 112 and SEQ ID NO: 131: (g) SEQ ID NO: 113 and SEQ ID NO: 132; (h) SEQ ID NO: 114 and SEQ ID NO: 133: (i) SEQ ID NO: 115 and SEQ ID NO: 134: (j) SEQ ID NO: 116 and SEQ ID NO: 135: (k) SEQ ID NO: 117 and SEQ ID NO: 136; and (1) SEQ ID NO: 118 and SEQ ID NO: 137.

In some embodiments of the antibodies of the disclosure, the heavy chain variable domain of the antibody comprises the amino acid sequence of SEQ ID NO: 104 or an amino acid sequence with at least 80% sequence identity thereto; and/or wherein the light chain variable domain of the antibody comprises the amino acid sequence of SEQ ID NO: 123, or an amino acid sequence with at least 80% sequence identity thereto. In some embodiments, the heavy chain variable domain of the antibody comprises the amino acid sequence of SEQ ID NO: 106 or an amino acid sequence with at least 80% sequence identity thereto; and/or wherein the light chain variable domain of the antibody comprises the amino acid sequence of SEQ ID NO: 125, or an amino acid sequence with at least 80% sequence identity thereto. In some embodiments the heavy chain variable domain of the antibody comprises the amino acid sequence of SEQ ID NO: 107 or an amino acid sequence with at least 80% sequence identity thereto; and/or wherein the light chain variable domain of the antibody comprises the amino acid sequence of SEQ ID NO: 126, or an amino acid sequence with at least 80% sequence identity thereto. In some embodiments, the heavy chain variable domain of the antibody comprises the amino acid sequence of SEQ ID NO: 110 or an amino acid sequence with at least 80% sequence identity thereto; and/or wherein the light chain variable domain of the antibody comprises the amino acid sequence of SEQ ID NO: 129, or an amino acid sequence with at least 80% sequence identity thereto. In some embodiments, the heavy chain variable domain of the antibody comprises the amino acid sequence of SEQ ID NO: 111 or an amino acid sequence with at least 80% sequence identity thereto; and/or wherein the light chain variable domain of the antibody comprises the amino acid sequence of SEQ ID NO: 130, or an amino acid sequence with at least 80% sequence identity thereto. In some embodiments, the heavy chain variable domain of the antibody comprises the amino acid sequence of SEQ ID NO: 112 or an amino acid sequence with at least 80% sequence identity thereto; and/or wherein the light chain variable domain of the antibody comprises the amino acid sequence of SEQ ID NO: 131, or an amino acid sequence with at least 80% sequence identity thereto. In some embodiments, the heavy chain variable domain of the antibody comprises the amino acid sequence of SEQ ID NO: 113 or an amino acid sequence with at least 80% sequence identity thereto; and/or wherein the light chain variable domain of the antibody comprises the amino acid sequence of SEQ ID NO: 132, or an amino acid sequence with at least 80% sequence identity thereto. In some embodiments, the heavy chain variable domain of the antibody comprises the amino acid sequence of SEQ ID NO: 114 or an amino acid sequence with at least 80% sequence identity thereto; and/or wherein the light chain variable domain of the antibody comprises the amino acid sequence of SEQ ID NO: 133, or an amino acid sequence with at least 80% sequence identity thereto. In some embodiments, the heavy chain variable domain of the antibody comprises the amino acid sequence of SEQ ID NO: 115 or an amino acid sequence with at least 80% sequence identity thereto; and/or wherein the light chain variable domain of the antibody comprises the amino acid sequence of SEQ ID NO: 134, or an amino acid sequence with at least 80% sequence identity thereto. In some embodiments, the heavy chain variable domain of the antibody comprises the amino acid sequence of SEQ ID NO: 116 or an amino acid sequence with at least 80% sequence identity thereto; and/or wherein the light chain variable domain of the antibody comprises the amino acid sequence of SEQ ID NO: 135, or an amino acid sequence with at least 80% sequence identity thereto. In some embodiments, the heavy chain variable domain of the antibody comprises the amino acid sequence of SEQ ID NO: 117 or an amino acid sequence with at least 80% sequence identity thereto; and/or wherein the light chain variable domain of the antibody comprises the amino acid sequence of SEQ ID NO: 136, or an amino acid sequence with at least 80% sequence identity thereto. In some embodiments, the heavy chain variable domain of the antibody comprises the amino acid sequence of SEQ ID NO: 118 or an amino acid sequence with at least 80% sequence identity thereto; and/or wherein the light chain variable domain of the antibody comprises the amino acid sequence of SEQ ID NO: 137, or an amino acid sequence with at least 80% sequence identity thereto. In some embodiments, the antibody comprises an Fc domain.

In some embodiments of the antibodies of the disclosure, the antibody is an Fc-containing antibody, and the binding of the antibody to one or more of SIRPα, SIRPβ1, and SIRPγ on a cell induces depletion of the cell. In some embodiments, the cell depletion involves antibody dependent cellular phagocytosis (ADCP). In some embodiments, the cell depletion involves antibody dependent cellular cytotoxicity (ADCC). In some embodiments, the cell depletion involves depletion of SIRPγ positive cells. In some embodiments, the SIRPγ cells are lymphocytes. In some embodiments, the lymphocytes are T cells or NK cells. In some embodiments, the T cells are cytotoxic T cells, helper T cells, memory T cells, regulatory T cells, natural killer T cells, mucosal associated invariant T cells, gamma delta T cells, or a combination thereof. In some embodiments, the cell depletion involves depletion of SIRPγ positive cells and SIRPα and/or SIRPβ1 positive cells. In some embodiments, the SIRPα and/or SIRPβ1 cells are myeloid cells or myeloid progenitor cells. In some embodiments, the SIRPα and/or SIRPβ1 cells are selected from the group consisting of monocytes, macrophages, dendritic cells, basophils, eosinophils, neutrophils, and mast cells.

In some embodiments of the antibodies of the disclosure, the antibody is a monoclonal antibody. In some embodiments, the antibody is an antibody fragment. In some embodiments, the antibody is a human antibody. In some embodiments, the antibody is a humanized antibody. In some embodiments, the antibody is a chimeric antibody. In some embodiments, the antibody is a full-length antibody.

In some embodiments of the antibodies of the disclosure, the Fc domain is selected from the group consisting of human IgG1, IgG2, IgG3, and IgG4. In some embodiments, the Fc domain comprises SEQ ID NO: 3, SEQ ID NO: 4 or SEQ ID NO: 26. In some embodiments, the Fc domain comprises one or more amino acid substitutions relative to SEQ ID NO: 3, SEQ ID NO: 4 or SEQ ID NO: 26. In some embodiments, the Fc domain of the antibody is human IgG1 and comprises at least one amino acid substitution at a position selected from the group consisting of: 214, 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330), 332, 333, 334, 345, 356, 358, 396, 428, 430, 433, 434, and 440) wherein the position numbers of the amino acid residues are of the EU numbering scheme. In some embodiments, the IgG1 Fc comprises a sequence selected from the group consisting of: (a) SEQ ID NO: 19; (b) SEQ ID NO: 20, wherein $X_1$ is V or A; (c) SEQ ID NO: 21, wherein $X_1$ is V or A; $X_2$ is G or A; $X_3$ is S or D; and $X_4$ is I or E; (d) SEQ ID NO: 22, wherein $X_1$ is V or A; (e) SEQ ID NO: 25, wherein $X_1$ is V or A; $X_2$ is M or L; and $X_3$ is N or S; and (f) SEQ ID NO: 26, wherein $X_1$ is K or R; $X_2$ is D or E; and $X_3$ is L or M. In some embodiments, the IgG4 Fc comprises a sequence of SEQ ID NO: 34, 35 or 37, wherein $X_1$ in SEQ ID NO: 37 is S or P; and $X_2$ in SEQ ID NO: 37 is L or E.

In some embodiments of the antibodies of the disclosure, the binding of the antibody does not disrupt the interaction between CD47 and SIRPα, and/or the interaction between CD47 and SIRPγ. In some embodiments, binding of the antibody disrupts the interaction between CD47 and SIRPα, and/or the interaction between CD47 and SIRPγ. In some embodiments, the antibody binds SIRPα, SIRPβ1 and SIRPγ. In some embodiments, the antibody binds SIRPα and SIRPγ and exhibits little or no binding to SIRPβ1. In some embodiments, the antibody binds SIRPβ1 and SIRPγ and exhibits little or no binding to SIRPα.

In some embodiments of the antibodies of the disclosure, the antibody comprises a binding affinity for SIRPα of about 100 μm, about 1 nM, about 5 nM, about 10 nM, about 50 nM, about 100 nM, about 500 nM, or about 1 μM. In some embodiments, the antibody comprises a binding affinity for SIRPβ1 of about 0.5 nM, about 0.1 nM, about 5 nM, about 10) nM, about 50) nM, about 100 nM, about 500 nM, about 1 μM, about 5 μM, or about 10 μM. In some embodiments, the antibody comprises a binding affinity for SIRPγ of about 0.0001 nM about 0.0005 nM, about 0.001 nM, about 0.005 nM, about 0.1 nM, about 0.05 nM, about 0.1 nM, about 0.5 nM, about 1 nM, about 5 nM, about 10 nM, about 50 nM, about 100 nM, about 500 nM, about 1 μM, about 2 μM, or about 3 μM.

The disclosure provides a pharmaceutical composition comprising an antibody of the disclosure, and optionally a pharmaceutically acceptable carrier.

The disclosure provides a nucleic acid encoding for the antibody of the disclosure. In some embodiments, the nucleic acid comprises nucleic acid sequence selected from the group consisting of SEQ ID NOS: 142, 144-145, 148-156, 161, 163-164, and 167-175. In some embodiments, the heavy chain variable domain is encoded by the nucleic acid sequence of SEQ ID NO: 142, or a nucleic acid sequence with at least 80% sequence identity thereto; and/or wherein the light chain variable domain is encoded by the nucleic acid sequence of SEQ ID NO: 161, or a nucleic acid sequence with at least 80% sequence identity thereto. In some embodiments, the heavy chain variable domain is encoded by the nucleic acid sequence of SEQ ID NO: 144, or a nucleic acid sequence with at least 80% sequence identity thereto; and/or wherein the light chain variable domain is encoded by the nucleic acid sequence of SEQ ID NO: 163, or a nucleic acid sequence with at least 80% sequence identity thereto. In some embodiments, the heavy chain variable domain is encoded by the nucleic acid sequence of SEQ ID NO: 145, or a nucleic acid sequence with at least 80% sequence identity thereto; and/or wherein the light chain variable domain is encoded by the nucleic acid sequence of SEQ ID NO: 164, or a nucleic acid sequence with at least 80% sequence identity thereto. In some embodiments, the heavy chain variable domain is encoded by the nucleic acid sequence of SEQ ID NO: 148, or a nucleic acid sequence with at least 80% sequence identity thereto; and/or wherein the light chain variable domain is encoded by the nucleic acid sequence of SEQ ID NO: 167, or a nucleic acid sequence with at least 80% sequence identity thereto. In some embodiments, the heavy chain variable domain is encoded by the nucleic acid sequence of SEQ ID NO: 149, or a nucleic acid sequence with at least 80% sequence identity thereto; and/or wherein the light chain variable domain is encoded by the nucleic acid sequence of SEQ ID NO: 168, or a nucleic acid sequence with at least 80% sequence identity thereto. In some embodiments, the heavy chain variable domain is encoded by the nucleic acid sequence of SEQ ID NO: 150, or a nucleic acid sequence with at least 80% sequence identity thereto; and/or wherein the light chain variable domain is encoded by the nucleic acid sequence of SEQ ID NO: 169, or a nucleic acid sequence with at least 80% sequence identity thereto. In some embodiments, the heavy chain variable domain is encoded by the nucleic acid sequence of SEQ ID NO: 151, or a nucleic acid sequence with at least 80% sequence identity thereto; and/or wherein the light chain variable domain is encoded by the nucleic acid sequence of SEQ ID NO: 170, or a nucleic acid sequence with at least 80% sequence identity thereto. In some embodiments, the heavy chain variable domain is encoded by the nucleic acid sequence of SEQ ID NO: 152, or a nucleic acid sequence with at least 80% sequence identity thereto; and/or wherein the light chain variable domain is encoded by the nucleic acid sequence of SEQ ID NO: 171, or a nucleic acid sequence with at least 80% sequence identity thereto. In some embodiments, the heavy chain variable domain is encoded by the nucleic acid sequence of SEQ ID NO: 153, or a nucleic acid sequence with at least 80% sequence identity thereto; and/or wherein the light chain variable domain is encoded by the nucleic acid sequence of SEQ ID NO: 172, or a nucleic acid sequence with at least 80% sequence identity thereto. In some embodiments, the heavy chain variable domain is encoded by the nucleic acid sequence of SEQ ID NO: 154, or a nucleic acid sequence with at least 80% sequence identity thereto; and/or wherein the light chain variable domain is encoded by the nucleic acid sequence of SEQ ID NO: 173, or a nucleic acid sequence with at least 80% sequence identity thereto. In some embodiments, the heavy chain variable domain is encoded by the nucleic acid sequence of SEQ ID NO: 155, or a nucleic acid sequence with at least 80% sequence identity thereto; and/or wherein the light chain variable domain is encoded by the nucleic acid sequence of SEQ ID NO: 174, or a nucleic acid sequence with at least 80% sequence identity thereto. In some embodiments, the heavy chain variable domain is encoded by the nucleic acid sequence of SEQ ID NO: 156, or a nucleic acid sequence with at least 80% sequence identity thereto; and/or wherein the light chain variable domain is encoded by the nucleic acid sequence of SEQ ID NO: 175, or a nucleic acid sequence with at least 80% sequence identity thereto.

The disclosure provides vectors comprising the nucleic acid of the disclosure.

The disclosure provides methods of inducing the depletion of a population of cells, the methods comprising contacting the population of cells with the antibody of the disclosure.

In some embodiments of the methods of the disclosure, at least a subset of the population of cells expresses SIRPγ. In some embodiments, the population of cells that express SIRPγ comprise lymphocytes. In some embodiments, the lymphocytes comprise T cells or NK cells. In some embodiments, at least a subset of the population of cells expresses SIRPα and/or SIRPβ1. In some embodiments, the population of cells that express SIRPα and/or SIRPβ1 comprise myeloid cells or myeloid progenitor cells. In some embodiments, the population of cells that express SIRPα and/or SIRPβ1 comprise monocytes, macrophages, dendritic cells, basophils, eosinophils, neutrophils, or mast cells. In some embodiments, the method is in vitro. In some embodiments, the method is in vivo. In some embodiments, the population of cells comprises tissue-resident cells. In some embodiments, the population of cells comprises circulating cells.

In some embodiments of the methods of the disclosure, the cell depletion involves ADCC. In some embodiments the cell depletion involves ADCP. In some embodiments, the cell depletion involves ADCC and ADCP.

The disclosure provides methods of treating a disease or condition in a subject in need thereof, comprising administering to the subject a therapeutically effective amount of the antibody or pharmaceutical composition of the disclosure.

In some embodiments of the methods of treating a disease or condition of the disclosure, the disease or condition is characterized by overactivation and/or hyperproliferation of lymphocytes, and the antibody induces depletion of lymphocytes. In some embodiments, the lymphocytes are T cells. In some embodiments, the disease or condition comprises aplastic anemia, cell mediated rejection of solid organ transplant, graft failure post-HSCT (hematopoietic stem cell transplant), lymphocyte-variant hypereosinophilia, atopic dermatitis, lymphocytic myocarditis, axial spondyloarthritis, celiac disease, or Rasmussen's encephalitis.

In some embodiments of the methods of treating a disease or condition of the disclosure, the disease or condition is characterized by overactivation and/or hyperproliferation of myeloid cells, and the antibody induces depletion of myeloid cells. In some embodiments, the myeloid cells comprise monocytes, macrophages, dendritic cells, basophils, eosinophils, neutrophils, or mast cells. In some embodiments, the myeloid cells comprise eosinophils, and the disease or condition comprises acute eosinophilic pneumonia, chronic eosinophilic pneumonia, eosinophilic esophagitis, eosinophilic gastritis, eosinophilic gastroenteritis, eosinophilic enteritis, eosinophilic colitis, lymphocyte-variant hypereosinophilia, eosinophilic cardiomyopathy/Loeffler endocarditis, Löffler syndrome or episodic angioedema with eosinophilia/Gleich syndrome. In some embodiments, the myeloid cells comprise mast cells, and the disease or condition comprises cutaneous mastocytosis, mastocytic enterocolitis, systemic mastocytosis, mast cell activation syndrome, hereditary alpha tryptasemia syndrome, chronic urticaria or severe allergic conjunctivitis. In some embodiments, the myeloid cells comprise neutrophils, and the disease or condition comprises neutrophilic dermatoses, psoriatic arthritis, generalized pustular psoriasis, pyoderma gangrenosum, Sweet's syndrome, subcorneal pustular dermatosis, neutrophilic eccrine hidradenitis, bowel-associated dermatosis-arthritis syndrome (BADAS), rheumatoid neutrophilic dermatitis, or Behçet's disease.

In some embodiments of the methods of treating a disease or condition of the disclosure, the disease or condition comprises a disease or disorder associated with both lymphocytes and myeloid cells. In some embodiments, the disease or disorder comprises histiocytosis. In some embodiments, the histiocytosis comprises hemophagocytic lymphohistiocytosis (HLH) (including primary and secondary HLH), macrophage activation syndrome, Langerhans cell histiocytosis (LCH), indeterminate cell histiocytosis, Erdheim-Chester disease (ECD), mixed LCH/ECD, Rosai Dorfman disease, malignant histiocytosis, cutaneous non-LCH histiocytoses, juvenile xanthogranuloma, infection-associated HLH, or malignancy-triggered HLH. In some embodiments, the malignancy-triggered HLH includes an HLH triggered by a hematological malignancy or solid tumor. In some embodiments, the disease or disorder comprises a non-mendelian secondary HLH (secondary HLH, or sHLH). In some embodiments, the secondary HLH comprises an infection-associated HLH. In some embodiments, the infection-associated HLH comprises virus-associated HLH, bacteria-associated HLH, parasite-associated HLH, or fungal-associated (fungal induced) HLH. In some embodiments, the sHLH is associated with a rheumatologic condition. In some embodiments, the sHLH is associated with a kidney transplant or hematologic stem cell transplant.

In some embodiments of the methods of treating a disease or condition of the disclosure, the disease or condition comprises sHLH or cytokine release syndrome (CRS). In some embodiments, the sHLH or CRS is associated with iatrogenic immune activation, infection, T cell therapy, chimeric antigen receptor-T cell therapy (CAR-T), T cell receptor T cell therapy (TCR-T), T cell activating bispecific antibody therapy, or iatrogenic immune suppression.

In some embodiments of the methods of treating a disease or condition of the disclosure, the disease or condition comprises a granulomatous disease or condition, or a disease characterized by the presence of multinucleated giant cells. In some embodiments, the disease or condition comprises sarcoidosis, Crohn's disease, Takayasu arteritis, giant cell arteritis, psoriatic arthritis, granulomatosis with polyangiitis (Wegener's Granulomatosis), giant cell myocarditis, chronic granulomatous disease, eosinophilic granulomatosis with polyangiitis (Churg-Strauss Syndrome), or chronic beryllium disease (berylliosis).

In some embodiments of the methods of treating a disease or condition of the disclosure, the disease or condition comprises an autoimmune disorder or an inflammatory disorder. In some embodiments, the autoimmune disorder comprises presentation of self antigens by antigen presenting myeloid cells (e.g. dendritic cells) in germinal centers of secondary lymphoid tissue of the subject.

In some embodiments, the disease or condition comprises Guillain-Barre syndrome, chronic inflammatory demyelinating polyneuropathy (CIDP), Lambert-Eaton myasthenic syndrome (LEMS), myasthenia gravis (MG), neuromyelitis optica (NMO), bullous pemphigoid, epidermolysis bullosa acquisita, *Pemphigus foliaceus, Pemphigus vulgaris*, anti-glomerular basement membrane disease (Goodpasture Syndrome), membranous nephropathy, ankylosing spondylitis, rheumatoid arthritis, rheumatoid vasculitis, lupus nephritis, lupus vasculitis, systemic lupus erythematosus (SLE), scleroderma (systemic sclerosis), Behcet's disease, granulomatosis with polyangiitis (Wegener's Granulomatosis), eosinophilic granulomatosis with polyangiitis (Churg-Strauss Syndrome), microscopic polyangiitis (MPA), Kawasaki disease, anti-glomerular basement membrane disease (Goodpasture Syndrome), antiphospholipid syndrome and catastrophic antiphospholipid syndrome, Graves ophthalmopathy, Castleman disease, and antibody-mediated rejection (AMR), Sjögren's syndrome, multiple sclerosis, Hashimoto's thyroiditis, primary sclerosing cholangitis, primary biliary cirrhosis, autoimmune neutropenia, systemic juvenile idiopathic arthritis, axial spondyloarthritis, celiac disease, autoimmune hepatitis, or psoriatic arthritis.

In some embodiments, the disease or condition comprises disseminated encephalomyelitis, acute respiratory distress syndrome, Addison's disease, Adult-Onset Still's disease, ankylosing spondylitis, antibody-mediated rejection (AMR), anti-glomerular basement membrane disease (Goodpasture Syndrome), antiphospholipid syndrome, aplastic anemia, atopic dermatitis, autoimmune hemolytic anemia, autoimmune hepatitis, autoimmune lymphoproliferative syndrome, axial spondyloarthritis, Behcet's disease, bullous pemphigoid, Castleman disease, catastrophic antiphospholipid syndrome, celiac disease, cell mediated rejection of solid organ transplant. Chediak-Higashi syndrome, chronic inflammatory demyelinating polyneuropathy (CIDP), chronic neutrophilic leukemia, chronic urticaria, coronary artery disease (CAD)/peripheral artery disease (PAD), CoVID-19, cutaneous mastocytosis, eosinophilic cardiomyopathy/Loeffler endocarditis, epidermolysis bullosa acquisita. Evans syndrome, Felty's syndrome, general pustular psoriasis, giant cell myocarditis, graft failure post-HSCT (hematopoietic stem cell transplant), graft vs. host disease, Graves' disease, Graves ophthalmopathy, Guillain-Barre syndrome, Hashimoto's thyroiditis, hereditary alpha tryptasemia syndrome, hyper IgE syndrome, Idiopathic interstitial pneumonia, idiopathic pulmonary fibrosis, IgA nephropathy, immune/idiopathic thrombocytopenia purpura, inclusion body myositis, inflammatory bowel disease, Kawasaki disease, Lambert-Eaton myasthenic syndrome (LEMS), linear IgA disease, Löffler syndrome, lupus nephritis, lupus vasculitis, mast cell activation syndrome, mastocytic enterocolitis, membranous nephropathy, microscopic polyangiitis (MPA), multiple sclerosis, myasthenia gravis, myelodysplastic syndromes, myelofibrosis, myocarditis, neuromyelitis optica (NMO), neutrophilic dermatoses, paraneoplastic syndrome, *Pemphigus foliaceus, Pemphigus vulgaris*, primary biliary cholangitis, primary sclerosing cholangitis, pyoderma gangrenosum. Rasmussen's encephalitis, rheumatoid arthritis, rheumatoid vasculitis, Schmidt syndrome, scleroderma (systemic sclerosis), severe allergic conjunctivitis. Sjogren syndrome, Susac syndrome, systemic inflammatory response syndrome, systemic juvenile idiopathic arthritis, systemic lupus erythematosus, systemic mastocytosis, type 1 diabetes, ulcerative colitis, uveitis, vitiligo or X-linked lymphoproliferative disease.

In some embodiments of the methods of treating a disease or condition of the disclosure, the disease or disorder comprises a hematological malignancy. In some embodiments, the hematological malignancy comprises acute lymphoblastic leukemia, acute myelogenous leukemia, chronic myelogenous leukemia, chronic myelomonocytic leukemia, chronic neutrophilic leukemia, juvenile myelomonocytic leukemia, chronic eosinophilic leukemia, large granular lymphocyte leukemia. T-cell prolymphocytic leukemia, hepatosplenic lymphoma. Hodgkin's lymphomas. T-cell lymphoblastic lymphoma or leukemia. T-cell non-lymphoblastic lymphoma. NK-cell lymphoma/leukemia, myeloid neoplasia, or chronic neutrophilic leukemia.

In some embodiments of the methods of treating a disease or condition of the disclosure, the disease or disorder comprises hemophagocytic lymphohistiocytosis (HLH) (including primary and secondary HLH), macrophage activation syndrome. Langerhans cell histiocytosis (LCH), indeterminate cell histiocytosis. Erdheim-Chester disease (ECD), mixed LCH/ECD. Rosai Dorfman disease, malignant histiocytosis, cutaneous non-LCH histiocytosis, juvenile xanthogranuloma, virus-associated HLH, bacteria-associated HLH, parasite-associated HLH, fungal-associated/fungal-induced HLH, malignancy-triggered HLH. HLH occurring during chemotherapy. HLH associated with systemic-onset juvenile idiopathic arthritis (SoJIA), HLH associated with adult-onset Still's disease. HLH associated with systemic lupus erythematosus (SLE). HLH associated with vasculitis. HLH associated with auto-immune conditions. HLH associated with a kidney transplant. HLH associated with hematologic stem cell transplants, sHLH or CRS associated with checkpoint inhibitors for the treatment of malignancies, sHLH or CRS associated with associated with T cell therapy, sHLH or CRS associated with chimeric antigen receptor (CAR) T cell therapy, sHLH or CRS associated with T cell activating bispecific monoclonal antibody therapy, cytokine release syndrome (CRS), systemic mastocytosis, hypereosinophilic syndrome (including primary, secondary, and idiopathic), hyper IgE syndrome. X-linked lymphoproliferative disease, graft vs. host disease, type 1 diabetes, systemic lupus erythematosus, lupus nephritis, systemic inflammatory response syndrome, acute respiratory distress syndrome, autoimmune lymphoproliferative syndrome. X-linked hyper IgM syndrome, paraneoplastic syndrome. Susac syndrome, linear IgA disease, autoimmune neutropenia, idiopathic pulmonary fibrosis, inclusion body myositis, vitiligo, Addison's disease. Graves' disease. Hashimoto's thyroiditis. Schmidt syndrome, acute disseminated encephalomyelitis, sarcoidosis, ankylosing spondylitis, inflammatory bowel disease, ulcerative colitis. Crohn's disease, eosinophilic granulomatosis with polyangiitis, pyoderma gangrenosum, giant cell arteritis, rheumatoid arthritis, systemic juvenile idiopathic arthritis. Sjogren's syndrome, primary sclerosing cholangitis, primary biliary cholangitis, myasthenia gravis multiple sclerosis, Guillain-Barre syndrome, acute lymphoblastic leukemia, acute myelogenous leukemia, chronic myelogenous leukemia, chronic myelomonocytic leukemia, juvenile myelomonocytic leukemia, chronic eosinophilic leukemia, large granular lymphocyte leukemia, T-cell prolymphocytic leukemia, hepatosplenic lymphoma. Hodgkin's lymphoma, T-cell lymphoblastic lymphoma/leukemia. T-cell non-lymphoblastic lymphoma, B-cell leukemia, B-cell lymphoma (non-Hodgkin's), NK-cell lymphoma or leukemia, myeloid neoplasia, autoimmune hemolytic anemia, immune/idiopathic thrombocytopenia purpura. Evans syndrome, Felty's syndrome, chronic inflammatory demyelinating polyneuropathy (CIDP), Lambert-Eaton myasthenic syndrome (LEMS), neuromyelitis optica (NMO), bullous pemphigoid, epidermolysis bullosa acquisita, *Pemphigus foliaceus, Pemphigus vulgaris*, membranous nephropathy, rheumatoid vasculitis, lupus vasculitis, scleroderma (systemic sclerosis), Behcet's disease, granulomatosis with polyangiitis (Wegener's Granulomatosis), eosinophilic granulomatosis with polyangiitis (Churg-Strauss Syndrome), microscopic polyangiitis (MPA), Kawasaki disease, anti-glomerular basement membrane disease (Goodpasture Syndrome), antiphospholipid syndrome, catastrophic antiphospholipid syndrome, Graves ophthalmopathy, Castleman disease, antibody-mediated rejection (AMR), acute eosinophilic pneumonia, chronic eosinophilic pneumonia, eosinophilic esophagitis, eosinophilic gastritis, eosinophilic gastroenteritis, eosinophilic enteritis, eosinophilic colitis, uveitis, giant cell myocarditis, cutaneous mastocytosis, mastocytic enterocolitis, mast cell activation syndrome, IgA nephropathy, Chediak-Higashi syndrome, eosinophilic cardiomyopathy/Loeffler endocarditis, acute kidney injury, chronic kidney disease, coronary artery disease (CAD)/peripheral artery disease (PAD), myelofibrosis. IgG4-related disease, Löffler syndrome, chronic neutrophilic leukemia, myocarditis, episodic angioedema with eosinophilia/Gleich syndrome, idiopathic interstitial pneumonia, hereditary alpha tryptasemia syndrome, chronic urticaria, severe allergic conjunctivitis, Adult-onset Still's, aplastic Anemia, cell mediated rejection of solid organ transplant, graft failure Post-hematopoietic stem cell transplant (HSCT), lymphocyte-variant hypereosinophilia, myelodysplastic syndromes, atopic dermatitis, axial spondyloarthritis, celiac disease, hyperthyroidism. Rasmussen's encephalitis, chronic beryllium disease (Berylliosis), Takayasu arteritis, autoimmune hepatitis, neutrophilic dermatoses, psoriatic arthritis, Corona Virus Disease 2019 (CoVID-19), or general pustular psoriasis.

In some embodiments of the methods of treating a disease or condition of the disclosure, the subject is human.

In some embodiments of the methods of treating a disease or condition of the disclosure, the antibody or pharmaceutical composition is administered intravenously. In some embodiments, the antibody or pharmaceutical composition is administered subcutaneously.

The disclosure provides cells expressing SIRPγ, wherein the cells are bound to an antibody of the disclosure, wherein the antibody is bound to the SIRPγ.

The disclosure provides kits or articles of manufacture comprising the antibodies or pharmaceutical compositions of the disclosure.

The disclosure provides use of the antibodies or the pharmaceutical compositions of the disclosure for the treatment of a disease or disorder in a subject in need thereof.

The disclosure provides use of the antibodies or the pharmaceutical compositions of the disclosure for the manufacture of a medicament for the treatment of a disease or disorder in a subject in need thereof.

BRIEF DESCRIPTION OF THE DRAWINGS

FIGS. 2A-2B show binding curves of selected antibodies to human and cynomolgus monkey SIRPα by ELISA.

FIG. 2C shows binding curves of selected antibodies to human and cynomolgus monkey SIRPα (top row) and SIRPβ1 (bottom row) by ELISA.

FIG. 2E shows binding curves of selected antibodies to human and cynomolgus monkey SIRPα (top row) and SIRPβ1 (bottom row) by ELISA.

FIG. 3A shows binding curves of selected antibodies of the disclosure to human SIRPα and cynomolgus monkey SIRPα by ELISA.

FIG. 3B shows binding curves of selected antibodies of the disclosure to human SIRPβ1 and human SIRPγ by ELISA.

FIG. 3C shows binding curves of Antibody 29 to human SIRPα, SIRPβ1 and SIRPγ by ELISA.

FIG. 4E shows binding curves of selected antibodies of the disclosure to human SIRPγ-expressing CHO cells by flow cytometry.

FIG. 4F shows binding curves of selected antibodies of the disclosure to human SIRPα, SIRPβ1/DAP12 or SIRPγ-expressing CHO cells by flow cytometry.

FIG. 6C shows the effect of selected antibodies of the disclosure on ADCC of human and cynomolgus monkey (cyno) CD4+ T cells in vitro.

FIG. 6D shows the effect of selected antibodies of the disclosure on ADCC of human and cynomolgus monkey (cyno) CD8+ T cells in vitro.

FIG. 7 shows the effect of selected antibodies of the disclosure on antibody dependent cellular phagocytosis (ADCP) of MOLM-13 cells by THP-1 cells in vitro.

FIGS. 9A-9B show the effect of selected antibodies of the disclosure on monocyte depletion in vivo.

FIGS. 10A-10B show the effect of selected antibodies of the disclosure on neutrophil depletion in vivo.

FIGS. 12A-12B show the effect of selected antibodies of the disclosure on eosinophil depletion in vivo.

FIGS. 13A-13B show the effect of selected antibodies of the disclosure on basophil depletion in vivo.

DETAILED DESCRIPTION

Figure 1A:
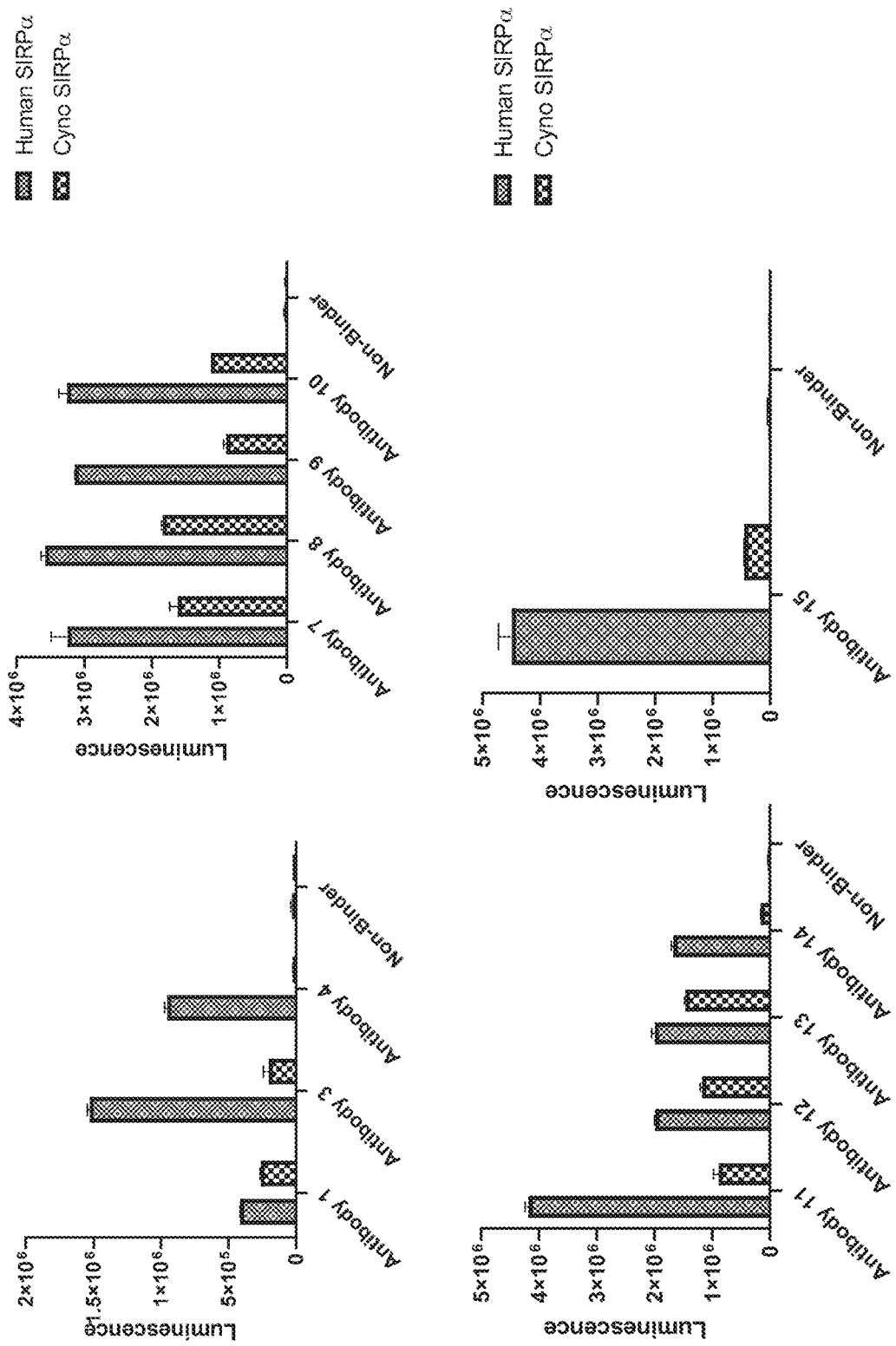
FIG. 1A shows binding of selected antibodies of the disclosure to human SIRPα and cynomolgus monkey (cyno) SIRPα by enzyme-linked immunosorbent assay (ELISA).

Provided herein are antibodies that bind to both (a) SIRPγ and (b) SIRPα and/or SIRPβ1. Also provided are methods of making and using such antibodies. The antibodies may be useful for treating diseases or conditions involving cells expressing SIRPγ, SIRPα and/or SIRPβ1. For example, in some embodiments, the antibodies may be used for treating diseases or conditions involving overactivation and/or hyperproliferation of SIRPα, SIRPβ1 (e.g., myeloid cells), or SIRPγ expressing cells (e.g. lymphocytes) as a part of the pathology.

Where elements are presented in a list format (e.g., in a Markush group), it should be understood that each possible subgroup of the elements is also disclosed, and that any one or more elements can be removed from the list or group.

It should be understood that, unless clearly indicated, in any method described or disclosed herein that includes more than one act, the order of the acts is not necessarily limited to the order in which the acts of the method are recited, but the disclosure encompasses exemplary embodiments in which the order of the acts is so limited.

The terms used throughout the specification are defined as follows unless otherwise limited in specific instances. As used in the specification and the claims, the singular forms "a," "an," and "the" include plural referents unless the context clearly dictates otherwise. All technical and scientific terms, acronyms, and abbreviates used in the specification and claims have the same meaning as commonly understood by one of ordinary skill in the art to which the disclosure pertains, unless defined or stated otherwise. All numerical ranges are inclusive of the values defining the range as well as all integer values in between, unless indicated or defined otherwise.

The terms "individual," "subject," and "patient" are used interchangeably herein and refer to any subject for whom treatment or therapy is desired. The subject may be a mammalian subject. Mammalian subjects include, e. g., humans, non-human primates, rodents, (e.g., rats, mice), lagomorphs (e.g., rabbits), ungulates (e.g., cows, sheep, pigs, horses, goats, and the like), etc. In some embodiments, the subject is a human. In some embodiments, the subject is a non-human primate, for example a cynomolgus monkey. In some embodiments, the subject is a companion animal (e.g. cats, dogs).

All publications, patents, and patent applications mentioned in this specification are herein incorporated by reference to the same extent as if each individual publication, patent, or patent application was specifically and individually indicated to be incorporated by reference.

I. Antibodies

A. SIRP Antibodies

Provided herein are antibodies that bind to SIRPγ, and also bind to SIRPα, SIRPβ1 or a combination of SIRPα and SIRPβ1. Thus, antibodies that bind to (a) SIRPγ and SIRPα, (b) SIRPγ and SIRPβ1, or (c) SIRPγ, SIRPα and SIRPβ1 are envisaged as within the scope of the instant disclosure, and are referred to herein collectively as "SIRP antibody," "SIRP antibodies" or "anti-SIRP antibodies" and the like. It is referred to throughout that the binding specificity of the SIRP antibodies of the disclosure is such that the SIRP antibodies show binding to SIRPγ, and one or more of SIRPα and/or SIRPβ1 (that is, the antibodies show binding to SIRPγ as well as SIRPα and/or SIRPβ1).

The skilled artisan will appreciate that, depending on context, a SIRP antibody of the disclosure that has the ability to bind to SIRPγ as well as SIRPα and/or SIRPβI will encounter a binding surface (e.g. a cell) that may express only a subset of the targets to which the antibody is capable of binding. For example, an antibody that can bind SIRPγ as well as SIRPα can bind to a cell expressing only SIRPγ, or a cell expressing only SIRPα. Alternatively, a binding surface, such as a cell, may express more than one, or all, of the targets to which the antibody can bind. In such a situation, the antibody is also expected to bind that surface. For example, an antibody that can bind to SIRPβ1 and SIRPγ can bind to a cell that expresses both SIRPβ1 and SIRPγ. Thus, although the SIRP antibodies of the disclosure bind SIRPγ as well as SIRPα and/or SIRPβ1, the binding of all of the targets simultaneously is not required for activity.

The term antibody as used herein throughout is used in the broadest sense and includes a monoclonal antibody, polyclonal antibody, human antibody, humanized antibody, non-human antibody, chimeric antibody, a monovalent antibody, and an antibody fragment.

In exemplary embodiments, the SIRP antibodies provided herein are monoclonal antibodies (mAbs). In exemplary embodiments, the SIRP antibodies provided herein are human antibodies. In exemplary embodiments, the SIRP antibodies provided herein are humanized antibodies. In exemplary embodiments, the SIRP antibodies provided herein are monoclonal human antibodies. In exemplary embodiments, the SIRP antibodies provided herein are chimeric antibodies. In exemplary embodiments, the SIRP antibodies provided herein are monoclonal chimeric antibodies.

In some embodiments, the SIRP antibodies provided herein are antibody fragments, retaining SIRPγ as well as SIRPβ1 and/or SIRPα antigen binding specificity. In some embodiments, the antibody fragments are antigen-binding fragments (Fab), variable fragments (Fv) containing VH and VL sequences, single chain variable fragments (scFv) containing VH and VL sequences linked together in one chain, single chain antibody fragments (scAb) or other antibody variable region fragments, such as Fab', F(ab')2, dsFv diabody, and Fd polypeptide fragments.

Also provided herein are SIRP antibody-drug conjugates, bispecific antibodies comprising at least one arm specific for SIRPγ as well as SIRPα and/or SIRPβ1, and multispecific antibodies that exhibit binding for SIRPγ as well as SIRPα and/or SIRPβ1.

The SIRPα protein has been characterized to be highly polymorphic but does not appear to affect ligand binding properties. At least thirteen variants (polymorphs) have been characterized in humans, Variants 1-13, with V1 and V2 the most common. (Hatherley et al. JBC 289: 10024-10028, 2014). SIRPα also has at least three isoforms. Accordingly, the term "SIRPα" as used herein is inclusive of all variants and isoforms of SIRPα.

The amino acid sequence of human SIRPα (hSIRPα) isoform 1, variant 1 (V1) is provided in SEQ ID NO: 1 and referred to herein as hSIRPα V1.

(SEQ ID NO: 1)

```
  1    MEPAGPAPGR LGPLLCLLLA ASCAWSGVAG EEELQVIQPD KSVLVAAGET ATLRCTATSL

61    IPVGPIQWFR GAGPGRELIY NQKEGHFPRV TTVSDLTKRN NMDFSIRIGN ITPADAGTYY

121    CVKFRKGSPD DVEFKSGAGT ELSVRAKPSA PVVSGPAARA TPQHTVSFTC ESHGFSPRDI

181    TLKWFKNGNE LSDFQTNVDP VGESVSYSIH STAKVVLTRE DVHSQVICEV AHVTLQGDPL

241    RGTANLSETI RVPPTLEVTQ QPVRAENQVN VTCQVRKFYP QRLQLTWLEN GNVSRTETAS

301    TVTENKDGTY NWMSWLLVNV SAHRDDVKLT CQVEHDGQPA VSKSHDLKVS AHPKEQGSNT

361    AAENTGSNER NIYIVVGVVC TLLVALLMAA LYLVRIRQKK AQGSTSSTRL HEPEKNAREI

421    TQDTNDITYA DLNLPKGKKP APQAAEPNNH TEYASIQTSP QPASEDTLTY ADLDMVHLNR

481    TPKQPAPKPE PSFSEYASVQ VPRK
```

The amino acid sequence of hSIRPα isoform 1, variant 2 (V2) is provided in SEQ ID NO: 2 and referred to herein as hSIRPα V2.

```
                                                             (SEQ ID NO: 2)
  1    MEPAGPAPGR LGPLLCLLLA ASCAWSGVAG EEELQVIQPD KSVSVAAGES AILHCTVTSL
 61    IPVGPIQWFR GAGPARELIY NQKEGHFPRV TTVSESTKRE NMDFSISISN ITPADAGTYY
121    CVKFRKGSPD TEFKSGAGTE LSVRAKPSAP VVSGPAARAT PQHTVSFTCE SHGFSPRDIT
181    LKWFKNGNEL SDFQTNVDPV GESVSYSIHS TAKVVLTRED VHSQVICEVA HVTLQGDPLR
241    GTANLSETIR VPPTLEVTQQ PVRAENQVNV TCQVRKFYPQ RLQLTWLENG NVSRTETAST
301    VTENKDGTYN WMSWLLVNVS AHRDDVKLTC QVEHDGQPAV SKSHDLKVSA HPKEQGSNTA
361    AENTGSNERN IYIVVGVVCT LLVALLMAAL YLVRIRQKKA QGSTSSTRLH EPEKNAREIT
421    QVQSLDTNDI TYADLNLPKG KKPAPQAAEP NNHTEYASIQ TSPQPASEDT LTYADLDMVH
481    LNRTPKQPAP KPEPSFSEYA SVQVPRK
```

The amino acid sequence of hSIRPα isoform 2 is provided herein as SEQ ID NO: 6.

```
                                                             (SEQ ID NO: 6)
  1    MEPAGPAPGR LGPLLCLLLA ASCAWSGVAG EEELQVIQPD KSVLVAAGET ATLRCTATSL
 61    IPVGPIQWFR GAGPGRELIY NQKEGHFPRV TTVSDLTKRN NMDFSIRIGN ITPADAGTYY
121    CVKFRKGSPD DVEFKSGAGT ELSVRAKPSA PVVSGPAARA TPQHTVSFTC ESHGFSPRDI
181    TLKWFKNGNE LSDFQTNVDP VGESVSYSIH STAKVVLTRE DVHSQVICEV AHVTLQGDPL
241    RGTANLSETI RVPPTLEVTQ QPVRAENQVN VTCQVRKFYP QRLQLTWLEN GNVSRTETAS
301    TVTENKDGTY NWMSWLLVNV SAHRDDVKLT CQVEHDGQPA VSKSHDLKVS AHPKEQGSNT
361    AAENTGSNER NIYIVVGVVC TLLVALLMAA LYLVRIRQKK AQGSTSSTRL HEPEKNAREI
421    TQVQSLDTND ITYADLNLPK GKKPAPQAAE PNNHTEYASI QTSPQPASED TLTYADLDMV
481    HLNRTPKQPA PKPEPSFSEY ASVQVPRK
```

The amino acid sequence of human SIRPα isoform 4 is provided in SEQ ID NO: 40.

```
                                                             (SEQ ID NO: 40)
  1    MEPAGPAPGR LGPLLCLLLA ASCAWSGVAG EEELQVIQPD KSVLVAAGET ATLRCTATSL
 61    IPVGPIQWFR GAGPGRELIY NQKEGHFPRV TTVSDLTKRN NMDFSIRIGN ITPADAGTYY
121    CVKFRKGSPD VEFKSGAGTE LSVRAKPSAP VVSGPAARAT PQHTVSFTCE SHGFSPRDIT
181    LKWFKNGNEL SDFQTNVDPV GESVSYSIHS TAKVVLTRED VHSQVICEVA HVTLQGDPLR
241    GTANLSETIR VPPTLEVTQQ PVRAENQVNV TCQVRKFYPQ RLQLTWLENG NVSRTETAST
301    VTENKDGTYN WMSWLLVNVS AHRDDVKLTC QVEHDGQPAV SKSHDLKVSA HPKEQGSNTA
361    AENTGSNERN IYIVVGVVCT LLVALLMAAL YLVRIRQKKA QGSTSSTRLH EPEKNAREIT
421    QDTNDITYAD LNLPKGKKPA PQAAEPNNHT EYASIQTSPQ PASEDTLTYA DLDMVHLNRT
481    PKQPAPKPEP SFSEYASVQV PRK
```

In some embodiments, the SIRP antibodies also bind to one or more variants or isoforms of a SIRPα of a single species. In some embodiments, the SIRP antibodies also bind to one or more variants or isoforms of a SIRPα of more than one species. In some embodiments, the SIRP antibodies also bind to one or more variants or isoforms of human SIRPα. In some embodiments, the SIRP antibodies also bind to one or more variants or isoforms of a non-human primate SIRPα, e.g. a cynomolgus monkey SIRPα.

In some embodiments, the SIRP antibodies also bind to a plurality of SIRPα variants found in a particular species, e.g. the SIRP antibodies bind to more than one of SIRPα human variants 1-13. In some embodiments the SIRP antibodies also bind to hSIRPα V1. In some embodiments, the SIRP antibodies also bind to hSIRPα V2. In some embodiments, the SIRP antibodies also bind to hSIRPα V1 and V2. In some embodiments, the SIRP antibodies also bind the extracellular domain of SIRPα, e.g. hSIRPα V1 (e.g. Met1-Arg370 of V1, Gly27-Arg370 of V1, or Glu31-Arg370 of V1), or e.g. hSIRPα V2 (Met1-Arg369).

In some embodiments, the SIRP antibodies of the disclosure bind a plurality of SIRPα isoforms. For example, the SIRP antibodies of the disclosure may bind to two or more SIRPα isoforms, or all SIRPα isoforms. In some embodiments, the SIRP antibodies bind to isoform 1, 2 and 4 of SIRPα.

In some embodiments, the SIRP antibodies also bind specifically to hSIRPα V1. In some embodiments, the SIRP antibodies also bind specifically to hSIRPα V2. In some embodiments, the SIRP antibodies also bind specifically to hSIRPα V1 and hSIRPα V2. In some embodiments, the SIRP antibodies also bind specifically to one or more variants of SIRPα, but show little or no binding to SIRPβ1.

Human SIRPβ1 (hSIRPβ1) has at least 3 isoforms. The amino acid sequence of hSIRPβ1 isoform 1 is provided in SEQ ID NO: 9.

In some embodiments, the SIRP antibodies bind to one or more variants or isoforms of a SIRPγ of a single species. In some embodiments, the SIRP antibodies bind to one or more variants or isoforms of a SIRPγ of more than one species. In some embodiments, the SIRP antibodies bind to one or more variants or isoforms of human SIRPγ. In some embodiments, the SIRP antibodies bind to one or more variants or isoforms of a non-human primate SIRPγ, e.g. a cynomolgus monkey SIRPγ.

In some embodiments, the SIRP antibodies bind to a plurality of SIRPγ variants or isoforms found in a particular species, e.g. the SIRP antibodies bind to more than one of SIRPγ human isoforms 1-3. In some embodiments, the SIRP antibodies bind the extracellular domain of SIRPγ (e.g. amino acids 1-360 of SEQ ID NO: 10).

The skilled artisan will recognize that antibodies that exhibit little or no binding to a target antigen can be

```
                                                           (SEQ ID NO: 8)
  1    MPVPASWPHL  PSPFLLMTLL  LGRLTGVAGE  DELQVIQPEK  SVSVAAGESA  TLRCAMTSLI

61    PVGPIMWFRG  AGAGRELIYN  QKEGHFPRVT  TVSELTKRNN  LDFSISISNI  TPADAGTYYC

121    VKFRKGSPDD  VEFKSGAGTE  LSVRAKPSAP  VVSGPAVRAT  PEHTVSFTCE  SHGFSPRDIT

181    LKWFKNGNEL  SDFQTNVDPA  GDSVSYSIHS  TARVVLTRGD  VHSQVICEIA  HITLQGDPLR

241    GTANLSEAIR  VPPTLEVTQQ  PMRAENQANV  TCQVSNFYPR  GLQLTWLENG  NVSRTETAST

301    LIENKDGTYN  WMSWLLVNTC  AHRDDVVLTC  QVEHDGQQAV  SKSYALEISA  HQKEHGSDIT

361    HEAALAPTAP  LLVALLLGPK  LLLVVGVSAI  YICWKQKA
```

In some embodiments, the SIRP antibodies also bind to one or more variants or isoforms of a SIRPβ1 of a single species. In some embodiments, the SIRP antibodies also bind to one or more variants or isoforms of a SIRPβ1 of more than one species. In some embodiments, the SIRP antibodies also bind to one or more variants or isoforms of human SIRPβ1. In some embodiments, the SIRP antibodies also bind to one or more variants or isoforms of a non-human primate SIRPβ1, e.g. a cynomolgus monkey SIRPβ.

In some embodiments, the SIRP antibodies also bind to a plurality of SIRPβ1 variants or isoforms found in a particular species, e.g. the SIRP antibodies bind to more than one of SIRPβ1 human isoforms 1-3. In some embodiments, the SIRP antibodies also bind the extracellular domain of SIRPβ1 (e.g. amino acids 1-371 of SEQ ID NO: 9). In some embodiments, the SIRP antibodies also bind specifically to one or more variants or isoforms of SIRPα, in addition to binding to SIRPγ and SIRPβ1.

Human SIRPγ has at least 4 isoforms. The amino acid of hSIRPγ isoform 1 is provided as SEQ ID NO: 10.

described as having a low affinity, and a high equilibrium dissociation constant (KD) for the target antigen, for example a KD of about 10 μM or greater, about 100 μM or greater, about 1 mM or greater, or about 10 mM or greater. For example, a SIRP antibody that binds to SIRPγ and SIRPα may bind to SIRPβ1 with low affinity. A SIRP antibody of the disclosure with low affinity for SIRPβ1 may bind to SIRPβ1 with a $K_D$ of about 10 UM or greater, about 100 μM or greater, about 1 mM or greater, or about 10 mM or greater but retain higher binding affinity for SIRPγ and SIRPα. As a further example, a SIRP antibody that binds to SIRPγ and SIRPβ1 may bind to SIRPα with low affinity.

In some embodiments, provided herein are SIRP antibodies comprising a binding affinity (KD) to SIRPα of about 0.05 nM, about 0.1 nM, about 0.5 nM, about 1 nM, about 5 nM, about 10 nM, about 50 nM, about 100 nM, about 500 nM, or about 1 μM.

In some embodiments, provided herein are SIRP antibodies comprising a binding affinity (KD) to SIRPα of between

```
                                                           (SEQ ID NO: 9)
  1    MPVPASWPHP  PGPFLLLTLL  LGLTEVAGEE  ELQMIQPEKL  LLVTVGKTAT  LHCTVTSLLP

61    VGPVLWFRGV  GPGRELIYNQ  KEGHFPRVTT  VSDLTKRNNM  DFSIRISSIT  PADVGTYYCV

121    KFRKGSPENV  EFKSGPGTEM  ALGAKPSAPV  VLGPAARTTP  EHTVSFTCES  HGFSPRDITL

181    KWFKNGNELS  DFQTNVDPTG  QSVAYSIRST  ARVVLDPWDV  RSQVICEVAH  VTLQGDPLRG

241    TANLSEAIRV  PPTLEVTQQP  MRVGNQVNVT  CQVRKFYPQS  LQLTWSENGN  VCQRETASTL

301    TENKDGTYNW  TSWFLVNISD  QRDDVVLTCQ  VKHDGQLAVS  KRLALEVTVH  QKDQSSDATP

361    GPASSLTALL  LIAVLLGPIY  VPWKQKT
``` about 0.05 nM and 1 µM, between about 0.5 nM and 1 µM, between about 1 nM and 1 µM, between about 5 nM and 1 µM, between about 0.05 nM and 500 nM, between about 0.5 nM and 500 nM, between about 1 nM and 500 nM, between about 5 nM and 500 nM, between about 0.05 nM and 50 nM, between about 0.5 nM and 50 nM, between about 1 nM and 50 nM, or between about 5 nM and 50 nM.

In some embodiments, provided herein are SIRP antibodies comprising a binding affinity (KD) to SIRPβ1 of about 0.05 nM, about 0.1 nM, about 0.5 nM, about 1 nM, about 5 nM, about 10 nM, about 50) nM, about 100 nM, about 500 nM, about 1 µM, about 2 µM, about 3 µM, about 5 µM, or about 10 µM.

In some embodiments, provided herein are SIRP antibodies comprising a binding affinity (KD) to SIRPβ1 of between about 0.05 nM and 10 µM, between about 0.5 nM and 10 µM, between about 1 nM and 10 µM, between about 5 nM and 10 µM, between about 10 nM and 10 µM, between about 50 nM and 10 µM, between about 100 nM and 10 µM, between about 0.05 nM and 1 µM, between about 0.5 nM and 1 µM, between about 1 nM and 1 µM, between about 5 nM and 1 µM, between about 10 nM and 1 µM, between 50 nM and 1 µM, between about 0.05 nM and 500 nM, between about 0.5 nM and 500 nM, between about 1 nM and 500 nM, between about 5 nM and 500 nM, between 10 nM and 500 nM, between about 0.001 nM and 50 nM, between about 0.005 nM and 50 nM, between about 0.05 nM and 50 nM, between about 0.5 nM and 50 nM, between about 1 nM and 50 nM, or between about 5 nM and 50 nM.

In some embodiments, provided herein are SIRP antibodies comprising a binding affinity (KD) to SIRPγ of about 0.0001 nM, about 0.0005 nM, about 0.001 nM, about 0.005 nM, about 0.1 nM, about 0.05 nM, about 0.1 nM, about 0.5 nM, about 1 nM, about 5 nM, about 10) nM, about 50) nM, about 100 nM, about 500 nM, about 1 µM, about 2 µM or about 3 µM.

In some embodiments, provided herein are SIRP antibodies comprising a binding affinity (KD) to SIRPγ of between about 0.0001 nM and 5 µM, between about 0.0005 nM and 5 µM, between about 0.05 nM and 5 µM, between about 0.5 nM and 5 µM, between about 1 nM and 5 µM, between about 5 nM and 5 µM, 0.0001 nM and 2 µM, between about 0.0005 nM and 2 µM, between about 0.05 nM and 2 µM, between about 0.5 nM and 2 µM, between about 1 nM and 2 µM, between about 5 nM and 2 µM, 0.0001 nM and 1 µM, between about 0.0005 nM and 1 µM, between about 0.05 nM and 1 µM, between about 0.5 nM and 1 µM, between about 1 nM and 1 µM, between about 5 nM and 1 µM, between about 0.0001 nM and 500 nM, between about 0.0005 nM and 500 nM, between about 0.05 nM and 500 nM, between about 0.5 nM and 500 nM, between about 1 nM and 500 nM, between about 5 nM and 500 nM, between about 0.0001 nM and 50 nM, between about 0.0005 nM and 50 nM, between about 0.05 nM and 50 nM, between about 0.5 nM and 50 nM, between about 1 nM and 50 nM, or between about 5 nM and 50 nM.

In some embodiments, a SIRP antibody of the disclosure competes with CD47 for binding to SIRPα or SIRPγ on a cell or other surface. In some embodiments, a SIRP antibody of the disclosure partially competes with CD47 for binding to SIRPα or SIRPγ on a cell or other surface. In other embodiments, a SIRP antibody of the disclosure does not compete with CD47 for binding to SIRPα or SIRPγ on a surface, e.g a cell. Exemplary antibodies of the disclosure that do not compete with CD47 binding of SIRPα include Antibodies 1 and 13 referring to Table 11. Exemplary antibodies of the disclosure that partially inhibit the binding of CD47 to SIRPα include Antibodies 3 and 7, referring to Table 11.

In some embodiments, the constant region of a SIRP antibody (referred to interchangeably as a Fc domain, a Fc sequence or simply as a Fc) is a human Fc domain. In some embodiments, the Fc domain of a SIRP antibody is human IgG1, human IgG2, human IgG3, or human IgG4. In some embodiments, the Fc domain of a SIRP antibody is that of a mouse. In some embodiments, the Fc domain of a SIRP antibody is mouse IgG1 or mouse IgG2a. In some embodiments, the Fc domain of a SIRP antibody is that of a rat. In some embodiments, the Fc domain of a SIRP antibody is rat IgG1 or rat IgG2b. In some embodiments, the Fc domain of a SIRP antibody is rat IgG2b. In embodiments, the Fc domain of a SIRP antibody is that of a non-human primate, e.g. it is a cynomolgus monkey Fc domain.

In some embodiments, the SIRP antibodies provided herein are full-length antibodies. In some embodiments, the constant region of a full-length antibody (referred to interchangeably as a Fc domain, a Fc sequence or simply as a Fc) of the full-length SIRP antibodies is a human Fc domain. In some embodiments, the Fc domain of a full-length SIRP antibody is human IgG1, human IgG2, human IgG3, or human IgG4. In some embodiments, the Fc domain of a full-length SIRP antibody is that of a mouse. In some embodiments, the Fc domain of a full-length SIRP antibody is mouse IgG1 or mouse IgG2a. In some embodiments, the Fc domain of a full-length SIRP antibody is that of a rat. In some embodiments, the Fc domain of a full-length SIRP antibody is rat IgG1 or rat IgG2b. In embodiments, the Fc domain of a full-length SIRP antibody is that of a non-human primate, e.g. it is a cynomolgus monkey Fc domain.

In some embodiments, the SIRP antibody contains an Fc domain, and the Fc domain of a SIRP antibody is a human IgG1 Fc. Exemplary, but non-limiting, human IgG1 Fc domain sequences are provided as SEQ ID NOS: 3-4, 19-22, 25-26, 41, 50-53, 55, 57-58, 66-69, 71, and 73-74.

```
                                                           (SEQ ID NO: 3)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKKVEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPIEKTIS KAKGQPREPQ VYTLPPSRDE

241    LTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK
```

```
                                                      (SEQ ID NO: 4)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKAEP KSCDKTHTCP PCPAPELLGG

121   PSVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPIEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK (SEQ ID NO: 19)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKAEP KSCDKTHTCP PCPAPELLAG

121   PDVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPEEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK (SEQ ID NO: 41)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKVEP KSCDKTHTCP PCPAPELLAG

121   PDVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPEEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK (SEQ ID NO: 50)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKVEP KSCDKTHTCP PCPAPELLGG

121   PDVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPEEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK (SEQ ID NO: 51)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKVEP KSCDKTHTCP PCPAPELLGG

121   PSVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPEEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK (SEQ ID NO: 52)
  1   ASTKGPSVFP LAPSSKSTSG GTAALGCLVK DYFPEPVTVS WNSGALTSGV HTFPAVLQSS

61   GLYSLSSVVT VPSSSLGTQT YICNVNHKPS NTKVDKKVEP KSCDKTHTCP PCPAPELLGG

121   PDVFLFPPKP KDTLMISRTP EVTCVVVDVS HEDPEVKFNW YVDGVEVHNA KTKPREEQYN

181   STYRVVSVLT VLHQDWLNGK EYKCKVSNKA LPAPIEKTIS KAKGQPREPQ VYTLPPSRDE

241   LTKNQVSLTC LVKGFYPSDI AVEWESNGQP ENNYKTTPPV LDSDGSFFLY SKLTVDKSRW

301   QQGNVFSCSV MHEALHNHYT QKSLSLSPGK
```

```
                                                                 (SEQ ID NO: 53)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKKAEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV MHEALHNHYT QKSLSLSPGK (SEQ ID NO: 55)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKKVEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV LHEALHNHYT QKSLSLSPGK (SEQ ID NO: 57)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKKVEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV MHEALHSHYT QKSLSLSPGK (SEQ ID NO: 58)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKKAEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV LHEALHNHYT QKSLSLSPGK (SEQ ID NO: 66)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKKAEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV MHEALHSHYT QKSLSLSPGK (SEQ ID NO: 67)
  1    ASTKGPSVFP LAPSSKSTSG GTAALGCLVK DYFPEPVTVS WNSGALTSGV HTFPAVLQSS
 61    GLYSLSSVVT VPSSSLGTQT YICNVNHKPS NTKVDKRVEP KSCDKTHTCP PCPAPELLGG
121    PSVFLFPPKP KDTLMISRTP EVTCVVVDVS HEDPEVKFNW YVDGVEVHNA KTKPREEQYN
181    STYRVVSVLT VLHQDWLNGK EYKCKVSNKA LPAPIEKTIS KAKGQPREPQ VYTLPPSRDE
241    LTKNQVSLTC LVKGFYPSDI AVEWESNGQP ENNYKTTPPV LDSDGSFFLY SKLTVDKSRW
301    QQGNVFSCSV MHEALHNHYT QKSLSLSPGK
```

```
                                                       (SEQ ID NO: 68)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKRVEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPIEKTIS KAKGQPREPQ ENNYKTTPPV

241    LTKNQVSLTC LVKGFYPSDI AVEWESNGQP VYTLPPSREE LDSDGSFFLY SKLTVDKSRW

301    QQGNVFSCSV MHEALHNHYT QKSLSLSPGK (SEQ ID NO: 69)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKKVEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPIEKTIS KAKGQPREPQ VYTLPPSREE

241    LTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK (SEQ ID NO: 71)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKRVEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPIEKTIS KAKGQPREPQ VYTLPPSRDE

241    MTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK (SEQ ID NO: 73)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKKAEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPIEKTIS KAKGQPREPQ VYTLPPSRDE

241    MTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK (SEQ ID NO: 74)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKKAEP KSCDKTHTCP PCPAPELLGG

121    PSVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPEEKTIS KAKGQPREPQ VYTLPPSRDE

241    LTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK
```

In some embodiments, the human IgG1 Fc domain sequence is SEQ ID NO: 20, wherein $X_1$ is V or A.

```
                                                       (SEQ ID NO: 20)
  1    ASTKGPSVFP LAPSSKSTSG GTAALGCLVK DYFPEPVTVS WNSGALTSGV HTFPAVLQSS

61    GLYSLSSVVT VPSSSLGTQT YICNVNHKPS NTKVDKKX₁EP KSCDKTHTCP PCPAPELLAG

121    PDVFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPEEKTIS KAKGQPREPQ VYTLPPSRDE
```

```
241    LTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK
```

In some embodiments, the human IgG1 Fc domain sequence is SEQ ID NO: 21, wherein $X_1$ is V or A; $X_2$ is G or A; $X_3$ is S or D; and $X_4$ is I or E.

```
                                                         (SEQ ID NO: 21)
1      ASTKGPSVFP LAPSSKSTSG GTAALGCLVK DYFPEPVTVS WNSGALTSGV HTFPAVLQSS

61     GLYSLSSVVT VPSSSLGTQT YICNVNHKPS NTKVDKKX₁EP KSCDKTHTCP PCPAPELLX₂G

121    PX₃VFLFPPKP KDTLMISRTP EVTCVVVDVS HEDPEVKFNW YVDGVEVHNA KTKPREEQYN

181    STYRVVSVLT VLHQDWLNGK EYKCKVSNKA LPAPX₄EKTIS KAKGQPREPQ VYTLPPSRDE

241    LTKNQVSLTC LVKGFYPSDI AVEWESNGQP ENNYKTTPPV LDSDGSFFLY SKLTVDKSRW

301    QQGNVFSCSV MHEALHNHYT QKSLSLSPGK
```

In some embodiments, the human IgG1 Fc domain sequence is SEQ ID NO: 22, wherein $X_1$ is V or A.

```
                                              (SEQ ID NO: 22)
1      ASTKGPSVFP LAPSSKSTSG GTAALGCLVK DYFPEPVTVS
       WNSGALTSGV HTFPAVLQSS

61     GLYSLSSVVT VPSSSLGTQT YICNVNHKPS NTKVDKKX₁EP
       KSCDKTHTCP PCPAPELLGG

121    PSVFLFPPKP KDTLMISRTP EVTCVVVDVS HEDPEVKFNW
       YVDGVEVHNA KTKPREEQYN

181    STYRVVSVLT VLHQDWLNGK EYKCKVSNKA LPAPIEKTIS
       KAKGQPREPQ VYTLPPSRDE

241    LTKNQVSLTC LVKGFYPSDI AVEWESNGQP ENNYKTTPPV
       LDSDGSFFLY SKLTVDKSRW

301    QQGNVFSCSV LHEALHSHYT QKSLSLSPGK
```

In some embodiments, the human IgG1 Fc domain sequence is SEQ ID NO: 25, wherein $X_1$ is V or A; $X_2$ is M or L; and $X_3$ is N or S.

```
                                              (SEQ ID NO: 25)
1      ASTKGPSVFP LAPSSKSTSG GTAALGCLVK DYFPEPVTVS
       WNSGALTSGV HTFPAVLQSS

61     GLYSLSSVVT VPSSSLGTQT YICNVNHKPS NTKVDKKX₁EP
       KSCDKTHTCP PCPAPELLGG

121    PSVFLFPPKP KDTLMISRTP EVTCVVVDVS HEDPEVKFNW
       YVDGVEVHNA KTKPREEQYN

181    STYRVVSVLT VLHQDWLNGK EYKCKVSNKA LPAPIEKTIS
       KAKGQPREPQ VYTLPPSRDE

241    LTKNQVSLTC LVKGFYPSDI AVEWESNGQP ENNYKTTPPV
       LDSDGSFFLY SKLTVDKSRW

301    QQGNVFSCSV X₂HEALHX₃HYT QKSLSLSPGK
```

In some embodiments, the human IgG1 Fc domain sequence is SEQ ID NO: 26, wherein $X_1$ is K or R; $X_2$ is D or E; and $X_3$ is L or M.

```
                                              (SEQ ID NO: 26)
1      ASTKGPSVFP LAPSSKSTSG GTAALGCLVK DYFPEPVTVS
       WNSGALTSGV HTFPAVLQSS
```

```
                           -continued
61     GLYSLSSVVT VPSSSLGTQT YICNVNHKPS NTKVDKX₁VEP
       KSCDKTHTCP PCPAPELLGG

121    PSVFLFPPKP KDTLMISRTP EVTCVVVDVS HEDPEVKFNW
       YVDGVEVHNA KTKPREEQYN

181    STYRVVSVLT VLHQDWLNGK EYKCKVSNKA LPAPIEKTIS
       KAKGQPREPQ VYTLPPSRX₂E

241    X₃TKNQVSLTC LVKGFYPSDI AVEWESNGQP ENNYKTTPPV
       LDSDGSFFLY SKLTVDKSRW

301    QQGNVFSCSV MHEALHNHYT QKSLSLSPGK
```

In some embodiments, the SIRP antibody contains an Fc domain, and the Fc domain of a SIRP antibody is a human IgG4 Fc. Exemplary human IgG4 heavy chain Fc domain sequences are provided as SEQ ID NO: 34-35, 37, 82-85 and 87.

```
                                                         (SEQ ID NO: 34)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
                                                         (SEQ ID NO: 35)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK
```

(SEQ ID NO: 82)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFEGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (SEQ ID NO: 83)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPPCPAPEFLGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (SEQ ID NO: 84)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEALGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (SEQ ID NO: 85)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEAAGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK (SEQ ID NO: 87)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPSCPAPEFAGGPSVFLFPPKPKDTLMISRTPEVTCVVVDVSQED

PEVQFNWYVDGVEVHNAKTKPREEQFNSTYRVVSVLTVLHQDWLNGKEYK

CKVSNKGLPSSIEKTISKAKGQPREPQVYTLPPSQEEMTKNQVSLTCLVK

GFYPSDIAVEWESNGQPENNYKTTPPVLDSDGSFFLYSRLTVDKSRWQEG

NVFSCSVMHEALHNHYTQKSLSLSLGK

In some embodiments, the human IgG4 Fc domain sequence is SEQ ID NO: 37, wherein $X_1$ is S or P; AND $X_2$ is L or E.

(SEQ ID NO: 37)
ASTKGPSVFPLAPCSRSTSESTAALGCLVKDYFPEPVTVSWNSGALTSGV

HTFPAVLQSSGLYSLSSVVTVPSSSLGTKTYTCNVDHKPSNTKVDKRVES

KYGPPCPX$_1$CPAPEFX$_2$GGPSVFLFPPKPKDTLMISRTPEVTCVVVDVSQ

EDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCL

VKGFYPSDIAVEWESNGQPENNYKTTPPVLDSDGSFFLYSRLTVDKSRWQ

EGNVFSCSVMHEALHNHYTQKSLSLSLGK

In some embodiments, the SIRP antibodies provided herein are chimeric and comprise a variable region from one species, and a constant region from another species, e.g. comprise a human variable region and a rat constant region. In some embodiments, the rat constant region is rat IgG1 or IgG2b. In some embodiments, the rat constant region is IgG2b. In some embodiments, the antibodies comprise a human variable region and a mouse constant region. In some embodiments, the mouse constant region is mouse IgG2a. In some embodiments, the antibodies comprise a human variable region and a human constant region. In exemplary embodiments, the human constant region is human IgG1 or human IgG4.

The EU numbering scheme is one of many available antibody numbering schemes based on the residue numbers assigned to a canonical antibody sequence. Accordingly, a skilled artisan would understand that reference to a particular residue using the EU numbering scheme may or may not be exactly the residue in one of the SIRP antibodies of the disclosure. For example, if a SIRP antibody of the disclosure comprises a V215A substitution in the Fc, wherein the position number of the amino acid residue is of the EU numbering scheme, the residue may not be the actual residue 215 in that particular SIRP antibody. It may be actual residue number 213, or 214, or 215, or 216 or others. Accordingly, a skilled artisan will understand how to correspond the recited residue using the EU numbering scheme, to the actual residue in a SIRP antibody of the disclosure. The EU numbering system for antibodies is known in the art and is described, for example, at imgt.org/IMGTScientificChart/Numbering/Hu_IGHGnber.html.

In some embodiments, the Fc domain of a SIRP antibody is an IgG1 Fc domain (e.g. SEQ ID NOS: 3-4, 19-22 or 25-26) or IgG4 human Fc domain (e.g. SEQ ID NOS: 34, 35 or 37), and comprises at least one amino acid substitution at a position selected from the group consisting of: 214, 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 356, 358, 396, 428, 430, 433, 434, and 440 wherein the position numbers of the amino acid residues are of the EU numbering scheme.

In some embodiments, the Fc domain of a SIRP antibody comprises SEQ ID NOS: 3-4, 19-22 or 25-26, optionally with one or more Fc amino acid substitutions, for example at least one amino acid substitution at a position selected from the group consisting of: 214, 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 356, 358, 396, 428, 430, 433, 434, and 440 wherein the position numbers of the amino acid residues are of the EU numbering scheme. Exemplary substitutions include one or more of K214R, V215A, G236A, S239D, I332E, D356E, L358M, M428L, N434S, wherein the position numbers of the amino acid residues are of the EU numbering scheme.

In some embodiments, the Fc domain of a SIRP antibody is a human IgG1 (e.g. SEQ ID NO: 3-4, 19-22 or 25-26), and substitutions are introduced to increase effector function, selected from the group consisting of V215A, G236A, S239D, I332E, G236A/S239D, G236A/I332E, S239D/I332E, G236A/S239D/I332E, K326W/E333S, S267E/H268F/S324T, and E345R/E430G/S440Y, F243L/R292P/Y300L/V305I/P396L, S239D/I332E, S298A/E333A/K334A, L234Y/L235Q/G236W/S239M/H268D/D270E/S298A, and D270E/K326D/A330M/K334E wherein the position numbers of the amino acid residues are of the EU numbering scheme.

In some embodiments, the Fc domain of a SIRP antibody is a human IgG1 (e.g. SEQ ID NO: 3-4, 19-22 or 25-26), and substitutions are introduced to reduce effector function, including one or more of N297A, N297Q, N297G, L235E, L234A, L235A, K214R, D356E, and L358M, wherein the position numbers of the amino acid residues are of the EU numbering scheme.

In some embodiments, the Fc domain of a SIRP antibody is human IgG4 (e.g. SEQ ID NOS: 34, 35 or 37), and substitutions are introduced to reduce effector function, including one or more of L235E, and F234A/L235A, wherein the position numbers of the amino acid residues are of the EU numbering scheme.

In some embodiments, the Fc domain of a SIRP antibody is human IgG2, and substitutions are introduced to reduce effector function, including H268Q/V309L/A330S/P331S and V234A/G237A/P238S/H268A/V309L/A330S/P331S, wherein the position numbers of the amino acid residues are of the EU numbering scheme.

In some embodiments, the Fc domain of a SIRP antibody is an IgG4 human Fc domain (e.g. SEQ ID NOS: 34, 35 or 37), and the antibody is prone to the dynamic process of Fab-arm exchange. Accordingly, in some embodiments the IgG4 Fc domain comprises a S228P substitution, resulting in the reduction of this process, wherein the position number of the amino acid residues are of the EU numbering scheme.

In some embodiments, the Fc domain of a SIRP antibody is human IgG4 (e.g. SEQ ID NO: 34, 35 or 37), and one or more of the following substitution are introduced: L235A, L235E, S228P, L235E/S228P, S228P/F234A, S228P/F234A/L235A, wherein the position numbers of the amino acid residues are of the EU numbering scheme.

In other embodiments, the Fc domain of a SIRP antibody is altered to increase its serum half-life. Such alterations include substitutions of a human IgG1, IgG2, IgG3 or IgG4 such as M428L, N343S, T250Q/M428L, M252Y/S254T/T256E, M428L/N434S, S267E/L328F, N325S/L328F, and H433K/N434F, wherein the position number of the amino acid residues are of the EU numbering scheme.

i. SIRP Antibody-Mediated Cell Depletion

The SIRP antibodies that contain Fc domains provided herein are capable of targeting a variety of cell types and inducing the depletion of those cells. An exemplary non-limiting list of antibodies of the disclosure that exhibit cell depletion include Antibodies 23, 25, and 28-31, as provided in Table 11.

In some embodiments, the SIRP antibodies containing Fc domains provided herein are capable of depleting SIRPγ expressing cells. In some embodiments, the SIRP antibodies provided herein are capable of inducing the depletion of lymphocytes. In some embodiments, the SIRP antibodies provided herein are capable of inducing the depletion of SIRPα- and/or SIRPβ1-expressing cells such as myeloid cells and myeloid progenitor cells, and include, but are not limited to, monocytes, macrophages, dendritic cells, mast cells, eosinophils, basophil, and neutrophils. In some embodiments, for example wherein the SIRP antibody binds to SIRPγ and SIRPα, the SIRP antibody is capable of inducing the depletion of SIRPα as well as SIRPγ expressing cells. In some embodiments, for example wherein the SIRP antibody binds to SIRPβ1, the SIRP antibody is capable of inducing the depletion of SIRPβ1 as well as SIRPγ expressing cells. In some embodiments, for example where the SIRP antibody binds to SIRPγ. SIRPα and SIRPβ1, the SIRP antibody is capable of inducing the depletion of SIRPα and SIRPβ1 expressing cells, as well as SIRPγ expressing cells.

Without being held to any theory, it is envisioned that the SIRP antigen binding domain allows for the antigen-binding fragments (Fab) of the antibody to bind to the SIRP expressing cell, and that the Fc portion of the antibody induces depletion. Accordingly in some embodiments, the cell depletion involves antibody dependent cellular cytotoxicity (ADCC). In some embodiments, the cell depletion involves antibody dependent cellular phagocytosis (ADCP). In some embodiments, the cell depletion involves ADCC and ADCP. An Fc-containing SIRP antibody of the disclosure includes a full-length antibody, or an antibody fragment that is linked to a Fc domain, e.g. a VH-VL-Fc single chain antibody.

ii. Exemplary SIRP Antibodies—Complementarity Determining Region (CDR) Sequences Provided herein are sequences for exemplary SIRP antibodies of the disclosure. Exemplary CDR-L1, L2, L3, H1, H2, and H3 sequences that make up the SIRP antigen binding domain are presented below in Tables 1-6. As referred below, a light chain variable (VL) domain CDR1 region is referred to as CDR-L1: a VL CDR2 region is referred to as CDR-L2: a VL CDR3 region is referred to as CDR-L3: a heavy chain variable (VH) domain CDR1 region is referred to as CDR-H1: a VH CDR2 region is referred to as CDR-H2; and a VH CDR3 region is referred to as CDR-H3. Tables 7 and 8 provide exemplary CDR triplets for the light chains and heavy chains of SIRPα antibodies of the disclosure. Table 9 provides exemplary CDR combinations of antibodies of the disclosure.

TABLE 1

Exemplary SIRP antibody CDR-L1 Sequences

| CDR-L1 | SEQ ID NO: |
|---|---|
| QSLLHGNGFNY | 5 |
| QGISGY | 7 |
| QDFSNY | 8 |
| NIGSKS | 11 |
| KLGDKY | 12 |
| KLGDRY | 13 |
| QDISSW | 14 |
| QSVSSN | 15 |
| QSVSRN | 16 |

TABLE 1-continued

Exemplary SIRP antibody CDR-L1 Sequences

| CDR-L1 | SEQ ID NO: |
|---|---|
| QTVLNSSNNKNY | 17 |
| QDINRY | 18 |

TABLE 2

Exemplary SIRP antibody CDR-L2 Sequences

| CDR-L2 | SEQ ID NO: |
|---|---|
| LGS | 23 |
| AAS | 24 |
| DDS | 27 |
| HDD | 28 |
| QDD | 29 |
| QDT | 30 |
| GAS | 31 |
| WAS | 32 |
| RAN | 33 |

TABLE 3

Exemplary SIRP antibody CDR-L3 Sequences

| CDR-L3 | SEQ ID NO: |
|---|---|
| MQGLQTPRT | 36 |
| QQFTSDLIT | 38 |
| QQYDNLPYT | 39 |
| QVWDSSSDHYV | 42 |
| QTWDSSTVV | 43 |
| QAWDSSTAV | 44 |
| QACDSSTAV | 45 |
| QEANSFPYT | 46 |
| QQYNNWPYT | 47 |
| QQYYNTPPWT | 48 |
| LQYDEFPFT | 49 |

TABLE 4

Exemplary SIRP antibody CDR-H1 Sequences

| CDR-H1 | SEQ ID NO: |
|---|---|
| GGSISSSNW | 54 |
| DYSISSGYY | 56 |
| GFTFSKFG | 59 |

TABLE 4-continued

Exemplary SIRP antibody CDR-H1 Sequences

| CDR-H1 | SEQ ID NO: |
|---|---|
| GGSFSGYY | 60 |
| GGSFSTYY | 61 |
| GFTFSSYA | 62 |
| GFTFSSYW | 63 |
| GFIFSNYG | 64 |
| GYTFRNFG | 65 |

TABLE 5

Exemplary SIRP antibody CDR-H2 Sequences

| CDR-H2 | SEQ ID NO: |
|---|---|
| IYHSGST | 70 |
| IYHSGNT | 72 |
| ISYDGNNK | 75 |
| INHSGST | 76 |
| ISGSGGDT | 77 |
| IHNDGSRT | 78 |
| ISGSGSST | 79 |
| ISYDGRNE | 80 |
| IDTNTGEP | 81 |

TABLE 6

Exemplary SIRP antibody CDR-H3 Sequences

| CDR-H3 | SEQ ID NO: |
|---|---|
| ARRGIWFGVGP | 86 |
| AREGIEGYYFYYGMDV | 88 |
| ARDKCSTTTCSFDY | 89 |
| WAAAGAFYI | 92 |
| SRVDSGSYPYYDGLDV | 93 |
| ASSHYGSGSFPDSYGMDV | 94 |
| AKDGGSYYPPFDY | 95 |
| TRDPPPYDILTGYPFDY | 96 |
| AAYSGSYYYYGMDV | 97 |
| AKGSGSYYFDY | 98 |
| ARSRGNYFAMEY | 99 |

TABLE 7

Exemplary SIRP antibody Light Chain CDR Triplets

| CDR-L1 | SEQ ID NO: | CDR-L2 | SEQ ID NO: | CDR-L3 | SEQ ID NO: |
|---|---|---|---|---|---|
| QSLLHGNGFNY | 5 | LGS | 23 | MQGLQTPRT | 36 |
| QGISGY | 7 | AAS | 24 | QQFTSDLIT | 38 |
| QDFSNY | 8 | AAS | 24 | QQYDNLPYT | 39 |
| NIGSKS | 11 | DDS | 27 | QVWDSSSDHYV | 42 |
| KLGDKY | 12 | HDD | 28 | QTWDSSTVV | 43 |
| KLGDRY | 13 | QDD | 29 | QAWDSSTAV | 44 |
| KLGDRY | 13 | QDT | 30 | QACDSSTAV | 45 |
| QDISSW | 14 | GAS | 31 | QEANSFPYT | 46 |
| QSVSSN | 15 | GAS | 31 | QQYNNWPYT | 47 |
| QSVSRN | 16 | GAS | 31 | QQYNNWPYT | 47 |
| QTVLNSSNNKNY | 17 | WAS | 32 | QQYYNTPPWT | 48 |
| QDINRY | 18 | RAN | 33 | LQYDEFPFT | 49 |

TABLE 8

Exemplary SIRP antibody Heavy Chain CDR Triplets

| CDR-H1 | SEQ ID NO: | CDR-H2 | SEQ ID NO: | CDR-H3 | SEQ ID NO: |
|---|---|---|---|---|---|
| GGSISSSNW | 54 | IYHSGST | 70 | ARRGIWFGVGP | 86 |
| GGSISSSNW | 54 | IYHSGNT | 72 | AREGIEGYYFYYGMDV | 88 |
| DYSISSGYY | 56 | IYHSGNT | 72 | ARDKCSTTTCSFDY | 89 |
| GFTFSKFG | 59 | ISYDGNNK | 75 | WAAAGAFYI | 92 |
| GGSFSGYY | 60 | INHSGST | 76 | SRVDSGSYPYYDGLDV | 93 |
| GGSFSTYY | 61 | INHSGST | 76 | ASSHYGSGSFPDSYGMDV | 94 |
| GFTFSSYA | 62 | ISGSGGDT | 77 | AKDGGSYYPPFDY | 95 |
| GFTFSSYW | 63 | IHNDGSRT | 78 | TRDPPPYDILTGYPFDY | 96 |
| GFTFSSYA | 62 | ISGSGSST | 79 | AAYSGSYYYYGMDV | 97 |
| GFIFSNYG | 64 | ISYDGRNE | 80 | AKGSGSYYFDY | 98 |
| GYTFRNFG | 65 | IDTNTGEP | 81 | ARSRGNYFAMEY | 99 |

TABLE 9

Exemplary SIRP antibody CDR Combinations, Antibodies 1, 3-4 and 7-15

| Antibody No. | CDR-L1 | CDR-L2 | CDR-L3 | CDR-H1 | CDR-H2 | CDR-H3 |
|---|---|---|---|---|---|---|
| Antibody 1 | QSLLHGNGFNY (SEQ ID NO: 5) | LGS (SEQ ID NO: 23) | MQGLQTPRT (SEQ ID NO: 36) | GGSISSSNW (SEQ ID NO: 54) | IYHSGST (SEQ ID NO: 70) | ARRGIWFGVGP (SEQ ID NO: 86) |
| Antibody 3 | QGISGY (SEQ ID NO: 7) | AAS (SEQ ID NO: 24) | QQFTSDLIT (SEQ ID NO: 38) | GGSISSSNW (SEQ ID NO: 54) | IYHSGNT (SEQ ID NO: 72) | AREGIEGYYFYYGMDV (SEQ ID NO: 88) |
| Antibody 4 | QDFSNY (SEQ ID NO: 8) | AAS (SEQ ID NO: 24) | QQYDNLPYT (SEQ ID NO: 39) | DYSISSGYY (SEQ ID NO: 56) | IYHSGNT (SEQ ID NO: 72) | ARDKCSTTTCSFDY (SEQ ID NO: 89) |
| Antibody 7 | NIGSKS (SEQ ID NO: 11) | DDS (SEQ ID NO: 27) | QVWDSSSDHYV (SEQ ID NO: 42) | GFTFSKFG (SEQ ID NO: 59) | ISYDGNNK (SEQ ID NO: 75) | WAAAGAFYI (SEQ ID NO: 92) |
| Antibody 8 | KLGDKY (SEQ ID NO: 12) | HDD (SEQ ID NO: 28) | QTWDSSTVV (SEQ ID NO: 43) | GGSFSGYY (SEQ ID NO: 60) | INHSGST (SEQ ID NO: 76) | SRVDSGSYPYYDGLDV (SEQ ID NO: 93) |
| Antibody 9 | KLGDRY (SEQ ID NO: 13) | QDD (SEQ ID NO: 29) | QAWDSSTAV (SEQ ID NO: 44) | GGSFSTYY (SEQ ID NO: 61) | INHSGST (SEQ ID NO: 76) | ASSHYGSGSFPDSYGMDV (SEQ ID NO: 94) |
| Antibody 10 | KLGDRY (SEQ ID NO: 13) | QDT (SEQ ID NO: 30) | QACDSSTAV (SEQ ID NO: 45) | GFTFSSYA (SEQ ID NO: 62) | ISGSGGDT (SEQ ID NO: 77) | AKDGGSYYPPFDY (SEQ ID NO: 95) |
| Antibody 11 | QDISSW (SEQ ID NO: 14) | GAS (SEQ ID NO: 31) | QEANSFPYT (SEQ ID NO: 46) | GFTFSSYW (SEQ ID NO: 63) | IHNDGSRT (SEQ ID NO: 78) | TRDPPPYDILTGYPFDY (SEQ ID NO: 96) |
| Antibody 12 | QSVSSN (SEQ ID NO: 15) | GAS (SEQ ID NO: 31) | QQYNNWPYT (SEQ ID NO: 47) | GFTFSSYA (SEQ ID NO: 62) | ISGSGSST (SEQ ID NO: 79) | AAYSGSYYYYGMDV (SEQ ID NO: 97) |

TABLE 9-continued

Exemplary SIRP antibody CDR Combinations, Antibodies 1, 3-4 and 7-15

| Antibody No. | CDR-L1 | CDR-L2 | CDR-L3 | CDR-H1 | CDR-H2 | CDR-H3 |
|---|---|---|---|---|---|---|
| Antibody 13 | QSVSRN (SEQ ID NO: 16) | GAS (SEQ ID NO: 31) | QQYNNWPYT (SEQ ID NO: 47) | GFTFSSYA (SEQ ID NO: 62) | ISGSGSST (SEQ ID NO: 79) | AAYSGSYYY YGMDV (SEQ ID NO: 97) |
| Antibody 14 | QTVLNSSNN KNY (SEQ ID NO: 17) | WAS (SEQ ID NO: 32) | QQYYNTPPWT (SEQ ID NO: 48) | GFIFSNYG (SEQ ID NO: 64) | ISYDGRNE (SEQ ID NO: 80) | AKGSGSYYF DY (SEQ ID NO: 98) |
| Antibody 15 | QDINRY (SEQ ID NO: 18) | RAN (SEQ ID NO: 33) | LQYDEFPFT (SEQ ID NO: 49) | GYTFRNFG (SEQ ID NO: 65) | IDTNTGEP (SEQ ID NO: 81) | ARSRGNYFA MEY (SEQ ID NO: 99) |

In some embodiments, the SIRP antibodies provided herein include any one or more of the amino acid sequences of the CDR sequences provided in Tables 1-6.

In some embodiments, provided herein is a SIRP antibody, wherein the antibody comprises:
(a) any one of the CDR-L1 amino acid sequences of SEQ ID NOS: 5, 7-8 or 11-18 as set forth in Table 1;
(b) any one of the CDR-L2 amino acid sequences of SEQ ID NOS: 23-24, or 27-33 as set forth in Table 2;
(c) any one of the CDR-L3 amino acid sequences of SEQ ID NOS: 36, 38-39 or 42-49 as set forth in Table 3;
(d) any one of the CDR-H1 amino acid sequences of SEQ ID NOS: 54, 56, or 59-65 as set forth in Table 4;
(e) any one of the CDR-H2 amino acid sequences of SEQ ID NOS: 70, 72, or 75-81 as set forth in Table 5; and/or
(f) any one of the CDR-H3 amino acid sequences of SEQ ID NOS: 86, 88-89 or 92-99 as set forth in Table 6.

In some embodiments, provided herein is a SIRP antibody, wherein the light chain variable domain of the antibody comprises:
(g) a CDR-L1 comprising any one of the amino acid sequences of SEQ ID NOs: 5, 7-8, or 11-18;
(h) a CDR-L2 comprising any one of the amino acid sequences of SEQ ID NOs: 23-24, or 27-33; and
(i) a CDR-L3 comprising any one of the amino acid sequences of SEQ ID NOs: 36, 38-39, or 42-49.

In some embodiments, provided herein is a SIRP antibody, wherein the heavy chain variable domain of the antibody comprises:
(j) a CDR-H1 comprising any one of the amino acid sequences of SEQ ID NOs: 54, 56, or 59-65;
(k) a CDR-H2 comprising any one of the amino acid sequences of SEQ ID NOs: 70, 72, or 75-81; and
(l) a CDR-H3 comprising any one of the amino acid sequences of SEQ ID NOs: 86, 88-89, or 92-99.

In some embodiments, provided herein is a SIRP antibody, wherein the light chain variable domain of the antibody comprises any one of the sequences provided in Tables 1-3, and wherein the heavy chain variable domain of the antibody comprises:
(m) a CDR-H1 comprising any one of the amino acid sequences of SEQ ID NOs: 54, 56, or 59-65;
(n) a CDR-H2 comprising any one of the amino acid sequences of SEQ ID NOs: 70, 72, or 75-81; and
(o) a CDR-H3 comprising any one of the amino acid sequences of SEQ ID NOs: 86, 88-89, or 92-99.

In some embodiments, provided herein is a SIRP antibody, wherein the heavy chain variable domain of the antibody comprises any one of the sequences provided in Tables 4-6, and wherein the light chain variable domain of the antibody comprises:
(p) a CDR-L1 comprising any one of the amino acid sequences of SEQ ID NOs: 5, 7-8, or 11-18;
(q) a CDR-L2 comprising any one of the amino acid sequences of SEQ ID NOs: 23-24, or 27-33; and
(r) a CDR-L3 comprising any one of the amino acid sequences of SEQ ID NOs: 36, 38-39, or 42-49.

In some embodiments, provided herein is a SIRP antibody, wherein the light chain of the antibody comprises the amino acid sequences of:
a. SEQ ID NO: 5, SEQ ID NO: 23, and SEQ ID NO: 36;
b. SEQ ID NO: 7, SEQ ID NO: 24, and SEQ ID NO: 38;
c. SEQ ID NO: 8, SEQ ID NO: 24, and SEQ ID NO: 39;
d. SEQ ID NO: 11, SEQ ID NO: 27, and SEQ ID NO: 42;
e. SEQ ID NO: 12, SEQ ID NO: 28, and SEQ ID NO: 43;
f. SEQ ID NO: 13, SEQ ID NO: 29, and SEQ ID NO: 44;
g SEQ ID NO: 13, SEQ ID NO: 30, and SEQ ID NO: 45;
h. SEQ ID NO: 14, SEQ ID NO: 31, and SEQ ID NO: 46;
i. SEQ ID NO: 15, SEQ ID NO: 31, and SEQ ID NO: 47;
j. SEQ ID NO: 16, SEQ ID NO: 31, and SEQ ID NO: 47;
k. SEQ ID NO: 17, SEQ ID NO: 32, and SEQ ID NO: 48; or
l. SEQ ID NO: 18, SEQ ID NO: 33, and SEQ ID NO: 49.

In some embodiments, provided herein is a SIRP antibody, wherein the heavy chain of the antibody comprises the amino acid sequences of:
a. SEQ ID NO: 54, SEQ ID NO: 70, and SEQ ID NO: 86;
b. SEQ ID NO: 54, SEQ ID NO: 72, and SEQ ID NO: 88;
c. SEQ ID NO: 56, SEQ ID NO: 72, and SEQ ID NO: 89;
d. SEQ ID NO: 59, SEQ ID NO: 75, and SEQ ID NO: 92;
e. SEQ ID NO: 60, SEQ ID NO: 76, and SEQ ID NO: 93;
f. SEQ ID NO: 61, SEQ ID NO: 76, and SEQ ID NO: 94;
g SEQ ID NO: 62, SEQ ID NO: 77, and SEQ ID NO: 95;
h SEQ ID NO: 63, SEQ ID NO: 78, and SEQ ID NO: 96;
i. SEQ ID NO: 62, SEQ ID NO: 79, and SEQ ID NO: 97;
j. SEQ ID NO: 62, SEQ ID NO: 79, and SEQ ID NO: 97;
k SEQ ID NO: 64, SEQ ID NO: 80, and SEQ ID NO: 98; or
l. SEQ ID NO: 65, SEQ ID NO: 81, and SEQ ID NO: 99.

In some embodiments, provided herein is a SIRP antibody, wherein the antibody comprises the amino acid sequences of:
a. SEQ ID NO: 5, SEQ ID NO: 23, SEQ ID NO: 36, SEQ ID NO: 54, SEQ ID NO: 70, and SEQ ID NO: 86;
b. SEQ ID NO: 7, SEQ ID NO: 24, SEQ ID NO: 38, SEQ ID NO: 54, SEQ ID NO: 72, and SEQ ID NO: 88;

c. SEQ ID NO: 8, SEQ ID NO: 24, SEQ ID NO: 39, SEQ ID NO: 56, SEQ ID NO: 72, and SEQ ID NO: 89;
d. SEQ ID NO: 11, SEQ ID NO: 27, SEQ ID NO: 42, SEQ ID NO: 59, SEQ ID NO: 75, and SEQ ID NO: 92;
e. SEQ ID NO: 12, SEQ ID NO: 28, SEQ ID NO: 43, SEQ ID NO: 60, SEQ ID NO: 76, and SEQ ID NO: 93;
f. SEQ ID NO: 13, SEQ ID NO: 29, SEQ ID NO: 44, SEQ ID NO: 61, SEQ ID NO: 76, and SEQ ID NO: 94;
g. SEQ ID NO: 13, SEQ ID NO: 30, SEQ ID NO: 45, SEQ ID NO: 62, SEQ ID NO: 77, and SEQ ID NO: 95;
h. SEQ ID NO: 14, SEQ ID NO: 31, SEQ ID NO: 46, SEQ ID NO: 63, SEQ ID NO: 78, and SEQ ID NO: 96;
i. SEQ ID NO: 15, SEQ ID NO: 31, SEQ ID NO: 47, SEQ ID NO: 62, SEQ ID NO: 79, and SEQ ID NO: 97;
j. SEQ ID NO: 16, SEQ ID NO: 31, SEQ ID NO: 47, SEQ ID NO: 62, SEQ ID NO: 79, and SEQ ID NO: 97;
k. SEQ ID NO: 17, SEQ ID NO: 32, SEQ ID NO: 48, SEQ ID NO: 64, SEQ ID NO: 80, and SEQ ID NO: 98; or
l. SEQ ID NO: 18, SEQ ID NO: 33, SEQ ID NO: 49, SEQ ID NO: 65, SEQ ID NO: 81, and SEQ ID NO: 99.

iv. Exemplary SIRP Antibodies—Variable Region Sequences

The term variable region and variable domain are used interchangeably and refer to the portions of the light and heavy chains of an antibody that include the complementarity determining regions and framework regions (FRs).

Table 10 provides amino acid sequences for the variable domains of exemplary SIRP antibodies of the disclosure. Accordingly, in some embodiments a SIRP antibody of the disclosure comprises a variable heavy chain comprising an amino acid sequence selected from SEQ ID NOS: 104, 106-107, and 110-118, or at least 80% sequence identity thereto. In some embodiments a SIRP antibody of the disclosure comprises a variable light chain comprising an amino acid sequence selected from SEQ ID NOS: 123, 125-126, and 129-137, or at least 80% sequence identity thereto. In some embodiments a SIRP antibody of the disclosure comprises a variable heavy chain comprising an amino acid sequence selected from SEQ ID NOS: 104, 106-107, and 110-118, or at least 80% sequence identity thereto and comprises a variable light chain comprising an amino acid sequence selected from SEQ ID NOS: 123, 125-126, and 129-137, or at least 80% sequence identity thereto.

In some embodiments, a SIRP antibody of the disclosure comprises the combination of VH/VL variable chain sequences of any one Antibodies 1, 3-4 and 7-15 presented in Table 10.

TABLE 10

Exemplary Variable Heavy Chain and Variable Light Chain Amino Acid Sequences VH/VL pairs of SIRP antibodies

| Antibody No. | Variable Heavy Chain Amino Acid Sequence | Variable Light Chain Amino Acid Sequence |
|---|---|---|
| 1 | QVQLQESGPGLVKPSGTLSLTCAVSGG SISSSNWWSWVRQPPGKGLEWIGEIY HSGSTNYNPSLKSRVTISVDKSKNQFSL KLSSVTAADTAVYYCARRGIWFGVGP WGQGTLVTVSS (SEQ ID NO: 104) | DIVMTQSPLSLPVTPGEPASISCRSSQSLLHG NGFNYLDWYLQKPGQSPQLLIYLGSNRASG VPDRFTGSGSGTDFTLKISRVEAEDVGVYYC MQGLQTPRTFGQGTKVEIK (SEQ ID NO: 123) |
| 3 | QVQLQESGPGLVKPSGTLSLTCAVSGG SISSSNWWSWVRQPPGKGLEWIGEIY HSGNTNYNPSLKSRVTISVDKSKNQFS LKLSSVTAADTAVYYCAREGIEGYYFYY GMDVWGQGTTVTVSS (SEQ ID NO: 106) | DIQLTQSPSFLSASVGDRVTITCRASQGISGY LDWYQQKPGKAPKLLIYAASTLQRGVPSRFS GSGSGTDFNLTISSLOPEDFATYYCQQFTSD LITFGQGTRLEIK (SEQ ID NO: 125) |
| 4 | QVQLQESGPGLLKPSETLSLTCAVSDYS ISSGYYWGWIRQPPGKGLEWIGSIYHS GNTYYNPSLKSRVTILVDTSKNQFSLKL SSVTAADTAVYYCARDKCSTTTCSFDY WGQGTLVTVSS (SEQ ID NO: 107) | DIQMTQSPSSLSASVGDRVTITCQASQDFS NYLNWYQQKPGKAPKLLIYAASNLETGVPS RFSGSGSGTDFTFTISSLQPEDIAVYYCQQYD NLPYTFGQGTKLEIK (SEQ ID NO: 126) |
| 7 | QVQLVESGGGVVQPGRSLRLSCAASG FTFSKFGMHWVRQAPGKGLEWVAVI SYDGNNKYYTDSVKGRFTISRDNSRNT LYLQMDSVKPEDTAVYYSWAAAGAFY IWGQGTMVTVSS (SEQ ID NO: 110) | SYVLTQPPSVSVAPGQTARITCGGYNIGSKS VHWYQQKAGQAPVLVVYDDSGRPSGIPER LSGSKSGNTATLTISRVEAGDEADYYCQVW DSSSDHYVFGTGTKVTVL (SEQ ID NO: 129) |
| 8 | QVQLQQWGAGLLKPSETLSLTCAVYG GSFSGYYWSWIRQPPGKGLEWIGEIN HSGSTNFNPSLKSRVTISVDTSKNQFSL KLRSVTAADTAVYYCSRVDSGSYPYYD GLDVWGQGTTVTVSS (SEQ ID NO: 111) | SSELTQPPSVSVSPGQTASITCSGDKLGDKY VYWYQQKPGQSPVLVIYHDDRRPAGIPERF AGSASGNTATLTISGTQAMDEADYYCQTW DSSTVVFGGGTKLTVL (SEQ ID NO: 130) |
| 9 | QVQLQQWGAGLLKPSETLSLTCAVYG GSFSTYYWNWIRQPPGKGLEWIGEIN HSGSTNYNPSLKSRVIISVDTSKNQFSL KLSSVTAADTAVYYCASSHYGSGSFPD SYGMDVWGQGTTVTVSA (SEQ ID NO: 112) | SYELTQSPSVSVSPGQTASITCSGDKLGDRY AWWYQQKPGQSPVLVIYQDDKRPSGIPER FSGSNSGNTATLTISGTQAMDEADYYCQA WDSSTAVFGGGTKLTVL (SEQ ID NO: 131) |
| 10 | EVQLLESGGGLVQPGGSLRLSCAASGF TFSSYAMSWVRQAPGKGLEWVSAISG | SYELTQPPSVSVSPGQTASITCSGDKLGDRY ACWYQQKPGQSPVLVIYQDTKRPSGIPERF |

TABLE 10-continued

Exemplary Variable Heavy Chain and Variable Light Chain Amino Acid Sequences VH/VL pairs of SIRP antibodies

| Antibody No. | Variable Heavy Chain Amino Acid Sequence | Variable Light Chain Amino Acid Sequence |
|---|---|---|
|  | SGGDTYYADSVKGRFTISRDNSKSTLYL QMNSLRAEDTAVYYCAKDGGSYYPPF DYWGQGTLVTVSS (SEQ ID NO: 113) | SGSNSGNTATLTISGTQAMDEADYYCQACD SSTAVFGGGTKLTVL (SEQ ID NO: 132) |
| 11 | EVQLVESGGGLVQPGGSLRLSCAASGF TFSSYWMHWVRQAPGKGLVWVSRI HNDGSRTSYADSVKGRFTISRDNAKNT LYLQMSSLRAEDTAVYYCTRDPPPYDIL TGYPFDYWGQGTLVTVSS (SEQ ID NO: 114) | DIQMTQSPSSVSASVGDRVTITCRASQDISS WLAWFQQKPGKAPKLLIYGASSLQSGVPSR FSGSGSGTDFTLTISSLQPEDFATYYCQEANS FPYTFGQGTKLEIK (SEQ ID NO: 133) |
| 12 | EVQVLESGGGLVQPGGSLRLSCAASGF TFSSYAMSWVRQAPGKGLEWVSAISG SGSSTHYADSVKGRFTISRDNSKNTLYL QMNSLRAEDTAVYYCAAYSGSYYYYG MDVWGQGTTVTVSS (SEQ ID NO: 115) | EIVMTQSPATLSVSPGERATLSCRASQSVSS NLAWYQQKSGQAPRLLIYGASTRATGIPAR FSGSGSGTEFTLTISSLQSEDFAGYYCQQYN NWPYTFGQGTKLEIK (SEQ ID NO: 134) |
| 13 | EVQMLESGGGLVQPGGSLRLSCAASG FTFSSYAMSWVRQAPGKGLEWVSAIS GSGSSTHYADSVKGRFTISRDNSKNTL YLQMNSLRAEDTAVYYCAAYSGSYYYY GMDVWGQGTTVTVSS (SEQ ID NO: 116) | EIVMTQSPATLSVSPGERATLSCRASQSVSR NLAWYQQKSGQAPRLLIYGASTRATGIPAR FSGSGSGTEFTLTISSLQSEDFAGYYCQQYN NWPYTFGQGTKLEIK (SEQ ID NO: 135) |
| 14 | QVQLVESGGGVVQPGRSLRLSCVASG FIFSNYGMHWVRQAPGKGLEWVAVI SYDGRNEDHVDSVKGRFTISRDNSKN TLYLQMNSLRAEDTAVYYCAKGSGSYY FDYWGQGTLVTVSS (SEQ ID NO: 117) | DIVLTQSPDSLAVSLGERATINCKSSQTVLNS SNNKNYLAWYQQKPGQPPKLLIYWASIRES GVPDRFSGSGSGTDFTLTISSLQAEDVAVYY CQQYYNTPPWTFGQGTKVEIK (SEQ ID NO: 136) |
| 15 | QIQLVQSGPELKKPGETVKISCKGSGYT FRNFGMNWVKQAPGMGLKWMVWI DTNTGEPTYAEEFKGRFAFSLETSASTA YLQINNLKNEDTATYFCARSRGNYFA MEYWGQGTSVTVSS (SEQ ID NO: 118) | DIKMTQSPSSMYASLGERVTVTCKASQDIN RYLSWFQQKPGKSPKTLIYRANRLVDGVPSR FSGSGSGQDYSLTISSLEYEDMGFYYCLQYD EFPFTFGSGTKLEIK (SEQ ID NO: 137) |

In some embodiments, provided herein is a SIRP antibody, wherein the heavy chain variable domain of the antibody comprises the amino acid sequence of SEQ ID NO: 104 or an amino acid sequence with at least 80%. 81%. 82%. 83%. 84%. 85%. 86%, 87%. 88%, 89%. 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 123, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 104, and the light chain variable domain of the antibody comprises the amino acid sequence of SEQ ID NO: 123. In some embodiments, the light chain variable domain comprises CDR sequences of SEQ ID NOS: 5, 23 and 36, and the heavy chain variable domain comprises CDR sequences of SEQ ID NOS: 54, 70 and 86.

In some embodiments, provided herein is a SIRP antibody, wherein the heavy chain variable domain of the antibody comprises the amino acid sequence of SEQ ID NO: 106 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 125, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 106, and the light chain variable domain of the antibody comprises the amino acid sequence of SEQ ID NO: 125. In some embodiments, the light chain variable domain comprises CDR sequences of SEQ ID NOS: 7, 24 and 38, and the heavy chain variable domain comprises CDR sequences of SEQ ID NOS: 54, 72 and 88.

In some embodiments, provided herein is a SIRP antibody, wherein the heavy chain variable domain of the antibody comprises the amino acid sequence of SEQ ID NO: 107 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 126, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 107, and the light chain variable domain of the antibody comprises the amino acid sequence of SEQ ID NO: 126. In some embodiments, the light chain variable domain comprises CDR sequences of SEQ ID NOS: 8, 24 and 39, and the heavy chain variable domain comprises CDR sequences of SEQ ID NOS: 56, 72 and 89.

In some embodiments, provided herein is a SIRP antibody, wherein the heavy chain variable domain of the antibody comprises the amino acid sequence of SEQ ID NO: 110 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 129, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 110, and the light chain variable domain of the antibody comprises the amino acid sequence of SEQ ID NO: 129. In some embodiments, the light chain variable domain comprises CDR sequences of SEQ ID NOS: 11, 27 and 42, and the heavy chain variable domain comprises CDR sequences of SEQ ID NOS: 59, 75 and 92.

In some embodiments, provided herein is a SIRP antibody, wherein the heavy chain variable domain of the antibody comprises the amino acid sequence of SEQ ID NO: 111 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 130, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 111, and the light chain variable domain of the antibody comprises the amino acid sequence of SEQ ID NO: 130. In some embodiments, the light chain variable domain comprises CDR sequences of SEQ ID NOS: 12, 28 and 43, and the heavy chain variable domain comprises CDR sequences of SEQ ID NOS: 560, 76 and 93.

In some embodiments, provided herein is a SIRP antibody, wherein the heavy chain variable domain of the antibody comprises the amino acid sequence of SEQ ID NO: 112 or an 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 131, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 112, and the light chain variable domain of the antibody comprises the amino acid sequence of SEQ ID NO: 131. In some embodiments, the light chain variable domain comprises CDR sequences of SEQ ID NOS: 13, 29 and 44, and the heavy chain variable domain comprises CDR sequences of SEQ ID NOS: 61, 76 and 94.

In some embodiments, provided herein is a SIRP antibody, wherein the heavy chain variable domain of the antibody comprises the amino acid sequence of SEQ ID NO: 113 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 132, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 113, and the light chain variable domain of the antibody comprises the amino acid sequence of SEQ ID NO: 132. In some embodiments, the light chain variable domain comprises CDR sequences of SEQ ID NOS: 13, 30 and 45, and the heavy chain variable domain comprises CDR sequences of SEQ ID NOS: 62, 77 and 95.

In some embodiments, provided herein is a SIRP antibody, wherein the heavy chain variable domain of the antibody comprises the amino acid sequence of SEQ ID NO: 114 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 133, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 114, and the light chain variable domain of the antibody comprises the amino acid sequence of SEQ ID NO: 133. In some embodiments, the light chain variable domain comprises CDR sequences of SEQ ID NOS: 14, 31 and 46, and the heavy chain variable domain comprises CDR sequences of SEQ ID NOS: 63, 78 and 96.

In some embodiments, provided herein is a SIRP antibody, wherein the heavy chain variable domain of the antibody comprises the amino acid sequence of SEQ ID NO: 115 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 134, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 115, and the light chain variable domain of the antibody comprises the amino acid sequence of SEQ ID NO: 134. In some embodiments, the light chain variable domain comprises CDR sequences of SEQ ID NOS: 15, 31 and 47, and the heavy chain variable domain comprises CDR sequences of SEQ ID NOS: 62, 79 and 97.

In some embodiments, provided herein is a SIRP antibody, wherein the heavy chain variable domain of the antibody comprises the amino acid sequence of SEQ ID NO: 116 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 135, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 116, and the light chain variable domain of the antibody comprises the amino acid sequence of SEQ ID NO: 135. In some embodiments, the light chain variable domain comprises CDR sequences of SEQ ID NOS: 16, 31 and 47, and the heavy chain variable domain comprises CDR sequences of SEQ ID NOS: 62, 79 and 97.

In some embodiments, provided herein is a SIRP antibody, wherein the heavy chain variable domain of the antibody comprises the amino acid sequence of SEQ ID NO: 117 or an 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 136, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 117, and the light chain variable domain of the antibody comprises the amino acid sequence of SEQ ID NO: 136. In some embodiments, the light chain variable domain comprises CDR sequences of SEQ ID NOS: 17, 32 and 48, and the heavy chain variable domain comprises CDR sequences of SEQ ID NOS: 64, 80 and 98.

In some embodiments, provided herein is a SIRP antibody, wherein the heavy chain variable domain of the antibody comprises the amino acid sequence of SEQ ID NO: 118 or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody comprises the amino acid sequence of SEQ ID NO: 137, or an amino acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody comprises the amino acid sequence of SEQ ID NO: 118, and the light chain variable domain of the antibody comprises the amino acid sequence of SEQ ID NO: 137. In some embodiments, the light chain variable domain comprises CDR sequences of SEQ ID NOS: 18, 33 and 49, and the heavy chain variable domain comprises CDR sequences of SEQ ID NOS: 65, 81 and 99.

Table 11 provides full-length exemplary SIRP antibodies of the disclosure.

TABLE 11

Exemplary Combinations of Amino Acid with Fc Regions of SIRP Antibodies

| Antibody No. | VH/VL Pair Amino Acid | Fc |
| --- | --- | --- |
| Antibody 1 | SEQ ID NO: 104/SEQ ID NO: 123 | Rat IgG2b Fc |
| Antibody 3 | SEQ ID NO: 106/SEQ ID NO: 125 | Rat IgG2b Fc |
| Antibody 4 | SEQ ID NO: 107/SEQ ID NO: 126 | Rat IgG2b Fc |
| Antibody 7 | SEQ ID NO: 110/SEQ ID NO: 129 | Rat IgG2b Fc |
| Antibody 8 | SEQ ID NO: 111/SEQ ID NO: 130 | Rat IgG2b Fc |
| Antibody 9 | SEQ ID NO: 112/SEQ ID NO: 131 | Rat IgG2b Fc |
| Antibody 10 | SEQ ID NO: 113/SEQ ID NO: 132 | Rat IgG2b Fc |
| Antibody 11 | SEQ ID NO: 114/SEQ ID NO: 133 | Rat IgG2b Fc |
| Antibody 12 | SEQ ID NO: 115/SEQ ID NO: 134 | Rat IgG2b Fc |
| Antibody 13 | SEQ ID NO: 116/SEQ ID NO: 135 | Rat IgG2b Fc |

TABLE 11-continued

Exemplary Combinations of Amino Acid with Fc Regions of SIRP Antibodies

| Antibody No. | VH/VL Pair Amino Acid | Fc |
| --- | --- | --- |
| Antibody 14 | SEQ ID NO: 117/SEQ ID NO: 136 | Rat IgG2b Fc |
| Antibody 15 | SEQ ID NO: 118/SEQ ID NO: 137 | Mouse IgG2a Fc |
| Antibody 21 | SEQ ID NO: 110/SEQ ID NO: 129 | Human IgG1 Fc |
| Antibody 23 | SEQ ID NO: 104/SEQ ID NO: 123 | Human IgG1 Fc |
| Antibody 24 | SEQ ID NO: 106/SEQ ID NO: 125 | Human IgG1 Fc |
| Antibody 25 | SEQ ID NO: 116/SEQ ID NO: 135 | Human IgG1 Fc |
| Antibody 26 | SEQ ID NO: 110/SEQ ID NO: 129 | Human IgG1 Fc with increased affinity for FcγR |
| Antibody 28 | SEQ ID NO: 104/SEQ ID NO: 123 | Human IgG1 Fc with increased affinity for FcγR |
| Antibody 29 | SEQ ID NO: 116/SEQ ID NO: 135 | Human IgG1 Fc with increased affinity for FcγR |
| Antibody 30 | SEQ ID NO: 104/SEQ ID NO: 123 | Human IgG1 Fc with increased affinity for FcγR + extended half life |
| Antibody 31 | SEQ ID NO: 116/SEQ ID NO: 135 | Human IgG1 Fc with increased affinity for FcγR + extended half life |
| Antibody 32 | SEQ ID NO: 106/SEQ ID NO: 125 | Human IgG1 Fc with increased affinity for FcγR |

B. Generation of SIRP Antibodies

Production of the antibodies provided herein may be by use of any method known to those of ordinary skill in the art. In some embodiments, the antibodies are produced by hybridomas. In some embodiments, the antibodies are encoded by a nucleic acid and are expressed, purified, and isolated.

The terms polynucleotide and nucleic acid are used interchangeably herein, and refer to a polymeric form of nucleotides of any length, which may be ribonucleotides or deoxyribonucleotides. The terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivative nucleotide bases. The terms encompass nucleic acids containing known analogues of natural nucleotides and having similar binding properties, and are metabolized in a manner similar to naturally-occurring nucleotides, unless specifically limited or stated otherwise.

Accordingly, provided herein are nucleic acids encoding any of the antibodies disclosed herein, vectors comprising any of the nucleic acids encoding such antibodies, and host cells comprising any such vectors. Also provided herein are exemplary nucleic acid sequences encoding for the variable heavy chains and variable light chains of the SIRP antibodies disclosed herein.

Table 12 provides exemplary nucleic acid sequences for the SIRP antibodies of the disclosure. Accordingly, in some embodiments a nucleic acid sequence encoding for a SIRP antibody of the disclosure comprises a variable heavy chain nucleic acid sequence selected from SEQ ID NOS: 142, 144-145, and 148-156, or at least 80% sequence identity thereto. In some embodiments a nucleic acid sequence encoding for a SIRP antibody of the disclosure comprises a variable light chain nucleic acid sequence selected from SEQ ID NOS: 161, 163-164, and 167-175, or at least 80% sequence identity thereto. In some embodiments a nucleic acid sequence encoding for a SIRP antibody of the disclosure comprises a variable heavy chain nucleic acid sequence selected from SEQ ID NOS: 142, 144-145, and 148-156, or at least 80% sequence identity thereto, and a variable light chain nucleic acid sequence selected from SEQ ID NOS: 161, 163-164, 167-175, or at least 80% sequence identity thereto. The person of ordinary skill in the art will appreciate that, because of redundancy in the triplet code, multiple nucleic acids may encode the same amino acid sequence. Thus, nucleic acid sequences that are not identical to those set forth in Table 12 may still encode the amino acid sequences set forth in Table 10.

TABLE 12

Variable Heavy Chain and Variable Light Chain Nucleic Acid Sequences of Exemplary SIRP Antibodies

| Antibody No. | Variable Heavy Chain Nucleic Acid Sequence | Variable Light Chain Nucleic Acid Sequence |
|---|---|---|
| 1 | CAGGTGCAGCTGCAGGAGTCGGGCCC AGGACTGGTGAAGCCTTCGGGGACCCT GTCCCTCACCTGCGCTGTCTCTGGTGG CTCCATCAGCAGTAGTAACTGGTGGAG TTGGGTCCGCCAGCCCCCAGGGAAGG GGCTGGAATGGATTGGGGAAATCTATC ATAGTGGGAGCACCAACTACAACCCGT CCCTCAAGAGTCGAGTCACCATATCAG TAGACAAGTCCAAGAACCAGTTCTCCC TGAAGCTGAGTTCTGTGACCGCCGCGG ACACGGCCGTGTATTACTGTGCGAGAA GGGGGATATGGTTCGGGGTCGGTCCC TGGGGCCAGGGAACCCTGGTCACCGTC TCCTCA (SEQ ID NO: 142) | GATATTGTGATGACTCAGTCTCCACTC TCCCTGCCCGTCACCCCTGGAGAGCC GGCCTCCATCTCCTGCAGGTCTAGTCA GAGCCTCCTACATGGTAATGGATTCA ACTATTTGGATTGGTACCTGCAGAAG CCAGGGCAGTCTCCACAGCTCCTGAT CTATTTGGGTTCTAATCGGGCCTCCGG GGTCCCTGACAGGTTCACTGGCAGTG GATCAGGCACAGATTTTACACTGAAA ATCAGCAGAGTGGAGGCTGAGGATG TTGGGGTTTATTACTGCATGCAAGGTC TACAAACTCCTCGGACGTTCGGCCAA GGGACCAAGGTGGAAATCAAA (SEQ ID NO: 161) |
| 3 | CAGGTGCAGCTGCAGGAGTCGGGCCC AGGACTGGTGAAGCCTTCGGGGACCCT GTCTCTCACCTGCGCTGTCTCTGGTGGC TCCATCAGCAGTAGTAACTGGTGGAGT TGGGTCCGCCAGCCCCCAGGGAAGGG GCTGGAGTGGATTGGGGAAATCTATCA TAGTGGGAACACCAACTACAACCCGTC CCTCAAGAGTCGAGTCACCATATCAGT AGACAAGTCCAAGAACCAGTTCTCCCT GAAGCTGAGCTCTGTGACCGCCGCGG ACACGGCCGTGTATTACTGTGCGAGAG AGGGTATAGAGGGGTACTACTTCTACT ACGGTATGGACGTCTGGGGCCAAGGG ACCACGGTCACCGTCTCCTCA (SEQ ID NO: 144) | GACATCCAGTTGACCCAGTCTCCATCC TTCCTGTCTGCATCTGTAGGAGACAG AGTCACCATCACTTGCCGGGCCAGTC AGGGCATTAGCGGTTATTTAGACTGG TATCAGCAAAAACCAGGGAAAGCCCC TAAGCTCCTGATCTATGCTGCATCCAC TTTACAAAGAGGGGTCCCATCAAGGT TCAGCGGCAGTGGATCTGGGACAGAT TTCAATCTCACAATCAGCAGCCTGCAG CCTGAAGATTTTGCAACTTATTACTGT CAACAGTTTACTAGTGACCTCATCACC TTCGGCCAAGGGACACGACTGGAGAT TAAA (SEQ ID NO: 163) |
| 4 | CAGGTGCAGCTGCAGGAGTCGGGCCC AGGACTGCTGAAGCCTTCGGAGACCCT GTCCCTCACCTGCGCTGTCTCTGATTAC TCCATCAGCAGTGGTTACTACTGGGGC TGGATCCGGCAGCCCCCGGGGAAGGG GCTGGAGTGGATTGGGAGTATCTATCA TAGTGGGAATACCTATTATAACCCGTC CCTCAAGAGTCGAGTCACCATATTAGT AGACACGTCCAAGAACCAGTTCTCCCT GAAGCTGAGCTCTGTGACCGCCGCAGA CACGGCCGTGTATTACTGTGCGAGAGA TAAATGTAGTACTACAACCTGCTCCTTT GACTACTGGGGCCAGGGAACCCTGGT CACCGTCTCCTCA (SEQ ID NO: 145) | GACATCCAGATGACCCAGTCTCCATCC TCCCTGTCTGCATCTGTAGGAGACAG AGTCACCATCACTTGCCAGGCGAGTC AGGACTTTAGCAACTATTTAAATTGGT ATCAGCAGAAACCAGGGAAAGCCCCT AAGCTCCTGATCTACGCTGCATCCAAT TTGGAAACAGGGGTCCCATCGAGGTT CAGTGGAAGTGGATCTGGGACAGATT TTACTTTCACCATCAGCAGCCTGCAGC CTGAAGATATTGCAGTATATTACTGTC AACAGTATGATAATCTCCCGTACACTT TTGGCCAGGGGACCAAGCTGGAGATC AAA (SEQ ID NO: 164) |
| 7 | CAGGTGCAGCTGGTGGAGTCTGGGGG AGGCGTGGTCCAGCCTGGGAGGTCCCT GAGACTCTCCTGTGCAGCCTCTGGATT CACCTTCAGTAAATTTGGCATGCACTG GGTCCGCCAGGCTCCAGGCAAGGGGC TGGAGTGGGTGGCAGTTATATCATATG ATGGAAATAATAAATACTATACAGACT CCGTGAAGGGCCGATTCACCATCTCCA GAGACAATTCCAGGAACACGCTGTATC TGCAAATGGACAGCGTGAAACCTGAG GACACGGCTGTGTACTATTCCTGGGCA GCAGCTGGTGCTTTTTATATCTGGGGC CAAGGGACAATGGTCACCGTCTCTTCA (SEQ ID NO: 148) | TCCTATGTGCTGACTCAGCCACCCTCG GTGTCAGTGGCCCCAGGACAGACGGC CAGGATTACCTGTGGGGGATACAACA TTGGAAGTAAAAGTGTGCACTGGTAC CAGCAGAAGGCAGGCCAGGCCCCTGT GCTGGTCGTCTATGATGATAGCGGCC GGCCCTCAGGGATCCCTGAGCGATTG TCTGGCTCCAAGTCTGGGAACACGGC CACCCTGACCATCAGCAGGGTCGAAG CCGGGGATGAGGCCGACTATTACTGT CAGGTGTGGGATAGTAGTAGTGATCA TTATGTCTTCGGAACTGGGACCAAGG TCACCGTCCTA (SEQ ID NO: 167) |
| 8 | CAGGTGCAGCTACAGCAGTGGGGCGC AGGACTGTTGAAGCCTTCGGAGACCCT GTCCCTCACCTGCGCTGTCTATGGTGG GTCCTTCAGTGGTTACTACTGGAGCTG GATTCGCCAGCCCCCAGGGAAGGGGC | TCCTCTGAATTGACTCAGCCACCCTCA GTGTCCGTGTCCCAGGACAGACAGC CAGCATCACCTGCTCTGGAGATAAATT GGGGGATAAATATGTTTACTGGTATC AACAGAAGCCAGGCCAGTCCCCTGTG |

TABLE 12-continued

Variable Heavy Chain and Variable Light Chain Nucleic Acid Sequences of Exemplary SIRP Antibodies

| Antibody No. | Variable Heavy Chain Nucleic Acid Sequence | Variable Light Chain Nucleic Acid Sequence |
|---|---|---|
|  | TGGAGTGGATTGGGGAAATCAATCATA GTGGAAGCACCAACTTCAACCCGTCCC TCAAGAGTCGAGTCACCATATCAGTAG ACACGTCCAAGAACCAGTTCTCCCTGA AGCTGAGGTCTGTGACCGCCGCGGAC ACGGCTGTGTATTACTGTTCGAGAGTC GATAGTGGGAGCTATCCCTACTACGAC GGTTTGGACGTCTGGGGCCAAGGGAC CACGGTCACCGTCTCCTCA (SEQ ID NO: 149) | TTGGTCATCTATCATGATGATCGGCG GCCCGCTGGGATCCCTGAGCGATTCG CTGGCTCCGCTTCTGGGAACACAGCC ACTCTGACCATCAGCGGGACCCAGGC TATGGATGAGGCTGACTATTACTGTC AGACGTGGGACAGCAGCACTGTGGTT TTCGGCGGAGGGACCAAGCTGACCGT CCTA (SEQ ID NO: 168) |
| 9 | CAGGTGCAGCTACAGCAGTGGGGCGC AGGACTGTTGAAGCCTTCGGAGACCCT GTCCCTCACCTGCGCTGTCTATGGTGG GTCCTTCAGTACTTACTACTGGAACTGG ATCCGCCAGCCCCCAGGGAAGGGGCT GGAGTGGATTGGGGAAATCAATCATA GTGGAAGCACCAACTACAACCCGTCCC TCAAGAGTCGAGTCATCATATCAGTAG ACACGTCCAAGAACCAGTTCTCCCTGA AGCTGAGCTCTGTGACCGCCGCGGACA CGGCTGTGTATTACTGTGCGAGCAGTC ATTATGGTTCGGGGAGTTTTCCCGACT CCTACGGTATGGACGTCTGGGGCCAAG GGACCACGGTCACCGTCTCCGCA (SEQ ID NO: 150) | TCCTATGAATTGACTCAGTCACCCTCA GTGTCCGTGTCCCAGGACAGACAGC CAGCATCACCTGCTCTGGAGATAAATT GGGGGATAGATATGCTTGGTGGTATC AGCAGAAGCCAGGCCAGTCCCCTGTG CTGGTCATCTATAAGATGACAAGCG GCCCTCAGGGATCCCTGAGCGATTCT CTGGCTCCAACTCTGGGAACACAGCC ACTCTGACCATCAGCGGGACCCAGGC TATGGATGAGGCTGACTATTACTGTC AGGCGTGGGACAGCAGCACTGCGGT ATTCGGCGGAGGGACCAAGCTGACC GTCCTA (SEQ ID NO: 169) |
| 10 | GAGGTGCAGCTGTTGGAGTCTGGGGG AGGCTTGGTACAGCCTGGGGGGTCCCT GAGACTCTCCTGTGCAGCCTCTGGATT CACGTTTAGCAGCTATGCCATGAGCTG GGTCCGCCAGGCTCCAGGGAAGGGGC TGGAGTGGGTCTCAGCTATTAGTGGTA GTGGTGGTGACACTTACTACGCAGACT CCGTGAAGGGCCGGTTCACCATCTCCA GAGACAATTCCAAGAGCACGCTGTATC TGCAAATGAACAGCCTGAGAGCCGAG GACACGGCCGTATATTACTGTGCGAAA GACGGTGGGAGCTACTACCCCCCCTTT GACTACTGGGGCCAGGGAACCCTGGT CACCGTCTCCTCA (SEQ ID NO: 151) | TCCTATGAGCTGACTCAGCCACCCTCA GTGTCCGTGTCCCAGGACAGACAGC CAGCATCACCTGCTCTGGAGATAAATT GGGGGATAGATATGCTTGCTGGTATC AGCAGAAGCCAGGCCAGTCCCCTGTA CTGGTCATCTATAAGATACCAAGCG GCCCTCAGGGATCCCTGAGCGATTCT CTGGCTCCAACTCTGGGAACACAGCC ACTCTGACCATCAGCGGGACCCAGGC TATGGATGAGGCTGACTATTACTGTC AGGCGTGCGACAGCAGCACTGCGGT GTTCGGCGGAGGGACCAAGCTGACC GTCCTA (SEQ ID NO: 170) |
| 11 | GAGGTGCAGCTGGTGGAGTCCGGGGG AGGCTTAGTTCAGCCTGGGGGGTCCCT GAGACTCTCTTGTGCAGCCTCTGGATT CACCTTCAGTAGCTACTGGATGCACTG GGTCCGCCAAGCTCCAGGGAAGGGGC TGGTGTGGGTCTCACGTATTCATAATG ATGGGAGTAGAACAAGTTACGCGGAC TCCGTGAAGGGCCGATTCACTATCTCC AGAGACAACGCCAAGAACACGCTGTAT CTGCAAATGAGCAGTCTGCGAGCCGA GGACACGGCTGTGTATTACTGTACAAG AGATCCCCTCCTTACGATATTTTGACT GGTTACCCCTTTGACTACTGGGGCCAG GGAACCCTGGTCACCGTCTCCTCA (SEQ ID NO: 152) | GACATCCAGATGACCCAGTCTCCGTCT TCCGTGTCTGCATCTGTAGGAGACAG AGTCACCATCACTTGTCGGGCGAGTC AGGATATTAGCAGCTGGTTAGCCTGG TTTCAGCAGAAACCAGGGAAAGCCCC TAAGCTCCTGATCTATGGTGCATCCAG TTTGCAAAGTGGGGTCCCATCAAGGT TCAGCGGCAGTGGATCTGGGACAGAT TTCACTCTCACCATCAGCAGCCTGCAG CCTGAAGATTTTGCAACTTACTATTGT CAAGAGGCTAACAGTTTCCCGTATACT TTTGGCCAGGGGACCAAGCTGGAGAT CAAA (SEQ ID NO: 171) |
| 12 | GAGGTGCAGGTGTTGGAGTCTGGGGG AGGCTTGGTACAGCCTGGGGGGTCCCT GAGACTCTCCTGTGCAGCCTCTGGATT CACCTTTAGCAGCTATGCCATGAGCTG GGTCCGCCAGGCTCCAGGGAAGGGGC TGGAGTGGGTCTCAGCTATTAGTGGTA GTGGTAGTAGCACACACTACGCAGACT CCGTGAAGGGCCGGTTCACCATCTCCA GAGACAATTCCAAGAACACGCTGTATC TGCAAATGAACAGCCTGAGAGCCGAG GACACGGCCGTATATTACTGTGCGGCG TATAGTGGGAGCTACTACTACTATGGA ATGGACGTCTGGGGACAAGGGACCAC GGTCACCGTCTCCTCA (SEQ ID NO: 153) | GAAATAGTGATGACGCAGTCTCCAGC CACCCTGTCTGTGTCTCCAGGGGAAA GAGCCACCCTCTCCTGCAGGGCCAGT CAGAGTGTTAGCAGCAACTTAGCCTG GTACCAGCAGAAATCTGGCCAGGCTC CCAGGCTCCTCATCTATGGTGCATCCA CCAGGGCCACTGGTATCCCAGCCAGG TTCAGTGGCAGTGGGTCTGGGACAGA GTTCACTCTCACCATCAGCAGCCTGCA GTCTGAAGATTTTGCAGGTTATTACTG CCAGCAGTATAATAACTGGCCGTACA CTTTTGGCCAGGGGACCAAGCTGGAG ATCAAA (SEQ ID NO: 172) |

TABLE 12-continued

Variable Heavy Chain and Variable Light Chain Nucleic Acid Sequences of Exemplary SIRP Antibodies

| Antibody No. | Variable Heavy Chain Nucleic Acid Sequence | Variable Light Chain Nucleic Acid Sequence |
|---|---|---|
| 13 | GAGGTGCAGATGTTGGAGTCTGGGGG AGGCTTGGTTCAGCCTGGGGGGTCCCT GAGACTCTCCTGTGCAGCCTCTGGATT CACCTTTAGCAGCTATGCCATGAGCTG GGTCCGCCAGGCTCCAGGGAAGGGGC TGGAGTGGGTCTCAGCTATTAGTGGTA GTGGTAGTAGCACACACTACGCAGACT CCGTGAAGGGCCGGTTCACCATCTCCA GAGACAATTCCAAGAACACGCTGTATC TGCAAATGAACAGCCTGAGAGCCGAG GACACGGCCGTTTATTACTGTGCGGCG TATAGTGGGAGCTACTACTACTATGGA ATGGACGTCTGGGGACAGGGGACCAC GGTCACCGTCTCCTCA (SEQ ID NO: 154) | GAAATAGTGATGACGCAGTCTCCAGC CACCCTGTCTGTGTCTCCAGGGGAAA GAGCCACCCTCTCCTGCAGGGCCAGT CAGAGTGTTAGTAGGAATTTAGCCTG GTACCAGCAGAAATCTGGCCAGGCTC CCAGGCTCCTCATCTATGGTGCATCCA CCAGGGCCACTGGTATCCCAGCCAGG TTCAGTGGCAGTGGGTCTGGGACAGA GTTCACTCTCACCATCAGCAGCCTGCA GTCTGAAGATTTTGCAGGTTATTACTG CCAGCAGTATAATAACTGGCCGTACA CTTTTGGCCAGGGGACCAAGCTGGAG ATCAAA (SEQ ID NO: 173) |
| 14 | CAGGTGCAGCTGGTGGAGTCTGGGGG AGGCGTGGTCCAGCCTGGGAGGTCCCT GAGACTCTCCTGTGTAGCCTCTGGATT CATCTTCAGTAACTATGGCATGCACTG GGTCCGCCAGGCTCCAGGCAAGGGGC TGGAGTGGGTGGCAGTTATATCATATG ATGGAAGAAATGAAGACCATGTAGAC TCCGTGAAGGGCCGATTCACCATCTCC AGAGACAATTCCAAGAACACGCTGTAT CTGCAAATGAACAGCCTGAGAGCTGA GGACACGGCTGTATATTACTGTGCGAA AGGGTCGGGGAGCTACTACTTTGACTA CTGGGGCCAGGGAACCCTGGTCACCGT CTCCTCA (SEQ ID NO: 155) | GACATCGTGCTGACCCAGTCTCCAGA CTCCCTGGCTGTGTCTCTGGGCGAGA GGGCCACCATCAACTGCAAGTCCAGC CAGACTGTTTTAAACAGCTCCAACAAT AAGAACTACCTAGCTTGGTACCAGCA GAAACCAGGACAGCCTCCTAAGCTGC TCATTTACTGGGCATCTATCCGGGAAT CCGGGGTCCCTGACCGATTCAGTGGC AGCGGGTCTGGGACAGATTTCACTCT CACCATCAGCAGCCTGCAGGCTGAAG ATGTGGCAGTTTATTACTGTCAGCAAT ATTATAATACTCCTCCGTGGACGTTCG GCCAAGGGACCAAGGTGGAAATCAA A (SEQ ID NO: 174) |
| 15 | CAGATCCAGTTGGTGCAGTCTGGACCT GAGCTGAAGAAGCCTGGAGAGACAGT CAAGATCTCCTGCAAGGGTTCTGGGTA TACCTTCAGAAACTTTGGAATGAATTG GGTGAAGCAGGCTCCAGGAATGGGTT TAAAGTGGATGGTGTGGATAGACACC AACACTGGAGAGCCAACATATGCTGAA GAGTTCAAGGGACGGTTTGCCTTCTCT TTGGAAACCTCTGCCAGCACTGCCTATT TGCAGATCAACAACCTCAAAAATGAGG ACACGGCTACATATTTCTGTGCAAGAT CGAGAGGTAACTACTTTGCTATGGAGT ATTGGGGCAAGGAACCTCAGTCACC GTCTCCTCA (SEQ ID NO: 156) | GACATCAAGATGACCCAGTCTCCATCT TCCATGTATGCATCTCTAGGAGAGAG AGTCACTGTCACTTGCAAGGCGAGTC AGGACATTAATCGCTATTTAAGCTGGT TCCAGCAGAAACCAGGGAAATCTCCT AAGACCCTGATCTATCGTGCAAACAG ATTGGTAGATGGGGTCCCATCAAGGT TCAGTGGCAGTGGATCTGGGCAAGAT TATTCTCTCACCATCAGCAGCCTGGAG TATGAAGATATGGGATTTTATTATTGT CTACAGTATGATGAGTTTCCATTCACG TTCGGCTCGGGGACAAAGTTGGAAAT AAAA (SEQ ID NO: 175) |

In some embodiments, provided herein is a nucleic acid encoding any of the SIRP antibodies disclosed herein. In some embodiments, provided herein is a nucleic acid comprising any one or more of the nucleic acid sequences of Table 12. In some embodiments, the heavy and light chain variable domains of the SIRP antibodies disclosed herein are encoded by a nucleic acid comprising any one or more of the nucleic acid sequences of Table 12.

In some embodiments, the heavy chain variable domain of the SIRP antibodies of the disclosure are encoded by a nucleic acid by the nucleic acid sequence of SEQ ID NO: 142, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or the light chain variable domain of the antibody is encoded by the nucleic acid sequence of SEQ ID NO: 161, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 142, or a nucleic acid sequence with at least 97%, sequence identity thereto; and/or wherein the light chain variable domain of the antibody is encoded by the nucleic acid sequence of SEQ ID NO: 161, or a nucleic acid sequence with at least 97% sequence identity thereto. In some embodiments, the heavy chain variable domain of the antibody is encoded by the nucleic acid sequence of SEQ ID NO: 142, and the light chain variable domain of the antibody is encoded by the nucleic acid sequence of SEQ ID NO: 161.

In some embodiments, the heavy chain variable domain of the SIRP antibodies of the disclosure is encoded by the nucleic acid sequence of SEQ ID NO: 144, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or the light chain variable domain of the antibody is encoded by the nucleic acid sequence of SEQ ID NO: 163, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 144, or a nucleic acid sequence with at least 97%, sequence identity thereto; and/or wherein the light chain variable domain of the antibody is encoded by the nucleic acid sequence of SEQ ID NO: 163, or a nucleic acid sequence with at least 97% sequence identity thereto. In some embodiments, the heavy chain variable domain of the antibody is encoded by the nucleic acid sequence of SEQ ID NO: 144, and the light chain variable domain of the antibody is encoded by the nucleic acid sequence of SEQ ID NO: 163.

In some embodiments, the heavy chain variable domain of the SIRP antibodies of the disclosure is encoded by the nucleic acid sequence of SEQ ID NO: 145, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or the light chain variable domain of the antibody is encoded by the nucleic acid sequence of SEQ ID NO: 164, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 145, or a nucleic acid sequence with at least 97%, sequence identity thereto; and/or wherein the light chain variable domain of the antibody is encoded by the nucleic acid sequence of SEQ ID NO: 164, or a nucleic acid sequence with at least 97% sequence identity thereto. In some embodiments, the heavy chain variable domain of the antibody is encoded by the nucleic acid sequence of SEQ ID NO: 145, and the light chain variable domain of the antibody is encoded by the nucleic acid sequence of SEQ ID NO: 164.

In some embodiments, the heavy chain variable domain of the SIRP antibodies of the disclosure is encoded by the nucleic acid sequence of SEQ ID NO: 148, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 167, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 148, or a nucleic acid sequence with at least 97%, sequence identity thereto; and/or wherein the light chain variable domain of the antibody is encoded by the nucleic acid sequence of SEQ ID NO: 167, or a nucleic acid sequence with at least 97% sequence identity thereto. In some embodiments, the heavy chain variable domain of the antibody is encoded by the nucleic acid sequence of SEQ ID NO: 148, and the light chain variable domain of the antibody is encoded by the nucleic acid sequence of SEQ ID NO: 167.

In some embodiments, the heavy chain variable domain of the SIRP antibodies of the disclosure is encoded by the nucleic acid sequence of SEQ ID NO: 149, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 168, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 149, or a nucleic acid sequence with at least 97%, sequence identity thereto; and/or wherein the light chain variable domain of the antibody is encoded by the nucleic acid sequence of SEQ ID NO: 168, or a nucleic acid sequence with at least 97% sequence identity thereto. In some embodiments, the heavy chain variable domain of the antibody is encoded by the nucleic acid sequence of SEQ ID NO: 149, and the light chain variable domain of the antibody is encoded by the nucleic acid sequence of SEQ ID NO: 168.

In some embodiments, the heavy chain variable domain of the SIRP antibodies of the disclosure is encoded by the nucleic acid sequence of SEQ ID NO: 150, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 169, or a nucleic acid sequence with at least 80%, 81%, 82%, 83%, 84%, 85%, 86%, 87%. 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 150, or a nucleic acid sequence with at least 97%, sequence identity thereto; and/or wherein the light chain variable domain of the antibody is encoded by the nucleic acid sequence of SEQ ID NO: 169, or a nucleic acid sequence with at least 97% sequence identity thereto. In some embodiments, the heavy chain variable domain of the antibody is encoded by the nucleic acid sequence of SEQ ID NO: 150, and the light chain variable domain of the antibody is encoded by the nucleic acid sequence of SEQ ID NO: 169.

In some embodiments, the heavy chain variable domain of the SIRP antibodies of the disclosure is encoded by the nucleic acid sequence of SEQ ID NO: 151, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 170, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 151, or a nucleic acid sequence with at least 97%, sequence identity thereto; and/or wherein the light chain variable domain of the antibody is encoded by the nucleic acid sequence of SEQ ID NO: 170 or a nucleic acid sequence with at least 97% sequence identity thereto. In some embodiments, the heavy chain variable domain of the antibody is encoded by the nucleic acid sequence of SEQ ID NO: 151, and the light chain variable domain of the antibody is encoded by the nucleic acid sequence of SEQ ID NO: 170.

In some embodiments, the heavy chain variable domain of the SIRP antibodies of the disclosure is encoded by the nucleic acid sequence of SEQ ID NO: 152, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 171, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 152, or a nucleic acid sequence with at least 97%, sequence identity thereto; and/or wherein the light chain variable domain of the antibody is encoded by the nucleic acid sequence of SEQ ID NO: 171, or a nucleic acid sequence with at least 97% sequence identity thereto. In some embodiments, the heavy chain variable domain of the antibody is encoded by the nucleic acid sequence of SEQ ID NO: 152, and the light chain variable domain of the antibody is encoded by the nucleic acid sequence of SEQ ID NO: 171.

In some embodiments, the heavy chain variable domain of the SIRP antibodies of the disclosure is encoded by the nucleic acid sequence of SEQ ID NO: 153, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 172, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 153, or a nucleic acid sequence with at least 97%, sequence identity thereto; and/or wherein the light chain variable domain of the antibody is encoded by the nucleic acid sequence of SEQ ID NO: 172, or a nucleic acid sequence with at least 97% sequence identity thereto. In some embodiments, the heavy chain variable domain of the antibody is encoded by the nucleic acid sequence of SEQ ID NO: 153, and the light chain variable domain of the antibody is encoded by the nucleic acid sequence of SEQ ID NO: 172.

In some embodiments, the heavy chain variable domain of the SIRP antibodies of the disclosure is encoded by the nucleic acid sequence of SEQ ID NO: 154, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 173, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 154, or a nucleic acid sequence with at least 97%, sequence identity thereto; and/or wherein the light chain variable domain of the antibody is encoded by the nucleic acid sequence of SEQ ID NO: 173, or a nucleic acid sequence with at least 97% sequence identity thereto. In some embodiments, the heavy chain variable domain of the antibody is encoded by the nucleic acid sequence of SEQ ID NO: 154, and the light chain variable domain of the antibody is encoded by the nucleic acid sequence of SEQ ID NO: 173.

In some embodiments, the heavy chain variable domain of the SIRP antibodies of the disclosure is encoded by the nucleic acid sequence of SEQ ID NO: 155, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 174, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 155, or a nucleic acid sequence with at least 97%, sequence identity thereto; and/or wherein the light chain variable domain of the antibody is encoded by the nucleic acid sequence of SEQ ID NO: 174, or a nucleic acid sequence with at least 97% sequence identity thereto. In some embodiments, the heavy chain variable domain of the antibody is encoded by the nucleic acid sequence of SEQ ID NO: 155, and the light chain variable domain of the antibody is encoded by the nucleic acid sequence of SEQ ID NO: 174.

In some embodiments, the heavy chain variable domain of the SIRP antibodies of the disclosure=is encoded by the nucleic acid sequence of SEQ ID NO: 156, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto; and/or wherein the light chain variable domain of the antibody is encoded by the nucleic acid sequence of SEQ ID NO: 175, or a nucleic acid sequence with at least 80%, 81%, 82%, 83%, 84%, 85%, 86%, 87%, 88%, 89%, 90%, 91%, 92%, 93%, 94%, 95%, 96%, 97%, 98%, or 99% sequence identity thereto. In some embodiments, the heavy chain variable domain of the antibody is encoded by the nucleic acid sequence of SEQ ID NO: 156, or a nucleic acid sequence with at least 97%, sequence identity thereto; and/or wherein the light chain variable domain of the antibody is encoded by the nucleic acid sequence of SEQ ID NO: 175, or a nucleic acid sequence with at least 97% sequence identity thereto. In some embodiments, the heavy chain variable domain of the antibody is encoded by the nucleic acid sequence of SEQ ID NO: 156, and the light chain variable domain of the antibody is encoded by the nucleic acid sequence of SEQ ID NO: 175.

The disclosure also provides vectors comprising any nucleic acid of the disclosure. In some embodiments, the nucleic acid of the vector comprises any one or more of the nucleic acid sequences selected from Table 12. In some embodiments, the vector is an expression vector or an expression construct. In some embodiments, the vector is a mammalian vector. In some embodiments, the vector is a viral vector.

In some embodiments, the SIRP antibodies provided herein are produced by culturing a cell under suitable conditions for leading to the expression of the SIRP antibody, wherein the cell comprises a vector.

II. Uses of SIRP Antibodies

A. SIRP Antibody-Mediated Cell Depletion

Provided herein are methods of inducing cell depletion, the method comprising contacting the cell with any of the Fc containing SIRP antibodies of the disclosure. The method may be carried out in vitro or in vivo. In some embodiments, the cell depletion involves ADCC. In some embodiments, the cell depletion involves ADCP. In some embodiments, the cell depletion involves both ADCC and ADCP.

In some embodiments, the cells are SIRPγ-expressing cells. In some embodiments, the cells comprise a first population of SIRPγ-expressing cells, and a second population of SIRPα- and/or SIRPβ1-expressing cells. In some embodiments, the cells comprise a first population of SIRPγ-expressing cells, second population of SIRPα-expressing cells, and a third population of SIRPβ1-expressing cells.

In some embodiments, the SIRPγ-expressing cells comprise lymphocytes. In some embodiments, the lymphocytes comprise B cells, T cells or natural killer (NK) cells. In some embodiments, the SIRPγ-expressing cell is a T cell. In some embodiments, the T cell is a cytotoxic T cell, helper T cell, a memory T cell, a regulatory T cell, a natural killer T cell, a mucosal associated invariant T cell or a gamma delta T cell. In some embodiments, the SIRPγ-expressing cell is an NK cell. In some embodiments, the SIRPγ-expressing cell is an activated T cell or an activated NK cell. In some embodiments, the SIRPγ-expressing cell is a fibroblast. In some embodiments, the SIRPγ-expressing cell is not a myeloid cell. Markers for identifying T cells, NK cells, and B cells, as well as specific populations of T cells, will be known to persons of ordinary skill in the art. For example, cytotoxic T cells express CD8, helper T cells express CD4, regulatory T cells express CD4 as well as additional markers such as CTLA-4, CCR4 or CXCR4, and memory T cells express CD8, as well as CD95. B cells express IgM and CD19, and activated B cells express CD19, CD25 and CD30. NK cells can be identified based on high CD56 expression.

In some embodiments, the SIRPα-expressing cell is a myeloid cell. Myeloid, or myelogenous, cells are blood cells that arise from progenitor cells for granulocytes, or monocytes. In some embodiments, the SIRPα-expressing cell is a monocyte, macrophage, dendritic cell, mast cell, eosinophil, basophil, or neutrophil. In some embodiments, the SIRPα-expressing cell is a myeloid progenitor cell.

In some embodiments, the SIRPβ1-expressing cells are myeloid cells. In some embodiments, the SIRPβ1-expressing cells are granulocytes, for example eosinophils or neutrophils. In some embodiments, the SIRPβ1-expressing cells are monocytes. In some embodiments, the monocytes are classical, intermediate, non-classical, or a combination thereof. In some embodiments, the SIRPβ1-expressing cells are macrophages. In some embodiments, the SIRPβ1-expressing cells are Kupffer cells or Hofbauer cells. In some embodiments, the SIRPβ1-expressing cells are dendritic cells. In some embodiments, the SIRPβ1-expressing cells are alveolar cells.

In some embodiments, the depleted cells comprise lymphocytes. In some embodiments, for example those embodiments where the antibody is specific to SIRPγ and SIRPα and/or SIRPβ1, the depleted cells comprise lymphocytes and at least one other cell type. In some embodiments, the depleted cells comprise lymphocytes and myeloid cells. In some embodiments, the depleted cells comprise lymphocytes and granulocytes, monocytes and/or dendritic cells. In some embodiments, cell depletion is antibody dose-dependent. Exemplary antibodies of the disclosure that induce cell depletion include Antibodies 23, 25, and 28-31, referring to Table 11.

Also provided herein are methods of depleting a population of cells in a subject, comprising administering to a subject any of the Fc containing SIRP antibodies of the disclosure. Exemplary antibodies of the disclosure that exhibit such an effect include Antibodies 23, and 28-31, referring to Table 11. In some embodiments, the cell depletion involves ADCC. In some embodiments, the cell depletion involves ADCP. In some embodiments, the cell depletion involves ADCP and ADCC. In some embodiments, the cells comprise SIRPγ-expressing cells. In some embodiments, the SIRPγ-expressing cells comprise lymphocytes. In some embodiments, the lymphocytes comprise B cells, T cells or NK cells. In some embodiments, the cells further comprise SIRPα-expressing cells. In some embodiments, the SIRPα-expressing cells are myeloid cells. In some embodiments, the SIRPα-expressing myeloid cell is a monocyte, macrophage, dendritic cell, mast cell, eosinophil, basophil, or neutrophil. In some embodiments, the SIRPα-expressing cell is a myeloid progenitor cell. In some embodiments, the cells are not SIRPα-expressing cells, e.g. lymphocytes, but are depleted by the SIRP antibodies of the disclosure. In some embodiments, the cells comprise SIRPβ1-expressing cells. In some embodiments, the SIRPβ1-expressing cells comprise myeloid cells. In some embodiments, the SIRPβ1-expressing cells comprise granulocytes, monocytes, macrophages or dendritic cells. In some embodiments, the granulocytes are eosinophils, basophils or neutrophils. In some embodiments, the SIRPβ1-expressing cells comprise macrophages. In some embodiments, the SIRPβ1-expressing cells comprise Kupffer cells or Hofbauer cells. In some embodiments, the cells are tissue-resident cells. In some embodiments, the cells are circulating cells. In some embodiments, the cell depletion is antibody dose-dependent.

In some embodiments, methods lead to ADCC in vitro, and the SIRP antibody increases ADCC by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Exemplary antibodies of the disclosure that exhibit such an effect include Antibodies 23, 28, and 31-32, referring to Table 11.

In some embodiments, methods lead to ADCP in vitro, and the SIRP antibody increases ADCP by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Exemplary antibodies of the disclosure that exhibit such an effect include Antibodies 23, 25, and 28-31, referring to Table 11.

In some embodiments, the methods lead to ADCC and/or ADCP in vitro, and the SIRP antibody increases ADCC and/or ADCP by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Exemplary antibodies of the disclosure that exhibit such an effect include Antibodies 23, 25, and 28-32, referring to Table 11.

In some embodiments, SIRP antibodies of the disclosure induce ADCC of SIRPγ-expressing lymphocytes cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCP of SIRPγ-expressing lymphocytes in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCC and ADCP of SIRPγ-expressing lymphocytes in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCC of SIRPγ-expressing T cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCP of SIRPγ-expressing T cells in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCC and/or ADCP of SIRPγ-expressing T cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCC of SIRPγ-expressing NK cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCP of SIRPγ-expressing NK cells in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCC and/or ADCP of SIRPγ-expressing NK cells in vitro. In some embodiments, the ADCC and ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies bind SIRPα and also induce ADCC of SIRPα-expressing cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing myeloid cells in vitro. Exemplary antibodies of the disclosure that exhibit such an effect include Antibodies 23, 28, and 31-32, referring to Table 11. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing myeloid cells in vitro. Exemplary antibodies of the disclosure that exhibit such an effect include Antibodies 23, 25, and 28-31, referring to Table 11. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP and ADCC of SIRPα-expressing myeloid cells in vitro. Exemplary antibodies of the disclosure that exhibit such an effect include Antibodies 23, 25, and 28-32, referring to Table 11. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing monocyte cells in vitro. Exemplary antibodies of the disclosure that exhibit such an effect include Antibodies 23, 28, 31-32, referring to Table 11. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing monocyte cells in vitro. Exemplary antibodies of the disclosure that exhibit such an effect include Antibodies 23, 25, and 28-31, referring to Table 11. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing monocyte cells in vitro. Exemplary antibodies of the disclosure that exhibit such an effect include Antibodies 23, 25, and 28-32, referring to Table 11. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing myeloid progenitor cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing myeloid progenitor cells in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing myeloid progenitor cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing macrophages in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce ADCP of SIRPα-expressing macrophages in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing macrophages in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing dendritic cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing dendritic cells in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing dendritic cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing basophils in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing basophils in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing basophils in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing neutrophils in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing neutrophils in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing neutrophils in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing eosinophils in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing eosinophils in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP and ADCC of SIRPα-expressing eosinophils in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC of SIRPα-expressing mast cells in vitro. In some embodiments, the ADCC is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCP of SIRPα-expressing mast cells in vitro. In some embodiments, the ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce ADCC and ADCP of SIRPα-expressing mast cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce ADCC and/or ADCP of SIRPβ1-expressing cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce ADCC and/or ADCP of SIRPβ1-expressing myeloid cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce ADCC and/or ADCP of SIRPβ1-expressing granulocytes in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the granulocytes are eosinophils, neutrophils or a combination thereof.

In some embodiments, SIRP antibodies of the disclosure are also specific to SIRPβ1 and also induce ADCC and/or ADCP of SIRPβ1-expressing monocytes in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the monocytes are classical, intermediate, non-classical, or a combination thereof.

In some embodiments, SIRP antibodies of the disclosure are also specific to SIRPβ1 and also induce ADCC and/or ADCP of SIRPβ1-expressing dendritic cells in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce ADCC and/or ADCP of SIRPβ1-expressing macrophages in vitro. In some embodiments, the ADCC and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce antibody-mediated depletion of cells where the cells do not express SIRPα, or express SIRPα only under certain physiological conditions such as when activated (e.g. activated lymphocytes). In some embodiments, SIRP antibodies of the disclosure induce antibody-mediated depletion of cells where the cells do not express SIRPβ1, or express SIRPβ1 only under certain physiological conditions. In some embodiments, SIRP antibodies of the disclosure induce ADCC of lymphocytes in vitro. In some embodiments, SIRP antibodies of the disclosure induce ADCP of lymphocytes in vitro. In some embodiments, SIRP antibodies of the disclosure induce ADCC and ADCP of lymphocytes in vitro. In some embodiments, the ADCC, and/or ADCP is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, the methods lead to ADCC in vivo, and the SIRP antibody increases ADCC by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, the methods lead to ADCP in vivo, and the SIRP antibody increases ADCP by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, the methods lead to ADCC and/or ADCP in vivo, and the SIRP antibody increases ADCC and/or ADCP by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, the methods lead to cell depletion in vivo, and the SIRP antibody increases ADCC and ADCP by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. Exemplary antibodies of the disclosure that exhibit such an effect include Antibodies 23, and 28-31, referring to Table 11.

In some embodiments, SIRP antibodies of the disclosure induce cell depletion (e.g. ADCC and/or ADCP) of SIRPγ-expressing cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce cell depletion (e.g. ADCC and/or ADCP) of SIRPγ-expressing lymphocytes in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce cell depletion (e.g. ADCC and/or ADCP) of SIRPγ-expressing T cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce cell depletion (e.g. ADCC and/or ADCP) of SIRPγ-expressing NK cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing myeloid cells in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing monocyte cells in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing neutrophils in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing eosinophils in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing basophils in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce antibody-mediated depletion of cells where the cells do not express SIRPα, or express SIRPα only under certain physiological conditions, for example such as when activated (e.g. lymphocytes). Accordingly, in some embodiments, SIRP antibodies of the disclosure induce cell depletion (e.g. ADCC and/or ADCP) of lymphocytes in vivo. Exemplary antibodies of the disclosure that exhibit such an effect include Antibodies 23, and 28-31, referring to Table 11. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure induce are also specific to SIRPα and also cell depletion (e.g. ADCC and/or ADCP) of SIRPα-expressing myeloid progenitor cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing macrophages in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing dendritic cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPα and also induce cell depletion (e.g. ADCC and/or ADCP) of SIRPα-expressing mast cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce cell depletion (e.g. ADCC and/or ADCP) of SIRPβ1-expressing cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce cell depletion (e.g. ADCC and/or ADCP) of SIRPβ1-expressing myeloid cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce cell depletion (e.g. ADCC and/or ADCP) of SIRPβ1-expressing granulocytes cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%. In some embodiments, the granulocytes comprise eosinophils, neutrophils or a combination thereof.

In some embodiments, SIRP antibodies of the disclosure are also specific to SIRPβ1 and also induce cell depletion (e.g. ADCC and/or ADCP) of SIRPβ1-expressing monocytes cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce cell depletion (e.g. ADCC and/or ADCP) of SIRPβ1-expressing macrophages in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

In some embodiments, SIRP antibodies of the disclosure are also specific to SIRPβ1 and also induce cell depletion (e.g. ADCC and/or ADCP) of SIRPβ1-expressing dendritic cells in vivo. In some embodiments, the cell depletion is increased by at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99%.

B. Therapeutic SIRP Antibodies

As discussed in Section IA above, provided herein are antibodies that recognize and bind to SIRPγ, in combination with SIRPα and/or SIRPβ1. The antibodies disclosed herein may be used for therapeutics in a subject.

Accordingly, provided herein are methods of treating a disease or condition in a subject in need thereof, the method comprising administering to the subject a therapeutically effective amount of a SIRP antibody of the disclosure, or pharmaceutical compositions thereof. In some embodiments, the subject is a mammalian subject. In some embodiments, the mammalian subject is a human subject. In some embodiments, the mammalian subject is a non-human primate, e.g. a cynomolgus monkey.

i. Treatment of Diseases/Conditions

In some embodiments, the SIRP antibodies provided herein are useful for depleting a population of cells in the subject, for the treatment of a disease or condition in the subject. In some embodiments, the therapeutic SIRP antibodies provided herein are useful for treating a disease or condition involving the overactivation or hyperproliferation of certain cells, e.g. SIRPγ-expressing cells (e.g. lymphocyte cells), optionally in combination with SIRPα and/or SIRPβ1 expressing cells (e.g., myeloid cells) as a part of the pathology.

In some embodiments, a therapeutically effective amount of the antibody or the pharmaceutical composition is sufficient to deplete a population of cells in the subject, e.g. by ADCC and/or ADCP. In some embodiments, the cells are overactivated or hyperproliferative. In some embodiments, the cells are SIRPγ-expressing cells. In some embodiments, the SIRPγ-expressing cells are lymphocytes. In some embodiments, the SIRPγ-expressing lymphocytes are selected from the group consisting of B cells, T cells and NK cells. In some embodiments, the cells are tissue resident cells. In other embodiments, the cells are circulating cells. In some embodiments, the cell depletion is antibody dose-dependent.

In some embodiments, a therapeutically effective amount of the antibody or the pharmaceutical composition is sufficient to deplete a population of SIRPα and/or SIRPβ1-expressing cells in a subject. In some embodiments, the cells are overactivated or hyperproliferative. In some embodiments, the SIRPα and/or SIRPβ1-expressing cells comprise myeloid cells. In some embodiments, the SIRPα and/or SIRPβ1-expressing cells comprise monocytes, macrophages, dendritic cells, mast cells, eosinophils, basophils and neutrophils.

In some embodiments, the disease or condition is characterized by overactivation and/or hyperproliferation of lymphocytes cells (including lymphoblast cells). In some embodiments, the disease or condition is characterized by overactivation and/or hyperproliferation of myeloid cells (including myeloid progenitor cells), and other SIRPα and/or SIRPβ1-expressing cells. Exemplary diseases associated with overactivation and/or hyperproliferation include, but are not limited to, histiocytic disorders, cytokine release syndrome (CRS), granulomatous diseases, autoimmune disorders, and hematological malignancies.

In some embodiments, the disease or disorder comprises a disease or disorder associated with lymphocytes. In some embodiments, the disease or disorder comprises a disease or disorder associated with myeloid cells. In some embodiments, the disease or disorder comprises a disease or disorder associated with both lymphocytes and myeloid cells.

In some embodiments, the disease or disorder comprises a disease or disorder associated with both lymphocytes and myeloid cells. In some embodiments, the disease or condition is a type of histiocytoses, for example hemophagocytic lymphohistiocytosis (HLH) (including primary and secondary HLH), macrophage activation syndrome, Langerhans cell histiocytosis (LCH), indeterminate cell histiocytosis, Erdheim-Chester disease (ECD), mixed LCH/ECD, Rosai Dorfman disease, malignant histiocytosis, cutaneous non-LCH histiocytoses, juvenile xanthogranuloma, virus-associated HLH, bacteria-associated HLH, parasite-associated HLH, fungal-associated (fungal induced) HLH, autoimmune disease associated HLH, or malignancy-triggered HLH.

In some embodiments, the disease or condition is associated with a non-mendelian secondary HLH (sHLH). In some embodiments, such sHLH is an infection-associated HLH, such as virus-associated HLH, bacteria-associated HLH, parasite-associated HLH, or fungal-associated HLH. Examples of virus-associated HLH include, but are not limited to, EBV-associated HLH, CMV-associated HLH, HLH associated with other defined herpes virus infections, HIV-associated HLH, Influenza-associated HLH, and HLH associated with other virus infections. In exemplary embodiments, the infection-associated sHLH is associated with an infection from a coronavirus (e.g. CoVID19, SARS (SARS-CoV), MERS), or Ebola. Examples of bacteria-associated HLH include *mycobacterium* associated HLH. Examples of parasite-associated HLH include *Leishmania*-associated or *Plasmodium*-associated HLH. Examples of fungal-induced HLH include Histoplasmosis-associated HLH.

In other embodiments, such sHLH is a malignancy-associated HLH, such as a malignancy-triggered HLH (HLH at onset of malignancy) and include hematological malignancies (e.g. T-cell lymphoblastic lymphoma/leukemia, T-cell non-lymphoblastic lymphomas, B-cell leukemias, B-cell lymphomas (non-Hodgkin's), Hodgkin's lymphomas, NK-cell lymphomas/leukemias, myeloid neoplasia, other hematological malignancies), as well as solid tumors. In other embodiments, such sHLH is a HLH occurring during chemotherapy (not associated with initial diagnosis of malignancy).

In other embodiments, such sHLH is associated with defined rheumatologic conditions (e.g. Macrophage Activation Syndrome-HLH, or MAS-HLH). These include, but are not limited to HLH associated with systemic-onset juvenile idiopathic arthritis (SoJIA), HLH associated with adult-onset Still's disease, HLH associated with systemic lupus erythematosus (SLE), HLH associated with vasculitis, HLH associated with rheumatoid arthritis, as well as HLH associated with other defined autoimmune conditions and HLH associated with an undefined autoimmune condition.

In other embodiments, such sHLH is a transplant-related HLH, such as HLH associated with a kidney transplant, or hematologic stem cell transplants.

In some embodiments, the disease or condition comprises comprises a sHLH or a cytokine release syndrome (CRS). In some embodiments, the disease or condition comprises CRS. In some embodiments, the sHLH or CRS is associated with iatrogenic immune activation, e.g. associated with checkpoint inhibitors for the treatment of malignancies, associated with T cell therapy, for example chimeric antigen receptor-T cell therapy (CAR-T) or T cell receptor T cell therapy (TCR-T), associated with NK cell activating bispecific monoclonal antibody therapy, or associated with T cell activating bispecific monoclonal antibody therapy. In other embodiments, such sHLH or CRS is associated with iatrogenic immune suppression. In other embodiments, the sHLH or CRS is associated with an infection, such as a viral infection, for example CoVID-19.

In other embodiments, the therapeutic SIRP antibodies provided herein are useful for treating a granulomatous disease or condition, or a disease characterized by the presence of multinucleated giant cells. In some embodiments, the granulomatous diseases or conditions, or giant cell diseases or conditions, comprise sarcoidosis, inflammatory bowel disease (IBD), ulcerative colitis, Crohn's disease, Takayasu arteritis, giant cell arteritis, psoriatic arthritis, granulomatosis with polyangiitis (Wegener's Granulomatosis), giant cell myocarditis, chronic granulomatous disease, eosinophilic granulomatosis with polyangiitis (Churg-Strauss Syndrome), or chronic beryllium disease (berylliosis).

In some embodiments, the disease or condition comprises a T-cell mediated disorder, including, but not limited to, aplastic anemia, cell mediated rejection of solid organ transplant, graft failure post-HSCT (hematopoietic stem cell transplant), lymphocyte-variant hypereosinophilia, atopic dermatitis, lymphocytic myocarditis, axial spondyloarthritis, celiac disease, or Rasmussen's encephalitis.

In some embodiments, the disease or condition comprises a disease or condition characterized by the aberrant activity and/or proliferation of granulocytes. In some embodiments, the granulocytes comprise eosinophils, basophils, mast cells or neutrophils.

In some embodiments, the disease or condition comprises a disease or condition is characterized by the aberrant activity and/or proliferation of eosinophils. In some embodiments, the disease or condition comprises hypereosinophilic syndrome (including primary, secondary, and idiopathic), acute eosinophilic pneumonia, chronic eosinophilic pneumonia, eosinophilic esophagitis, eosinophilic gastritis, eosinophilic gastroenteritis, eosinophilic enteritis, eosinophilic colitis, lymphocyte-variant hypereosinophilia, eosinophilic granulomatosis with polyangiitis (Churg-Strauss Syndrome), eosinophilic cardiomyopathy/Loeffler endocarditis, Löffler syndrome or episodic angioedema with eosinophilia/Gleich syndrome or lymphocyte-variant hypereosinophilia.

In some embodiments, the disease or condition comprises a disease or condition that is characterized by the aberrant activity and/or proliferation of mast cells. In some embodiments, the disease or condition comprises cutaneous mastocytosis, mastocytic enterocolitis, systemic mastocytosis, mast cell activation syndrome, hereditary alpha tryptasemia syndrome, chronic urticaria or severe allergic conjunctivitis.

In some embodiments, the disease or condition comprises a disease or condition that is characterized by the aberrant activity and/or proliferation of neutrophils. In some embodiments, the disease or condition comprises neutrophilic dermatoses, psoriatic arthritis, generalized pustular psoriasis, pyoderma gangrenosum, Sweet's syndrome, subcorneal pustular dermatosis, neutrophilic eccrine hidradenitis, bowel-associated dermatosis-arthritis syndrome (BADAS), rheumatoid neutrophilic dermatitis, or Behçet's disease.

In some embodiments, the disease or condition comprises an autoimmune disorder. In some embodiments, the autoimmune disorder involves the presentation of self antigens by antigen presenting cells occurring in germinal centers of secondary lymphoid tissue that results in the activation of autoreactive T and B cells, the latter of which produce autoantibodies that mediate cytokine release and sometimes IgG-induced phagocytosis. By targeting and depleting these antigen presenting dendritic cells and autoreactive lymphocytes, the antibodies described here can treat these diseases by halting this process of self-antigen presentation.

In some embodiments, the therapeutic SIRP antibodies provided herein are useful for treating an autoimmune or inflammatory (chronic or acute) disorder such as acute disseminated encephalomyelitis, acute respiratory distress syndrome. Addison's disease. Adult-Onset Still's disease, ankylosing spondylitis, antibody-mediated rejection (AMR), anti-glomerular basement membrane disease (Goodpasture Syndrome), catastrophic antiphospholipid syndrome, antiphospholipid syndrome, aplastic anemia, allograft transplant rejection, atopic dermatitis, atherosclerosis, autoimmune hemolytic anemia, autoimmune hepatitis, autoimmune lymphoproliferative syndrome, autoimmune neutropenia, axial spondyloarthritis. Behcet's disease, bullous pemphigoid. Castleman disease, catastrophic antiphospholipid syndrome, celiac disease, cell mediated rejection of solid organ transplant, chronic obstructive pulmonary disease (COPD). Chediak-Higashi syndrome, chronic inflammatory demyelinating polyneuropathy (CIDP), chronic neutrophilic leukemia, chronic urticaria, coronary artery disease (CAD)/peripheral artery disease (PAD). CoVID-19, cutaneous mastocytosis, eosinophilic cardiomyopathy/Loeffler endocarditis. Crohn's disease, epidermolysis bullosa acquisita. Evans syndrome, eosinophilic granulomatosis with polyangiitis (Churg-Strauss Syndrome). Felty's syndrome, general pustular psoriasis, giant cell myocarditis, graft failure post-HSCT (hematopoietic stem cell transplant), graft vs. host disease. Graves' disease. Graves ophthalmopathy, granulomatosis with polyangiitis (Wegener's Granulomatosis). Guillain-Barre syndrome. Hashimoto's thyroiditis, hereditary alpha tryptasemia syndrome, hyper IgE syndrome. Idiopathic interstitial pneumonia, idiopathic pulmonary fibrosis. IgA nephropathy, immune/idiopathic thrombocytopenia purpura, inclusion body myositis, inflammatory bowel disease. Kawasaki disease. Lambert-Eaton myasthenic syndrome (LEMS), myasthenia gravis (MG), linear IgA disease. Löffler syndrome, lupus nephritis, lupus vasculitis, systemic lupus erythematosus (SLE), mast cell activation syndrome, mastocytic enterocolitis, membranous nephropathy, microscopic polyangiitis (MPA), multiple sclerosis, myelodysplastic syndromes, myelofibrosis, myocarditis, neuromyelitis optica (NMO), neutrophilic dermatoses, paraneoplastic syndrome, *Pemphigus foliaceus, pemphigus* vulgaris, primary biliary cholangitis, primary biliary cirrhosis, primary sclerosing cholangitis, psoriatic arthritis, pyoderma gangrenosum. Rasmussen's encephalitis, rheumatoid arthritis, rheumatoid vasculitis. Schmidt syndrome, scleroderma (systemic sclerosis), Sjögren's syndrome, severe allergic conjunctivitis, Sjogren syndrome. Susac syndrome, systemic inflammatory response syndrome, systemic juvenile idiopathic arthritis, systemic lupus erythematosus, systemic mastocytosis, type 1 diabetes, ulcerative colitis, uveitis, vitiligo or X-linked lymphoproliferative disease.

In some embodiments, the therapeutic SIRP antibodies provided herein are useful for treating a hematological malignancy. In some embodiments, the hematological malignancy is selected from the group consisting of acute lymphoblastic leukemia, acute myelogenous leukemia, chronic myelogenous leukemia, chronic myelomonocytic leukemia, chronic neutrophilic leukemia, juvenile myelomonocytic leukemia, chronic eosinophilic leukemia, large granular lymphocyte leukemia. T-cell prolymphocytic leukemia, hepatosplenic lymphoma, Hodgkin's lymphomas. T-cell lymphoblastic lymphoma or leukemia, T-cell non-lymphoblastic lymphoma. NK-cell lymphoma/leukemia, myeloid neoplasia, chronic neutrophilic leukemia, and other hematological malignancies.

In other embodiments, the therapeutic SIRP antibodies provided herein are useful for treating a disease or condition associated with pathological alloantibodies or autoantibodies including myasthenia gravis, Guillain-Barre syndrome, autoimmune hemolytic anemia, immune/idiopathic thrombocytopenia purpura. Evans syndrome. Felty's syndrome, chronic inflammatory demyelinating polyneuropathy (CIDP), Lambert-Eaton myasthenic syndrome (LEMS), neuromyelitis optica (NMO), bullous pemphigoid, epidermolysis bullosa acquisita, *Pemphigus foliaceus, pemphigus* vulgaris, anti-glomerular basement membrane disease (Goodpasture Syndrome), membranous nephropathy, rheumatoid vasculitis, lupus vasculitis, scleroderma (systemic sclerosis), Behcet's disease, microscopic polyangiitis (MPA), Kawasaki disease, antiphospholipid syndrome, catastrophic antiphospholipid syndrome, Graves ophthalmopathy, Castleman disease and antibody-mediated rejection (AMR).

In some embodiments, the disease or condition comprises the disease or condition comprises hemophagocytic lymphohistiocytosis (HLH) (including primary and secondary HLH), macrophage activation syndrome. Langerhans cell histiocytosis (LCH), indeterminate cell histiocytosis, Erdheim-Chester disease (ECD), mixed LCH/ECD, Rosai Dorfman disease, malignant histiocytosis, cutaneous non-LCH histiocytosis, juvenile xanthogranuloma, virus-associated HLH, bacteria-associated HLH, parasite-associated HLH, fungal-associated/fungal-induced HLH, malignancy-triggered HLH. HLH occurring during chemotherapy. HLH associated with systemic-onset juvenile idiopathic arthritis (SoJIA), HLH associated with adult-onset Still's disease. HLH associated with systemic lupus erythematosus (SLE), HLH associated with vasculitis. HLH associated with autoimmune conditions. HLH associated with a kidney transplant. HLH associated with hematologic stem cell transplants, sHLH or CRS associated with checkpoint inhibitors for the treatment of malignancies, sHLH or CRS associated with associated with T cell therapy, sHLH or CRS associated with chimeric antigen receptor (CAR) T cell therapy, sHLH or CRS associated with T cell activating bispecific monoclonal antibody therapy, cytokine release syndrome (CRS), systemic mastocytosis, hypereosinophilic syndrome (including primary, secondary, and idiopathic), hyper IgE syndrome. X-linked lymphoproliferative disease, graft vs. host disease, type 1 diabetes, systemic lupus erythematosus, lupus nephritis, systemic inflammatory response syndrome, acute respiratory distress syndrome, autoimmune lymphoproliferative syndrome. X-linked hyper IgM syndrome, paraneoplastic syndrome. Susac syndrome, linear IgA disease, autoimmune neutropenia, idiopathic pulmonary fibrosis, inclusion body myositis, vitiligo. Addison's disease. Graves' disease. Hashimoto's thyroiditis. Schmidt syndrome, acute disseminated encephalomyelitis, sarcoidosis, ankylosing spondylitis, inflammatory bowel disease, ulcerative colitis. Crohn's disease, eosinophilic granulomatosis with polyangiitis, pyoderma gangrenosum, giant cell arteritis, rheumatoid arthritis, systemic juvenile idiopathic arthritis. Sjogren's syndrome, primary sclerosing cholangitis, primary biliary cholangitis, myasthenia gravis, multiple sclerosis. Guillain-Barre syndrome, acute lymphoblastic leukemia, acute myelogenous leukemia, chronic myelogenous leukemia, chronic myelomonocytic leukemia, juvenile myelomonocytic leukemia, chronic eosinophilic leukemia, large granular lymphocyte leukemia. T-cell prolymphocytic leukemia, hepatosplenic lymphoma. Hodgkin's lymphoma. T-cell lymphoblastic lymphoma/leukemia. T-cell non-lymphoblastic lymphoma. B-cell leukemia. B-cell lymphoma (non-Hodgkin's). NK-cell lymphoma or leukemia, myeloid neoplasia, autoimmune hemolytic anemia, immune/idiopathic thrombocytopenia purpura. Evans syndrome. Felty's syndrome, chronic inflammatory demyelinating polyneuropathy (CIDP). Lambert-Eaton myasthenic syndrome (LEMS), neuromyelitis optica (NMO), bullous pemphigoid, epidermolysis bullosa acquisita, *Pemphigus foliaceus, pemphigus* vulgaris, anti-glomerular basement membrane disease (Goodpasture Syndrome), membranous nephropathy, rheumatoid vasculitis, lupus vasculitis, scleroderma (systemic sclerosis). Behcet's disease, granulomatosis with polyangiitis (Wegener's Granulomatosis), eosinophilic granulomatosis with polyangiitis (Churg-Strauss Syndrome), microscopic polyangiitis (MPA), Kawasaki disease, antiphospholipid syndrome, catastrophic antiphospholipid syndrome, Graves ophthalmopathy, Castleman disease, antibody-mediated rejection (AMR), acute eosinophilic pneumonia, chronic eosinophilic pneumonia, eosinophilic esophagitis, eosinophilic gastritis, eosinophilic gastroenteritis, eosinophilic enteritis, eosinophilic colitis, uveitis, giant cell myocarditis, cutaneous mastocytosis, mastocytic enterocolitis, mast cell activation syndrome, IgA nephropathy, Chediak-Higashi syndrome, eosinophilic cardiomyopathy/Loeffler endocarditis, acute kidney injury, chronic kidney disease, coronary artery disease (CAD)/peripheral artery disease (PAD), myelofibrosis, IgG4-related disease, Löffler syndrome, chronic neutrophilic leukemia, myocarditis, episodic angioedema with eosinophilia/Gleich syndrome, idiopathic interstitial pneumonia, hereditary alpha tryptasemia syndrome, chronic urticaria, severe allergic conjunctivitis, Adult-onset Still's, aplastic Anemia, cell mediated rejection of solid organ transplant, graft failure Post-hematopoietic stem cell transplant (HSCT), lymphocyte-variant hypereosinophilia, myelodysplastic syndromes, atopic dermatitis, axial spondyloarthritis, celiac disease, hyperthyroidism, Rasmussen's encephalitis, chronic beryllium disease (Berylliosis), Takayasu arteritis, autoimmune hepatitis, neutrophilic dermatoses, psoriatic arthritis, Corona Virus Disease 2019 (CoVID-19), or general pustular psoriasis.

D. Pharmaceutical Compositions

The disclosure also provides pharmaceutical compositions comprising any one of the SIRP antibodies disclosed herein, and optionally a pharmaceutical acceptable excipient or carrier. In some embodiments, the pharmaceutical composition is sterile. The pharmaceutical compositions may be formulated to be compatible with their intended routes of administration. In some embodiments, the pharmaceutical compositions of the disclosure are suitable for administration to a human subject.

E. Combination Therapies

The administration of any one of the therapeutic SIRP antibodies provided herein may be in combination with any other known drugs or treatments for diseases or conditions as described in IIC. In some embodiments, the disease or condition is associated with overactivation and/or hyperproliferation of myeloid cells, lymphocytes, or other cells expressing SIRPα, SIRPβ1, or SIRPγ. In some embodiments, the disease or condition is an autoimmune disease or condition. In some embodiments, the disease or condition is a neoplastic disorder or malignancy. In exemplary embodiments, the disease or condition being treated is a hyperinflammatory syndrome such as HLH, or CRS (e.g. an autoimmune related CRS, or CRS associated with adoptive cell therapy) in which a therapeutic SIRP antibody may be used in combination with corticosteroids (e.g.—dexamethasone).

In some embodiments, a therapeutic SIRP antibody is provided to treat a CRS or sHLH that occurs due to infections, in combination with the appropriate antiviral for the treatment of a viral infection, or in combination with the appropriate antibiotic therapy for the treatment of a bacterial infection. By way of example only, a therapeutic antibody of the disclosure could be administered in combination with an antiviral therapy for example, an antiviral therapy for CoVID-19, SARS (SARS-CoV), MERS, Ebola, or Epstein Barr virus, or in combination with an antibiotic therapy, for example an antibiotic therapy for the treatment of sepsis. In some embodiments, the SIRP antibody is administered in combination with a standard therapy for the infection.

In some embodiments, a therapeutic SIRP antibody provided herein to treat a CRS or sHLH that occurs due to malignancies, is used in combination with the appropriate chemotherapeutic or malignancy-associated treatment of an oncological indication. In some embodiments, a therapeutic SIRP antibody provided herein to treat a CRS or sHLH that occurs due to an autoimmune disorder, such as a rheumatological disorder including systemic lupus erythematosus or rheumatoid arthritis, in combination with the appropriate treatment of such a disorder. Exemplary appropriate treatments include, but are not limited to, corticosteroids.

F. Administration of Therapeutic SIRP Antibodies

The in vivo administration of the therapeutic SIRP antibodies described herein may be carried out intravenously, intramuscularly, subcutaneously, topically, orally, transdermally, intraperitoneally, intraorbitally, intrathecally, intraventricularly, intranasally, transmucosally, through implantation, or through inhalation. Intravenous administration may be carried out via injection or infusion. In some embodiments, the SIRP antibodies of the disclosure are administered intravenously. In some embodiments, the SIRP antibodies of the disclosure are administered subcutaneously. Administration of the therapeutic SIRP antibodies may be performed with any suitable excipients, carriers, or other agents to provide suitable or improved tolerance, transfer, delivery, and the like.

G. Diagnostic Antibodies

The antibodies provided herein may also be used for diagnostic purposes. For example, for those SIRP antibodies which bind to SIRPα, diagnostic antibodies could be used for detecting the presence of a SIRPα mediated disorder, or for detecting SIRPα levels in a subject prior to dosing (e.g. as a companion diagnostic).

III. Kits and Articles of Manufacture

The disclosure also provides a kit or article of manufacture comprising any one of the antibodies disclosed herein, or any pharmaceutical composition disclosed herein. In some embodiments, the kits may further include instructional materials for carrying out any of the methods disclosed herein. In some embodiments, the kits may further include sterile containers or vials for holding the antibodies and/or pharmaceutical compositions disclosed herein. In some embodiments, the kits may further include sterile delivery devices for administering the antibodies and/or pharmaceutical compositions disclosed herein. In some embodiments, an article of manufacture comprises any pharmaceutical composition of the disclosure.

EXAMPLES

Example 1: Hybridoma Library Screens for Identification of Anti-Human SIRP Antibodies Anti-human SIRP monoclonal antibodies (referred to interchangeably in these examples as SIRP antibodies) were identified from various rodent models of immunization. Rodent strains were immunized with the extracellular domain of human SIRPα (hSIRPα). Using standard techniques, hybridoma libraries (six libraries) were generated from the splenocytes of immunized animals. Anti-hSIRPα antibody-producing clones were identified by flow cytometric analyses of hSIRPα-expressing cells incubated in the supernatant of individual clones. Twelve individual clones were identified (Antibodies 1, 3, 4, and 7-15). Antibodies 1, 3-4 and 7-14 have a human variable region and a rat IgG2b Fc domain. Antibody 15 has a mouse variable region and a mouse IgG2a Fc domain.

Example 2: Binding of SIRP Antibodies to SIRPα Protein

Selected hybridoma supernatants of Example 1 were further tested for binding to human SIRPα V1 and cynomolgus monkey SIRPα by enzyme-linked immunosorbent assay (ELISA). Briefly, 1 μg/mL of the extracellular domain of the SIRPα was coated onto high protein-binding plates and blocked. Supernatants were diluted 1:5 and added to coated plates. The antibodies were detected by anti-rat or anti-mouse IgG antibodies and a chemiluminescent substrate. FIG. 1A shows the results of binding of Antibodies 1, 3, 4, 7-15. The data depict the relative luminescence units read by a plate-reader capable of detecting chemiluminescence.

Figure 1B:
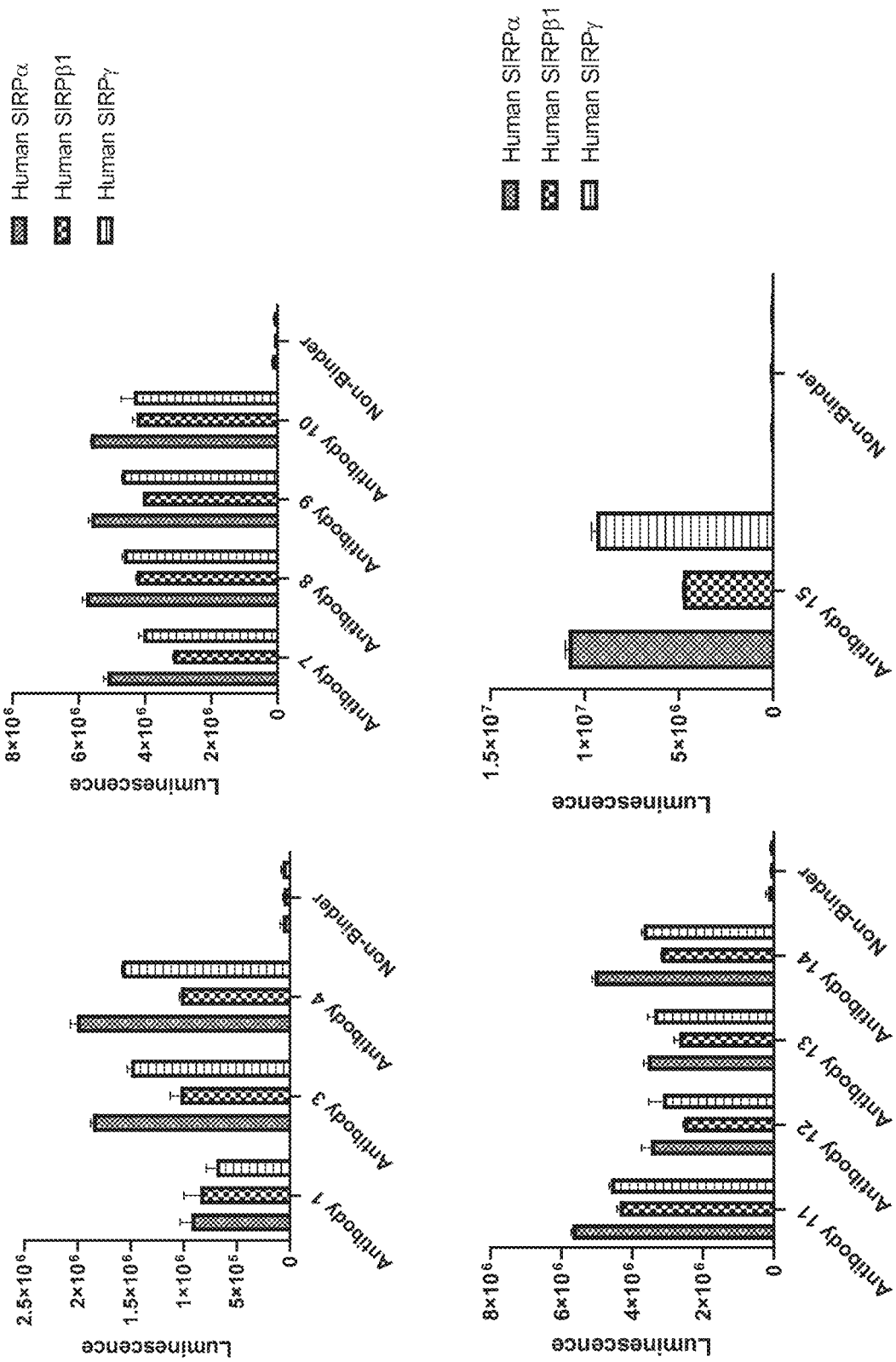
FIG. 1B shows binding of selected antibodies of the disclosure to human SIRPα, SIRPβ1 and SIRPγ by ELISA.

Selected hybridoma supernatants of Example 1 were further tested for binding to human SIRPα V1, SIRPβ1, and SIRPγ by enzyme-linked immunosorbent assay (ELISA). Briefly, 2 μg/mL of the extracellular domain of each of the SIRPs was coated onto high protein-binding plates and blocked. Supernatants were added undiluted to coated plates. The antibodies were detected by anti-rat or anti-mouse IgG antibodies and a chemiluminescent substrate. FIG. 1B shows the results of binding of Antibodies 1, 3, 4, 7-15. The data depict the relative luminescence units read by a plate-reader capable of detecting chemiluminescence.

Figure 2D:
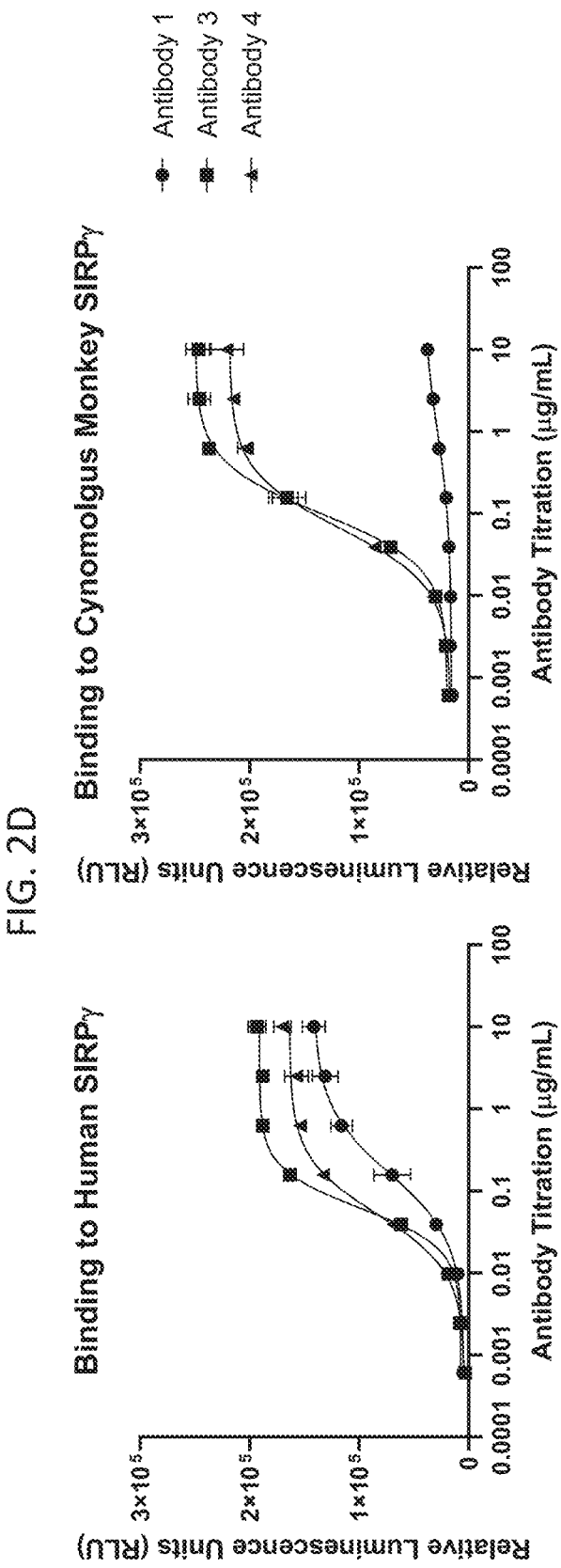
FIG. 2D shows binding curves of selected antibodies to human and cynomolgus monkey SIRPγ by ELISA.
Figure 2F:
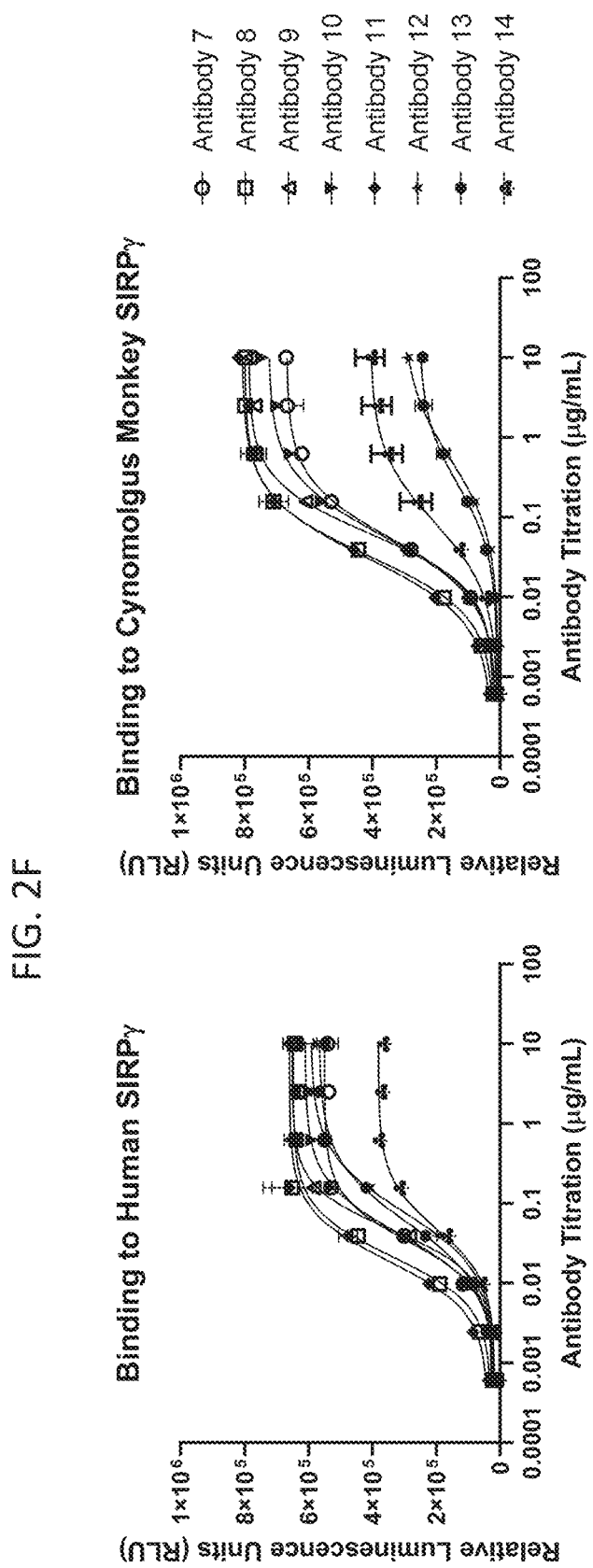
FIG. 2F shows binding curves of selected antibodies to human and cynomolgus monkey SIRPγ by ELISA.
Figure 2G:
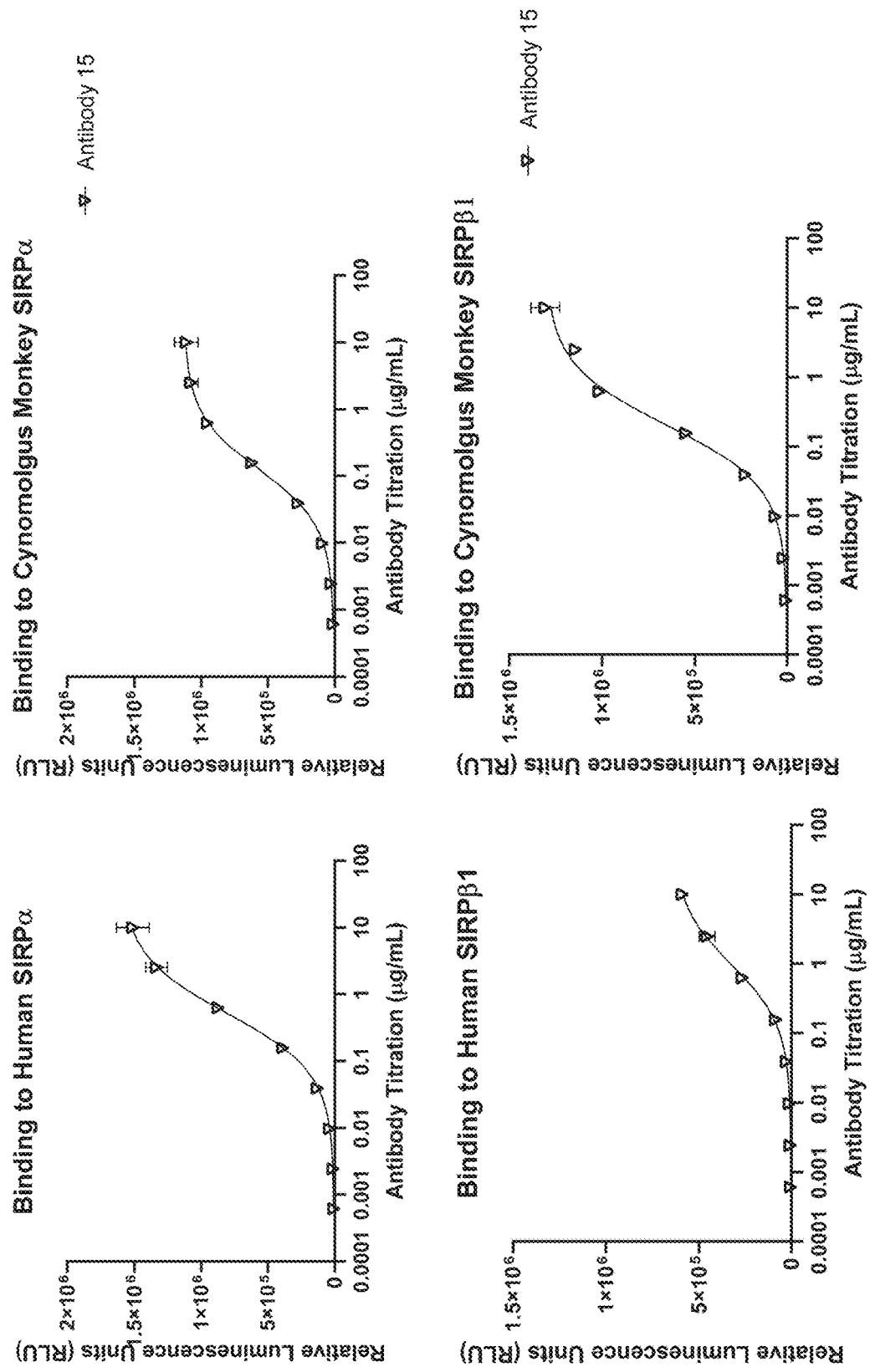
FIG. 2G shows binding curves of Antibody 15 to human and cynomolgus monkey SIRPα (top row) and SIRPβ1 (bottom row) by ELISA.
Figure 2H:
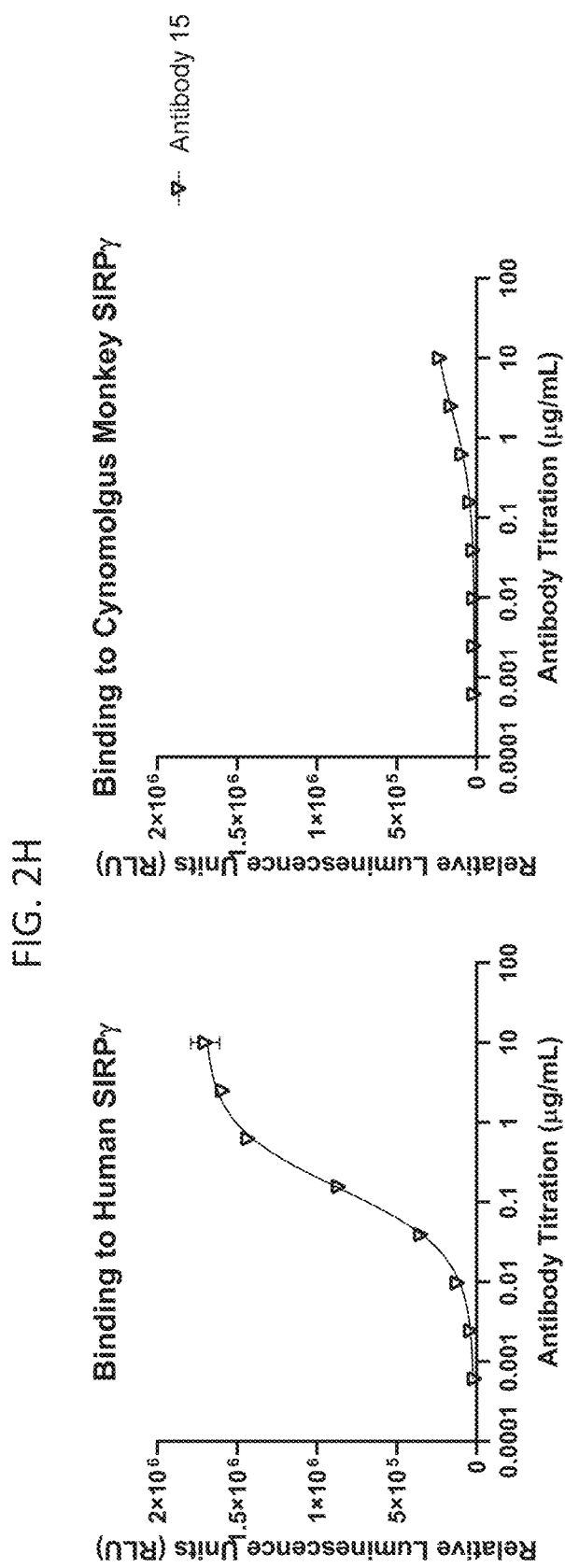
FIG. 2H shows binding curves of Antibody 15 to human and cynomolgus monkey SIRPγ by ELISA.

FIGS. 2A-2B shows binding curves of SIRP antibodies to human SIRPα V1 and cynomolgus monkey SIRPα by ELISA. Select SIRP antibodies were purified by Protein G from hybridoma supernatants and analyzed in a titration via ELISA. Briefly, 1 μg/mL of extracellular domain SIRPα was coated onto high protein-binding plates and blocked. Purified antibodies were added in a titration to the coated plates.

The antibodies were detected by an anti-rat IgG antibody and a chemiluminescent substrate.

FIGS. 2C-2H shows binding curves of SIRP antibodies to human SIRPα V1, human SIRPβ1, human SIRPγ, cynomolgus monkey SIRPα, cynomolgus monkey SIRPβ1, and cynomolgus monkey SIRPγ by ELISA. Select SIRP antibodies were purified by Protein G from hybridoma supernatants and analyzed in a titration via ELISA. Briefly, 2 μg/mL of extracellular domain of each of the SIRPs was coated onto high protein-binding plates and blocked. Purified antibodies were added in a titration to the coated plates. The antibodies were detected by an anti-rat IgG or an anti-mouse IgG antibody and a chemiluminescent substrate.

FIGS. 3A-3C show binding curves of SIRP antibodies and two isotype controls with human Fc to human SIRPα V1, human SIRPβ1, human SIRPγ and cynomolgus monkey SIRPα by ELISA. Select SIRP antibodies from Example 1 were fully made human. Isotype control 1 was an unrelated human IgG1 antibody with irrelevant CDRs. Isotype control 2 was the same as isotype control 1 but contained the same amino acid substitutions in the Fc region as some of the selected SIRP antibodies for increased FcγR binding (referring to Table 11). DNA was transiently transfected into CHO cells for 7 days. Antibodies were purified by Protein A from cell supernatants and analyzed in a titration via ELISA as previously described in FIGS. 2A-2B using an anti-human IgG antibody as the detection antibody.

Figure 3D:
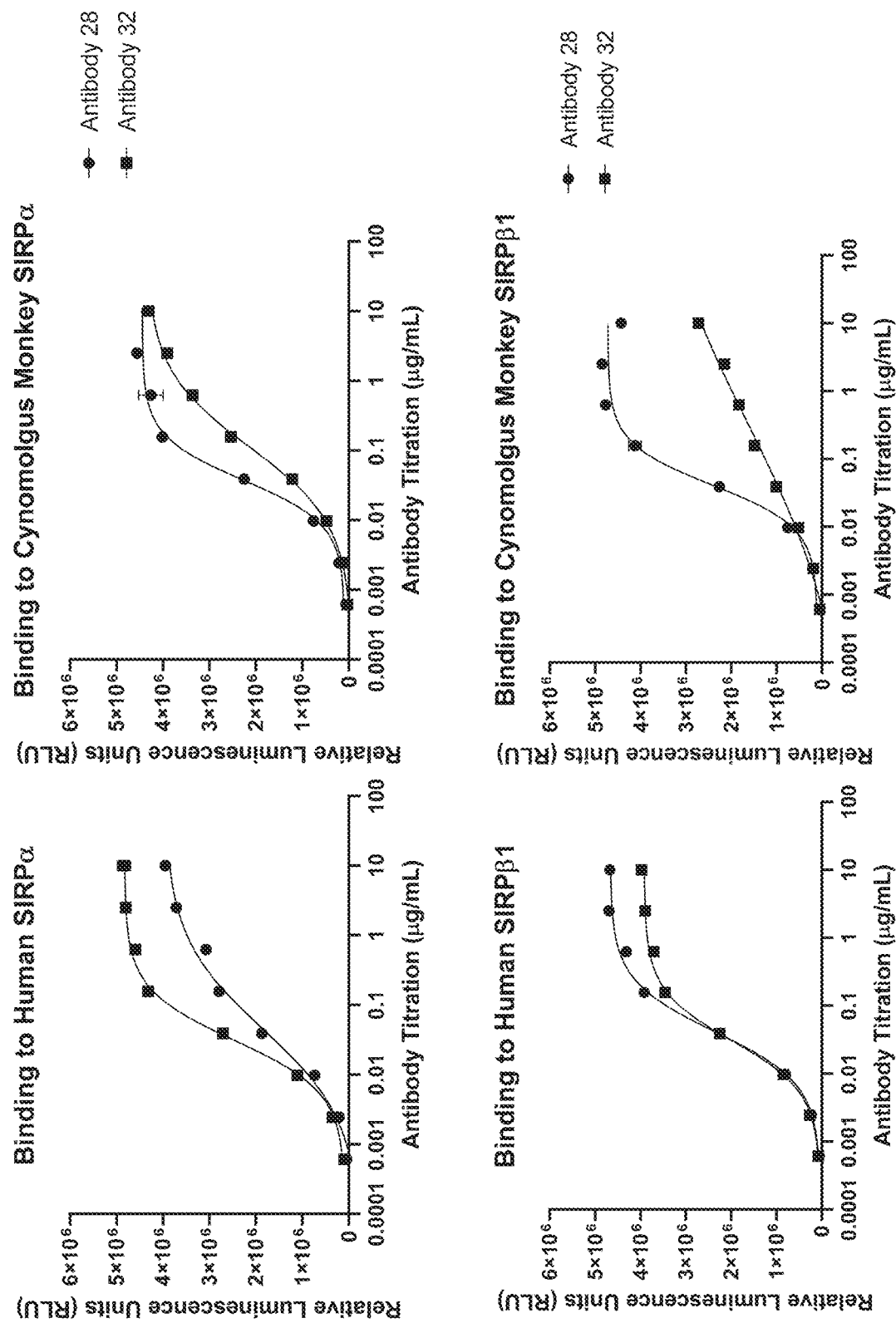
FIG. 3D shows binding curves of selected antibodies of the disclosure to human and cynomolgus monkey SIRPα (top row) and SIRPβ1 (bottom row) by ELISA.
Figure 3E:
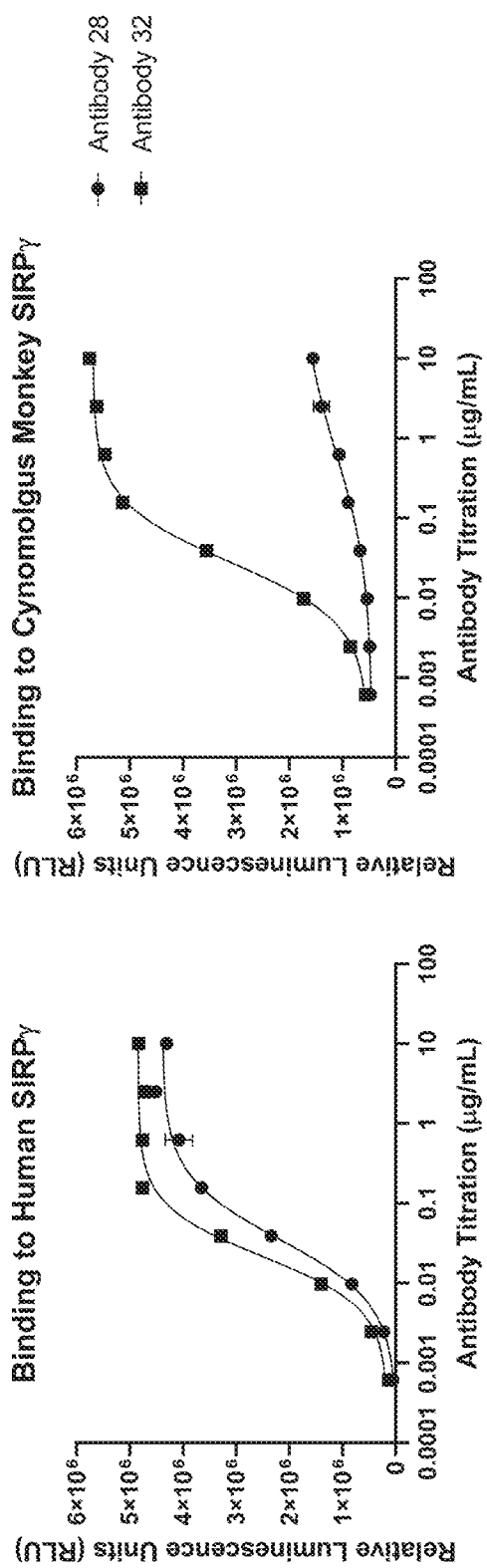
FIG. 3E shows binding curves of selected antibodies of the disclosure to human and cynomolgus monkey SIRPγ by ELISA.

FIGS. 3D-3E shows binding curves of SIRP antibodies with human Fc to human SIRPα V1, human SIRPβ1, human SIRPγ, cynomolgus monkey SIRPα, cynomolgus monkey SIRPβ, and cynomolgus monkey SIRPγ by ELISA. Select SIRP antibodies from Example 1 were fully made human. DNA was transiently transfected into CHO cells for 7 days. Antibodies were purified by Protein A from cell supernatants and analyzed in a titration via ELISA as previously described in FIG. 2C-2H using an anti-human IgG antibody as the detection antibody.

Selected antibodies were tested for their affinities to two hSIRPα variants (V1 and V2), and to cynomolgus monkey (herein referred to as "cyno") SIRPα. The composition of these antibodies is presented in Tables 10 and 11. The affinities of these SIRP antibodies were determined using surface plasmon resonance. The SIRP antibodies were flowed onto a chip and captured by an anti-mouse IgG or an anti-human IgG covalently coupled to the surface of the chip. A three-point titration of the extracellular binding domain of hSIRPα was performed per the manufacturer's recommended protocols. The resulting kinetic data were analyzed and fitted globally using a 1:1 binding model and calculated affinities are presented in Table 13 and Table 14 below: The tables show the KD (affinity) of binding of selected antibodies to monomeric human SIRPα and monomeric cynomolgus monkey SIRPα, as assayed by BIACORE.

Select SIRP antibodies were tested for their affinities to human SIRPα, SIRPβ1, and SIRPγ using a biolayer interferometry (BLI) Octet system (Pall ForteBio). The composition of these antibodies is presented in Tables 10 and 11. Each SIRP antibody with rat or mouse Fc was immobilized on a biosensor tip by an anti-mouse IgG capture (AMC). Antibodies with human Fc were digested with gingipain K enzyme to yield monomeric F(ab'), biotinylated, then coated onto streptavidin biosensors. SIRP-His monomer protein at three concentrations (100 nM, 33.3 nM, 11.1 nM) was exposed to the biosensor to measure on-rate kinetics of SIRP antibodies binding to SIRP-His protein. The biosensors were then exposed to wash buffer to measure off-rate kinetics. The resulting kinetic data were analyzed and fitted using a 1:1 binding model with $k_{on}$ and $k_{dis}$ fitted separately at each SIRP-His protein concentration. KD affinities were calculated as $k_{dis}$ to $k_{on}$ ratio at each concentration of SIRP-His and averaged. This average of the KD affinities for each antibody is presented in Table 15 below. The table shows the KD of binding of selected antibodies to monomeric human SIRPα, SIRPβ1, and SIRPγ, as assayed by ForteBio Octet.

TABLE 13

Affinities ($K_D$) of SIRP Antibodies with rat Fc to Human SIRPα V1 and Cyno SIRPα

| Antibody No. | Human SIRPα V1 (M) | Cyno SIRPα (M) |
|---|---|---|
| 1 | 5.79E−07 | 5.81E−07 |
| 3 | 4.57E−09 | 5.13E−07 |
| 7 | 4.98E−08 | 5.61E−08 |
| 13 | 1.26E−08 | 1.67E−08 |

TABLE 14

Affinities ($K_D$) of SIRP Antibodies with human Fc to Human SIRPα V1 and Cyno SIRPα

| Antibody No. | Human SIRPα V1 (M) | Human SIRPα V2 (M) | Cyno SIRPα (M) |
|---|---|---|---|
| 21 | 3.01E−08 | 3.66E−08 | 7.54E−08 |
| 23 | 3.23E−07 | 3.74E−07 | 3.84E−07 |
| 24 | 2.89E−09 | 2.26E−08 | 1.50E−08 |
| 25 | 1.14E−08 | 9.09E−09 | 1.26E−08 |
| 26 | 3.89E−08 | not tested | 6.60E−08 |
| 28 | 3.11E−07 | 3.73E−07 | 3.61E−07 |
| 29 | 8.32E−9 | 1.03E−08 | 1.11E−08 |

TABLE 15

Affinities ($K_D$) of SIRP Antibodies with rat, mouse, or human Fcs to Human SIRPα V1, SIRPβ1, and SIRPγ

| Antibody No. | Human SIRPα V1 (M) | Human SIRPβ1 (M) | Human SIRPγ (M) |
|---|---|---|---|
| 1 | 3.71E−08 | 3.52E−06 | 9.73E−07 |
| 3 | 3.10E−09 | 7.50E−06 | 1.03E−07 |
| 4 | 4.61E−08 | N/A | 2.41E−08 |
| 7 | 3.83E−08 | N/A | 3.27E−07 |
| 8 | 4.66E−08 | 7.89E−08 | 5.00E−08 |
| 9 | 1.24E−09 | 1.36E−08 | 8.05E−09 |
| 10 | 5.76E−08 | N/A | 1.37E−09 |
| 11 | 3.74E−09 | 6.19E−08 | 1.33E−08 |
| 12 | 5.31E−09 | N/A | <1.0E−12 [+] |
| 13 | 9.22E−10 | 2.99E−06 | <1.0E−12 [+] |
| 14 | 9.84E−06 | N/A | 3.87E−08 |
| 15 | 2.44E−10 | N/A | 5.44E−08 |
| 28 | 1.49E−08 | 5.55E−07 | 1.34E−06 |

Figure 4A:
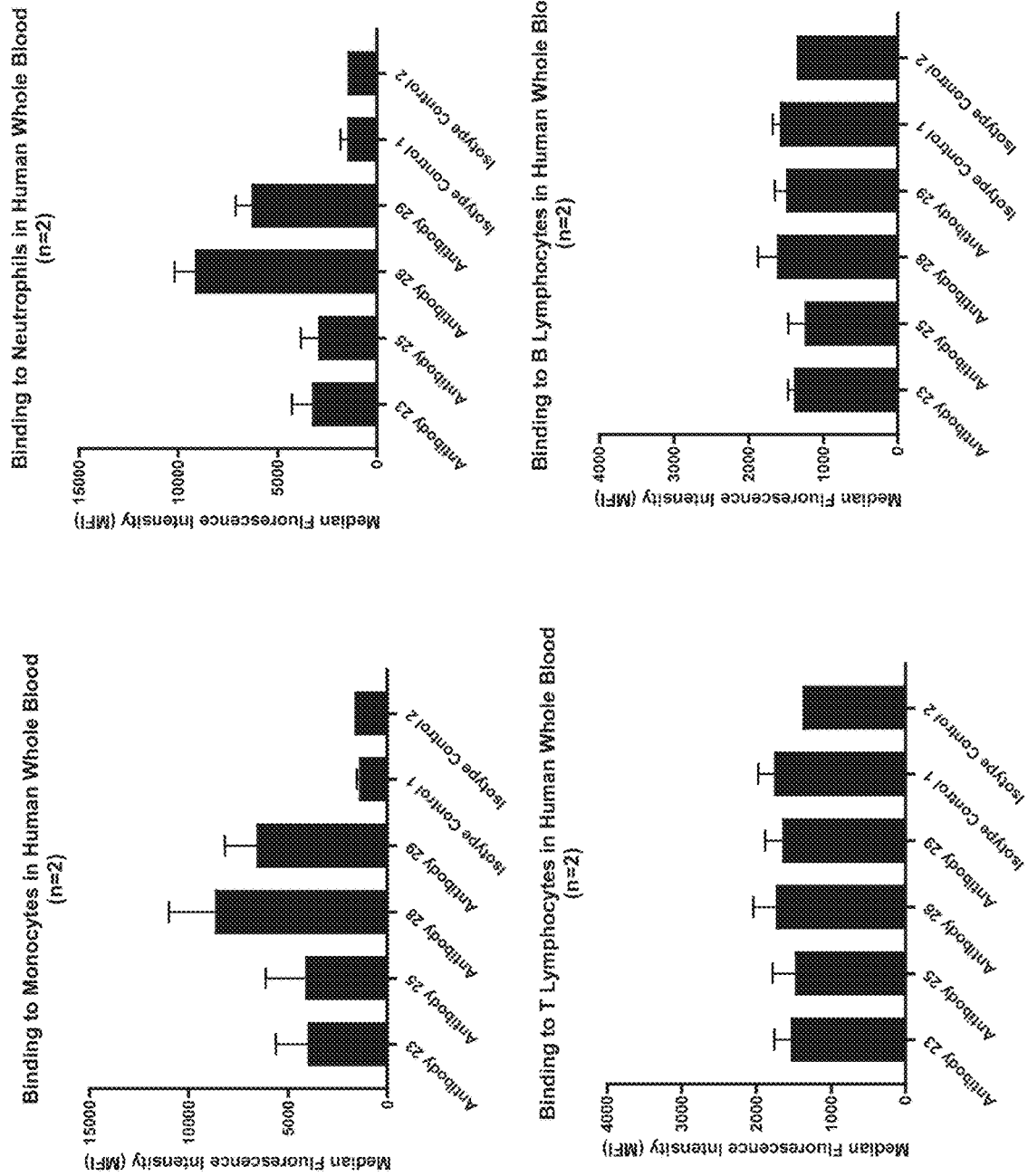
FIG. 4A shows the binding curves of selected antibodies of the disclosure to monocytes, neutrophils, T lymphocytes and B lymphocytes in human whole blood by flow cytometry.
Figure 4B:
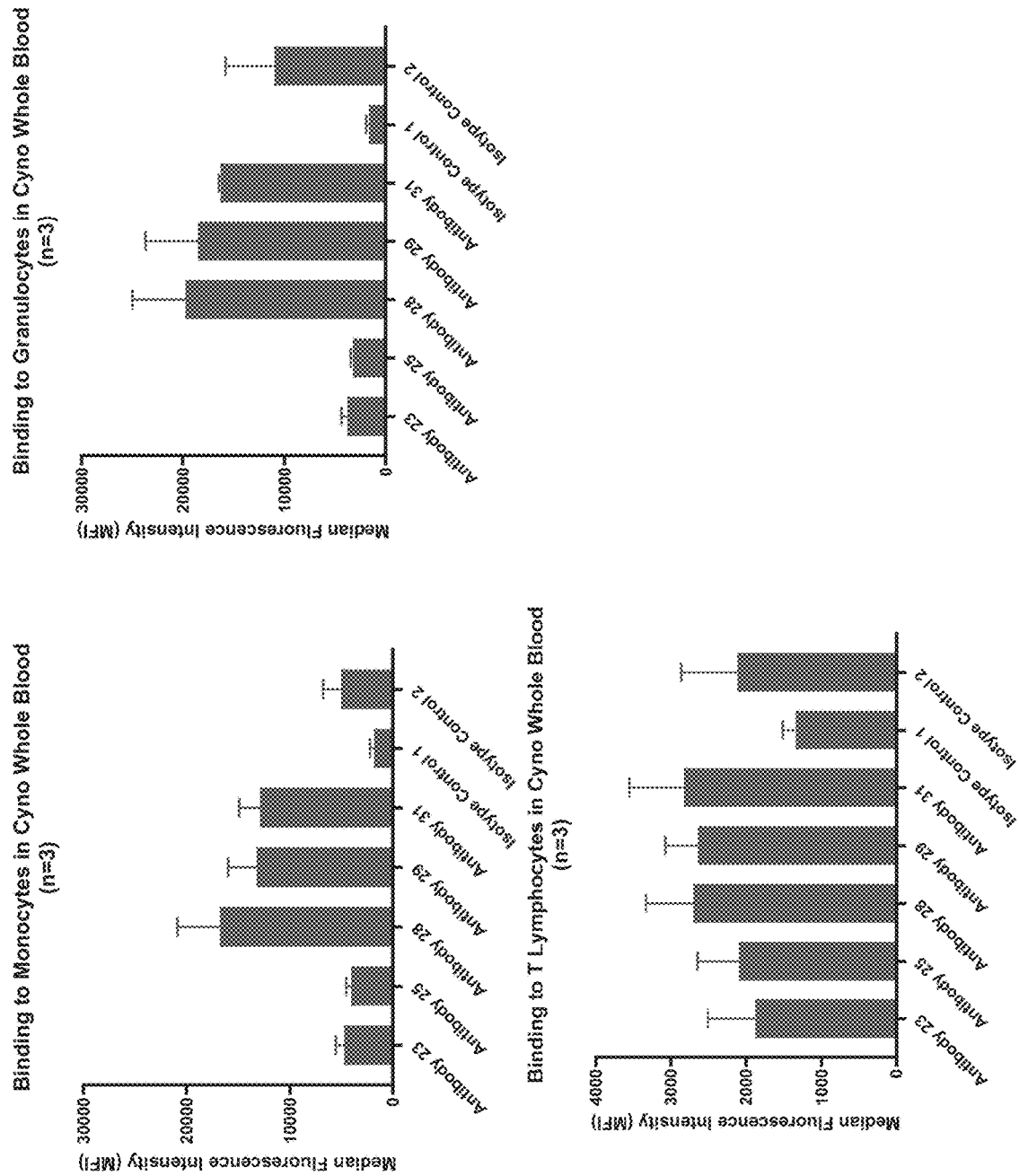
FIG. 4B shows the binding curves of selected antibodies of the disclosure to monocytes, granulocytes and T lymphocytes in cynomolgus monkey (cyno) whole blood by flow cytometry.

N/A = Not applicable, fit $R^2 < 0.75$
[+] No dissociation was seen in the time frame (600 seconds) of the assay Example 3: Binding of SIRP Antibodies to Cells In Vitro Via Flow Cytometry Selected antibodies and two isotype controls were tested for binding to human monocytes, neutrophils, T lymphocytes, and B lymphocytes. FIG. 4A shows the results of binding studies performed with SIRP antibodies to monocytes, neutrophils, T lymphocytes, and B lymphocytes in human whole blood compared to two isotype controls. 50 μg/mL fluorescent dye-conjugated SIRP antibodies or isotype controls were incubated with whole blood from two normal donors. Positive signal was detected on monocytes and neutrophils via flow cytometry. No signal was detected for T lymphocytes and B lymphocytes when compared to isotype controls. Monocytes were identified as the CD45+ and CD14+ population. Neutrophils were identified as the CD45+, CD14+, CD19−, SSC$^{high}$, and CD16+ population. T lymphocytes were identified as the CD45+, CD14−, CD19−, SSC$^{low}$, CD3+, and CD16− population. B lymphocytes were identified as the CD45+, SSC$^{low}$, and CD19+ population. Graphs depict the median fluorescence intensity (MFI) of each population. Selected antibodies and two isotype controls were tested for binding to cynomolgus monkey monocytes, granulocytes, and T lymphocytes. Isotype controls used were the same as for human binding experiments. FIG. 4B shows the results of binding studies performed with SIRP antibodies and isotype controls to monocytes, granulocytes, and T lymphocytes in cyno whole blood. 50 µg/mL fluorescent dye-conjugated SIRP antibodies were incubated with whole blood from three normal donors. Positive signal was detected on monocytes, granulocytes, and T lymphocytes via flow cytometry. Monocytes were identified as the CD45+ and CD14+ population. Granulocytes were identified as the CD45+, CD14−, CD19−, and SSC$^{high}$ population. T lymphocytes were identified as the CD45+, CD14−. CD19−, SSC$^{low}$, CD3+, and CD16− population. Graph depicts the median fluorescence intensity (MFI) of each population.

Figure 4C:
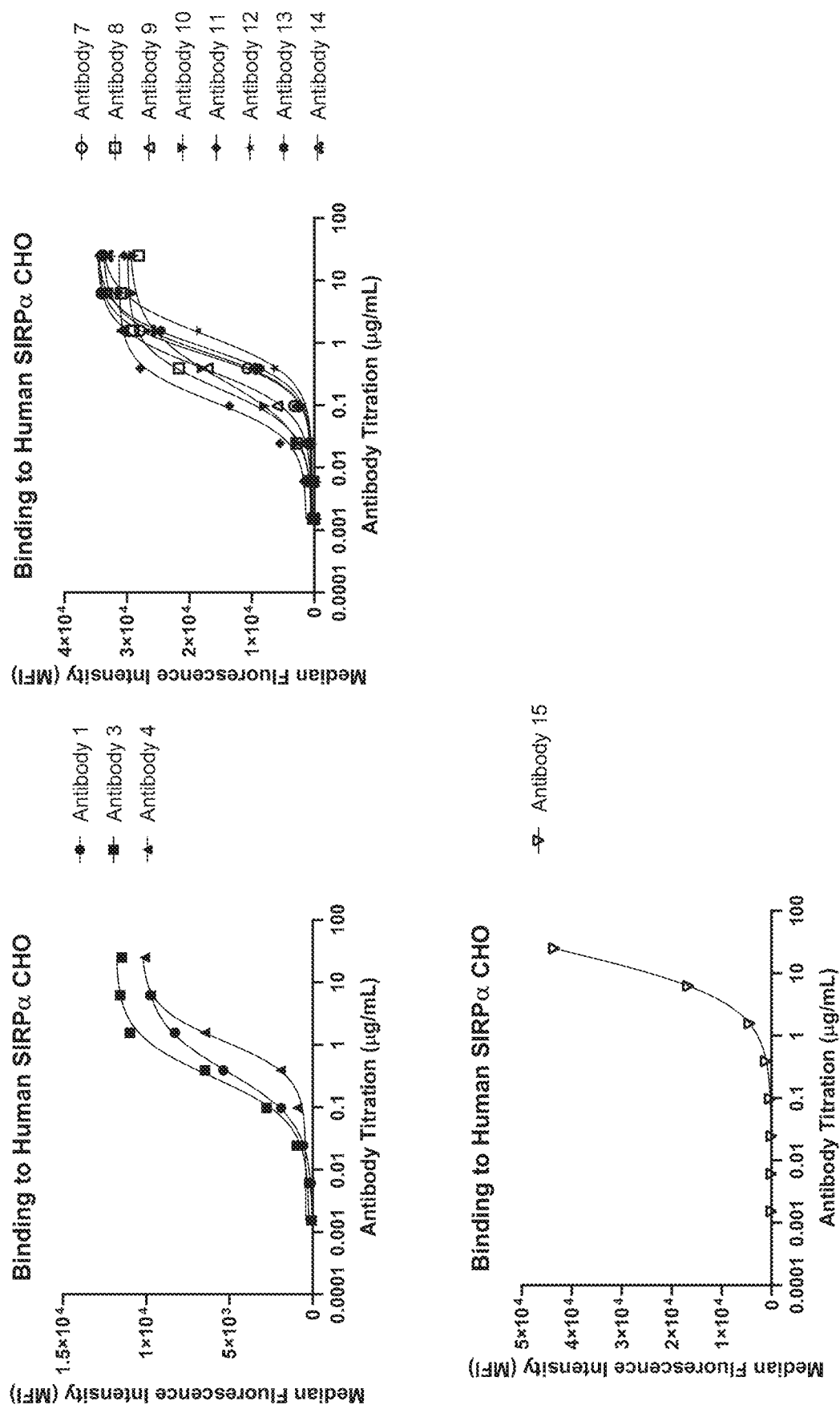
FIG. 4C shows binding curves of selected antibodies of the disclosure to human SIRPα-expressing CHO cells by flow cytometry.
Figure 4D:
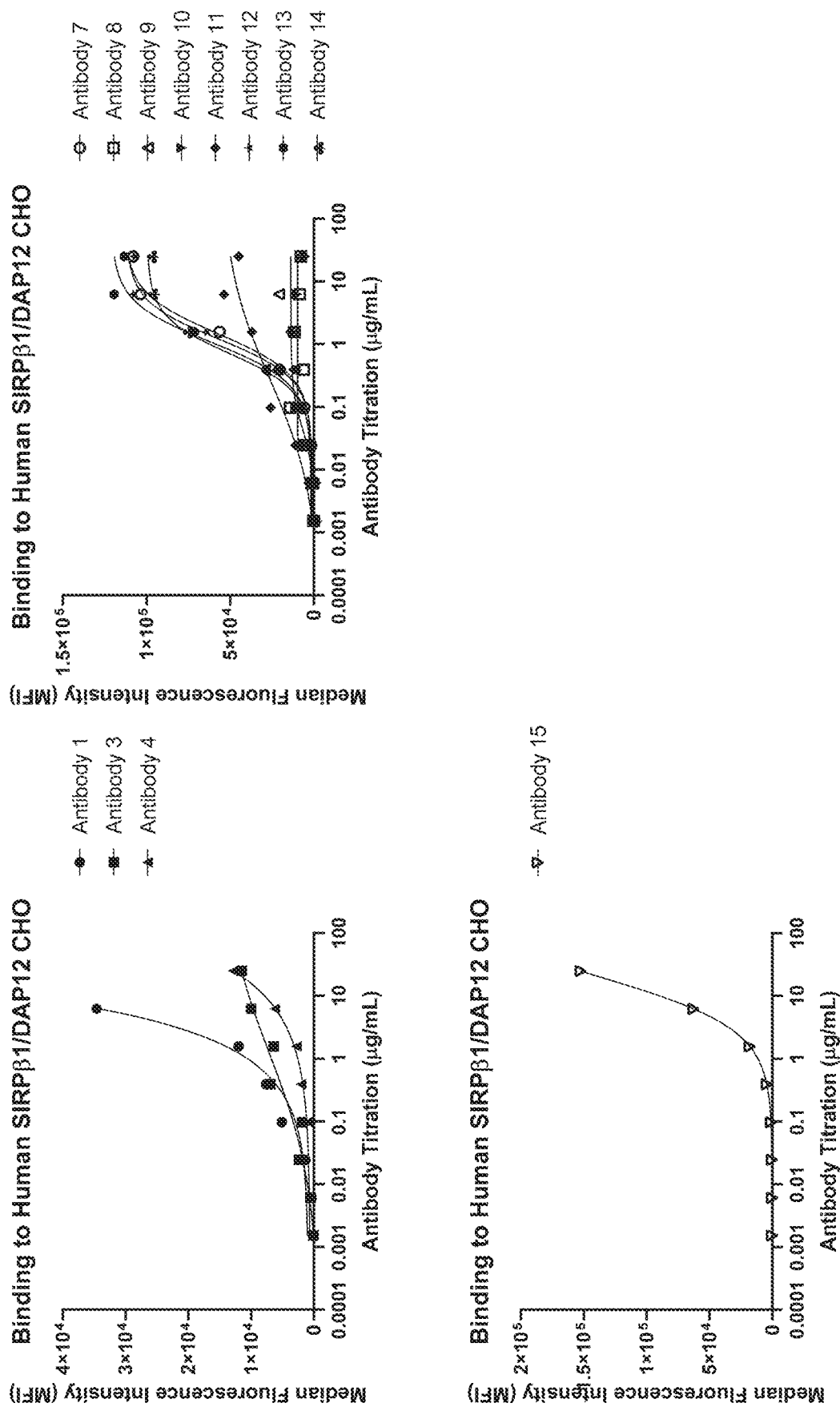
FIG. 4D shows binding curves of selected antibodies of the disclosure to human SIRPβ1/DAP12-expressing CHO cells by flow cytometry.

Selected antibodies were tested for binding to stably transfected human SIRPα, SIRPβ1 (co-transfected with DAP12), or SIRPγ Chinese hamster ovary (CHO) cells via flow cytometry. A titration of SIRP antibodies was added to the cells and detected using a fluorescently labelled secondary antibody. Graph depicts the median fluorescence intensity (MFI) at each concentration. FIGS. 4C-4E shows the binding curves of SIRP antibodies to human SIRPα. SIRPβ, or SIRPγ-expressing CHO cells detected using an anti-rat or anti-mouse IgG antibody. FIG. 4F shows the binding curves of SIRP antibodies to human SIRPα, SIRPβ, or SIRPγ-expressing CHO cells detected using an anti-human IgG antibody.

Example 4: Effect of SIRP Antibodies on ADCC

Figure 5:
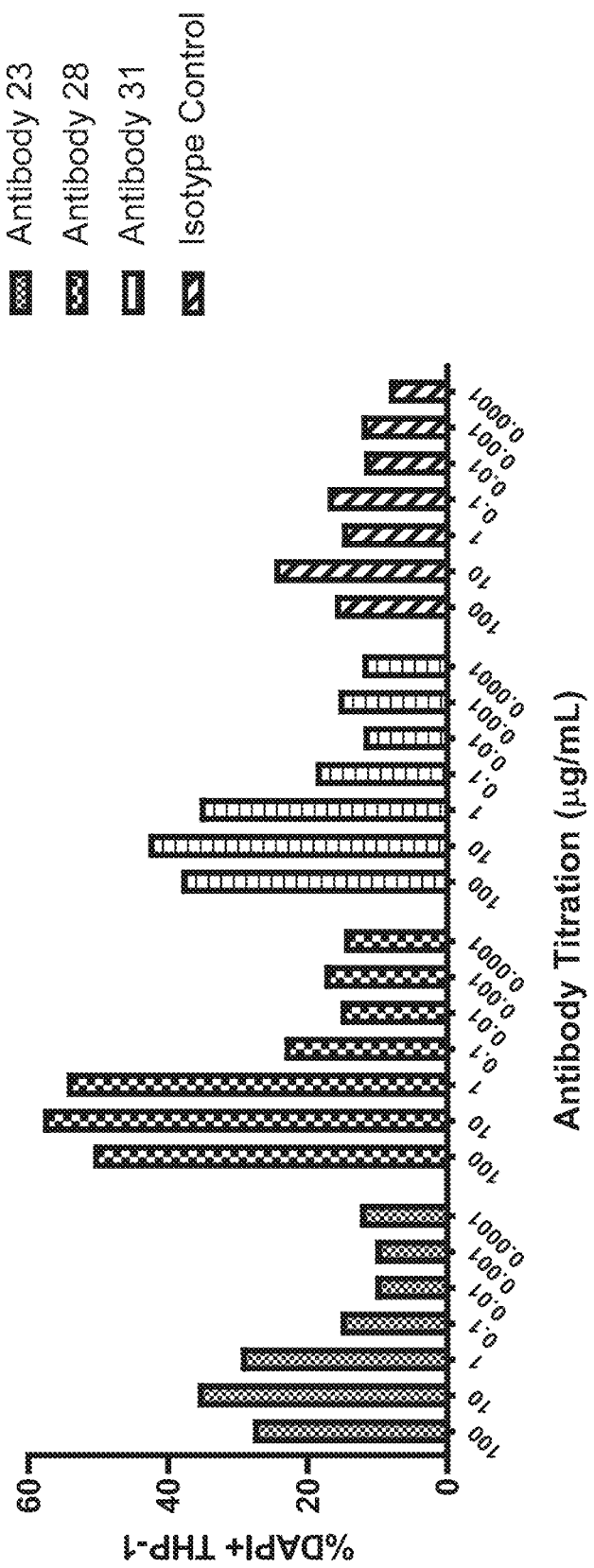
FIG. 5 shows the effect of selected antibodies of the disclosure on antibody dependent cellular cytotoxicity (ADCC) of THP-1 cells in vitro.

Antibody-dependent cell-mediated cytotoxicity (ADCC) induced by selected SIRP antibodies of a SIRPα-expressing human monocyte cell line was evaluated. An immortalized human monocyte-like cell line, THP-1, was stained using an intracellular dye (CellTracker™) and exposed to test article (SIRPα antibodies or isotype control) at various concentrations. Human NK (effector) cells were then co-incubated with the SIRP antibody-opsonized THP-1 (target) cells at an effector cell to target cell ratio of 1:1 for 4 hours at 37° C. Dead cells were stained using DAPI and samples analyzed via flow cytometry. FIG. 5 depicts percent of dual DAPI+ and CellTracker+ THP-1 cells. The data show ADCC of THP-1 cells induced by selected antibodies of the disclosure. The ADCC effect is antibody-dose dependent. The results are presented as compared to an isotype control, an unrelated IgG1 antibody with an irrelevant CDR.

Figure 6A:
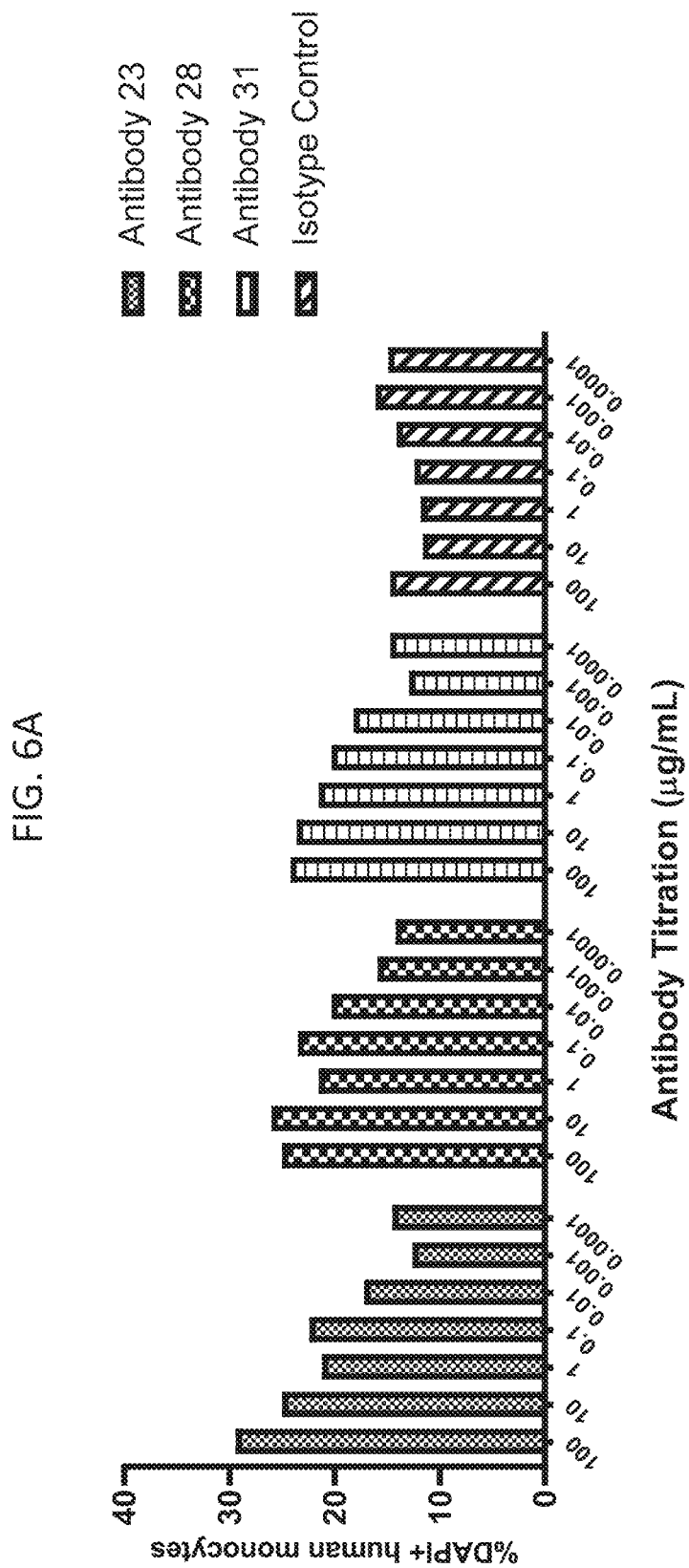
FIG. 6A shows the effect of selected antibodies of the disclosure on ADCC of human monocytes in vitro.

Antibody-dependent cell-mediated cytotoxicity (ADCC) induced by selected SIRP antibodies on primary monocytes was evaluated. SIRPα expressing-human primary monocyte (target) cells were exposed to test article at various concentrations, washed, and then co-incubated with human NK (effector) cells at an effector cell to target cell ratio of 1:1 for 4 hours at 37° C. Samples were stained with anti-CD14 antibody followed by DAPI and analyzed via flow cytometry. The graphs in FIG. 6A depicts percent of dual DAPI+ and CD14+ cells. FIG. 6A shows ADCC of human monocytes induced by selected antibodies of the disclosure. The ADCC effect is antibody-dose dependent. The results are presented as compared to an isotype control, 1, an unrelated IgG1 antibody with an irrelevant CDR.

Figure 6B:
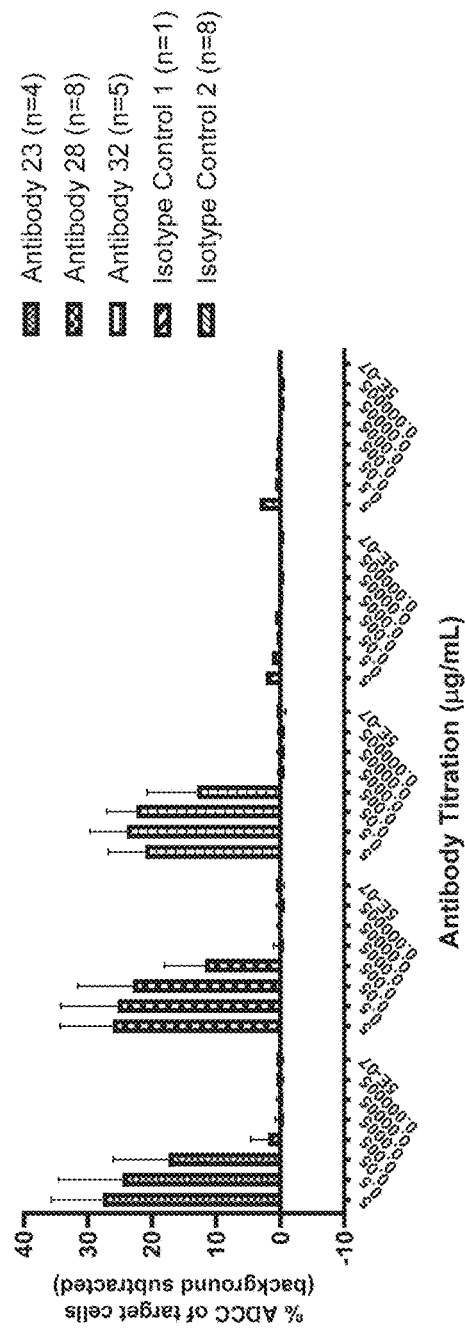
FIG. 6B shows the effect of selected antibodies of the disclosure on ADCC of human and cynomolgus monkey (cyno) monocytes in vitro.

ADCC induced by selected SIRP antibodies on primary human and cynomolgus monkey monocytes and resting T lymphocytes were evaluated. SIRP expressing-human and cynomolgus monkey primary monocyte or resting T lymphocytes (target) cells were stained with intracellular CellTracker™ Green, washed, and exposed to SIRP antibodies at various concentrations. The target cells were incubated with human NK (effector) cells at an effector-cell to target-cell ratio of 2:1 for 4 hours at 37° C. Samples were stained with Zombie Violet dye and analyzed via flow cytometry. The graph in FIGS. 6B-6D depict percent of cells positive for Zombie Violet dye with respect to total cells positive for CellTracker™ Green (% ADCC). FIG. 6B shows ADCC of human and cyno monocytes induced by selected antibodies of the disclosure. FIG. 6C shows ADCC of human and cyno CD4+ T cells induced by selected antibodies. FIG. 6D shows ADCC of human and cyno CD8+ T cells induced by selected antibodies. The ADCC effect is antibody-dose dependent. The results are presented as compared to isotype controls. Isotype control 1 was an unrelated IgG1 antibody with an irrelevant CDR. Isotype control 2 was the same as isotype control 1 but contained the same high affinity substitutions in the Fc region as some of the selected SIRP antibodies.

Example 5: Effect of SIRP Antibodies on ADCP

The antibody-dependent cellular phagocytosis (ADCP) of a monocytic cell line induced by selected SIRPα antibodies was evaluated. Two human monocytic cell lines, MOLM-13 and THP-1, were labelled with different colored intracellular dyes (CellTracker™ Green and CellTracker™ Deep Red). MOLM-13 (target) cells were opsonized with SIRP antibodies at the indicated concentrations and co-incubated with THP-1 (phagocytes) at a target cell to phagocyte ratio of 1:1 for 2 hours at 37° C. Cells were analyzed by flow cytometry. Graph depicts percent of THP-1 cells positive for two colors. FIG. 7 shows ADCP of MOLM-13 cells by THP-1 cells induced by selected antibodies of the disclosure.

Figure 8:
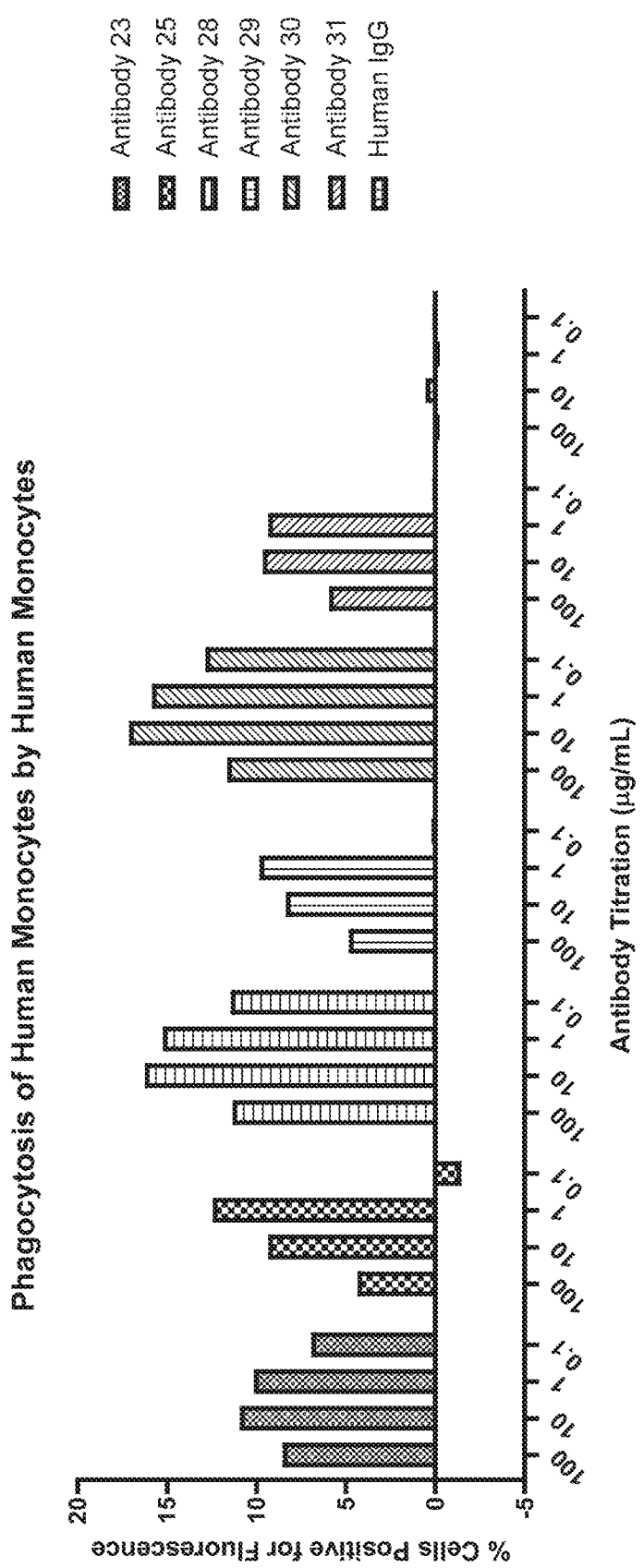
FIG. 8 shows the effect of selected antibodies of the disclosure on ADCP of human monocytes by human monocytes in vitro.

The antibody-dependent cellular phagocytosis (ADCP) of primary monocytes induced by SIRPα antibodies was evaluated. Primary human CD14+ monocytes were split into two sets and labelled with different colored intracellular dyes (CellTracker™ Green and CellTracker™ Deep Red). One set (target cells) was opsonized with SIRP antibodies at the indicated concentrations and co-incubated with the other set (phagocytes) at a target cell to phagocyte ratio of 1:1 for 2 hours at 37° C. Cells were analyzed by flow cytometry. Graph depicts percent of phagocytes positive for two colors. FIG. 8 shows ADCP of human monocytes by human monocytes induced by selected antibodies of the disclosure.

Figure 9A:
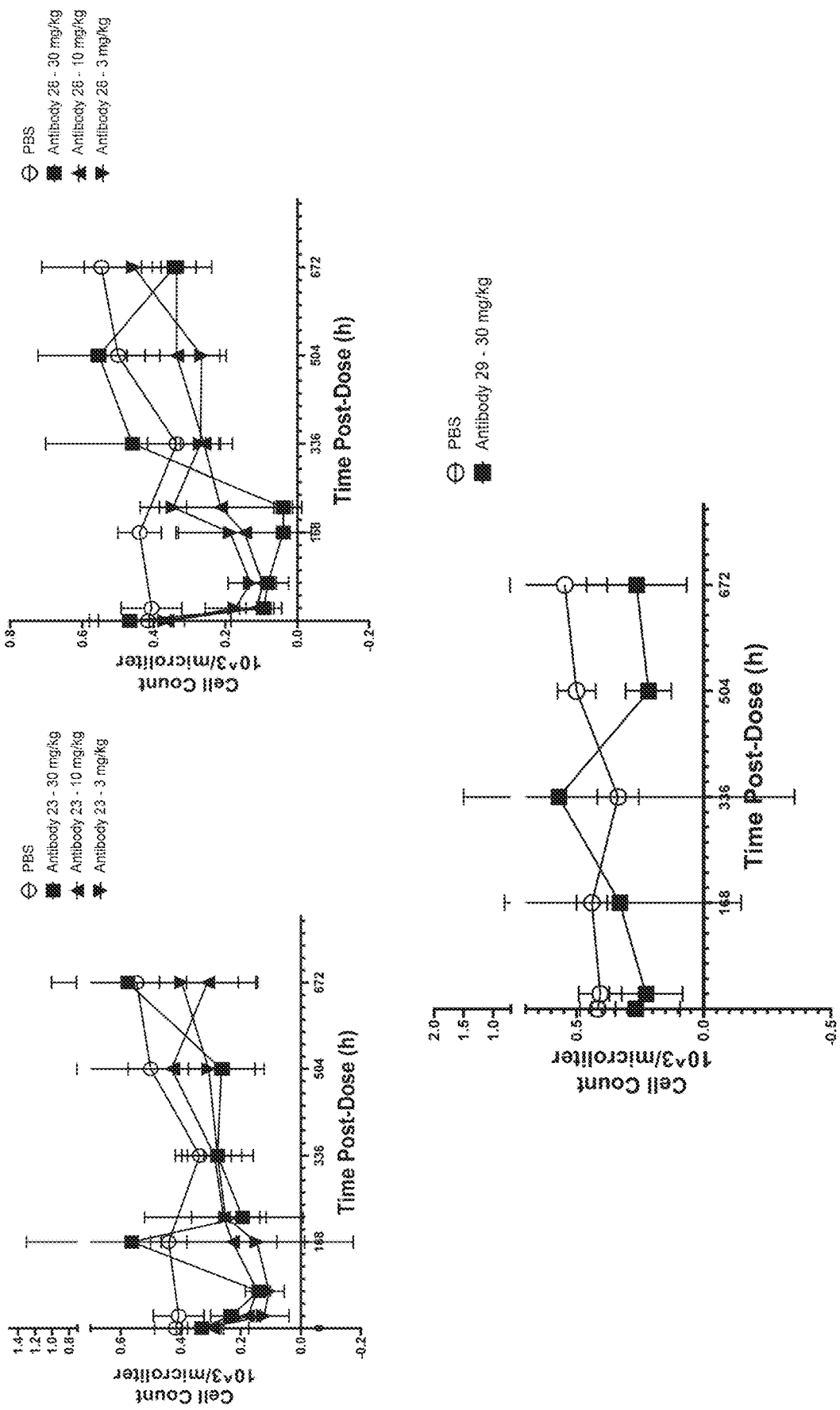

Example 6: Effect of SIRP Antibodies on In Vivo Depletion of Selected Cell Types The effect on monocytes in cynomolgus monkeys dosed intravenously with selected SIRP antibodies was evaluated. Data were generated from whole blood samples collected at different times post-dose and processed according to test facility's Standard Operating Procedures (SOPs). Samples were analyzed on an automated hematology analyzer. Graph depicts average (n=3 monkeys) of absolute monocyte number per microliter of whole blood sample plotted against time. Depletion of monocytes was observed. The effect was transient, but reversible. FIG. 9 shows that intravenous administration of selected antibodies of the disclosure resulted in transient in vivo monocyte depletion in cynomolgus monkeys at the doses indicated.

Figure 10A:
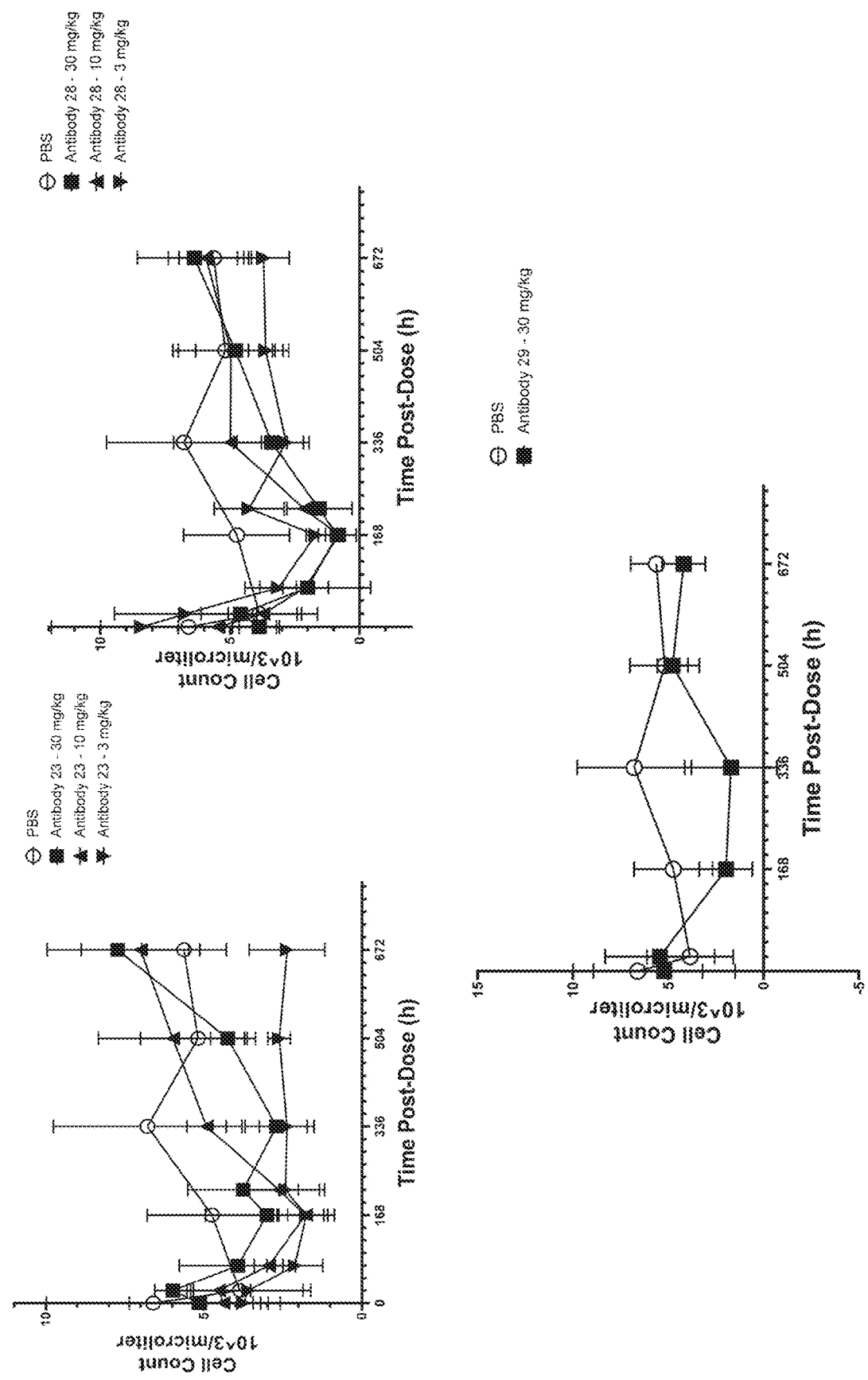

The effect on neutrophils in cynomolgus monkeys dosed intravenously with selected SIRP antibodies was evaluated. Data were generated from whole blood samples collected at different times post-dose and processed according to test facility's Standard Operating Protocols (SOPs). Samples were analyzed on an automated hematology analyzer. Graph depicts average (n=3 monkeys) of absolute neutrophil number per microliter of whole blood sample plotted against time. FIG. 10 shows that intravenous administration of selected antibodies of the disclosure resulted in transient in vivo neutrophil depletion in cynomolgus monkeys at the doses indicated.

Figure 11A:
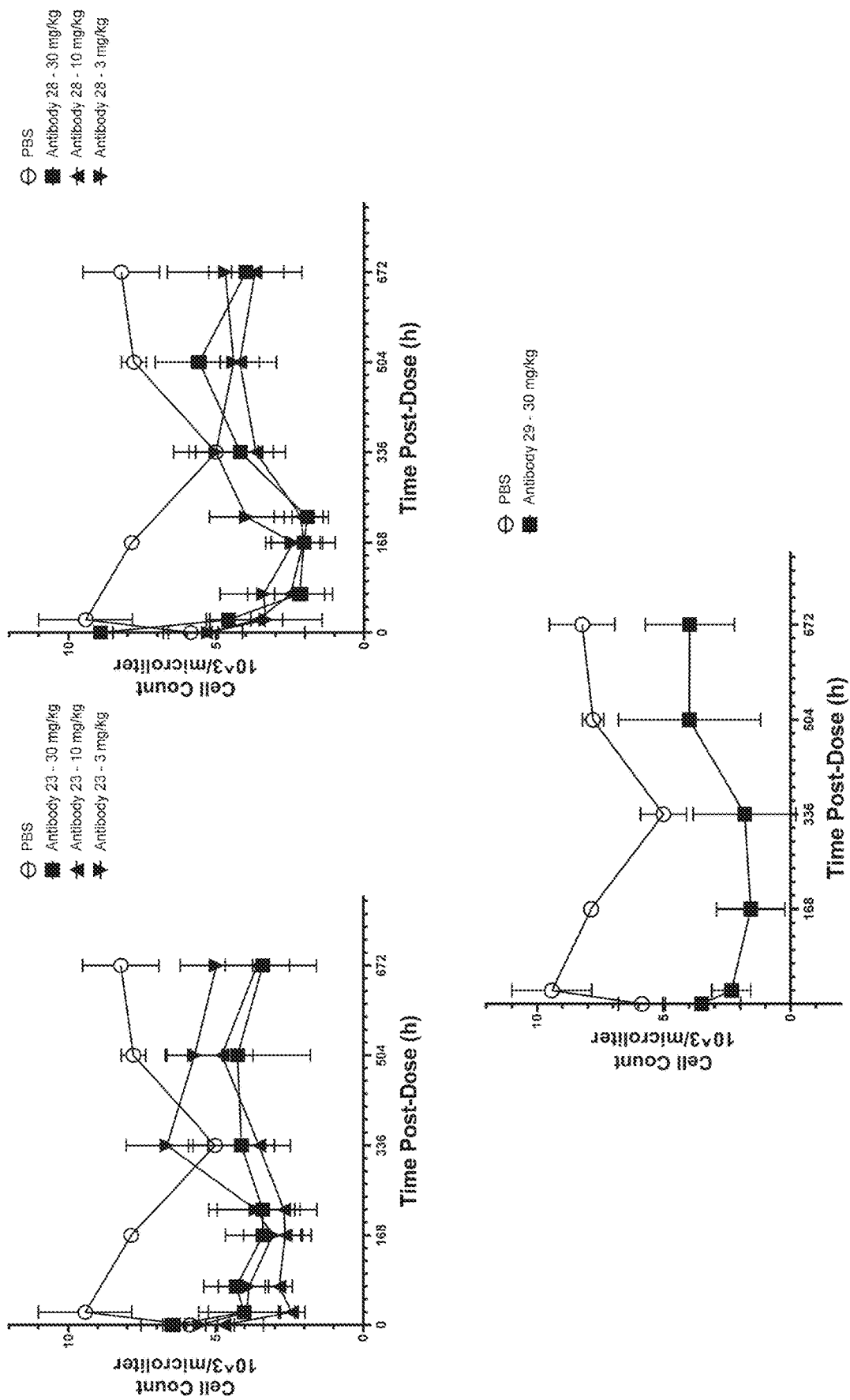
FIGS. 11A-11B show the effect of selected antibodies of the disclosure on lymphocyte depletion in vivo.
Figure 11B:
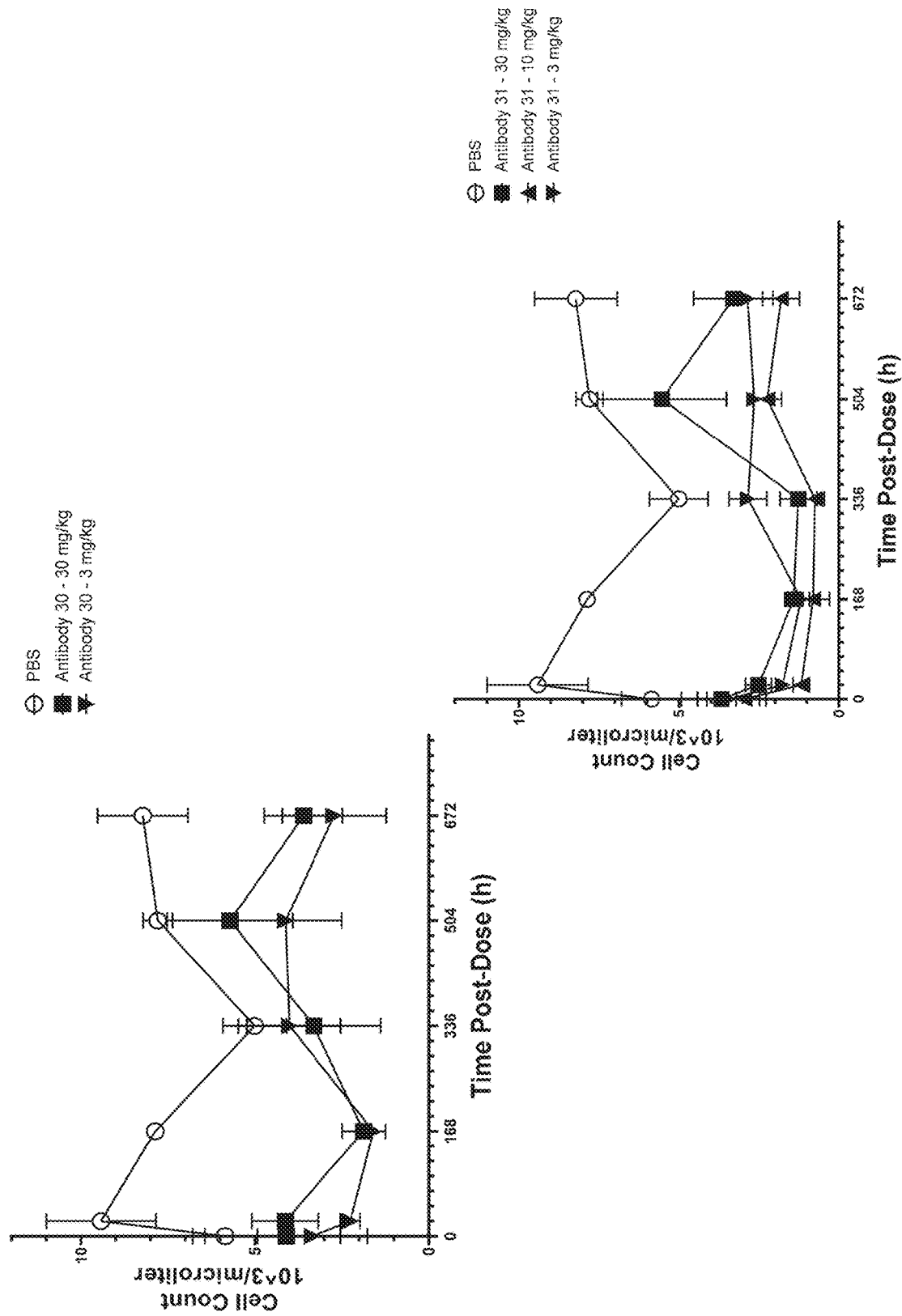

The effect on lymphocytes in cynomolgus monkeys dosed intravenously with selected SIRP antibodies was evaluated. Data were generated from whole blood samples collected at different times post-dose and processed according to test facility's Standard Operating Protocols (SOPs). Samples were analyzed on an automated hematology analyzer. Graph depicts average (n=3 monkeys) of absolute lymphocyte number per microliter of whole blood sample plotted against time. FIG. 11 shows that intravenous administration of selected antibodies of the disclosure resulted in transient in vivo lymphocyte depletion in cynomolgus monkeys at the doses indicated.

Figure 12A:
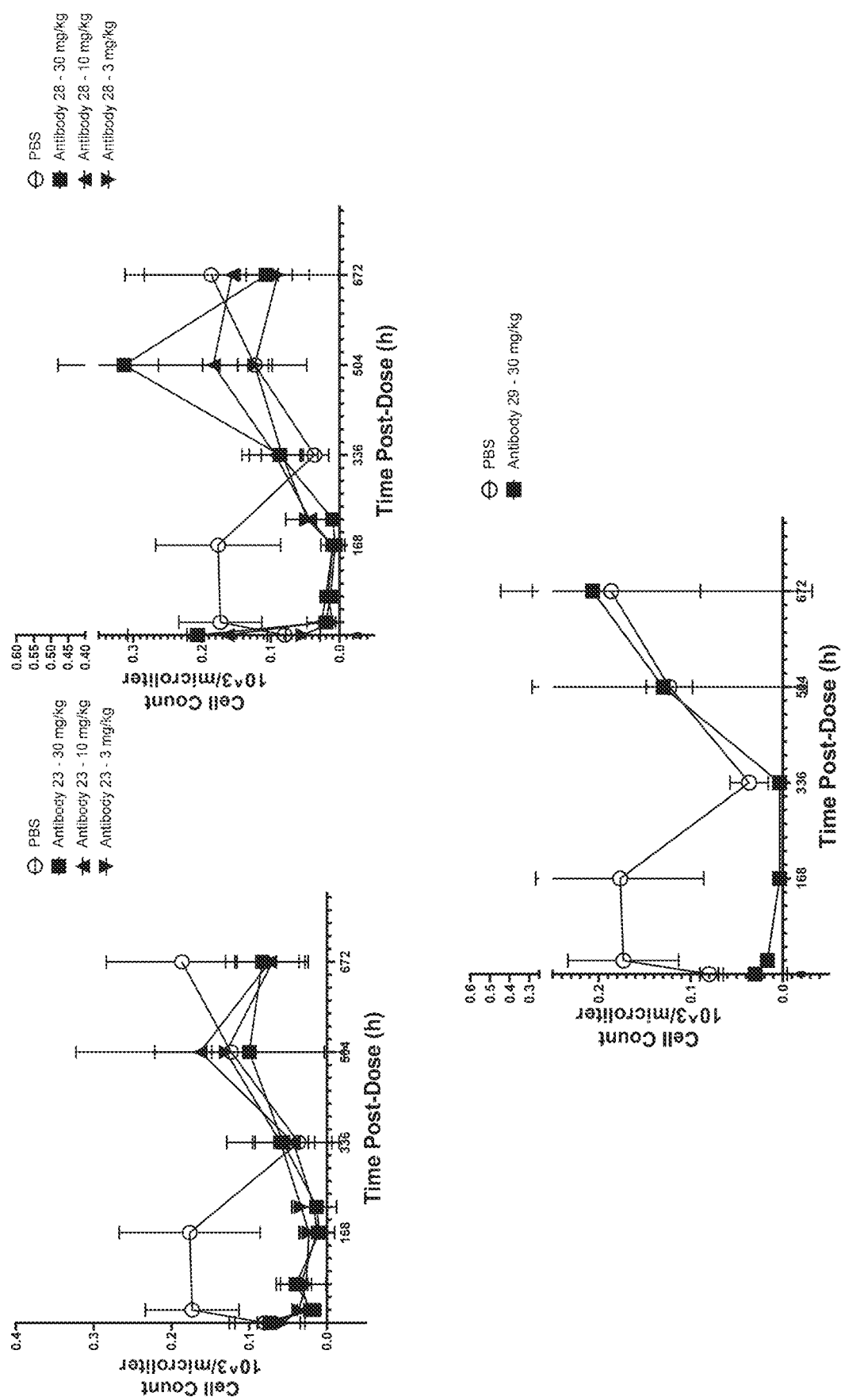

The effect on eosinophils in cynomolgus monkeys dosed intravenously with selected SIRP antibodies was evaluated. Data was generated from whole blood samples collected at different times post-dose and processed according to test facility's Standard Operating Protocols (SOPs). Samples were analyzed on an automated hematology analyzer. Graph depicts average (n=3 monkeys) of absolute eosinophil number per microliter of whole blood sample plotted against time. FIG. 12 shows that intravenous administration of selected antibodies of the disclosure resulted in transient in vivo eosinophil depletion in cynomolgus monkeys at the doses indicated.

Figure 13A:
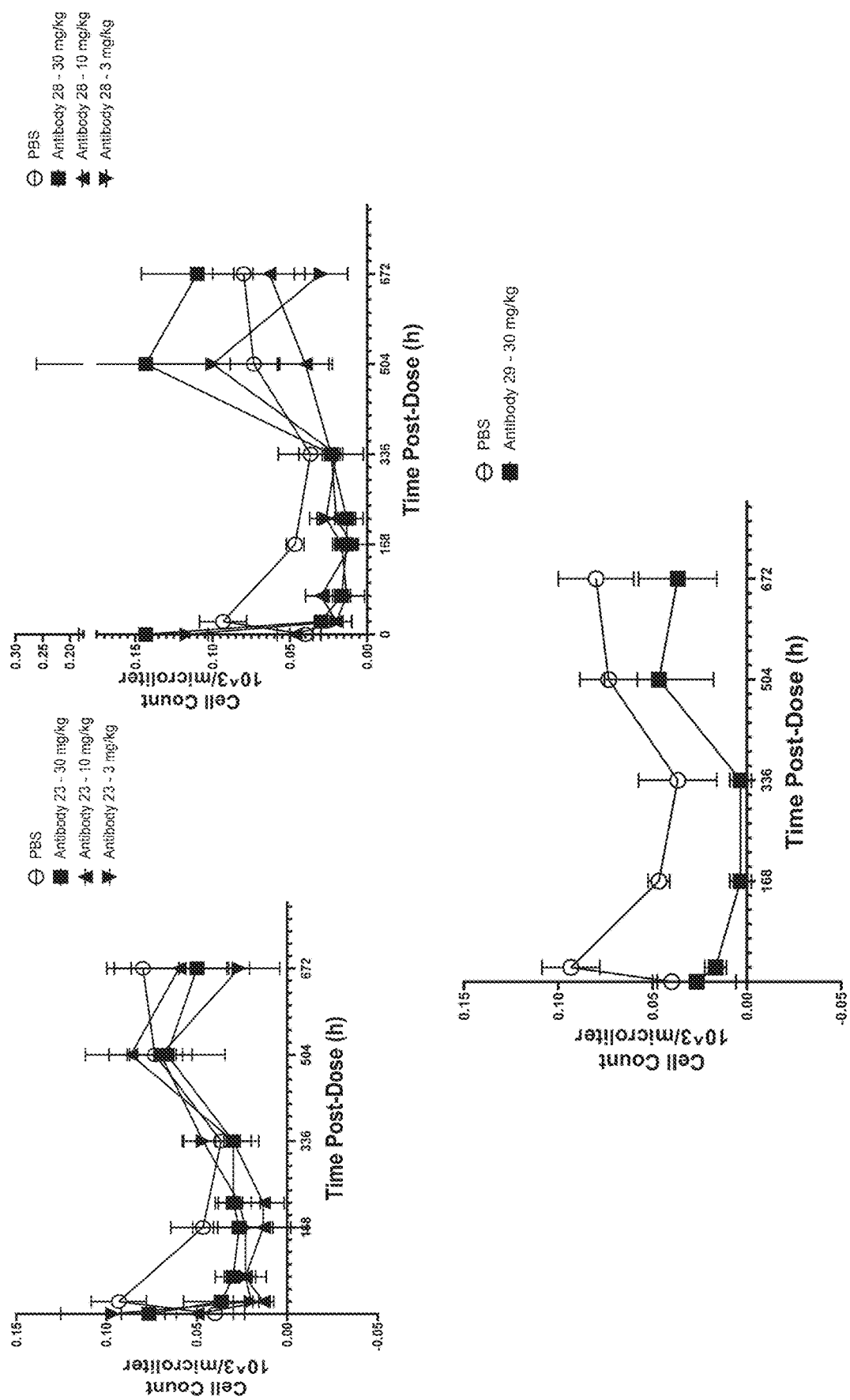

The effect on basophils in cynomolgus monkeys dosed intravenously with selected SIRP antibodies was evaluated. Data were generated from whole blood samples collected at different times post-dose and processed according to test facility's Standard Operating Protocols (SOPs). Samples were analyzed on an automated hematology analyzer. Graph depicts average (n=3 monkeys) of absolute basophil number per microliter of whole blood sample plotted against time. FIG. 13 shows that intravenous administration of selected antibodies of the disclosure resulted in transient in vivo basophil depletion in cynomolgus monkeys at the doses indicated.

Example 7: Determination of SIRP Antibody Competition with CD47 for Binding to SIRPα

Figure 14:
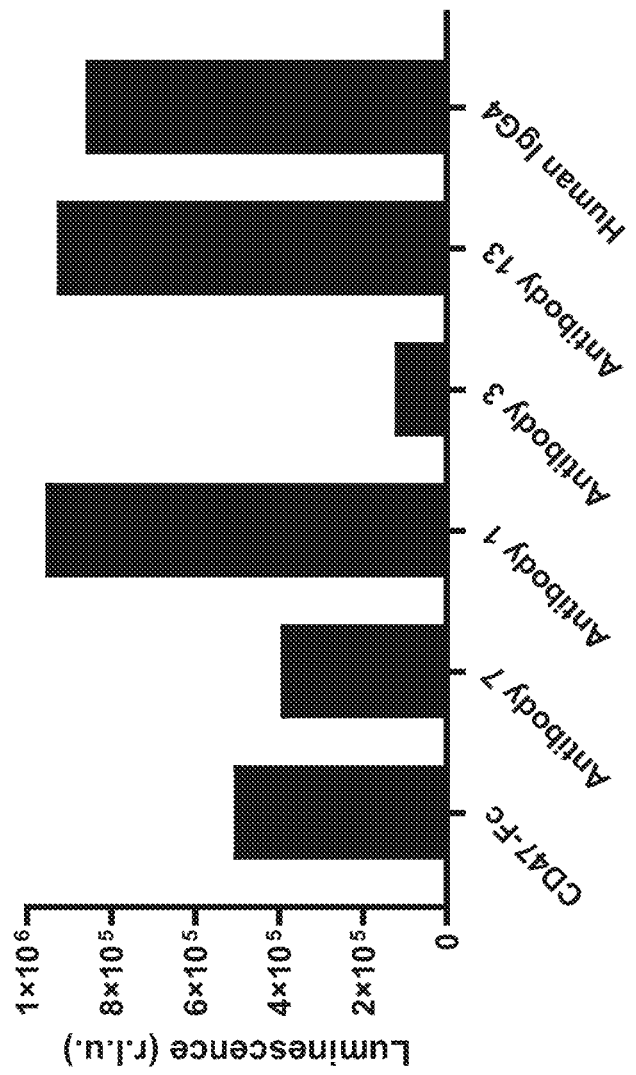
FIG. 14 is a graph depicting the results of an ELISA experiment assessing the ability of various antibodies to compete with CD47 for binding to human SIRPα.

ELISA analyses were performed to assess whether the SIRP antibodies of the disclosure compete with CD47-Fc for binding to hSIRPα, and whether any of the SIRP antibodies could displace CD47-Fc from binding to hSIRPα. To carry out the competition experiments, the extracellular binding domain of SIRPα was coated onto a 384-well plate and allowed to incubate overnight. Next, blocking solution was added. Next, each SIRP antibody at a concentration of 10 µg/mL was incubated on the plate for 1 hour. Biotinylated CD47-Fc at a concentration of 2.5 µg/mL was next added and allowed to equilibrate for 1 hour. Next, following a wash, streptavidin-HRP was added, and the plate was washed again, and next developed using substrate, following standard protocols. The plate was then read on a plate reader to assess the luminescence. A non-SIRPα-binding human IgG4 monoclonal antibody was used as a negative binding control. Non-biotinylated CD47-Fc was used as a positive control. A subset of the antibodies tested and shown in FIG. 14 showed significant disruption of the CD47-Fc binding to hSIRPα. A subset of the antibodies tested and shown in FIG. 14 show no or negligible disruption of the CD47-Fc binding to hSIRPα. Antibodies 1, and 13 do not disrupt the binding of CD47, they do not compete with CD47. Antibodies 3 and 7 inhibit the binding of CD47 to SIRPα at least partially. The competition data shown in FIG. 14 show varying degrees of luminescence for the antibodies tested, suggesting some antibodies bind to different regions on SIRPα.

SIRP antibodies were tested for their ability to interfere with SIRP-CD47 binding using the biolayer interferometry (BLI) Octet system (Pall ForteBio). Streptavidin (SA) biosensors were coated with biotinylated recombinant CD47-His. Human SIRPα or SIRPγ, conjugated to an Fc region, were tested to determine their ability to bind to CD47 immobilized on the biosensors and a response value during association is generated for each. To test for inhibition of SIRP-CD47 binding, select SIRP antibodies (200 nM) were each pre-incubated at a 10-fold molar excess with SIRP-Fc protein (20 nM) and then tested for their ability to block binding of SIRPα-Fc or SIRPγ-Fc to CD47-His-biotin immobilized on the biosensors. Table 16 shows total response values calculated during association for each antibody-SIRPα-Fc or SIRPγ-Fc complex measured and compared, as percent of response, to the binding of SIRPα-Fc or SIRPγ-Fc alone to CD47. A greater than or equal to 100% response indicates no blocking of the binding of the Antibody:SIRP antigen complex to the CD47 receptor. A less than 100% Response indicates blocking or partial blocking of Antibody:SIRP antigen complex to the CD47 receptor.

TABLE 16

Assessment of SIRP Antibodies to Block SIRPα-CD47 or SIRPγ-CD47 Interaction

| Antibody No. | SIRPα-CD47 Response (%) | SIRPγ-CD47 Response (%) |
| --- | --- | --- |
| 1  | 130.00 | 109.56 |
| 3  | −4.69  | −7.23  |
| 4  | −4.60  | −6.94  |
| 7  | 62.40  | 51.68  |
| 8  | −3.27  | −4.94  |
| 9  | −1.77  | −4.72  |
| 10 | −3.65  | −4.29  |
| 11 | −3.86  | −3.80  |
| 12 | 126.87 | 120.02 |
| 13 | 126.98 | 110.72 |
| 14 | 52.17  | 14.41  |
| 15 | 115.26 | 129.39 |
| 24 | −7.55  | −37.86 |
| 28 | 173.16 | 144.06 |

Example 8: Effect of SIRP Antibodies on Germinal Centers

Preliminary histological data from non-human primate studies indicate that in vivo administration of a SIRP antibody resulted in decreased germinal center cellularity in the spleen, characterized by decreased size of active germinal centers, fewer numbers of larger lymphocytes and tingible body macrophages, or complete absence of germinal centers. These observations are consistent with the mechanisms of action of the antibodies described herein that are capable of depleting SIRP-expressing cells found in the germinal centers, namely dendritic cells (SIRPα and SIRPβ1) and lymphocytes (SIRPγ). These observations suggest that the antibodies described herein may provide therapeutic effect in diseases where ectopic germinal centers or ectopic lymphoid like structures contribute to pathology including autoimmune disorders such as systemic lupus erythematosus, rheumatoid arthritis. Sjögren's syndrome, multiple sclerosis. Hashimoto's thyroiditis, primary sclerosing cholangitis and primary biliary cirrhosis, and Myasthenia gravis.

What is claimed is:

1. An antibody that is specific for one or more of SIRPα and SIRPβ1, and is specific for SIRPγ, wherein the antibody comprises a heavy chain variable region (VH) and a light chain variable region (VL), wherein the VH and VL comprise a combination of six complementarity determining regions (CDRs), wherein the CDR combination comprises the amino acid sequences of:
   a. SEQ ID NO: 5, SEQ ID NO: 23, SEQ ID NO: 36, SEQ ID NO: 54, SEQ ID NO: 70, and SEQ ID NO: 86; or
   b. SEQ ID NO: 16, SEQ ID NO: 31, SEQ ID NO: 47, SEQ ID NO: 62, SEQ ID NO: 79, and SEQ ID NO: 97.

2. The antibody of claim 1, wherein the binding of the antibody does not disrupt the interaction between CD47 and SIRPα, and/or the interaction between CD47 and SIRPγ.

3. The antibody of claim 1, wherein the antibody comprises an Fc domain, and wherein the Fc domain is selected from the group consisting of human IgG1, IgG2, IgG3, and IgG4.

4. The antibody of claim 1, wherein the antibody comprises an Fc domain, and wherein the Fc domain comprises SEQ ID NO: 3, SEQ ID NO: 4 or SEQ ID NO: 26.

5. The antibody of claim 1, wherein the antibody comprises an Fc domain, and wherein the Fc domain comprises SEQ ID NO: 3, SEQ ID NO: 4 or SEQ ID NO: 26 with one or more amino acid substitutions.

6. The antibody of claim 1, wherein the antibody comprises an Fc domain, and wherein the Fc domain of the antibody is human IgG1 and comprises at least one amino acid substitution at a position selected from the group consisting of: 214, 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 356, 358, 396, 428, 430, 433, 434, and 440 wherein the position numbers of the amino acid residues are of the EU numbering scheme.

7. The antibody of claim 1, wherein the antibody comprises an IgG1 Fc domain, and wherein the IgG1 Fc domain comprises a sequence selected from the group consisting of:
   a. SEQ ID NO: 19;
   b. SEQ ID NO: 20, wherein $X_1$ is V or A;
   c. SEQ ID NO: 21, wherein $X_1$ is V or A; $X_2$ is G or A; $X_3$ is S or D; and $X_4$ is I or E;
   d. SEQ ID NO: 22, wherein $X_1$ is V or A;
   e. SEQ ID NO: 25, wherein $X_1$ is V or A; $X_2$ is M or L; and $X_3$ is N or S; and
   f. SEQ ID NO: 26, wherein $X_1$ is K or R; $X_2$ is D or E; and $X_3$ is L or M.

8. The antibody of claim 1, wherein the antibody comprises an IgG4 Fc domain, and wherein the IgG4 Fc domain comprises a sequence of SEQ ID NO: 34, 35 or 37, wherein $X_1$ in SEQ ID NO: 37 is S or P; and $X_2$ in SEQ ID NO: 37 is L or E.

9. A pharmaceutical composition comprising the antibody of claim 1, and optionally a pharmaceutically acceptable carrier.

10. An antibody that is specific for one or more of SIRPα and SIRPβ1, and is specific for SIRPγ, wherein the antibody comprises a heavy chain variable region (VH) and a light chain variable region (VL), wherein:
   a. the VH comprises the amino acid sequence of SEQ ID NO: 104; and the VL comprises the amino acid sequence of SEQ ID NO: 123; or
   b. the VH comprises the amino acid sequence of SEQ ID NO: 116; and the VL comprises the amino acid sequence of SEQ ID NO: 135.

11. The antibody of claim 10, wherein the binding of the antibody does not disrupt the interaction between CD47 and SIRPα, and/or the interaction between CD47 and SIRPγ.

12. The antibody of claim 10, wherein the antibody comprises an Fc domain, and wherein the Fc domain is selected from the group consisting of human IgG1, IgG2, IgG3, and IgG4.

13. The antibody of claim 10, wherein the antibody comprises an Fc domain, and wherein the Fc domain comprises SEQ ID NO: 3, SEQ ID NO: 4 or SEQ ID NO: 26.

14. The antibody of claim 10, wherein the antibody comprises an Fc domain, and wherein the Fc domain comprises SEQ ID NO: 3, SEQ ID NO: 4 or SEQ ID NO: 26 with one or more amino acid substitutions.

15. The antibody of claim 10, wherein the antibody comprises an Fc domain, and wherein the Fc domain of the antibody is human IgG1 and comprises at least one amino acid substitution at a position selected from the group consisting of: 214, 215, 221, 222, 228, 234, 235, 236, 239, 240, 241, 243, 244, 245, 247, 250, 252, 254, 256, 262, 263, 264, 265, 266, 267, 268, 269, 270, 292, 296, 297, 298, 299, 300, 305, 313, 324, 325, 326, 327, 328, 329, 330, 332, 333, 334, 345, 356, 358, 396, 428, 430, 433, 434, and 440 wherein the position numbers of the amino acid residues are of the EU numbering scheme.

16. The antibody of claim 10, wherein the antibody comprises an IgG1 Fc domain, and wherein the IgG1 Fc domain comprises a sequence selected from the group consisting of:
   a. SEQ ID NO: 19;
   b. SEQ ID NO: 20, wherein $X_1$ is V or A;
   c. SEQ ID NO: 21, wherein $X_1$ is V or A; $X_2$ is G or A; $X_3$ is S or D; and $X_4$ is I or E;
   d. SEQ ID NO: 22, wherein $X_1$ is V or A;
   e. SEQ ID NO: 25, wherein $X_1$ is V or A; $X_2$ is M or L; and $X_3$ is N or S; and
   f. SEQ ID NO: 26, wherein $X_1$ is K or R; $X_2$ is D or E; and $X_3$ is L or M.

17. The antibody of claim 10, wherein the antibody comprises an IgG4 Fc domain, and wherein the IgG4 Fc domain comprises a sequence of SEQ ID NO: 34, 35 or 37, wherein $X_1$ in SEQ ID NO: 37 is S or P; and $X_2$ in SEQ ID NO: 37 is L or E.

18. A pharmaceutical composition comprising the antibody of claim 10, and optionally a pharmaceutically acceptable carrier.

19. A nucleic acid encoding for an antibody, wherein the antibody is specific for one or more of SIRPα and SIRPβ1, and is specific for SIRPγ, wherein the antibody comprises a heavy chain variable region (VH) and a light chain variable region (VL), wherein
   a. the VH comprises the nucleic acid sequence of SEQ ID NO: 142; and the VL comprises the nucleic acid sequence of SEQ ID NO: 161; or
   b. the VH comprises the nucleic acid sequence of SEQ ID NO: 154; and the VL comprises the nucleic acid sequence of SEQ ID NO: 173.

20. A method of treating a disease or condition in a subject in need thereof, comprising administering to the subject a therapeutically effective amount of an antibody that is specific for one or more of SIRPα and SIRPβ1, and is specific for SIRPγ, wherein the antibody comprises a heavy chain variable region (VH) and a light chain variable region (VL), wherein the VH and VL comprise a combination of six complementarity determining regions (CDRs), wherein the CDR combinations comprise the amino acid sequences of:
   a. SEQ ID NO: 5, SEQ ID NO: 23, SEQ ID NO: 36, SEQ ID NO: 54, SEQ ID NO: 70, and SEQ ID NO: 86; or
   b. SEQ ID NO: 16, SEQ ID NO: 31, SEQ ID NO: 47, SEQ ID NO: 62, SEQ ID NO: 79, and SEQ ID NO: 97.

21. The method of claim 20, wherein the antibody comprises a heavy chain variable region (VH) and a light chain variable region (VL), wherein:
   a. the VH comprises the amino acid sequence of SEQ ID NO: 104; and the VL comprises the amino acid sequence of SEQ ID NO: 123; or
   b. the VH comprises the amino acid sequence of SEQ ID NO: 116; and the VL comprises the amino acid sequence of SEQ ID NO: 135.

22. The method of claim 20, wherein the disease or condition is characterized by overactivation and/or hyperproliferation of lymphocytes, and the antibody induces depletion of lymphocytes, optionally wherein the lymphocytes are T cells, optionally wherein the disease or condition comprises aplastic anemia, cell mediated rejection of solid organ transplant, graft failure post-HSCT (hematopoietic stem cell transplant), lymphocyte-variant hypereosinophilia, atopic dermatitis, lymphocytic myocarditis, axial spondyloarthritis, celiac disease, or Rasmussen's encephalitis.

23. The method of claim 20, wherein the disease or condition is characterized by overactivation and/or hyperproliferation of myeloid cells, and the antibody induces depletion of myeloid cells, optionally wherein the myeloid cells comprise monocytes, macrophages, dendritic cells, basophils, eosinophils, neutrophils, or mast cells, optionally wherein the myeloid cells comprise:
   a. eosinophils, and the disease or condition comprises acute eosinophilic pneumonia, chronic eosinophilic pneumonia, eosinophilic esophagitis, eosinophilic gastritis, eosinophilic gastroenteritis, eosinophilic enteritis, eosinophilic colitis, lymphocyte-variant hypereosinophilia, eosinophilic cardiomyopathy/Loeffler endocarditis, Löffler syndrome or episodic angioedema with eosinophilia/Gleich syndrome;
   b. mast cells, and wherein the disease or condition comprises cutaneous mastocytosis, mastocytic enterocolitis, systemic mastocytosis, mast cell activation syndrome, hereditary alpha tryptasemia syndrome, chronic urticaria or severe allergic conjunctivitis; or
   c. neutrophils, and wherein the disease or condition comprises neutrophilic dermatoses, psoriatic arthritis, generalized pustular psoriasis, pyoderma gangrenosum, Sweet's syndrome, subcorneal pustular dermatosis, neutrophilic eccrine hidradenitis, bowel associated dermatosis-arthritis syndrome (BADAS), rheumatoid neutrophilic dermatitis, or Behçet's disease.

24. The method of claim 20, wherein the disease or condition comprises a disease or disorder associated with both lymphocytes and myeloid cells.

25. The method of claim 20, wherein the disease or condition comprises histiocytosis and is selected from the group consisting of: hemophagocytic lymphohistiocytosis (HLH) (including primary and secondary HLH), macrophage activation syndrome, Langerhans cell histiocytosis (LCH), indeterminate cell histiocytosis, Erdheim-Chester disease (ECD), mixed LCH/ECD, Rosai Dorfman disease, malignant histiocytosis, cutaneous non-LCH histiocytoses, juvenile xanthogranuloma, virus-associated HLH, bacteria-associated HLH, parasite-associated HLH, fungal-associated (fungal induced) HLH, autoimmune disease mediated HLH, and malignancy-triggered HLH.

26. The method of claim 20, wherein the disease or condition comprises a hematological malignancy.

27. The method of claim 20, wherein the disease or condition comprises a hematological malignancy selected from the group consisting of: Hodgkin's lymphoma, non-Hodgkin's lymphoma, T-cell lymphoblastic lymphoma, T-cell lymphoblastic leukemia, T-cell non-lymphoblastic lymphoma, B-cell lymphoma, acute lymphoblastic leukemia, large granular lymphocyte leukemia, NK-cell lymphoma, NK-cell leukemia, acute myelogenous leukemia, chronic myelogenous leukemia, chronic myelomonocytic leukemia, chronic eosinophilic leukemia, Chronic neutrophilic leukemia, autoimmune lymphoproliferative syndrome, X-linked lymphoproliferative disease, acute myelogenous leukemia, chronic myelogenous leukemia, chronic myelomonocytic leukemia, juvenile myelomonocytic leukemia, myeloid neoplasia, and myelofibrosis.

28. The method of claim 20, wherein the subject is human.

29. The method of claim 20, wherein the antibody is administered intravenously or subcutaneously.

* * * * *